(12) United States Patent
Mathew et al.

(10) Patent No.: US 12,359,215 B2
(45) Date of Patent: Jul. 15, 2025

(54) MODIFICATION OF UBIQUITIN BINDING PEPTIDASE GENES IN PLANTS FOR YIELD TRAIT IMPROVEMENT

(71) Applicant: Pairwise Plants Services, Inc., Durham, NC (US)

(72) Inventors: Lolita George Mathew, Cary, NC (US); Xiaoyu Zhang, Cary, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 15 days.

(21) Appl. No.: 17/822,822

(22) Filed: Aug. 29, 2022

(65) Prior Publication Data

US 2023/0074699 A1  Mar. 9, 2023

Related U.S. Application Data

(60) Provisional application No. 63/238,394, filed on Aug. 30, 2021.

(51) Int. Cl.
*C12N 15/82* (2006.01)
*C12N 15/11* (2006.01)

(52) U.S. Cl.
CPC .......... *C12N 15/8261* (2013.01); *C12N 15/11* (2013.01); *C12N 15/8213* (2013.01); *C12N 2310/20* (2017.05)

(58) Field of Classification Search
None
See application file for complete search history.

(56) References Cited

U.S. PATENT DOCUMENTS

2019/0300897 A1   10/2019  Li et al.
2019/0352660 A1*  11/2019  Bevan et al. ...... C12N 15/8261

FOREIGN PATENT DOCUMENTS

| WO | 2009047525 A1 | 4/2009 |
| WO | 2014161908 A1 | 10/2014 |
| WO | 2015022192 A1 | 2/2015 |
| WO | 2015067943 A1 | 5/2015 |

OTHER PUBLICATIONS

Zhao et al., Sequence and expression variations suggest an adaptive role for the DA1-like gene family in the evolution of soybeans, 2015, BMC Plant Biology, vol. 15(120), pp. 1-12. (Year: 2015).*
Li et al., Control of final seed and organ size by the DA1 gene family in Arabidopsis thaliana, 2008, Genes & Development, vol. 22, pp. 1331-1336. (Year: 2008).*
Zhao et al., Genome-Wide Analyses of a Plant-Specific LIM-Domain Gene Family Implicate Its Evolutionary Role in Plant Diversification, 2014, Genome Biol. Evol. 6(4), pp. 1000-1012 (Year: 2014).*
International Search Report and Written Opinion for International Application No. PCT/US2022/075555 dated Dec. 16, 2022 (17 pages).
Li, Yunhai, et al., "Control of final seed and organ size by the DAl gene family in *Arabidopsis thaliana*", Genes & Development, 22(10): 1331-1336 (2008).
Li, Na, et al., "Ubiquitin-mediated control of seed size in plants", Frontiers in Plant Science. vol. 5, Article 332 (2014).
Mora-Ramirez, Isabel, et al., "The da1 mutation in wheat increases grain size under ambient and elevated CO2 but not grain yield due to trade-off between grain size and grain number", Plant-Environment Interactions. 2: 61-73 (2021).
Wang, Jie-Li, et al., "Down-regulation of BnDA1, whose gene locus is associated with the seeds weight, improves the seeds weight and organ size in *Brassica napus*", Plant Biotechnology Journal. 15: 1024-1033 (2017).
Xia, Tian, et al., "The Ubiquitin Receptor DA1 Interacts with the E3 Ubiquitin Ligase DA2 to Regulate Seed and Organ Size in *Arabidopsis*", The Plant Cell. 25: 3347-3359 (2013).
Xie, Guangning, et al., "Over-expression of mutated ZmDA1 or ZmDAR1 gene improves maize kernel yield by enhancing starch synthesis", Plant Biotechnology Journal. 16: 234-244 (2018).
Yang, Hong, et al., "CRISPR/Cas9-mediated genome editing efficiently creates specific mutations at multiple loci using one sgRNA in *Brassica napus*", Scientific Reports. 7: 7489 (2017).
Zhao, Man, et al., "Sequence and expression variations suggest an adaptive role for the DA1-like gene family in the 9 evolution of soybeans", BMC Plant Biology. 15:120 (2015).

* cited by examiner

*Primary Examiner* — Amjad Abraham
*Assistant Examiner* — Christina L Meadows
(74) *Attorney, Agent, or Firm* — Myers Bigel, P.A.

(57) ABSTRACT

This invention relates to compositions and methods for modifying Ubiquitin Binding Peptidase (DA1) genes in plants, optionally to improve yield traits. The invention further relates to plants having increased improved yield traits produced using the methods and compositions of the invention.

20 Claims, No Drawings
Specification includes a Sequence Listing.

```
                         SEQUENCE LISTING

Sequence total quantity: 160
SEQ ID NO: 1            moltype = AA   length = 1228
FEATURE                 Location/Qualifiers
REGION                  1..1228
                        note = Lachnospiraceae bacterium
source                  1..1228
                        mol_type = protein
                        organism = unidentified
SEQUENCE: 1
MSKLEKFTNC YSLSKTLRFK AIPVGKTQEN IDNKRLLVED EKRAEDYKGV KKLLDRYYLS   60
FINDVLHSIK LKNLNNYISL FRKKTRTEKE NKELENLEIN LRKEIAKAFK GNEGYKSLFK  120
KDIIETILPE FLDDKDEIAL VNSFNGFTTA FTGFFDNREN MFSEEAKSTS IAFRCINENL  180
TRYISNMDIF EKVDAIFDKH EVQEIKEKIL NSDYDVEDFF EGEFFNFVLT QEGIDVYNAI  240
IGGFVTESGE KIKGLNEYIN LYNQKTKQKL PKFKPLYKQV LSDRESLSFY GEGYTSDEEV  300
LEVFRNTLNK NSEIFSSIKK LEKLFKNFDE YSSAGIFVKN GPAISTISKD IFGEWNVIRD  360
KWNAEYDDIH LKKKAVVTEK YEDDRRKSFK KIGSFSLEQL QEYADADLSV VEKLKEIIIQ  420
KVDEIYKVYG SSEKLFDADF VLEKSLKKND AVVAIMKDLL DSVKSFENYI KAFFGEGKET  480
NRDESFYGDF VLAYDILLKV DHIYDAIRNY VTQKPYSKDK FKLYFQNPQF MGGWDKDKET  540
DYRATILRYG SKYYLAIMDK KYAKCLQKID KDDVNGNYEK INYKLLPGPN KMLPKVFFSK  600
KWMAYYNPSE DIQKIYKNGT FKKGDMFNLN DCHKLIDFFK DSISRYPKWS NAYDFNFSET  660
EKYKDIAGFY REVEEQGYKV SFESASKKEV DKLVEEGKLY MFQIYNKDFS DKSHGTPNLH  720
TMYFKLLFDE NNHGQIRLSG GAELFMRRAS LKKEELVVHP ANSPIANKNP DNPKKTTTLS  780
YDVYKDKRFS EDQYELHIPI AINKCPKNIF KINTEVRVLL KHDDNPYVIG IDRGERNLLY  840
IVVVDGKGNI VEQYSLNEII NNFNGIRIKT DYHSLLDKKE KERFEARQNW TSIENIKELK  900
AGYISQVVHK ICELVEKYDA VIALEDLNSG FKNSRVKVEK QVYQKFEKML IDKLNYMVDK  960
KSNPCATGGA LKGYQITNKF ESFKSMSTQN GFIFYIPAWL TSKIDPSTGF VNLLKTKYTS 1020
IADSKKFISS FDRIMYVPEE DLFEFALDYK NFSRTDADYI KKWKLYSYGN RIRIFRNPKK 1080
NNVFDWEEVC LTSAYKELFN KYGINYQQGD IRALLCEQSD KAFYSSFMAL MSLMLQMRNS 1140
ITGRTDVDFL ISPVKNSDGI FYDSRNYEAQ ENAILPKNAD ANGAYNIARK VLWAIGQFKK 1200
AEDEKLDKVK IAISNKEWLE YAQTSVKH                                    1228

SEQ ID NO: 2            moltype = AA   length = 1307
FEATURE                 Location/Qualifiers
source                  1..1307
                        mol_type = protein
                        organism = Acidaminococcus sp.
SEQUENCE: 2
MTQFEGFTNL YQVSKTLRFE LIPQGKTLKH IQEQGFIEED KARNDHYKEL KPIIDRIYKT   60
YADQCLQLVQ LDWENLSAAI DSYRKEKTEE TRNALIEEQA TYRNAIHDYF IGRTDNLTDA  120
INKRHAEIYK GLFKAELFNG KVLKQLGTVT TTEHENALLR SFDKFTTYFS GFYENRKNVF  180
SAEDISTAIP HRIVQDNFPK FKENCHIFTR LITAVPSLRE HFENVKKAIG IFVSTSIEEV  240
FSFPFYNQLL TQTQIDLYNQ LLGGISREAG TEKIKGLNEV LNLAIQKNDE TAHIIASLPH  300
RFIPLFKQIL SDRNTLSFIL EEFKSDEEVI QSFCKYKTLL RNENVLETAE ALFNELNSID  360
LTHIFISHKK LETISSALCD HWDTLRNALY ERRISELTGK ITKSAKEKVQ RSLKHEDINL  420
QEIISAAGKE LSEAFKQKTS EILSHAHAAL DQPLPTTLKK QEEKEILKSQ LDSLLGLYHL  480
LDWFAVDESN EVDPEFSARL TGIKLEMEPS LSFYNKARNY ATKKPYSVEK FKLNFQMPTL  540
ASGWDVNKEK NNGAILFVKN GLYYLGIMPK QKGRYKALSF EPTEKTSEGF DYNVDYFPD  600
AAKMIPKCST QLKAVTAHFQ THTTPILLSN NFIEPLEITK EIYDLNNPEK EPKKFQTAYA  660
KKTGDQKGYR EALCKWIDFT RDFLSKYTKT TSIDLSSLRP SSQYKDLGEY YAELNPLLYH  720
ISFQRIAEKE IMDAVETGKL YLFQIYNKDF AKGHHGKPNL HTLYWTGLFS PENLAKTSIK  780
LNGQAELFYR PKSRMKRMAH RLGEKMLNKK LKDQKTPIPD TLYQELYDYV NHRLSHDLSD  840
EARALLPNVI TKEVSHEIIK DRRFTSDKFF FHVPITLNYQ AANSPSKFNQ RVNAYLKEHP  900
ETPIIGIDRG ERNLIYITVI DSTGKILEQR SLNTIQQFDY QKKLDNREKE RVAARQAWSV  960
VGTIKDLKQG YLSQVIHEIV DLMIHYQAVV VLENLNFGFK SKRTGIAEKA VYQQFEKMLI 1020
DKLNCLVLKD YPAEKVGGVL NPYQLTDQFT SFAKMGTQSG FLFYVPAPYT SKIDPLTGFV 1080
DPFVWKTIKN HESRKHFLEG FDFLHYDVKT GDFILHFKMN RNLSFQRGLP GFMPAWDIVF 1140
EKNETQFDAK GTPFIAGKRI VPVIENHRFT GRYRDLYPAN ELIALLEEKG IVFRDGSNIL 1200
PKLLENDDSH AIDTMVALIR SVLQMRNSNA ATGEDYINSP VRDLNGVCFD SRFQNPEWPM 1260
DADANGAYHI ALKGQLLLNH LKESKDLKLQ NGISNQDWLA YIQELRN               1307

SEQ ID NO: 3            moltype = AA   length = 1241
```

```
FEATURE              Location/Qualifiers
source               1..1241
                     mol_type = protein
                     organism = Butyrivibrio proteoclasticus
SEQUENCE: 3
MLLYENYTKR NQITKSLRLE LRPQGKTLRN IKELNLLEQD KAIYALLERL KPVIDEGIKD    60
IARDTLKNCE LSFEKLYEHF LSGDKKAYAK ESERLKKEIV KTLIKNLPEG IGKISEINSA   120
KYLNGVLYDF IDKTHKDSEE KQNILSDILE TKGYLALFSK FLTSRITTLE QSMPKRVIEN   180
FEIYAANIPK MQDALERGAV SFAIEYESIC SVDYYNQILS QEDIDSYNRL ISGIMDEDGA   240
KEKGINQTIS EKNIKIKSEH LEEKPFRILK QLHKQILEER EKAFTIDHID SDEEVVQVTK   300
EAFEQTKEQW ENIKKINGFY AKDPGDITLF IVVGPNQTHV LSQLIYGEHD RIRLLLEEYE   360
KNTLEVLPRR TKSEDARYDK FVNAVPKKVA KESHTFDGLQ KMTGDDRLFI LYRDELARNY   420
MRIKEAYGTF ERDILKSRRG IKGNRDVQES LVSFYDELTK FRSALRIINS GNDEKADPIF   480
YNTFDGIFEK ANRTYKAENL CRNYVTKSPA DDARIMASCL GTPARLRTHW WNGEENFAIN   540
DVAMIRRGDE YYYFVLTPDV KPVDLKTKDE TDAQIFVQRK GAKSFLGLPK ALFKCILEPY   600
FESPEHKNDK NCVIEEYVSK PLTIDRRAYD IFKNGTFKKT NIGIDGLTEE KFKDDCRYLI   660
DVYKEFIAVY TRYSCFNMSG LKRADEYNDI GEFFSDVDTR LCTMEWIPVS FERINDMVDK   720
KEGLLFLVRS MFLYNRPRKP YERTFIQLFS DSNMEHTSML LNSRAMIQYR AASLPRRVTH   780
KKGSILVALR DSNGEHIPMH IREAIYKMKN NFDISSEDFI MAKAYLAEHD VAIKKANEDI   840
IRNRRYTEDK FFLSLSYTKN ADISARTLDY INDKVEEDTQ DSRMAVIVTR NLKDLTYVAV   900
VDEKNNVLEE KSLNEIDGVN YRELLKERTK IKYHDKTRLW QYDVSSKGLK EAYVELAVTQ   960
ISKLATKYNA VVVVESMSST FKDKFSFLDE QIFKAFEARL CARMSDLSFN TIKEGEAGSI  1020
SNPIQVSNNN GNSYQDGVIY FLNNAYTRTL CPDTGFVDVF DKTRLITMQS KRQFFAKMKD  1080
IRIDDGEMLF TFNLEEYPTK RLLDRKEWTV KIAGDGSYFD KDKGEYVYVN DIVREQIIPA  1140
LLEDKAVFDG NMAEKFLDKT AISGKSVELI YKWFANALYG IITKKDGEKI YRSPITGTEI  1200
DVSKNTTYNF GKKFMFKQEY RGDGDFLDAF LNYMQAQDIA V                     1241

SEQ ID NO: 4         moltype = AA  length = 1238
FEATURE              Location/Qualifiers
source               1..1238
                     mol_type = protein
                     organism = Candidatus Methanoplasma termitum
SEQUENCE: 4
MNNYDEFTKL YPIQKTIRFE LKPQGRTMEH LETFNFFEED RDRAEKYKIL KEAIDEYHKK    60
FIDEHLTNMS LDWNSLKQIS EKYYKSREEK DKKVFLSEQK RMRQEIVSEF KKDDRFKDLF   120
SKKLFSELLK EEIYKKGNHQ EIDALKSFDK FSGYFIGLHE NRKNMYSDGD EITAISNRIV   180
NENFPKFLDN LQKYQEARKK YPEWIIKAES ALVAHNIKMD IVFSLEYFNK VLNQEGIQRY   240
NLALGGYVTK SGEKMMGLND ALNLAHQSEK SSKGRIHMTP LFKQILSEKE SFSYIPDVFT   300
EDSQLLPSIG GFFAQIENDK DGNIFDRALE LISSYAEYDT ERIYIRQADI NRVSNVIFGE   360
WGTLGGLMRE YKADSINDIN LERTCKKVDK WLDSKEFALS DVLEAIDRTG NNDAFNEYIS   420
KMRTAREKID AARKEMKFIS EKISGDEESI HIIKTLLDSV QQFLHFFNLF KARQDIPLDG   480
AFYAEFDEVH SKLFAIVPLY NKVRNYLTKN NLNTKKIKLN FKNPTLANGW DQNKVYDYAS   540
LIFLRDGNYY LGIINPKRKK NIKFEQGSGN GPFYRKMVYK QIPGPNKNLR PVFLTSTKGK   600
KEYKPSKEII EGYEADKHIR GDKFDLDFCH KLIDFFKESI EKHKDWSKFN FYFSPTESYG   660
DISEFYLDVE KQGYRMHFEN ISAETIDEYV EKGDLFLFQI YNKDFVKAAT GKKDMHTIYW   720
NAAFSPENLQ DVVVKLNGEA ELFYRDKSDI KEIVHREGEI LVNRTYNGRT PVPDKIHKKL   780
TDYHNGRTKD LGEAKEYLDK VRYFKAHYDI TDRRYLNDK IYPHVPLTLN FKANGKKNLN   840
KMVIEKFLSD EKAHIIGIDR GERNLLYYSI IDRSGKIIDQ QSLNVIDGFD YREKLNQREI   900
EMKDARQSWN AIGKIKDLKE GYLSKAVHEI TKMAIQYNAI VVMEELNYGF KRGRFKVEKQ   960
IYQKFENMLI DKMNYLVFKD APDESPGGVL NAYQLTNPLE SFAKLGKQTG ILFYVPAAYT  1020
SKIDPTTGFV NLFNTSSKTN AQERKEFLQK FESISYSAKD GGIFAFAFDY RKFGTSKTDH  1080
KNVWTAYTNG ERMRYIKEKK RNELFDPSKE IKEALTSSGI KYDGGQNILP DILRSNNNGL  1140
IYTMYSSFIA AIQMRVYDGK EDYIISPIKN SKGEFFRTDP KRRELPIDAD ANGAYNIALR  1200
GELTMRAIAE KFDPDSEKMA KLELKHKDWF EFMQTRGD                         1238

SEQ ID NO: 5         moltype = AA  length = 1281
FEATURE              Location/Qualifiers
source               1..1281
                     mol_type = protein
                     organism = Eubacterium eligens
SEQUENCE: 5
MNGNRSIVYR EFVGVIPVAK TLRNELRPVG HTQEHIIQNG LIQEDELRQE KSTELKNIMD    60
DYYREYIDKS LSGVTDLDFT LLFELMNLVQ SSPSKDNKKA LEKEQSKMRE QICTHLQSDS   120
NYKNIFNAKL LKEILPDFIK NYNQYDVKDK AGKLETLALF NGFSTYFTDF FEKRKNVFTK   180
EAVSTSIAYR IVHENSLIFL ANMTSYKKIS EKALDEIEVI EKNNQDKMGD WELNQIFNPD   240
FYNMVLIQSG IDFYNEICGV VNAHMNLYCQ QTKNNYNLFK MRKLHKQILA YTSTSFEVPK   300
MFEDDMSVYN AVNAFIDETE KGNIIGKLKD IVNKYDELDE KRIYISKDFY ETLSCFMSGN   360
WNLITGCVEN FYDENIHAKG KSKEEKVKKA VKEDKYKSLN DVNDLVEKYI DEKERNEFKN   420
SNAKQYIREI SNIITDTETA HLEYDDHISL IESEEKADEM KKRLDMYMNM YHWAKAFIVD   480
EVLDRDEMFY SDIDDIYNIL ENIVPLYNRV RNYVTQKPYN SKKIKLNFQS PTLANGWSQS   540
KEFDNNAIIL IRDNKYYLAI FNAKNKPDKK IIQGNSDKKN DNDYKKMVYN LLPGANKMLP   600
KVFLSKKGIE TFKPSDYIIS GYNAHKHIKT SENFDISFCR DLIDYFKNSI EKHAEWRKYE   660
FKFSATDSYS DISEFYREVE MQGYRIDWTY ISEADINKLD EEGKIYLFQI YNKDFAENST  720
GKENLHTMYF KNIFSEENLD KIIKLNGQAE LFYRRASVKN PVKHKKDSVL VNKTYKNQLD   780
NGDVVRIPIP DDIYNEIYKM YNGYIKESDL SEAAKEYLDK VEVRTAQKDI VKDYRYTVDK   840
YPFIHTPITIN YKVTARNNVN DMVVKYIAQN DDIHVIGIDR GERNLIYISV IDSHGNIVKQ   900
KSYNILNNYD YKKKLVEKEK TREYARKNWK SIGNIKELKE GYISGVVHEI AMLIVEYNAI   960
IAMEDLNYGF KRGRFKVERQ VYQKFESMLI NKLNYFASKE KSVDEPGGLL KGYQLTYVPD  1020
NIKNLGKQCG VIFYVPAAFT SKIDPSTGFI SAFNFKSIST NASRKQFFMQ FDEIRYCAEK  1080
```

-continued

```
DMFSFGFDYN NFDTYNITMG KTQWTVYTNG ERLQSEFNNA RRTGKTKSIN LTETIKLLLE  1140
DNEINYADGH DIRIDMEKMD EDKKSEFFAQ LLSLYKLTVQ MRNSYTEAEE QENGISYDKI  1200
ISPVINDEGE FFDSDNYKES DDKECKMPKD ADANGAYCIA LKGLYEVLKI KSEWTEDGFD  1260
RNCLKLPHAE WLDFIQNKRY E                                            1281

SEQ ID NO: 6            moltype = AA  length = 1300
FEATURE                 Location/Qualifiers
source                  1..1300
                        mol_type = protein
                        organism = Francisella novicida
SEQUENCE: 6
MSIYQEFVNK YSLSKTLRFE LIPQGKTLEN IKARGLILDD EKRAKDYKKA KQIIDKYHQF  60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKVNY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
AFKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE  1020
KQVYQKLEKM LIEKLNYLVF KDNEFDKTGG VLRAYQLTAP FETFKKMGKQ TGIIYYVPAG  1080
FTSKICPVTG FVNQLYPKYE SVSKSQEFFS KFDKICYNLD KGYFEFSFDY KNFGDKAAKG  1140
KWTIASFGSR LINFRNSDKN HNWDTREVYP TKELEKLLKD YSIEYGHGEC IKAAICGESD  1200
KKFFAKLTSV LNTILQMRNS KTGTELDYLI SPVADVNGNF FDSRQAPKNM PQDADANGAY  1260
HIGLKGLMLL GRIKNNQEGK KLNLVIKNEE YFEFVQNRNN                        1300

SEQ ID NO: 7            moltype = AA  length = 1206
FEATURE                 Location/Qualifiers
source                  1..1206
                        mol_type = protein
                        note = Lachnospiraceae sp.
                        organism = unidentified
SEQUENCE: 7
MYYESLTKQY PVSKTIRNEL IPIGKTLDNI RQNNILESDV KRKQNYEHVK GILDEYHKQL  60
INEALDNCTL PSLKIAAEIY LKNQKEVSDR EDFNKTQDLL RKEVVEKLKA HENFTKIGKK  120
DILDLLEKLP SISEDDYNAL ESFRNFYTYF TSYNKVRENL YSDKEKSSTV AYRLINENFP  180
KFLDNVKSYR FVKTAGILAD GLGEEEQDSL FIVETFNKTL TQDGIDTYNS QVGKINSSIN  240
LYNQKNQKAN GFRKIPKMKM LYKQILSDRE ESFIDEFQSD EVLIDNVESY GSVLIESLKS  300
SKVSAFFDAL RESKGKNVYV KNDLAKTAMS VIVFENWRTF DDLLNQEYDL ANENKKKDDK  360
YFEKRQKELK KNKSYSLEHL CNLSEDSCNL IENYIHQISD DIENIIINNE TFLRIVINEH  420
DRSRKLAKNR KAVKAIKDFL DSIKVLEREL KLINSSGQEL EKDLIVYSAH EELLVELKQV  480
DSLYNMTRNY LTKKPFSTEK VKLNFNRSTL LNGWDRNKET DNLGVLLLKD GKYYLGIMNT  540
SANKAFVNPP VAKTEKVFKK VDYKLLPVPN QMLPKVFFAK SNIDFYNPSS EIYSNYKKGT  600
HKKGNMFSLE DCHNLIDFFK ESISKHEDWS KFGFKFDTQA SYNDISEFYR EVEKQGYKLT  660
YTDIDETYIN DLIERNELYL FQIYNKDFSM YSKGKLNLHT LYFMMLFDQR NIDDVVYKLN  720
GEAEVFYRPA SISEDELIIH KAGEEIKNKN PNRARTKETS TFSYDIVKDK RYSKDKFTLH  780
IPITMNFGVD EVKRFNDAVN SAIRIDENVN VIGIDRGERN LLYVVVIDSK GNILEQISLN  840
SIINKEYDIE TDYHALLDER EGGRDKARKD WNTVENIRDL KAGLYLQVVN VVAKLVLKYN  900
AIICLEDLNF GFKRGRQKVE KQVYQKFEKM LIDKLNYLVI DKSREQTSPK ELGGALNALQ  960
LTSKFKSFKE LGKQSGVIYY VPAYLTSKID PTTGFANLFY MKCENVEKSK RFFDGFDFIR  1020
FNALENVFEF GFDYRSFTQR ACGINSKWTV CTNGERIIKY RNPDKNNMFD EKVVVVTDEM  1080
KNLFEQYKIP YEDGRNVKDM IISNEEAEFY RRLYRLLQQT LQMRNSTSDG TRDYIISPVK  1140
NKREAYFNSE LSDGSVPKDA DANGAYNIAR KGLWVLEQIR QKSEGEKINL AMTNAEWLEY  1200
AQTHLL                                                             1206

SEQ ID NO: 8            moltype = AA  length = 1233
FEATURE                 Location/Qualifiers
source                  1..1233
                        mol_type = protein
                        note = Lachnospiraceae sp.
                        organism = unidentified
SEQUENCE: 8
MDYGNGQFER RAPLTKTITL RLKPIGETRE TIREQKLLEQ DAAFRKLVET VTPIVDDCIR  60
KIADNALCHF GTEYDFSCLG NAISKNDSKA IKKETEKVEK LLAKVLTENL PDGLRKVNDI  120
NSAAFIQDTL TSFVQDDADK RVLIQELKGK TVLMQRFLTT RITALTVWLP DRVFENFNIF  180
IENAEKMRIL LDSPLNEKIM KFDPDAEQYA SLEFYGQCLS QKDIDSYNLI ISGIYADDEV  240
KNPGINEIVK EYNQQIRGDK DESPLPKLKK LHKQILMPVE KAFFVRVLSN DSDARSILEK  300
ILKDTEMLPS KIIEAMKEAD AGDIAVYGSR LHELSHVIYG DHGKLSQIIY DKESKRISEL  360
METLSPKERK ESKKRLEGLE EHIRKSTYTF DELNRYAEKN VMAAYIAAVE ESCAEIMRKE  420
KDLRTLLSKE DVKIRGNRHN TLIVKNYFNA WTVFRNLIRI LRRKSEAEID SDFYDVLDDS  480
VEVLSLTYKG ENLCRSYITK KIGSDLKPEI ATYGSALRPN SRWWSPGEKF NVKFHTIVRR  540
```

```
DGRLYYFILP KGAKPVELED MDGDIECLQM RKIPNPTIFL PKLVFKDPEA FFRDNPEADE    600
FVFLSGMKAP VTITRETYEA YRYKLYTVGK LRDGEVSEEE YKRALLQVLT AYKEFLENRM    660
IYADLNFGFK DLEEYKDSSE FIKQVETHNT FMCWAKVSSS QLDDLVKSGN GLLFEIWSER    720
LESYYKGYNE KVLRGYEGVL LSILKDENLV SMRTLLNSRP MLVYRPKESS KPMVVHRDGS    780
RVVDRFDKDG KYIPPEVHDE LYRFFNNLLI KEKLGEKARK ILDNKKVKVK VLESERVKWS    840
KFYDEQFAVT FSVKKNADCL DTTKDLNAEV MEQYSESNRL ILIRNTTDIL YYLVLDKNGK    900
VLKQRSLNII NDGARDVDWK ERFRQVTKDR NEGYNEWDYS RTSNDLKEVY LNYALKEIAE    960
AVIEYNAILI IEKMSNAFKD KYSFLDDVTF KGFETKKLAK LSDLHFRGIK DGEPCSFTNP   1020
LQLCQNDSNK ILQDGVIFMV PNSMTRSLDP DTGFIFAIND HNIRTKKAKL NFLSKFDQLK   1080
VSSEGCLIMK YSGDSLPTHN TDNRVWNCCC NHPITNYDRE TKKVEFIEEP VEELSRVLEE   1140
NGIETDTELN KLNERENVPG KVVDAIYSLV LNYLRGTVSG VAGQRAVYYS PVTGKKYDIS   1200
FIQAMNLNRK CDYYRIGSKE RGEWTDFVAQ LIN                                1233

SEQ ID NO: 9            moltype = AA   length = 1227
FEATURE                 Location/Qualifiers
source                  1..1227
                        mol_type = protein
                        note = Lachnospiraceae sp.
                        organism = unidentified
SEQUENCE: 9
MSKLEKFTNC YSLSKTLRFK AIPVGKTQEN IDNKRLLVED EKRAEDYKGV KKLLDRYYLS     60
FINDVLHSIK LKNLNNYISL FRKKTRTEKE NKELENLEIN LRKEIAKAFK GNEGYKSLFK    120
KDIIETILPE FLDDKDEIAL VNSFNGFTTA FTGFFDNREN MFSEEAKSTS IAFRCINENL    180
TRYISNMDIF EKVDAIFDKH EVQEIKEKIL NSDYDVEDFF EGEFFNFVLT QEGIDVYNAI    240
IGGFVTESGE KIKGLNEYIN LYNQKTKQKL PKFKPLYKQV LSDRESLSFY GEGYTSDEEV    300
LEVFRNTLNK NSEIFSSIKK LEKLFKNFDE YSSAGIFVKN GPAISTISKD IPGEWNVIRD    360
KWNAEYDDIH LKKKAVVTEK YEDDRRKSFK KIGSFSLEQL QEYADADLSV VEKLKEIIIQ    420
KVDEIYKVYG SSEKLFDADF VLEKSLKKND AVVAIMKDLL DSVKSFENYI KAFFGEGKET    480
NRDESFYGDF VLAYDILLKV DHIYDAIRNY VTQKPYSKDK FKLYFQNPQF MGGWDKDKET    540
DYRATILRYG SKYYLAIMDK KYAKCLQKID KDDVNGNYEK INYKLLPGPN KMLPKVFFSK    600
KWMAYYNPSE DIQKIYKNGT FKKGDMFNLN DCHKLIDFFK DSISRYPKWS NAYDFNFSET    660
EKYKDIAGFY REVEEQGYKV SFESASKKEV DKLVEEGKLY MFQIYNKDFS DKSHGTPNLH    720
TMYFKLLFDE NNHGQIRLSG GAELFMRRAS LKKEELVVHP ANSPIANKNP DNPKKTTTLS    780
YDVYKDKRFS EDQYIHIPI ANINKCPKNI FKINTEVRVL LKHDDNPYVI GIDRGERNLL     840
YIVVVDGKGN IVEQYSLNEI INNFNGIRIK TDYHSLLDKK EKERFEARQN WTSIENIKEL    900
KAGYISQVVH KICELVEKYD AVIALEDLNS GFKNSRVKVE KQVYQKFEKM LIDKLNYMVD    960
KKSNPCATGG ALKGYQITNK FESFKSMSTQ NGFIFYIPAW LTSKIDPSTG FVNLLKTKYT   1020
SIADKKFISS FDRIMYVPEE DLFEFALDYK NFSRTDADYI KKWKLYSYGN RIRIFRNPKK   1080
NNVFDWEEVC LTSAYKELFN KYGINYQQGD IRALLCEQSD KAFYSSFMAL MSLMLQMRNS   1140
ITGRTDVDFL ISPVKNSDGI FYDSRNYEAQ ENAILPKNAD ANGAYNIARK VLWAIGQFKK   1200
AEDEKLDKVK IASNKEWLEY AQTSVKH                                       1227

SEQ ID NO: 10           moltype = AA   length = 1264
FEATURE                 Location/Qualifiers
source                  1..1264
                        mol_type = protein
                        organism = Leptospira inadai
SEQUENCE: 10
MEDYSGFVNI YSIQKTLRFE LKPVGKTLEH IEKKGFLKKD KIRAEDYKAV KKIIDKYHRA     60
YIEEVFDSVL HQKKKKDKTR FSTQFIKEIK EFSELYYKTE KNIPDKERLE ALSEKLRKML    120
VGAFKGEFSE EVAEKYNKNL FSKELIRNEI EKFCETDEER KQVSNFKSFT TYFTGPHSNR    180
QNIYSDEKKS TAIGYRIIHQ NLPKFLDNLK IIESIQRRFK DFPWSDLKKN LKKIDKNIKL    240
TEYFSIDGFV NVLNQKGIDA YNTILGGKSE ESGEKIQGLN EYINLYRQKN NIDRKNPLNV    300
KILFKQILGD RETKSFIPEA FPDDQSVLNS ITEFAKYLKL DKKKSIIAE LKKFLSSFNR    360
YELDGIYLAN DNSLASISTF LFDDWSFIKK SVSFKYDESV GDPKKKIKSP LKYEKEKEKV    420
LKQKYYTISF LNDAIESYSK SQDEKRVKIR LEAYFAEFKS KDDAKKQFDL LERIEEAYAI    480
VEPLLGAEYP RDRNLKADKK EVGKIKDFLD SIKSLQFFLK PLLSAEIFDE KDLGFYNQLE    540
GYYEEIDISG HLYNKVRNYL TGKIYSKEKF KLNFENSTLL KGWDENREVA NLCVIFREDQ    600
KYYLGVMDKE NNTILGSDIPK VKPNELFYEK MVYKLIPTPH MQLPRIIFSS DNLSIYNPSK    660
SILKIREAKS FKEGKNFKLK DCHKFIDFYK ESISKNEDWS RFDFKFSKTS SYENISEFYR    720
EVERQGYNLD FKKVSKFYID SLVEDGKLYL FQIYNKDFSI FSKGKPNLHT IYFRSLFSKE    780
NLKDVCLKLN GEAEMFFRKK SINYDEKKKR EGHHPELFEK LKYPILKDKR YSEDKFQFHL    840
PISLNFKSKE RLNFNLKVNE FLKRNKDINI IGIDRGERNL LYLVMINQKG EILKQTLLDS    900
MQSGKGRPEI NYKEKLQEKE IERDKARKSW GTVENIKELK EGYLSIVIHQ ISKLMVENNA    960
IVVLEDLNIG FKRGRQKVER QVYQKFEKML IDKLNFLVFK ENKPTEPGGV LKAYQLTDEF   1020
QSFEKLSKQT GFLFYVPSWN TSKIDPRTGF IDFLHPAYEN IEKAKQWINK FDSIRFNSKM   1080
DWFEFTADTR KFSENLMLGK NRVWVICTTN VERYFTSKTA NSSIQYNSIQ ITEKLKELFV   1140
DIPFSNGQDL KPEILRKNDA VFFKSLLFYI KTTLSLRQNN GKKGEEEKDF ILSPVVDSKG   1200
RFFNSLEASD DEPKDADANG AYHIALKGLM NLLVLNETKE ENLSRPKWKI KNKDWLEFVW   1260
ERNR                                                               1264

SEQ ID NO: 11           moltype = AA   length = 1373
FEATURE                 Location/Qualifiers
source                  1..1373
                        mol_type = protein
                        organism = Moraxella bovoculi
SEQUENCE: 11
MLFQDFTHLY PLSKTVRFEL FIDRTLEHIH AKNFLSQDET MADMHQKVKV ILDDYHRDFI     60
ADMMGEVKLT KLAEFYDVYL KFRKNPKDDE LQKAQLKDLQ AVLRKEIVKP IGNGGKYKAG    120
```

```
YDRLFGAKLF KDGKELGDLA KFVIAQEGES SPKLAHLAHF EKFSTYFTGF HDNRKNMYSD    180
EDKHTAIAYR LIHENLPRFI DNLQILTTIK QKHSALYDQI INELTASGLD VSLASHLDGY    240
HKLLTQEGIT AYNTLLGGIS GEAGSPKIQG INELINSHHN QHCHKSERIA KLRPLHKQIL    300
SDGMSVSFLP SKFADDSEMC QAVNEFYRHY ADVFAKVQSL FDGFDDHQKD GIYVEHKNLN    360
ELSKQAFGDF ALLGRVLDGY YVDVVNPEFN ERFAKAKTDN AKAKLTKEKD KPFIKGVHSLA   420
SLEQAIEHYT ARHDDESVQA GKLGQYFKHG LAGVDNPIQK IHNNHSTIKG FLERERPAGE    480
RALPKIKSGK NPEMTQLRQL KELLDNALNV AHFAKLLTTK TTLDNQDGNF YGEFGVLYDE    540
LAKIPTLYNK VRDYLSQKPF STEKYKLNFG NPTLLNGWDL NKEKDNFGVI LQKDGCYYLA    600
LLDKAHKKVF DNAPNTGKSI YQKMIYKYLE VRKQFPKVFF SKEAIAINYH PSKELVEIKD    660
KGRQRSDDER LKLYRFILEC LKIHPKYDKK FEGAIGDIQL FKKDKKGREV PISEKDLFKD    720
INGIFSSKPK LEMEDFFIGE FKRYNPSQDL VDQYNIYKKI DSNDNRKKEN FYNNHPKFKK    780
DLVRYYYESM CKHEEWEESF EFSKKLQDIG CYVDVNELFT EIETRRLNYK ISFCNINADY    840
IDELVEQGQL YLFQIYNKDF SPKAHGKPNL HTLYFKALFS EDNLADPIYK LNGEAQIFYR    900
KASLDMNETT IHRAGEVLEN KNPDNPKKRQ FVYDIIKDKR YTQKDFMLHV PITMNFGVQG    960
MTIKEFNKKV NQSIQQYDEV NVIGIDRGER HLLYLTVINS KGEILEQCSL NDITTASANG   1020
TQMTTPYHKI LDKREIERLN ARVGWGEIET IKELKSGYLS HVVHQISQLM LKYNAIVVLE   1080
DLNFGFKRGR FKVEKQIYQN FENALIKKLN HLVLKDKADD EIGSYKNALQ LTNNFTDLKS   1140
IGKQTGFLFY VPAWNTSKID PETGFVDLLK PRYENIQASQ AFFGKFDKIC YNADKDYFEF   1200
HIDYAKFTDK AKNSRQIWTI CSHGDKRYVY DKTANQNKGA AKGINVNDIL KSLFARHHIN   1260
EKQPNLVMDI CQNNDKEFHK SLMYLLKTLL ALRYSNASSD EDFILSPVAN DEGVFFNSAL   1320
ADDTQPQNAD ANGAYHIALK GLWLLNELKN SDDLNKVKLA IDNQTWLNFA QNR           1373

SEQ ID NO: 12           moltype = AA  length = 1352
FEATURE                 Location/Qualifiers
source                  1..1352
                        mol_type = protein
                        note = Parcubacteria bacterium
                        organism = unidentified
SEQUENCE: 12
MENIFDQFIG KYSLSKTLRF ELKPVGKTED FLKINKVFEK DQTIDDSYNQ AKFYFDSLHQ     60
KFIDAALASD KTSELSFQNF ADVLEKQNKI ILDKKREMGA LRKRDKNAVG IDRLQKEIND    120
AEDIIQKEKE KIYKDVRTLF DNEAESWKTY YQEREVDGKK ITESKADLKQ KGADFLTAAG    180
ILKVLKYEFP EEKEKEFQAK NQPSLFVEEK ENPGQKRYIF DSFDKFAGYL TKFQQTKKNL    240
YAADGTSTAV ATRIADNFII FHQNTKVFRD KYKNNHTDLG FDEENIFEIE RYKNCLLQRE    300
IEHIKNENSY NKIIGRINKK IKEYRDQKAK DTKLTKSDFP FFKNLDKQIL GEVEKEKQLI    360
EKTREKTEED VLIERFKEFI ENNEERFTAA KKLMNAFCNG EFESEYEGIY LKNKAINTIS    420
RRWFVSDRDF ELKLPQQKSK NKSEKNEPKV KKFISIAEIK NAVEELDGDI FKAVFYDKKI    480
IAQGGSKLEQ FLVIWKYEFE YLFRDIEREN GEKLLGYDSC LKIAKQLGIF PQEKEAREKA    540
TAVIKNYADA GLGIFQMMKY FSLDDKDRKN TPGQLSTNFY AEYDGYYKDF EFIKYYNEFR    600
NPFITKKPFDE DKIKLNFENG ALLKGWDENK EYDFMGVILK KEGRLYLGIM HKNHRKLFQS    660
MGNAKGDNAN RYQKMIYKQI ADASKDVPRL LLTSKKAMEK FKPSQEILRI KKEKTFKRES    720
KNFSLRDLHA LIEYYRNCIP QYSNWSFYDF QFQDTGKYQN IKEFTDDVQK YGYKISFRDI    780
DDEYINQALN EGKMYLFEVV NKDIYNTKNG SKNLHTLYFK HILSAENLND PVFKLSGMAE    840
IFQRQPSVNE REKITTQKNQ CILDKGDRAY KYRRYTEKKI MPFHMSLVLNT GKGEIKQVQF    900
NKIINQRISS SDNEMRVNVI GIDRGEKNLL YYSVVKQNGE IIEQASLNEI NGVNYRDKLI    960
EREKERLKNR QSWKPVVKIK DLKKGYISHV IHKICQLIEK YSAIVVLEDL NMRFKQIRGG   1020
IERSVYQQFE KALIDKLGYL VFKDNRDLRA PGGVLNGYQL SAPFVSFEKM RKQTGILFYT   1080
QAEYTSKTDP ITGFRKNVYI SNSASLDKIK EAVKKFDAIG WDGKEQSYFF KYNPYNLADE   1140
KYKNSTVSKE WAIFASAPRI RRQKGEDGYW KYDRVKVNEE FEKLLVWNF VNPKATDIKQ    1200
EIIKKIKAGD LQGEKELDGR LRNFWHSFIY LFNLVLELRN SFSLQIKIKA GEVIAVDEGV   1260
DFIASPVKPF FTTPNPYIPS NLCWLAVENA DANGAYNIAR KGVMILKKIR EHAKKDPEFK   1320
KLPNLFISNA EWDEAARDWG KYAGTTALNL DH                                 1352

SEQ ID NO: 13           moltype = AA  length = 1260
FEATURE                 Location/Qualifiers
source                  1..1260
                        mol_type = protein
                        organism = Porphyromonas crevioricanis
SEQUENCE: 13
MDSLKDFTNL YPVSKTLRFE LKPVGKTLEN IEKAGILKED EHRAESYRRV KKIIDTYHKV     60
FIDSSLENMA KMGIENEIKA MLQSFCELYK KDHRTEGEDK ALDKIRAVLR GLIVGAFTGV    120
CGRRENTVQN EKYESLFKEK LIKEILPDFV LSTEAESLPF SVEEATRSLK EFDSFTSYFA    180
GFYENRKNIY STKPQSTAIA YRLIHENLPK FIDNILVFQK IKEPIAKELE HIRADFSAGG    240
YIKKDERLED IFSLNYYIHV LSQAGIEKYN ALIGKIVTEG DGEMKGLNEH INLYNQQRGR    300
EDRLPLFRPL YKQILSDREQ LSYLPESFEK DEELLRALKE FYDHIAEDIL GRTQQLMTSI    360
SEYDLSRIYV RNDSQLTDIS KKMLGDWNAI YMARERAYDH EQAPKRITAK YERDRIKALK    420
GEESISLANL NSCIAFLDNV RDCRVDTYLS TLGQKEGPHG LSNLVENVFA SYHEAEQLLS    480
FPYPEENNLI QDKDNVVLIK NLLDNISDLQ RFLKPLWGMG NEDKDERFY GEYNYIRGAL    540
DQVIPLYNKV RNYLTRKPYS TRKVKLNFGN SQLLSGWDRN KEKDNSCVIL RKGQNFYLAI    600
MNNRHKRSFE NKMLPEYKEG EPYFEKMDYK FLPDPNKMLP KVFLSKKGIE IYKPSPKLLE    660
QYGHGTHKKG DTFSMDDDLHE LIDFFKHSIE AHEDWKQFGF KFSDTATYEN VSSFYREVED    720
QGYKLSFRKV SESYVYSLID QGKLYLFQIY NKDFSPCSKG TPNLHTLYWR MLFDERNLAD    780
VIYKLDGKAE IFFREKSLKN DHPTHPAGKP IKKKSRQKEL EESLFEYDLV KDRRYTMDKF    840
QFHVPITMNF KCSAGSKVND MVNAHIREAK DMHVIGIDRG ERNLLYICVI DSRGTILDQI    900
SLNTINDIDY HDLLESRKKD RQQEHRNWQT IEGIKELKQG YLSQAVHRIA ELMVAYKAVV    960
ALEDLNMGFK RGRQKVESSV YQQFEKQLID KLNYLVDKKK RPEDIGGLLR AYQFTAPFKS   1020
FKEMGKQNGF LFYIPAWNTS NIDPTTGFVN LFHVQYENVD KAKSFFQKFD SISYNPKKDW   1080
FEFAFDYKNF TKKAEGSRSM WILCTHGSRI KNFRNSQKNG QWDSEEFALT EAFKSLFVRY   1140
EIDYTADLKT AIVDEKQKDF FVDLLKLFKL TVQMRNSWKE KDLDYLISPV AGADGRFFDT   1200
```

-continued

```
REGNKSLPKD ADANGAYNIA LKGLWALRQI RQTSEGGKLK LAISNKEWLQ FVQERSYEKD   1260

SEQ ID NO: 14          moltype = AA  length = 664
FEATURE                Location/Qualifiers
source                 1..664
                       mol_type = protein
                       organism = Prevotella disiens
SEQUENCE: 14
NSYKEDDKRL NKVIIAYIEQ IKQTNIKKSI IESISKYPNI SDDDKVTPSS LLEKIKKVSI     60
DSYNGILSFK SFQSVNKEVI DNLLKTISPL KNKAEFLDLI NKDYQIFTEV QAVIDEICKQ    120
KTFIYFPISN VELEKEMGDK DKPLCLFQIS NKDLSFAKTF SANLRKKRGA ENLHTMLFKA    180
LMEGNQDNLD LGSGAIFYRA KSLDGNKPTH PANEAIKCRN VANKDKVSLF TYDIYKNRRY    240
MENKFLFHLS IVQNYKAAND SAQLNSSATE YIRKADDLHI IGIDRGERNL LYYSVIDMKG    300
NIVEQDSLNI IRNNDLETDY HDLLDKREKE RKANRQNWEA VEGIKDLKKG YLSQAVHQIA    360
QLMLKYNAII ALEDLGQMFV TRGQKIEKAV YQQFEKSLVD KLSYLVDKKR PYNELGGILK    420
AYQLASSITK NNSDKQNGFL FYVPAWNTSK IDPVTGFTDL LRPKAMTIKE AQDFFGAFDN    480
ISYNDKGYFE FETNYDKFKI RMKSAQTRWT ICTFGNRIKR KKDKNYWNYE EVELTEEFKK    540
LFKDSNIDYE NCNLKEEIQN KDNRKFFDDL IKLLQLTLQM RNSDDKGNDY IISPVANAEG    600
QFFDSRNGDK KLPLDADANG AYNIARKGLW NIRQIKQTKN KDDLNLSISS TEWLDFVREK    660
PYLK                                                                664

SEQ ID NO: 15          moltype = AA  length = 1484
FEATURE                Location/Qualifiers
SITE                   1073
                       note = misc_feature - Xaa can be any naturally occurring
                        amino acid
source                 1..1484
                       mol_type = protein
                       note = Peregrinibacteria bacterium
                       organism = unidentified
SEQUENCE: 15
MSNFFKNFTN LYELSKTLRF ELKPVGDTLT NMKDHLEYDE KLQTFLKDQN IDDAYQALKP     60
QFDEIHEEFI TDSLESKKAK EIDFSEYLDL FQEKKELNDS EKKLRNKIGE TFNKAGEKWK    120
KEKYPQYEWK KGSKIANGAD ILSCQDMLQF IKYKNPEDEK IKNYIDDTLK GFFTYFGGFN    180
QNRANYYETK KEASTAVATR IVHENLPKFC DNVIQFKHII KRKKDGTVEK TERKTEYLNA    240
YQYLKNNNKI TQIKDAETEK MIESTPIAEK IFDVYYFSSC LSQKQIEEYN RIIGHYNLLI    300
NLYNQAKRSE GKHLSANEKK YKDLPKFKTL YKQIGCGKKK DLFYTIKCDT EEEANKSRNE    360
GKESHSVEEI INKAQEAINK YFKSNNDCEN INTVPDFINY ILTKENYEGV YWSKAAMNTI    420
SDKYFANYHD LQDRLKEAKV FQKADKKSED DIKIPEAIEL SGLFGVLDSL ADWQTTLFKS    480
SILSNEKLKI ITDSQTPSEA LLKMIFNDIE KNMESFLKET NDIITLKKYK GNKEGTEKIK    540
QWFDYTLAIN RMLKYFLVKE NKIKGNSLDT NISEALKTLI YSDDAEWFKW YDALRNYLTQ    600
KPQDEAKENK LKLNFDNPSL AGGWDVNKEC SNFCVILKDK NEKKYLAMIK KGENTLFQKE    660
WTEGRGKNLT KKSNPLFEIN NCEILSKMEY DFWADVSKMI PKCSTQLKAV VNHFKQSDNE    720
FIFPIGYKVT SGEKFREECK ISKQDFELNN KVFNKNELSV TAMRYDLSST QEKQYIKAFQ    780
KEYWELLFKQ EKRDTKLTNN EIFNEWINFC NKKYSELLSW ERKYKDALTN WINFCKYFLS    840
KYPKTTLFNY SFKESENYNS LDEFYRDVDI CSYKLNINTT INKSILDRLV EEGKLYLFEI    900
KNQDSNDGKS IGHKNNLHTI YWNAIFENFD NRPKLNGEAE IFYRKAISKD KLGIVKGKKT    960
KNGTWIIKNY RFSKEKFILH VPITLNFCSN NEYVNDIVNT KFYNFSNLHF LGIDRGEKHL   1020
AYYSLVNKNG EIVDQGTLNL PFTDKDGNQR SIKKEKYFYN KQEDKWEAKE VDXWNYNDLL   1080
DAMASNRDMA RKNWQRIGTI KEAKNGYVSL VIRKIADLAV NNERPAFIVL EDLNTGFKRS   1140
RQKIDKSVYQ KFELALAKKL NFLVDKNAKR DEIGSPTKAL QLTPPVNNYG DIENKKQAGI   1200
MLYTRANYTS QTDPATGWRK TIYLKAGPEE TTYKKDGKIK NKSVKDQIIE TFTDIGFDGK   1260
DYYFEYDKGE FVDEKTGEIK PKKWRLYSGE NGKSLDRFRG EREKDKYEWK IDKIDIVKIL   1320
DDLFVNFDKN ISLLKQLKEG VELTRNNEHG TGESLRFAIN LIQQIRNTGN NERDNDFILS   1380
PVRDENGKHF DSREYWDKET KGEKISMPSS GDANGAFNIA RKGIIMNAHI LANSDSKDLS   1440
LFVSDEEWDL HLNNKTEWKK QLNIFSSRKA MAKRKKKRPA ATKK                   1484

SEQ ID NO: 16          moltype = AA  length = 1245
FEATURE                Location/Qualifiers
source                 1..1245
                       mol_type = protein
                       organism = Porphyromonas macacae
SEQUENCE: 16
MKTQHFFEDF TSLYSLSKTI RFELKPIGKT LENIKKNGLI RRDEQRLDDY EKLKKVIDEY     60
HEDFIANILS SFSFSEEILQ SYIQNLSISE ARAKIEKTMR DTLAKAFSED ERYKSIFKKE    120
LVKKDIPVWC PAYKSLCKKF DNFTTSLVPF HENRKNLYTS NEITASIPYR IVHVNLPKFI    180
QNIEALCELQ KKMGADLYLE MMENLRNVWP SFVKTPDDLC NLKTYNHLMV QSSISEYNRF    240
VGGYSTEDGT KHQGINEWIN IYRQRNKEMR LPGLVFLHKQ ILAKVDSSSF ISDTLENDDQ    300
VFCVLRQFRK LFWNTVSSKE DDAASLKDLF CGLSGYDPEA IYVSDAHLAT ISKNIFDRWN    360
YISDAIRRKT EVLMPRKKES VERYAEKISK QIKKRQSYSL AELDDLLAHY SEESLPAGFS    420
LLSYFTSLGG QKYLVSDGEV ILYEEGSNIW DEVLIAFRDL QVILDKDFTE KKLGKDEEAV    480
SVIKKALDSA LRLRKFFDLL SGTGAEIRRD SSFYALYTDR MDKLKGLLKM YDKVRNYLTK    540
KPYSIEKFKL HFDNPSLLSG WDKNKELNNL SVIFRQNGYY YLGIMTPKGK NLFKTLPKLG    600
AEEMFYEKME YKQIAEPMLM LPKVFFPKKT KPAFAPDQSV VDIYNKKTFK TGQKGFNKKD    660
LYRLIDFYKE ALTVHEWKLF NFSFSPTEQY RNIGEFFDEV REQAYKVSMV NVPASYIDEA    720
VENGKLYLFQ IYNKDFSPYS KGIPNLHTLY WKALFSEQNQ SRVYKLCGGG ELFYRKASLH    780
MQDTTVHPKG ISIHKKNLNK KGETSLFNYD LVKDKRFTED KFFFHVPISI NYKNKKITNV    840
NQMVRDYIAQ NDDLQHGIDR GERNLLYISR IDTRGNLLEQ FSLNVIESDK GDLRTDYQKI    900
LGDREQERLR RRQEWKSIES IKDLKDGYMS QVVHKICNMV VEHKAIVVLE NLNLSFMKGR    960
```

-continued

```
KKVEKSVYEK FERMLVDKLN YLVVDKKNLS NEPGGLYAAY QLTNPLFSFE ELHRYPQSGI      1020
LFFVDPWNTS LTDPSTGFVN LLGRINYTNV GDARKFFDRF NAIRYDGKGN ILFDLDLSRF      1080
DVRVETQRKL WTLTTFGSRI AKSKKSGKWM VERIENLSLC FLELFEQFNI GYRVEKDLKK      1140
AILSQDRKEF YVRLIYLFNL MMQIRNSDGE EDYILSPALN EKNLQFDSRL IEAKDLPVDA      1200
DANGAYNVAR KGLMVVQRIK RGDHESIHRI GRAQWLRYVQ EGIVE                      1245

SEQ ID NO: 17          moltype = AA   length = 1250
FEATURE                Location/Qualifiers
source                 1..1250
                       mol_type = protein
                       organism = Smithella sp.
SEQUENCE: 17
MQTLFENFTN QYPVSKTLRF ELIPQGKTKD FIEQKGLLKK DEDRAEKYKK VKNIIDEYHK       60
DFIEKSLNGL KLDGLEKYKT LYLKQEKDDK DKKAFDKEKE NLRKQIANAF RNNEKFKTLF      120
AKELIKNDLM SFACEEDKKN VKEFEAFTTY FTGFHQNRAN MYVADEKRTA IASRLIHENL      180
PKFIDNIKIF EKMKKEAPEL LSPFNQTLKD MKDVIKGTTL EEIFSLDYFN KTLTQSGIDI      240
YNSVIGGRTP EEGKTKIKGL NEYINTDFNQ KQTDKKKRQP KFKQLYKQIL SDRQSLSFIA      300
EAFKNDTEIL EAIEKFYVNE LLHFSNEGKS TNVLDAIKNA VSNLESFNLT KMYFRSGASL      360
TDVSRKVFGE WSIINRALDN YYATTYPIKP REKSEKYEER KEKWLKQDFN VSLIQTAIDE      420
YDNETVKGKN SGKVIADYFA KFCDDKETDL IQKVNEGYIA VKDLLNTPCP ENEKLGSNKD      480
QVKQIKAFMD SIMDIMHFVR PLSLKDTDKE KDETFYSLFT PLYDHLTQTI ALYNKVRNYL      540
TQKPYSTEKI KLNFENSTLL GGWDLNKETD NTAIILRKDN LYYLGIMDKR HNRIFRNVPK      600
ADKKDFCYEK MVYKLLPGAN KMLPKVFFSQ SRIQEFTPSA KLLENYANET HKKGDNFNLN      660
HCHKLIDFFK DSINKHEDWK NFDFRFSATS TYADLSGFYH EVEHQGYKIS FQSVADSFID      720
DLVNEGKLYL FQIYNKDFSP FSKGKPNLHT LYWKMLFDEN NLKDVVYKLN GEAEVFYRKK      780
SIAEKNTTIH KANESIINKN PDNPKATSTF NYDIVKDKRY TIDKFQFHIP ITMNFKAEGI      840
FNMNQRVNQF LKANPDINII GIDRGERHLL YYALINQKGK ILKQDTLNVI ANEKQKVDYH      900
NLLDKKEGDR ATARQEWGVI ETIKELKEGY LSQVIHKLTD LMIENNAIIV MEDLNFGFKR      960
GRQKVEKQVY QKFEKMLIDK LNYLVDKNKK ANELGGLLNA FQLANKFESF QKMGKQNGFI     1020
FYVPAWNTSK TDPATGFIDF LKPRYENLNQ AKDFFEKFDS IRLNSKADYF EFAFDFKNFT     1080
EKADGGRTKW TVCTTNEDRY QWNRALNNNR GSQEKYDITA ELKSLFDGKV DYKSGKDLKQ     1140
QIASQESADF FKALMKNLSI TLSLRHNNGE KGDNEQDYIL SPVADSKGRF FDSRKADDDM     1200
PKNADANGAY HIALKGLWCL EQISKTDDLK KVKLAISNKE WLEFVQTLKG                1250

SEQ ID NO: 18          moltype = DNA   length = 3987
FEATURE                Location/Qualifiers
source                 1..3987
                       mol_type = other DNA
                       organism = synthetic construct
SEQUENCE: 18
atggccggga gcaagaagcg ccggataaag caggacacgc agttcgaggg cttcaccaac       60
ctgtaccaag tctccaagac gctccggttc gagcttatcc cgcaagggaa gaccctgaaa      120
cacatccagg aacaaggttt catcgaggag gacaaggccg caactgacca ctacaaggag      180
ctcaagccca taatcgatcg gatctacaag acgtaccgcg accagtgcct ccaactggtg      240
cagctcgact gggagaacct gagcgccgcc attgacagct accgcaagga aaagacggag      300
gagacgcgca acgcccttat tgaggagcaa gccacctacc gcaacgccat ccacgactac      360
ttcatcgggc gcaccgacaa cctgacggac gcgatccaca agccgcacgc ggaaatctac      420
aagggccttt tcaaggccga gctcttcaac gggaaggtcc taaaacagct cgggactgtc      480
acgacaaccg agcatgagaa cgccctcctt cgcagcttcg acaagttcac cacatacttc      540
tcgggcttct accggaaccg caagaacgtt ttcagcgccg aggacatctc caccgccatc      600
ccgcacagga tcgtccagga caacttcccc aagttcaagg agaactgcca catcttcacg      660
cgcctgatta cagccgtacc ttcacttcgt gagcacttcg agaacgtcaa aaaggccatc      720
gggatcttcg tctccacgtc catcgaggag gtattctctt tcccgttcta taaccagctc      780
ctgacccaga cgcagatcga cctctacaac cagctactgg cggcatcag ccgggaggcc       840
gggacctgaga aaataaaggg cctcaacgaa gttctcaacc tggccatcca gaagaacgac      900
gagaccgcgc atatcatcgc atccctgccg catcgcttca ttcctttgtt caagcagata      960
ttgagcgacc ggaacaccct ctcgttcatc ctcgaagaat tcaagagcga cgaggaggtc     1020
attcagtctt tctgcaagta caagacgctc tacggaatgg agatgtgct ggagaccgcg       1080
gaggcactct tcaatgagct gaactccatt gacctgaccc acatcttcat tagccacaag     1140
aaactggaga cgatctccag cgccctgtgc gaccactggg acactctccg caacgccctc     1200
tacgaacgcc ggatctccga acttaccggc aagataacta gtcggctaa ggagaaggtg       1260
caacggagcc tcaagcacga ggacatcaac cttcaggaaa tcatctcagc cgcgggcaag     1320
gagctgagcg aggcgtttaa gcagaaaaca tcggagatac tgagccacgc gcacgcggcc     1380
ctggatcaac cgctgccgac gactctcaag aagcaagagg caggaaat ccttaagtcc        1440
cagctcgact cgctgctcgg cctctatcac ttgctcgact ggttcgcggt tgatgagtcc     1500
aacgaggtgg acccggagtt ctcgcgcgcg ctcacgggta ttaagctgga gatgagccca     1560
agcttaagct tctacaacaa ggcccgcaac tacgcgacca aaaaaccgta ctcagtcgag     1620
aaattcaagc tgaatttcca gatgctacta ttggcgaggg ggtgggacgt gaaccgcag      1680
aagaacaatg agagccatcc tgttcgtcaaa aatgggttgt actacctggg catcatgccc     1740
aagcagaagg gccgttacaa ggccctgtca ttcgagccta ccgagaagac ctcggagggc     1800
ttcgacaaga tgtactacga ctatttcccg gacgccgcca agatgatccc cgaagtgctcc    1860
acgcagctca agccgtcac ggcccacttc agacgcata ccacgccgat acttctgagc       1920
aacaacttca ttgagccgct agagatcacg aaggagatat cgacctaaa caaccccgaa       1980
aaggagaagc agaagttcca tgacgcctac caggtagca gaagggatat                 2040
agggaggcac tctgcaagtg gatcgacttc acgcgcgact tcctgtcgaa atatacaaag     2100
acgaccagca ttgaccctaag ttctctccgc ccatcctccc agtacaagga tctgggcgag    2160
tattatgcgc agctgaaccc attgctgtac cacatcagct tccagaggat cgccgagaag     2220
gagattatgc acgcggtgga cgggggaaa ctataccctgt tccaaatata taacaaggac     2280
ttcgctaaag ggcaccacgg gaagcccaac ctgcacacac tctactggac gggcttgttt     2340
```

```
tcgccagaaa atttggccaa gacttcgatc aagctcaacg gccaggcgga gttgttttac    2400
cgtcccaagt ctcgcatgaa gcgcatggcg catcgcctcg gagagaaaat gcttaacaag    2460
aagctcaagg atcagaagac gcccatacct gatacgttgt accaggaatt gtacgactac    2520
gtgaaccacc gcctatcgca cgacctctca gacgaggccc gcgccctcct cccaaacgtg    2580
attactaagg aggtttccca tgaaataatc aaggaccgac ggttcaccag cgacaaattt    2640
tttttccacg tgcctatcac gctcaattac caggcggcca actccccatc gaagttcaac    2700
cagcgcgtga acgcctacct taaggagcac ccggagaccc caatcatcgg gatcgaccgt    2760
ggcgagcgga acctgatcta tattacggtg atcgatagca ccgggaagat cctggagcag    2820
cgctccctga acacaatcca gcagtttgac taccagaaga aactcgacaa ccgggagaag    2880
gagcgcgtcg cagcccggca agcatggagt gtggtcggca ccataaagga cctgaaacag    2940
ggttacctaa gtcaagttat ccacgagatc gttgacctga tgatacacta tcaagccgta    3000
gtcgtgctgg agaacctcaa cttcgggttt aagtccaagc gcaccggcat cgcggagaag    3060
gcggtgtacc agcagttcga gaagatgctg atcgacaagc tgaactgcct ggtgctcaag    3120
gactacctg cggagaaggt cggcgggtc ttgaaccgct aacgaccagttc    3180
acgagcttcg ccaaaatggg cacgcagtcc ggattcttgt tttatgtccc ggctccatat    3240
acaagtaaga tcgacccgct gacagggttt gttgacccat tcgtgtggaa gaccatcaag    3300
aaccacgaga gcaggaaaca cttcttagag ggcttcgact tcctgcatta cgacgttaag    3360
acaggcgact tcatcctgca cttcaagatg aaccgcaacc tgtcgttcca gaggggcctg    3420
cccggcttca tgcccgcctg ggatatcgtc tttgagaaga atgagacgca gttcgacgcg    3480
aaggggacgc cgttcatcgc tggaaagcgg atcgtgccgg tcatcgagaa ccaccgcttc    3540
acgggtcgct accgagattt ataccccgcc aacgaactaa ttgcgctgct ggaggagaag    3600
gggatcgtgt tccgagatgg cagcaacatt ctcccgaagc tgctggagaa cgacgactcg    3660
cacgctattg acacgatggt cgccctcata cggagcgtgc ttcagatgcg gaacagtaac    3720
gctgccacgg gcgaggacta cattaactcc ccgtccgcg acctcaacgg ggtctgcttc    3780
gatagccgct tccagaaccc ggagtggcct atggatgcgg acgcgaacgg ggcctaccac    3840
atcgccctca agggccaact cctgctcaac cacttgaagg aaagcaaaga cctcaaattg    3900
cagaatggca tcagtaacca ggactggctc gcgtacatcc aggaactgag aaacgggtcc    3960
aagaagcggc gtatcaagca agattga                                        3987

SEQ ID NO: 19           moltype = DNA  length = 3987
FEATURE                 Location/Qualifiers
source                  1..3987
                        mol_type = other DNA
                        organism = synthetic construct
SEQUENCE: 19
atggcgggaa gcaaaaagcg ccggattaag caagacacgc agttcgaggg cttcacgaac      60
ctctaccaag tcagcaagac cctccggttc gagctgatac cacagggaaa gacgctcaag     120
cacatccagg aacagggctt catcgaggag gacaaggcgc gcaacgacca ctacaaggag     180
ttgaaaccga tcatcgaccg catctacaag acgtacgccg accagtgcct ccagctcgtg     240
cagctcgact gggagaacct ctccgccgcc attgactcgt accggaagga gaagactgag     300
gagacccgca acgccctgat cgaggagcaa gcaacctacc ggaacgccat ccacgactac     360
ttcatcggcc gcaccgacaa cctcaccgac gcgatcaaca gcggcacgc ggagatatac      420
aaagggctgt tcaaggcgga gctgttcaac ggcaaggtgc tcaagcagct agggacggtg     480
accacgaccg agcacgagaa cgcgctcctc cgcagcttcg acaagttcac cacctacttc     540
agcggcttct accggaaccg caagaatgtg ttcagcgcgg aggacatcag cacggccatc     600
ccgcaccgca tcgtccagga caacttcccg aagttcaagg agaactgcca catcttcacc     660
cgcctgataa ccgccgtccc tccctgcgg gagcacttcg agaacgtcaa aaaggcaatt     720
gggatcttcg tctcgaccag cattgaggag gtgttcagct tcccttcta caaccagctc     780
ctcacccaga cgcagatcga cctgtacaat cagttgctcg gcgggataag ccgcgaggcg     840
ggaaccgaaa aaatcaaggg gctgaacgaa gtgttgaacc tcgccatcca gaagaacgac     900
gagaccgcgc acatcatcgc ctcccctgccc caccggttca tcccgctgtt caagcagatc     960
ctctctgacc ggaacaccct gtccttcatt cttgaggagt tcaagtcgga cgaggaggtc    1020
atccagagct tctgcaagta caagacgctg ctacggaacg agaacgtgct ggagacggcg    1080
gaggcactgt tcaacgagct aaacagcatc gacctcacgc acatcttcat cagtcacaag    1140
aaactggaga ccatctcctc cgcgctgtgc gaccactggg acacgctcag gaacgcgctc    1200
tacgagcgcc gaatcagtga gctgacgggc aagatcacga agtccgcgaa ggagaaggtg    1260
cagcggtccc tcaagcacga ggacatcaac ctccaggaga tcatctcagc ggctgggaaa    1320
gagctgtccg aggcgttcaa gcagaaacg agcgaaatcc tgtcccacgc gcacgcggcc    1380
ctggatcagc ctctgccgac gaccctcaag aaacaagaag aaaaggaaat cctcaagtcg    1440
cagctcgact cgctgctggg cctgtaccat ctcctcgact ggttcgccgt ggacgagagc    1500
aacgaggtgg acccccgagtt ctccgcgcgg cttacgggga tcaagctgga gatgagcccc    1560
agcctgtcct tctacaacaa ggcgcgcaac tacgccacca gaagcccta cagcgtggag    1620
aagttcaagc tcaacttcca gatgcccact ctcgcacgtg ggtgggacgt caaccgcgaa    1680
aaaaataatg gggcgatcct gttcgtcaag acggccgtgt actacttggg catcatgccg    1740
aaacagaagg gccgctacaa gggcctgagc ttcaaccgca ccgagaaaac gagcgagggg    1800
ttcgacaaga tgtactacga ctacttcccc gacgccgcga agatgattcc aaagtgctcc    1860
acgcagctta aggccgtgac ggcccacttc agacgcacg cgaccccgat cctcctcagc    1920
aacaacttca tcgagcccct ggagatcacg aaggagatat acgacctgaa caacccggag    1980
aaggagccca agaaattcca gaccgcctac gccaagaaga caggcgacca aaagggttac    2040
agggaggccc tctgcaagtg gatcgacttc actagggact tcctgtccaa gtacaccaag    2100
actacctcta tcgacctgtc cagcctccgc ccgtcgtccc agtacaaaga tttgggcgag    2160
tattacgcgg agctgaaccc actgctctac cacatcagct ccagcgcat cgcggagaag    2220
gagatcatgg acgcagtgga gacggggcaag ctataccctat ttcagatata caacaaagac    2280
ttcgctaagg gacaccacgg caagcctaac ctgcactcc tctactcgac ggggctcttc    2340
agcccggaga acctcgccaa gacctcgatc aagctcaacg gccaggccga gctgttctac    2400
cggcccaagt cccgcatgaa gcgcatggcc accggctcg gggagaaaat gctcaacaag    2460
aaattgaagg accaaaaaac gccgataccc gacaccctat accaggagct gtacgactat    2520
gtgaaccacc gcctgagcca cgacctcagc gacgaggcgc gggccctcct gccgaacgtc    2580
atcacaaagg aggtcagcca cgagatcatc aaggaccggc gcttcacctc cgacaagttt    2640
```

```
ttctttcacg tgcccatcac gctcaactac caggccgcca actcgccgtc caagttcaac    2700
cagcgcgtga acgcctacct caaggagcac cccgagaccc cgatcatcgg gattgaccga    2760
ggggagcgga acctcatcta catcaccgtc atcgacagca ccgggaagat ccttgaacag    2820
cggtcgctca acaccatcca gcagttcgac taccagaaga aactcgacaa ccgggagaag    2880
gagagagtgg cggcccgcca ggcttggtcc gtcgtcggca cgattaagga cttgaaacaa    2940
ggttacctgt cgcaagtgat ccacgagatc gttgacctga tgatccacta ccaagccgtc    3000
gtggtcctgg agaacctcaa cttcggcttc aagagcaaac gaaccggcat cgcggagaag    3060
gccgtgtacc agcagttcga aaaaatgctg atcgacaagc tgaactgcct cgtgctcaag    3120
gactacccog ctgagaaggt cggcggggtg ctgaacccgt accagctcac tgaccagttc    3180
accagcttcg caaagatggg cacccagtcc ggcttcctgt tctacgtgcc tgcgccatac    3240
acctcgaaga tcgacccgct caccgggttc gtggaccccc tcgtctggaa gaccatcaag    3300
aaccacgaga gccgcaagca cttcctggag ggcttcgact cctccacta cgacgtcaag    3360
accggggact tcatcctgca cttcaagatg aaccgcaacc tcagtttcca gcgcggcctg    3420
ccggggttca tgcccgcttg ggatatagtc ttcgagaaga atgagacgca gttcgacgcg    3480
aagggcaccc cgttcatcgc cgggaagcgc atcgtgccgg tcatcgagaa ccaccggttc    3540
accgggcgct accgcgacct ataccgggcg aacgagttga tcgccctcct ggaggagaag    3600
ggcatcgtgt tccgcgacgg ctccaacatc ctcccgaagc tgctcgaaaa cgacgactcc    3660
cacgccatcg acacgatggt cgcgctgatc cggtcggtgc tccagatgcg gaactccaac    3720
gccgcgacgg gcgaggacta catcaacagt ccggtccgcg atctgaacgg cgtctgcttc    3780
gactccggt tccagaaccc cgagtggccg atggacgcgg acgcgaacgg cgcataccac    3840
atcgccctaa aagggcaatt gctgctcaac cacctcaagg aatccaaaga cctaaagctc    3900
cagaacggca tctccaacca ggactggctg gcgtacatcc aggaactgcg gaacgggagc    3960
aaaaaacgtc ggatcaagca agattga                                       3987

SEQ ID NO: 20          moltype = DNA  length = 3987
FEATURE                Location/Qualifiers
source                 1..3987
                       mol_type = other DNA
                       organism = synthetic construct
SEQUENCE: 20
atggcgggct ccaagaaacg ccggattaag caagatacccc agttcgaggg gttcacgaac    60
ctctaccaag tgagcaagac cctccgattc gaactgattc ctcaggggaa gaccctcaag   120
cacatccagg agcaagggtt catcgaggag acaaggcgc ggaacgacca ctacaaggaa    180
ctcaaaccca tcatcgaccg catctacaag acctacgtcg atcagtgcct ccagctcgtg   240
cagttggact gggagaacct cagcgcggcc attgactcct accggaagga gaaaccggag   300
gagacgcgca acgcgctcat cgaggaacag gcaacctatc gcaacgccat ccacgactac   360
ttcatcggga ggactgacaa cctcactgac gcgattaaca agcgccacgc ggagatatac   420
aagggactct tcaaagcgga gctgtttaac ggcaaggttc tcaagcaact cggcactgtg   480
accacgaccg agcatgagaa cgccctgctc cgctccttcg acaagttcac cacctactc   540
tccggttct accgcaaccg caagaatgtc ttcagcgcgg aggacatcag cacggccatt   600
ccacatcgaa tcgtccaaga taccttcccg aagttcaagg agaactgcca catcttcacc   660
cgactcatta ctgctgtacc gtcgttacgc gaacacttcg agaacgtcaa gaaggcaatt   720
ggaatcttcg tctctacgtc aatagaggag tgtgttcatt tccctttcta caaccagctc   780
cttacgcaga cccagataga cctgtacaat cagctcctcg gtgggatcag ccgggaggcc   840
gggactgaga agattaaagg gctcaacgag gtcttgaacc tggccatcca aaaaaacgat   900
gagacggcgc acatcatcgc ctcgctgccc caccggttca tcccgctgtt caagcagatc   960
ctcagtgaca ggaacacctt gagctttatc ctagaggagt tcaagagcga cgaggaggtg  1020
atccagagct tctgcaagta caaaaccctg ctgaggaacg agaacgtcct ggagacggcg  1080
gaggcgctgt tcaacgagct gaactctatc gacttaactc acatattcat ctcgcacaag  1140
aagctggaga ctattagctc tgcactctgc gaccactggg acaccctccg caacgcgctc  1200
tacgacgcc gcatctcgga gctgaccggg aagatccaca atccgcgaa ggaaaagtc  1260
cagcgttcc ctcaaacacga ggatatttaac ttacaggaga ttatctcagc ggctgggaag  1320
gagttgtcag aggcgttcaa gcagaaaact tccgagatcc tgagccaccg cgcacgcagcg  1380
ctcgaccagc ctctgcccac caccctcaaa agcaggaag aaaagagat cctcaagagc  1440
cagttggact cccgtgctgg gctctatcac ctttctgact ggttcgccgt cgatgagtcg  1500
aacgaggtgg accccgagtt ctccgcccgg ctgaccggca tcaagctaga gatggagccg  1560
tccctcagct ctctacaataa ggccgcaac tacgcgacca aaaaaccccta cagcgtggag  1620
aagttcaagc tgaacttcca gatgccgacc ttagcacgcg gttgggacgt aaacagggag  1680
aagaacaatg gagccatcct gttcgtcaag aacgggctt actacctcgg gataatgcc   1740
aagcagaagg gccgctacaa ggccctttcc ttcgagccga cggagaaaac ctccgagggg  1800
ttcgacaaga tgtactacga ctacttcccc gacgccgcca agatgatccc gaagtgctca  1860
acgcagctaa aagccgtgac cgcccacttc cagacccaca cgacgccgat cctgctgagc  1920
aacaacttca tcgagcccct tgagatcact aaggagatat cgacctgaa caaccccgag  1980
aaggagccca agagtttca aaccgcctac gccaaaaaaa ctggcgacca aaagggctag  2040
agggaggcgc tgtgtaagtg gatcgacttc acacgcgact ccttcgaa gtatacgaag   2100
acaacctcta ttgacctgag cagcctgcgt cctagctccc agtacaaaga tttgggcgag  2160
tactacgcgg agcttaatcc actactctac cacatctcat ccagcgcat cgctgagaag  2220
gaaatcatgg acgcggtgga gacaggcaaa ctgtacctct tccagatata caacaaagac  2280
ttcgctaagg ggcaccacgg gaagccccaa cttccataacg tctactggac gggcctattc  2340
agcccccgaaa atctgccccaa gacctccatc aagctgaacg gccaagcgga gctgttctac  2400
agacccaaga gccggatgaa gcggatggcc cacaggctcg cgagaaaat gcttaacaaa   2460
aagttgaagg accagaaaac ccctatcccc gacaccctct accaggaact gtacgactac  2520
gtgaaccaca ggctctcgca cgacctttcc gacgaggccc gtgccctact cccgaacgtc  2580
attaccaaag aggtttcgca tgatcatc aaggaccgag ggttcacgag cgacaagttt  2640
ttctttcacg tccccatcac ccttaactac caggcggcca actccccatc caagttcaac  2700
cagcgtgtga atgcctacct caaggagcac ccagagaccc cgatcattgg gatcgaccgg  2760
ggcgagcgga acctgatcta catcaccgtc atcgactcga cggcaagat tcttgagcag  2820
agatcgttga ataccataca gcagttcgac taccagaaga aactcgacaa ccgcgagaag  2880
gagcgcgtgg cggcccgcca ggcgtggtcc gtcgttggga cgattaagga cttgaaacaa  2940
```

```
ggttatctgt cccaagtcat ccacgagatc gttgatctga tgatccacta tcaggcagtg    3000
gtggtgctgg agaatctcaa cttcggcttc aagagtaagc ggacgggaat cgccgagaag    3060
gccgtgtacc agcagttcga gaagatgctg atcgacaagc tcaactgcct tgtgctgaaa    3120
gactacccgg ccgagaaggt cggcggcgtc ctcaacccgt accaacttac cgaccagttc    3180
acctccttcg ccaagatggg cactcagtcc gggttcttgt tctacgtccc cgcaccttac    3240
acctctaaga tcgaccctct gactggcttc gtagatccat tcgtgtggaa gaccattaag    3300
aaccacgaga gccgcaagca cttcctggag ggcttcgact tcctgcacta cgacgtgaag    3360
accggggact tcatccttca cttcaagatg aaccggaacc tcagcttcca gcggggcctg    3420
ccgggggttca tgcccgcctg ggacatcgtg ttcgagaaga acgagaccca gttcgacgcg    3480
aagggcacgc ccttcatcgc cgggaagcgt atcgtgccgg tgatcgagaa ccatcgtttc    3540
acgggtcgct accgtgacct ctaccggcg aacgagctta tcgcactcct ggaggagaag    3600
ggcatcgtct tccgggacgg ctccaacatc ctcccgaaac tgctgaaaaa cgacgactct    3660
cacgccatcg acacgatggt ggccctcatc cggtccgtgc tccaaatgcg gaacagcaac    3720
gccgccaccg gtgaggacta catcaacagc ccggtccggg atctgaacgg ggtgtgcttc    3780
gattcgcggt tccagaatcc tgagtggccg atggacgcgg atgcaaacgg ggcgtaccac    3840
atcgcgctca agggccagtt acttctgaac caccttaagg agtctaaaga tttgaaactc    3900
cagaacggga tctcgaacca ggactggctg gcctacatcc aagagttgcg gaacggcagc    3960
aagaagcggc ggattaagca agattag                                        3987

SEQ ID NO: 21           moltype = DNA  length = 1592
FEATURE                 Location/Qualifiers
source                  1..1592
                        mol_type = other DNA
                        organism = Medicago truncatula
SEQUENCE: 21
actgttaata attttttaaac gtcagcgcac taaaaaaacg aaaagacgga cacgtgaaaa    60
taaaaaacac acactagttt atgacgcaat actatttttac ttatgatttg ggtacattag    120
acaaaaccgt gaaagagatg tatcagctat gaaacctgta tacttcaata cagagactta    180
ctcatatcgg atacgtacgc acgaagtatc atattaatta ttttaatttt taataaatat    240
tttatcggat acttatgtga tactctacat atacacaagg atatttctaa gatacttttat   300
agatacgtat cctagaaaaa catgaagagt aaaaaagtga acaatgttg taaaaattca    360
ttataaatgt atatgattca attttagata tgcatcagta taattgattc tcgatgaaac    420
acttaaaatt atatttcttg tggaagaacg tagcgagaga ggtgattcag ttagacaaca    480
ttaaataaaa ttaatgttaa gttctttaa tgatgtttct ctcaatatca catcatatga    540
aaatgtaata tgatttataa gaaaatttt aaaaaattta ttttaataat cacatgtact    600
atttttaaa aattgtatct tttataataa tacaataata aagagtaatc agtgttaatt    660
tttcttcaaa tataagtttt attataaatc attgttaacg tatcataagt cattaccgta    720
tcgtatctta atttttttt aaaaccgct aattcacgta cccgtattgt attgtacccg    780
cacctgtatc acaatcgatc ttagttagaa gaattgtctc gaggcggtgc aagacagcat    840
ataatagacg tggactctct tataccaaac gttgtcgtat cacaaagggt taggtaacaa    900
gtcacagttt gtccacgtgt cacgttttaa ttggaagagg tgccgttggc gtaatataac    960
agccaatcga tttttgctat aaaagcaaat caggtaaact aaacttcttc attctttct    1020
tccccatcgc tacaaaaccg gttcctttgg aaaagagatt cattcaaacc tagcacccaa    1080
ttccgtttca aggtataatc tactttctat tcttcgatta ttttattatt attagctact    1140
atcgtttaat cgatctttc ttttgatccg tcaaattaa attcaattag ggttttgttc    1200
ttttcttca tctgattgaa atccttctga attgaaccgt ttacttgatt ttactgttta    1260
ttgtatgatt taatccttg ttttcaaag acagtcttta gattgttatt aggggttcat    1320
ataaattttt agatttggat ttttgtattg tatgattcaa aaaatacgtc ctttaattag    1380
attagtacat ggatatttt tacccgattt attgattgtc agggagaatt tgatgagcaa    1440
gttttttga tgtctgttgt aaattgaatt gattataatt gctgatctgc tgcttccagt    1500
tttcataacc catattcttt taaccttgtt gtacacacaa tgaaaattg gtgattgatt    1560
catttgtttt tctttgtttt ggattataca gg                                  1592

SEQ ID NO: 22           moltype = DNA  length = 2000
FEATURE                 Location/Qualifiers
source                  1..2000
                        mol_type = other DNA
                        organism = Zea mays
SEQUENCE: 22
gtcgtgcccc tctctagaga taaagagcat tgcatgtcta aagtataaaa aattaccaca    60
tatttttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tattttgaca atctacagtt    240
ttatctttt agtgtgcatg tgatctctct gttttttttg caaatagctt gacctatata    300
atacttcatc cattttatta gtacatccat ttaggattta gggttgatgg tttctataga    360
ctaattttta gtacatccat tttattcttt ttagtctcta aatttttaa aactaaaact    420
ctatttagt tttttattta ataatttaga tataaaatga aataaaataa attgactaca    480
aataaaacaa ataccctta agaaataaaa aaactaagca aacattttc ttgttttcgag    540
tagataatga caggctgttc aacgccgtcg acgagtctaa cggacaccaa ccagcgaacg    600
agcagcgtcg cgtcgggcca agcgaagcag acggcacggc atctctgtag ctgcctctgg    660
acccctctcg agagttccgc tccaccgttg gacttgctcc gctgtcggca tccagaaatt    720
gcgtggcgga gcgcagacg tgaggcggca cggcaggcgg cctcttcctc ctctcacggc    780
accggcagct acggggggatt ccttcccac cgctccttcg ctttccctc ctcgcccgcc    840
gtaataaata gacacccct ccacaccctc tttcccaac cctcgtgcg                900
acacacacgc aaccagatct ccccaaatc cagccgcgg cacctccgct tcaaggtacg    960
ccgctcatcc tcccccccc cctctctcta ccttctctag atcggcgatc cggtccatgg    1020
ttagggcccg gtagttctac ttctgttcat gtttgtgtta gagcaaacat gttcatgttc    1080
atgtttgtga tgatgtggtc tggttgggcg gtcgttctag atcggagtag gatactgttt    1140
caagctacct ggtggattta ttaattttgt atctgtatgt gtgtgccata catcttcata    1200
```

```
gttacgagtt taagatgatg gatggaaata tcgatctagg ataggtatac atgttgatgc  1260
gggtttttact gatgcatata cagagatgct ttttttctcg cttggttgtg atgatatggt  1320
ctggttgggc ggtcgttcta gatcggagta gaatactgtt tcaaactacc tggtggattt  1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag  1620
atcggagtag aatactgttt caaactacct ggtggattta ttaattttgt atctttatgt  1680
gtgtgccata catcttcata gttacgagtt taagatgatg gatggaaata ttgatctagg  1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta tttatttgct tggtactgtt tcttttgtcc gatgctcacc  1980
ctgttgtttg gtgatacttc                                              2000

SEQ ID NO: 23          moltype = AA  length = 228
FEATURE                Location/Qualifiers
source                 1..228
                       mol_type = protein
                       organism = Rattus norvegicus
SEQUENCE: 23
SSETGPVAVD PTLRRRIEPH EFEVFFDPRE LRKETCLLYE INWGGRHSIW RHTSQNTNKH  60
VEVNFIEKFT TERYFCPNTR CSITWFLSWS PCGECSRAIT EFLSRYPHVT LFIYIARLYH  120
HADPRNRQGL RDLISSGVTI QIMTEQESGY CWRNFVNYSP SNEAHWPRYP HLWVRLYVLE  180
LYCIILGLPP CLNILRRKQP QLTFFTIALQ SCHYQRLPPH ILWATGLK               228

SEQ ID NO: 24          moltype = AA  length = 199
FEATURE                Location/Qualifiers
source                 1..199
                       mol_type = protein
                       organism = Homo sapiens
SEQUENCE: 24
MEASPASGPR HLMDPHIFTS NFNNGIGRHK TYLCYEVERL DNGTSVKMDQ HRGFLHNQAK  60
NLLCGFYGRH AELRFLDLVP SLQLDPAQIY RVTWFISWSP CFSWGCAGEV RAFLQENTHV  120
RLRIFAARIY DYDPLYKEAL QMLRDAGAQV SIMTYDEFKH CWDTFVDHQG CPFQPWDGLD  180
EHSQALSGRL RAILQNQGN                                               199

SEQ ID NO: 25          moltype = DNA  length = 621
FEATURE                Location/Qualifiers
source                 1..621
                       mol_type = other DNA
                       organism = Petromyzon marinus
SEQUENCE: 25
acagatgcag agtatgtgag aattcacgaa aagctggaca tctatacctt caagaagcag  60
ttctttaaca ataagaagtc tgtgagccat aggtgctacg tgctgttcga gctgaagaga  120
aggggtgaaa gaagggcatg ttttttgggg tatgctgtga acaagcccca gtctggaact  180
gagagaggca ttcacgccga aatttttcagc atcagaaagt tggaggaata ccctgagggat  240
aaccctggac agtttacaat taattggtat tctagctggt ctccatgcgc tgactgtgcc  300
gagaagatcc tggaatggta caaccaggag ctgagaggaa atggcctata cctgaagatt  360
tgggcctgca agctgtacta tgaaaagaac gcaagaaatc agatcggact gtggaacctg  420
agggataaatg gtgtggggct gaacgtgatg gtgtccgagc actatcagtg ctgtagaaag  480
atttttcattc agtcctcaca taatcagctg aacagagaata gatggctgga aaagactctg  540
aagagggctg agaagagaag gtccgaactg tcaattatga tccaggtgaa gatcctgcac  600
accactaagt cacctgccgt g                                           621

SEQ ID NO: 26          moltype = AA  length = 160
FEATURE                Location/Qualifiers
source                 1..160
                       mol_type = protein
                       organism = synthetic construct
SEQUENCE: 26
FERNYDPREL RKETYLLYEI KWGKSGKLWR HWCQNNRTQH AEVYFLENIF NARRFNPSTH  60
CSITWYLSWS PCAECSQKIV DFLKEHPNVL EIYVARLYYH EDERNRQGLR DLVNSGVTIR  120
IMDLPDYNYC WKTFVSDQGG DEDYWPGHFA PWIKQYSLKL                        160

SEQ ID NO: 27          moltype = AA  length = 207
FEATURE                Location/Qualifiers
source                 1..207
                       mol_type = protein
                       organism = synthetic construct
SEQUENCE: 27
TDAEYVRIHE KLDIYTFKKQ FSNNKKSVSH RCYVLFELKR RGERRACFWG YAVNKPQSGT  60
ERGIHAEIFS IRKVEEYLRD NPGQFTINWY SSWSPCADCA EKILEWYNQE LRGNGHTLKI  120
WVCKLYYEKN ARNQIGLWNL RDNGVGLNVM VSEHYQCCRK IFIQSSHNQL NENRWLEKTL  180
KRAEKRRSEL SIMFQVKILH TTKSPAV                                     207

SEQ ID NO: 28          moltype = AA  length = 228
FEATURE                Location/Qualifiers
source                 1..228
```

```
                            mol_type = protein
                            organism = synthetic construct
SEQUENCE: 28
SSKTGPVAVD  PTLRRRIEPH  EFEVFFDPRE  LRKETCLLYE  INWGGRHSIW  RHTSQNTNKH    60
VEVNFIEKFT  TERYFCPNTR  CSITWFLSWS  PCGECSRAIT  EFLSRYPNVT  LFIYIARLYH   120
LANPRNRQGL  RDLISSGVTI  QIMTEQESGY  CWHNFVNYSP  SNESHWPRYP  HLWVRLYVLE   180
LYCIILGLPP  CLNILRRKQS  QLTSFTIALQ  SCHYQRLPPH  ILWATGLK                 228

SEQ ID NO: 29               moltype = AA  length = 162
FEATURE                     Location/Qualifiers
source                      1..162
                            mol_type = protein
                            organism = synthetic construct
SEQUENCE: 29
SFERNYDPRE  LRKETYLLYE  IKWGKSGKLW  RHWCQNNRTQ  HAEVYFLENI  FNARRFNPST    60
HCSITWYLSW  SPCAECSQKI  VDFLKEHPNV  NLEIYVARLY  YPENERNRQG  LRDLVNSGVT   120
IRIMDLPDYN  YCWKTFVSDQ  GGDEDYWPGH  FAPWIKQYSL  KL                       162

SEQ ID NO: 30               moltype = AA  length = 166
FEATURE                     Location/Qualifiers
source                      1..166
                            mol_type = protein
                            organism = Escherichia coli
SEQUENCE: 30
SEVEFSHEYW  MRHALTLAKR  AWDEREVPVG  AVLVHNNRVI  GEGWNRPIGR  HDPTAHAEIM    60
ALRQGGLVMQ  NYRLIDATLY  VTLEPCVMCA  GAMIHSRIGR  VVFGARDAKT  GAAGSLMDVL   120
HHPGMNHRVE  ITEGILADEC  AALLSDFFRM  RRQEIKAQKK  AQSSTD                   166

SEQ ID NO: 31               moltype = AA  length = 166
FEATURE                     Location/Qualifiers
source                      1..166
                            mol_type = protein
                            organism = synthetic construct
SEQUENCE: 31
SEVEFSHEYW  MRHALTLAKR  ARDEREVPVG  AVLVLNNRVI  GEGWNRAIGL  HDPTAHAEIM    60
ALRQGGLVMQ  NYRLIDATLY  VTFEPCVMCA  GAMIHSRIGR  VVFGVRNAKT  GAAGSLMDVL   120
HYPGMNHRVE  ITEGILADEC  AALLCYFFRM  PRQVFNAQKK  AQSSTD                   166

SEQ ID NO: 32               moltype = AA  length = 166
FEATURE                     Location/Qualifiers
source                      1..166
                            mol_type = protein
                            organism = synthetic construct
SEQUENCE: 32
SEVEFSHEYW  MRHALTLAKR  AWDEREVPVG  AVLVLNNRVI  GEGWNRSIGL  HDPTAHAEIM    60
ALRQGGLVMQ  NYRLIDATLY  VTFEPCVMCA  GAMIHSRIGR  VVFGVRNAKT  GAAGSLMDVL   120
HYPGMNHRVE  ITEGILADEC  AALLCYFFRM  RRQVFNAQKK  AQSSTD                   166

SEQ ID NO: 33               moltype = AA  length = 166
FEATURE                     Location/Qualifiers
source                      1..166
                            mol_type = protein
                            organism = synthetic construct
SEQUENCE: 33
SEVEFSHEYW  MRHALTLAKR  ALDEREVPVG  AVLVLNNRVI  GEGWNRAIGL  HDPTAHAEIM    60
ALRQGGLVMQ  NYRLIDATLY  VTFEPCVMCA  GAMIHSRIGR  VVFGVRNAKT  GAAGSLMDVL   120
HYPGMNHRVE  ITEGILADEC  NALLCYFFRM  RRQVFNAQKK  AQSSTD                   166

SEQ ID NO: 34               moltype = AA  length = 166
FEATURE                     Location/Qualifiers
source                      1..166
                            mol_type = protein
                            organism = synthetic construct
SEQUENCE: 34
SEVEFSHEYW  MRHALTLAKR  ALDEREVPVG  AVLVLNNRVI  GEGWNRAIGL  HDPTAHAEIM    60
ALRQGGLVMQ  NYRLIDATLY  VTFEPCVMCA  GAMIHSRIGR  VVFGVRNAKT  GAAGSLMDVL   120
HYPGMNHRVE  ITEGILADEC  NALLCYFFRM  PRQVFNAQKK  AQSSTD                   166

SEQ ID NO: 35               moltype = AA  length = 1763
FEATURE                     Location/Qualifiers
source                      1..1763
                            mol_type = protein
                            organism = synthetic construct
SEQUENCE: 35
SEVEFSHEYW  MRHALTLAKR  AWDEREVPVG  AVLVHNNRVI  GEGWNRPIGR  HDPTAHAEIM    60
ALRQGGLVMQ  NYRLIDATLY  VTLEPCVMCA  GAMIHSRIGR  VVFGARDAKT  GAAGSLMDVL   120
HHPGMNHRVE  ITEGILADEC  AALLSDFFRM  RRQEIKAQKK  AQSSTDSGGS  SGGSSGSETP   180
GTSESATPES  SGGSSGGSSE  VEFSHEYWMR  HALTLAKRAW  DEREVPVGAV  LVLNNRVIGE   240
GWNRAIGLHD  PTAHAEIMAL  RQGGLVMQNY  RLIDATLYVT  FEPCVMCAGA  MIHSRIGRVV   300
```

```
FGVRNAKTGA AGSLMDVLHY PGMNHRVEIT EGILADECAA LLCYFFRMPR QVFNAQKKAQ   360
SSTDSGGSSG GSSGSETPGT SESATPESSG GSSGGSDKKY SIGLAIGTNS VGWAVITDEY   420
KVPSKKFKVL GNTDRHSIKK NLIGALLFDS GETAEATRLK RTARRRYTRR KNRICYLQEI   480
FSNEMAKVDD SFFHRLEESF LVEEDKKHER HPIFGNIVDE VAYHEKYPTI YHLRKKLVDS   540
TDKADLRLIY LALAHMIKFR GHFLIEGDLN PDNSDVDKLF IQLVQTYNQL FEENPINASG   600
VDAKAILSAR LSKSRRLENL IAQLPGEKKN GLFGNLIALS LGLTPNFKSN FDLAEDAKLQ   660
LSKDTYDDDL DNLLAQIGDQ YADLFLAAKN LSDAILLSDI LRVNTEITKA PLSASMIKRY   720
DEHHQDLTLL KALVRQQLPE KYKEIFFDQS KNGYAGYIDG GASQEEFYKF IKPILEKMDG   780
TEELLVKLNR EDLLRKQRTF DNGSIPHQIH LGELHAILER QEDFYPFLKD NREKIEKILT   840
FRIPYYVGPL ARGNSRFAWM TRKSEETITP WNFEEVVDKG ASAQSFIERM TNFDKNLPNE   900
KVLPKHSLLY EYFTVYNELT KVKYVTEGMR KPAFLSGEQK KAIVDLLFKT NRKVTVKQLK   960
EDYFKKIECF DSVEISGVED RFNASLGTYH DLLKIIKDKD FLDNEENEDI LEDIVLTLTL  1020
FEDREMIEER LKTYAHLFDD KVMKQLKRRR YTGWGRLSRK LINGIRDKQS GKTILDFLKS  1080
DGFANRFMQ LIHDDSLTFK EDIQKAQVSG QGDSLHEHIA NLAGSPAIKK GILQTVKVVD  1140
ELVKVMGRHK PENIVIEMAR ENQTTQKGQK NSRERMKRIE EGIKELGSQI LKEHPVENTQ  1200
LQNEKLYLYY LQNGRDMYVD QELDINRLSD YDVDHIVPQS FLKDDSIDNK VLTRSDKNRG  1260
KSDNVPSEEV VKKMKNYWRQ LLNAKLITQR KFDNLTKAER GGLSELDKAG FIKRQLVETR  1320
QITKHVAQIL DSRMNTKYDE NDKLIREVKV ITLKSKLVSD FRKDFQFYKV REINNYHHAH  1380
DAYLNAVVGT ALIKKYPKLE SEFVYGDYKV YDVRKMIAKS EQEIGKATAK YFFYSNIMNF  1440
FKTEITLANG EIRKRPLIET NGETGEIVWD KGRDFATVRK VLSMPQVNIV KKTEVQTGGF  1500
SKESILPKRN SDKLIARKKD WDPKKYGGFD SPTVAYSVLV VAKVEKGKSK KLKSVKELLG  1560
ITIMERSSFE KNPIDPLEAK GYKEVKKDLI IKLPKYSLFE LENGRKRMLA SAGELQKGNE  1620
LALPSKYVNF LYLASHYEKL KGSPEDNEQK QLFVEQHKHY LDEIIEQISE FSKRVILADA  1680
NLDKVLSAYN KHRDKPIREQ AENIIHLFTL TNLGAPAAFK YFDTTIDRKR YTSTKEVLDA  1740
TLIHQSITGL YETRIDLSQL GGD                                         1763

SEQ ID NO: 36          moltype = AA  length = 1565
FEATURE                Location/Qualifiers
source                 1..1565
                       mol_type = protein
                       organism = synthetic construct
SEQUENCE: 36
SEVEFSHEYW MRHALTLAKR ARDEREVPVG AVLVLNNRVI GEGWNRAIGL HDPTAHAEIM    60
ALRQGGLVMQ NYRLIDATLY VTFEPCVMCA GAMIHSLRGR VVFGVRNSKR GAAGSLMNVL   120
NYPGMNHRVE ITEGILADEC AALLCDFYRM PRQVFNAQKK AQSSINSGGS SGGSSGSETP   180
GTSESATPES SGGSSGGSDK KYSIGLAIGT NSVGWAVITD EYKVPSKKFK VLGNTDRHSI   240
KKNLIGALLF DSGETAEATR LKRTARRRYT RRKNRICYLQ EIFSNEMAKV DDSFFHRLEE   300
SFLVEEDKKH ERHPIFGNIV DEVAYHEKYP TIYHLRKKLV DSTDKADLRL IYLALAHMIK   360
FRGHFLIEGD LNPDNSDVDK LFIQLVQTYN QLFEENPINA SGVDAKAILS ARLSKSRRLE   420
NLIAQLPGEK KNGLFGNLIA LSLGLTPNFK SNFDLAEDAK LQLSKDTYDD LDNLLAQIG   480
DQYADLFLAA KNLSDAILLS DILRVNTEIT KAPLSASMIK RYDEHHQDLT LLKALVRQQL   540
PEKYKEIFFD QSKNGYAGYI DGGASQEEFY KFIKPILEKM DGTEELLVKL NREDLLRKQR   600
TFDNGSIPHQ IHLGELHAIL RRQEDFYPFL KDNREKIEKI LTFRIPYYVG PLARGNSRFA   660
WMTRKSEETI TPWNFEEVVD KGASAQSFIE RMTNFDKNLP NEKVLPKHSL LYEYFTVYNE   720
LTKVKYVTEG MRKPAFLSGE QKKAIVDLLF KTNRKVTVKQ LKEDYFKKIE CFDSVEISGV   780
EDRFNASLGT YHDLLKIIKD KDFLDNEENE DILEDIVLTL TLFEDREMIE ERLKTYAHLF   840
DDKVMKQLKR RRYTGWGRLS RKLINGIRDK QSGKTILDFL KSDGFANRFM QLIHDDSLT   900
FKEDIQKAQV SGQGDSLHEH IANLAGSPAI KKGILQTVKV VDELVKVMGR HKPENIVIEM   960
ARENQTTQKG QKNSRERMKR IEEGIKELGS QILKEHPVEN TQLQNEKLYL YYLQNGRDMY  1020
VDQELDINRL SDYDVDHIVP QSFLKDDSID NKVLTRSDKN RGKSDNVPSE EVVKKMKNYW  1080
RQLLNAKLIT QRKFDNLTKA ERGGLSELDK AGFIKRQLVE TRQITKHVAQ ILDSRMNTKY  1140
DENDKLIREV KVITLKSKLV SDFRKDFQFY KVREINNYHH AHDAYLNAVV GTALIKKYPK  1200
LESEFVYGDY KVYDVRKMIA KSEQEIGKAT AKYFFYSNIM NFFKTEITLA NGEIRKRPLI  1260
ETNGETGEIV WDKGRDFATV RKVLSMPQVN IVKKTEVQTG GFSKESILPK RNSDKLIARK  1320
KDWDPKKYGG FDSPTVAYSV LVVAKVEKGK SKKLKSVKEL LGITIMERSS FEKNPIDFLE  1380
AKGYKEVKKD LIIKLPKYSL FELENGRKRM LASAGELQKG NELALPSKYV NFLYLASHYE  1440
KLKGSPEDNE QKQLFVEQHK HYLDEIIEQI SEFSKRVILA DANLDKVLSA YNKHRDKPIR  1500
EQAENIIHLF TLTNLGAPAA FKYFDTTIDR KRYTSTKEVL DATLIHQSIT GLYETRIDLS  1560
QLGGD                                                              1565

SEQ ID NO: 37          moltype = AA  length = 1565
FEATURE                Location/Qualifiers
source                 1..1565
                       mol_type = protein
                       organism = synthetic construct
SEQUENCE: 37
SEVEFSHEYW MRHALTLAKR ARDEREVPVG AVLVLNNRVI GEGWNRAIGL HDPTAHAEIM    60
ALRQGGLVMQ NYRLYDATLY STFEPCVMCA GAMIHSRIGR VVFGVRNAKT GAAGSLMDVL   120
HHPGMNHRVE ITEGILADEC AALLCRFFRM PRRVFNAQKK AQSSTDSGGS SGGSSGSETP   180
GTSESATPES SGGSSGGSDK KYSIGLAIGT NSVGWAVITD EYKVPSKKFK VLGNTDRHSI   240
KKNLIGALLF DSGETAEATR LKRTARRRYT RRKNRICYLQ EIFSNEMAKV DDSFFHRLEE   300
SFLVEEDKKH ERHPIFGNIV DEVAYHEKYP TIYHLRKKLV DSTDKADLRL IYLALAHMIK   360
FRGHFLIEGD LNPDNSDVDK LFIQLVQTYN QLFEENPINA SGVDAKAILS ARLSKSRRLE   420
NLIAQLPGEK KNGLFGNLIA LSLGLTPNFK SNFDLAEDAK LQLSKDTYDD LDNLLAQIG   480
DQYADLFLAA KNLSDAILLS DILRVNTEIT KAPLSASMIK RYDEHHQDLT LLKALVRQQL   540
PEKYKEIFFD QSKNGYAGYI DGGASQEEFY KFIKPILEKM DGTEELLVKL NREDLLRKQR   600
TFDNGSIPHQ IHLGELHAIL RRQEDFYPFL KDNREKIEKI LTFRIPYYVG PLARGNSRFA   660
WMTRKSEETI TPWNFEEVVD KGASAQSFIE RMTNFDKNLP NEKVLPKHSL LYEYFTVYNE   720
LTKVKYVTEG MRKPAFLSGE QKKAIVDLLF KTNRKVTVKQ LKEDYFKKIE CFDSVEISGV   780
```

```
EDRFNASLGT YHDLLKIIKD KDFLDNEENE DILEDIVLTL TLFEDREMIE ERLKTYAHLF    840
DDKVMKQLKR RRYTGWGRLS RKLINGIRDK QSGKTILDFL KSDGFANRNF MQLIHDDSLT    900
FKEDIQKAQV SGQGDSLHEH IANLAGSPAI KKGILQTVKV VDELVKVMGR HKPENIVIEM    960
ARENQTTQKG QKNSRERMKR IEEGIKELGS QILKEHPVEN TQLQNEKLYL YYLQNGRDMY   1020
VDQELDINRL SDYDVDHIVP QSFLKDDSID NKVLTRSDKN RGKSDNVPSE EVVKKMKNYW   1080
RQLLNAKLIT QRKFDNLTKA ERGGLSELDK AGFIKRQLVE TRQITKHVAQ ILDSRMNTKY   1140
DENDKLIREV KVITLKSKLV SDFRKDFQFY KVREINNYHH AHDAYLNAVV GTALIKKYPK   1200
LESEFVYGDY KVYDVRKMIA KSEQEIGKAT AKYFFYSNIM NFFKTEITLA NGEIRKRPLI   1260
ETNGETGEIV WDKGRDFATV RKVLSMPQVN IVKKTEVQTG GFSKESILPK RNSDKLIARK   1320
KDWDPKKYGG FDSPTVAYSV LVVAKVEKGK SKKLKSVKEL LGITIMERSS FEKNPIDFLE   1380
AKGYKEVKKD LIIKLPKYSL FELENGRKRM LASAGELQKG NELALPSKYV NFLYLASHYE   1440
KLKGSPEDNE QKQLFVEQHK HYLDEIIEQI SEFSKRVILA DANLDKVLSA YNKHRDKPIR   1500
EQAENIIHLF TLTNLGAPAA FKYFDTTIDR KRYTSTKEVL DATLIHQSIT GLYETRIDLS   1560
QLGGD                                                              1565

SEQ ID NO: 38            moltype = AA   length = 364
FEATURE                  Location/Qualifiers
source                   1..364
                         mol_type = protein
                         organism = synthetic construct
SEQUENCE: 38
SEVEFSHEYW MRHALTLAKR AWDEREVPVG AVLVHNNRVI GEGWNRPIGR HDPTAHAEIM     60
ALRQGGLVMQ NYRLIDATLY VTLEPCVMCA GAMIHSRIGR VVFGARDAKT GAAGSLMDVL    120
HHPGMNHRVE ITEGILADEC AALLSDFFRM RRQEIKAQKK AQSSTDSGGS SGGSSGSETP    180
GTSESATPES SGGSSGGSSE VEFSHEYWMR HALTLAKRAR DEREVPVGAV LVLNNRVIGE    240
GWNRAIGLHD PTAHAEIMAL RQGGLVMQNY RLIDATLYVT FEPCVMCAGA MIHSRIGRVV    300
FGVRNAKTGA AGSLMDVLHY PGMNHRVEIT EGILADECAA LLCYFFRMPR QVFNAQKKAQ    360
SSTD                                                                364

SEQ ID NO: 39            moltype = AA   length = 167
FEATURE                  Location/Qualifiers
source                   1..167
                         mol_type = protein
                         organism = synthetic construct
SEQUENCE: 39
MSEVEFSHEY WMRHALTLAK RARDEREVPV GAVLVLNNRV IGEGWNRAIG LHDPTAHAEI     60
MALRQGGLVM QNYRLYDATL YSTFEPCVMC AGAMIHSRIG RVVFGVRNAK TGAAGSLMDV    120
LHHPGMNHRV EITEGILADE CAALLCRFFR MPRRVFNAQK KAQSSTD                  167

SEQ ID NO: 40            moltype = AA   length = 167
FEATURE                  Location/Qualifiers
source                   1..167
                         mol_type = protein
                         organism = synthetic construct
SEQUENCE: 40
MSEVEFSHEY WMRHALTLAK RARDEREVPV GAVLVLNNRV IGEGWNRAIG LHDPTAHAEI     60
MALRQGGLVM QNYRLIDATL YVTFEPCVMC AGAMIHSRIG RVVFGVRNSK RGAAGSLMNV    120
LNYPGMNHRV EITEGILADE CAALLCDFYR MPRQVFNAQK KAQSSIN                  167

SEQ ID NO: 41            moltype = AA   length = 83
FEATURE                  Location/Qualifiers
source                   1..83
                         mol_type = protein
                         organism = Bacillus phage AR9
SEQUENCE: 41
TNLSDIIEKE TGKQLVIQES ILMLPEEVEE VIGNKPESDI LVHTAYDEST DENVMLLTSD     60
APEYKPWALV IQDSNGENKI KML                                            83

SEQ ID NO: 42            moltype = AA   length = 24
FEATURE                  Location/Qualifiers
source                   1..24
                         mol_type = protein
                         organism = synthetic construct
SEQUENCE: 42
EELLSKNYHL ENEVARLKKG SGSG                                           24

SEQ ID NO: 43            moltype = AA   length = 241
FEATURE                  Location/Qualifiers
source                   1..241
                         mol_type = protein
                         organism = synthetic construct
SEQUENCE: 43
EEELLSKNYH LENEVARLKK GSGSGEELLS KNYHLENEVA RLKKGSGSGE ELLSKNYHLE     60
NEVARLKKGS GSGEELLSKN YHLENEVARL KKGSGSGEEL LSKNYHLENE VARLKKGSGS    120
GEELLSKNYH LENEVARLKK GSGSGEELLS KNYHLENEVA RLKKGSGSGE ELLSKNYHLE    180
NEVARLKKGS GSGEELLSKN YHLENEVARL KKGSGSGEEL LSKNYHLENE VARLKKGSGS    240
G                                                                   241

SEQ ID NO: 44            moltype = AA   length = 277
```

| FEATURE | Location/Qualifiers |
|---|---|
| source | 1..277<br>mol_type = protein<br>organism = synthetic construct |

SEQUENCE: 44
```
MGPDIVMTQS PSSLSASVGD RVTITCRSST GAVTTSNYAS WVQEKPGKLF KGLIGGTNNR    60
APGVPSRFSG SLIGDKATLT ISSLQPEDFA TYFCALWYSN HWVFGQGTKV ELKRGGGGSG   120
GGGSGGGGSS GGGSEVKLLE SGGGLVQPGG SLKLSCAVSG FSLTDYGVNW VRQAPGRGLE   180
WIGVIWGDGI TDYNSALKDR FIISKDNGKN TVYLQMSKVR SDDTALYYCV TGLFDYWGQG   240
TLVTVSSYPY DVPDYAGGGG GSGGGGSGGG GSGGGGS                           277
```

| SEQ ID NO: 45 | moltype = DNA   length = 66 |
|---|---|
| FEATURE | Location/Qualifiers |
| source | 1..66<br>mol_type = other DNA<br>organism = Saccharomyces bayanus |

SEQUENCE: 45
```
ttcttgtcgt acttatagat cgctacgtta tttcaatttt gaaaatctga gtcctgggag    60
tgcgga                                                               66
```

| SEQ ID NO: 46 | moltype = AA   length = 605 |
|---|---|
| FEATURE | Location/Qualifiers |
| source | 1..605<br>mol_type = protein<br>organism = Homo sapiens |

SEQUENCE: 46
```
MSGWESYYKT EGDEEAEEEQ EENLEASGDY KYSGRDSLIF LVDASKAMFE SQSEDELTPF    60
DMSIQCIQSV YISKIISSDR DLLAWFYGTE KDKNSVNFKI YVLQELDNPG AKRILELDQF   120
KGQQGQKRFQ DMMGHGSDYS LSEVLWVCAN LFSDVQFKMS HKRIMLFTNE DNPHGNDSAK   180
ASRARTKAGD LRDTGIFLDL HLKKPGGFDI SLFYRDIISI AEDEDLRVHF EESSKLEDLL   240
RKVRAKETRK RALSRLKLKL NKDIVISVGI YNLVQKALKP PPIKLYRETN EPVKTKTRTF   300
NTSTGGLLLP SDTKRSQIYG SRQIILEKEE TEELKRFDDP GLMLMGFKPL VLLKKHHYLR   360
PSLFVYPEES LVIGSSTLFS ALLIKCLEKE VAALCRYTPR RNIPPYFVAL VPQEEELDDQ   420
KIQVTPPGFQ LVFLPFADDK RKMPFTEKIM ATPEQVGMKK AIVEKLRFTY RSDSFENPVL   480
QQHFRNLEAL ALDLMEPEQA VDLTLPKVEA MNKRLGSLVD EFKELVYPPD YNPEGKVTKR   540
KHDNEGSGSK RPKVEYSEEE LKTHISKGTL GKFTVPLKEA CRAYGLKSGL KKQELLEALT   600
KHFQD                                                               605
```

| SEQ ID NO: 47 | moltype = AA   length = 482 |
|---|---|
| FEATURE | Location/Qualifiers |
| source | 1..482<br>mol_type = protein<br>organism = synthetic construct |

SEQUENCE: 47
```
MVRSGNKAAW LCMDVGFTMS NSIPGIESPF EQAKKVITMF VQRQVFAENK DEIALVLFGT    60
DGTDNPLSGG DQYQNITVHR HLMLPDFDLL EDIESKIQPG SQQADFLDAL IVSMDVIQHE   120
TIGKKFEKRH IEIFTDLSSR FSKSQLDIII HSLKKCDISE RHSIHWPCRL TIGSNLSIRI   180
AAYKSILQER VKKTTWDAKT LKKEDIQKET VYCLNDDDET EVLKEDIIQG FRYGSDIVPF   240
SKVDEEQMKY KSEGKCFSVL GFCKSSQVQR RFFMGNQVLK VFAARDDEAA AVALSSLIHA   300
LDDLDIWAIV RYAYDKRANP QVGVAFPHIK HNYECLVYVQ LPFMEDLRQY MFSSLKNSKK   360
YAPTEAQLNA VDALIDSMSL AKKDEKTDTL EDLFPTTKIP NPRFQRLFQC LLHRALHPRE   420
PLPPIQQHIW NMLNPPAEVT TKSQIPLSKI KTLFPLIEAK KKDQVTAQEI FQDNHEDGPT   480
AK                                                                 482
```

| SEQ ID NO: 48 | moltype = DNA   length = 10 |
|---|---|
| FEATURE | Location/Qualifiers |
| source | 1..10<br>mol_type = other DNA<br>organism = Methanobacterium thermoautotrophicum |

SEQUENCE: 48
```
aatttttgga                                                           10
```

| SEQ ID NO: 49 | moltype = AA   length = 83 |
|---|---|
| FEATURE | Location/Qualifiers |
| source | 1..83<br>mol_type = protein<br>organism = Methanobacterium thermoautotrophicum |

SEQUENCE: 49
```
GSVIDVSSQR VNVQRPLDAL GNSLNSPVII KLKGDREFRG VLKSFDLHMN LVLNDAEELE    60
DGEVTRRLGT VLIRGDNIVY ISP                                           83
```

| SEQ ID NO: 50 | moltype = DNA   length = 25 |
|---|---|
| FEATURE | Location/Qualifiers |
| source | 1..25<br>mol_type = other DNA<br>organism = Bacteriophage MS2 |

SEQUENCE: 50
```
gcgcacatga ggatcaccca tgtgc                                          25
```

```
SEQ ID NO: 51              moltype = AA   length = 116
FEATURE                    Location/Qualifiers
source                     1..116
                           mol_type = protein
                           organism = Bacteriophage MS2
SEQUENCE: 51
MASNFTQFVL VDNGGTGDVT VAPSNFANGI AEISSNSRSQ AYKVTCSVRQ SSAQNRKYTI   60
KVEVPKGAWR SYLNMELTIP IFATNSDCEL IVKAMQGLLK DGNPIPSAIA ANSGIY      116

SEQ ID NO: 52              moltype = DNA   length = 26
FEATURE                    Location/Qualifiers
source                     1..26
                           mol_type = other DNA
                           organism = Bacteriophage PP7
SEQUENCE: 52
ataaggagtt tatatggaaa cccctta                                       26

SEQ ID NO: 53              moltype = AA   length = 127
FEATURE                    Location/Qualifiers
source                     1..127
                           mol_type = protein
                           organism = Bacteriophage PP7
SEQUENCE: 53
MSKTIVLSVG EATRTLTEIQ STADRQIFEE KVGPLVGRLR LTASLRQNGA KTAYRVNLKL   60
DQADWDCSTS VCGELPKVRY TQVWSHDVTI VANSTEASRK SLYDLTKSLV ATSQVEDLVV   120
NLVPLGR                                                             127

SEQ ID NO: 54              moltype = DNA   length = 19
FEATURE                    Location/Qualifiers
source                     1..19
                           mol_type = other DNA
                           organism = Shigella phage
SEQUENCE: 54
ctgaatgcct gcgagcatc                                                19

SEQ ID NO: 55              moltype = AA   length = 62
FEATURE                    Location/Qualifiers
source                     1..62
                           mol_type = protein
                           organism = Shigella phage
SEQUENCE: 55
MKSIRCKNCN KLLFKADSFD HIEIRCPRCK RHIIMLNACE HPTEKHCGKR EKITHSDETV   60
RY                                                                  62

SEQ ID NO: 56              moltype = AA   length = 1367
FEATURE                    Location/Qualifiers
source                     1..1367
                           mol_type = protein
                           organism = synthetic construct
SEQUENCE: 56
DKKYSIGLAI GTNSVGWAVI TDEYKVPSKK FKVLGNTDRH SIKKNLIGAL LFDSGETAEA   60
TRLKRTARRR YTRRKNRICY LQEIFSNEMA KVDDSFFHRL EESFLVEEDK KHERHPIFGN  120
IVDEVAYHEK YPTIYHLRKK LVDSTDKADL RLIYLALAHM IKFRGHFLIE GDLNPDNSDV  180
DKLFIQLVQT YNQLFEENPI NASGVDAKAI LSARLSKSRR LENLIAQLPG EKKNGLFGNL  240
IALSLGLTPN FKSNFDLAED AKLQLSKDTY DDDLDNLLAQ IGDQYADLFL AAKNLSDAIL  300
LSDILRVNTE ITKAPLSASM IKRYDEHHQD LTLLKALVRQ QLPEKYKEIF FDQSKNGYAG  360
YIDGGASQEE FYKFIKPILE KMDGTEELLV KLNREDLLRK QRTFDNGSIP HQIHLGELHA  420
ILRRQEDFYP FLKDNREKIE KILTFRIPYY VGPLARGNSR FAWMTRKSEE TITPWNFEEV  480
VDKGASAQSF IERMTNFDKN LPNEKVLPKH SLLYEYFTVY NELTKVKYVT EGMRKPAFLS  540
GEQKKAIVDL LFKTNRKVTV KQLKEDYFKK IECFDSVEIS GVEDRFNASL GTYHDLLKII  600
KDKDFLDNEE NEDILEDIVL TLTLFEDREM IEERLKTYAH LFDDKVMKQL KRRRYTGWGR  660
LSRKLINGIR DKQSGKTILD FLKSDGFANR NFMQLIHDDS LTFKEDIQKA QVSGQGDSLH  720
EHIANLAGSP AIKKGILQTV KVVDELVKVM GRHKPENIVI EMARENQTTQ KGQKNSRERM  780
KRIEEGIKEL GSQILKEHPV ENTQLQNEKL YLYYLQNGRD MYVDQELDIN RLSDYDVDHI  840
VPQSFLKDDS IDNKVLTRSD KNRGKSDNVP SEEVVKKMKN YWRQLLNAKL ITQRKFDNLT  900
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM 1020
IAKSEQEIGK ATAKYFFYSN IMNFFKTEIT LANGEIRKRP LIETNGETGE IVWDKGRDFA 1080
TVRKVLSMPQ VNIVKKTEVQ TGGFSKESIL PKRNSDKLIA RKKDWDPKKY GGFDSPTVAY 1140
SVLVVAKVEK GKSKKLKSVK ELLGITIMER SSFEKNPIDF LEAKGYKEVK KDLIIKLPKY 1200
SLFELENGRK RMLASAGELQ KGNELALPSK YVNFLYLASH YEKLKGSPED NEQKQLFVEQ 1260
HKHYLDEIIE QISEFSKRVI LADANLDKVL SAYNKHRDKP IREQAENIIH LFTLTNLGAP 1320
AAFKYFDTTI DRKRYTSTKE VLDATLIHQS ITGLYETRID LSQLGGD              1367

SEQ ID NO: 57              moltype = AA   length = 1367
FEATURE                    Location/Qualifiers
source                     1..1367
                           mol_type = protein
                           organism = synthetic construct
```

```
SEQUENCE: 57
DKKYSIGLAI GTNSVGWAVI TDEYKVPSKK FKVLGNTDRH SIKKNLIGAL LFDSGETAEA    60
TRLKRTARRR YTRRKNRICY LQEIFSNEMA KVDDSFFHRL EESFLVEEDK KHERHPIFGN   120
IVDEVAYHEK YPTIYHLRKK LVDSTDKADL RLIYLALAHM IKFRGHFLIE GDLNPDNSDV   180
DKLFIQLVQT YNQLFEENPI NASGVDAKAI LSARLSKSRR LENLIAQLPG EKKNGLFGNL   240
IALSLGLTPN FKSNFDLAED AKLQLSKDTY DDDLDNLLAQ IGDQYADLFL AAKNLSDAIL   300
LSDILRVNTE ITKAPLSASM IKRYDEHHQD LTLLKALVRQ QLPEKYKEIF FDQSKNGYAG   360
YIDGGASQEE FYKFIKPILE KMDGTEELLV KLNREDLLRK QRTFDNGSIP HQIHLGELHA   420
ILRRQEDFYP FLKDNREKIE KILTFRIPYY VGPLARGNSR FAWMTRKSEE TITPWNFEEV   480
VDKGASAQSF IERMTNFDKN LPNEKVLPKH SLLYEYFTVY NELTKVKYVT EGMRKPAFLS   540
GEQKKAIVDL LFKTNRKVTV KQLKEDYFKK IECFDSVEIS GVEDRFNASL GTYHDLLKII   600
KDKDFLDNEE NEDILEDIVL TLTLFEDREM IEERLKTYAH LFDDKVMKQL KRRRYTGWGR   660
LSRKLINGIR DKQSGKTILD FLKSDGFANR NFMQLIHDDS LTFKEDIQKA QVSGQGDSLH   720
EHIANLAGSP AIKKGILQTV KVVDELVKVM GRHKPENIVI EMARENQTTQ KGQKNSRERM   780
KRIEEGIKEL GSQILKEHPV ENTQLQNEKL YLYYLQNGRD MYVDQELDIN RLSDYDVDHI   840
VPQSFLADDS IDNKVLTRSD KNRGKSDNVP SEEVVKKMKN YWRQLLNAKL ITQRKFDNLT   900
KAERGGLSEL DKAGFIKRQL VETRQITKHV AQILDSRMNT KYDENDKLIR EVKVITLKSK   960
LVSDFRKDFQ FYKVREINNY HHAHDAYLNA VVGTALIKKY PALESEFVYG DYKVYDVRKM  1020
IAKSEQEIGK ATAKYFFYSN IMNFFKTEIT LANGEIRKAP LIETNGETGE IVWDKGRDFA  1080
TVRKVLSMPQ VNIVKKTEVQ TGGFSKESIL PKRNSDKLIA RKKDWDPKKY GGFDSPTVAY  1140
SVLVVAKVEK GKSKKLKSVK ELLGITIMER SSFEKNPIDF LEAKGYKEVK KDLIIKLPKY  1200
SLFELENGRK RMLASAGELQ KGNELALPSK YVNFLYLASH YEKLKGSPED NEQKQLFVEQ  1260
HKHYLDEIIE QISEFSKRVI LADANLDKVL SAYNKHRDKP IREQAENIIH LFTLTNLGAP  1320
AAFKYFDTTI DRKRYTSTKE VLDATLIHQS ITGLYETRID LSQLGGD              1367

SEQ ID NO: 58           moltype = DNA   length = 4101
FEATURE                 Location/Qualifiers
source                  1..4101
                        mol_type = other DNA
                        organism = synthetic construct
SEQUENCE: 58
gacaagaagt acagcatcgg gctggcgatc gggaccaact ccgtcggctg ggctgtgatt    60
accgacgagt acaaggtgcc atccaagaag ttcaaggtcc tcggcaacac tgaccggcac   120
agcattaaga agaacctgat tggggcgctg ctgttcgatt cggggggagac tgcggaggcg   180
accaggctga agcggactgc gcgccggagg tacaccagga ggaagaatcg gatctgctac   240
ctccaggaga tttttctcgaa tgagatggcc aaggtggacg attccttctt ccatcgcctg   300
gaggagtcgt tcctcgttga ggaggacaag aagcatgaga gcatccat ttcgggaat   360
atcgttgacg aggtggctta ccatgagaag tacccgacca tctaccatct gcggaagaag   420
ctcgtcgatt cgaccgataa ggccgacctg cggctgatct acctggccct cgcgcacatg   480
attaagttcc ggggccattt cctcatcgag ggcgacctca cccggacaa ctcggacgtg   540
gataagctct tcattcagct cgtgcagaca taaccagc tcttgagga gaatcccatt   600
aacgcctcgg gggtcgacgc taaggctatt ctctcggctc ggctgtcgaa gtcgcgccgg   660
ctggaaatc tcattgccca gctcccaggc gagaagaaga acggcctctt cggcaacctg   720
attgccctgt cgctggggct cacaccgaat ttcaagtcga acttcgacct cgccgaggac   780
gctaagctcc agctcagcaa ggatacttac gatgatgacc tcgataacct gctcgcccag   840
attggggatc agtacgcgga tctgttcctc gcggccaaga atctcagcga tgctattctc   900
ctgtcggaca ttctccgcgt caacacagag attactaagg ccccactgtc ggcgagcatg   960
attaagaggt acgatgagca tcatcaggac ctgacactgc tcaaggcgct ggtccggcag  1020
cagctccccg agaagtacaa ggagattttc ttcgatcagt caaagaatgg gtacgcgggc  1080
tacattgatg gcggcgcgtc ccaggaggag ttctacaagt tcattaagcc catcctggag  1140
aagatggacg gaaccgagga gctgctggtg aagctcaatc gggaggacct gctccggaag  1200
cagcgcacat tcgacaatgg ctcgattcct caccagattc acctgggcga gctgcacgcc  1260
attctccgca ggcaggagga ctttctaccg ttcctcaagg acaaccgcga aagatcgag  1320
aagatcctga ccttccggat tccatactac gtggggccgc tcgcgcgggg gaactcccgg  1380
ttcgcgtgga tgactcgcaa gtccgaagaa acgattacac cgtggaattt cgaggaggtc  1440
gtcgacaagg gcgctagtgc gcagtcattc attgagagga tgaccaattt cgataagaac  1500
ctgcctaacg agaaggtgct gccgaagcat tcgctgctct acgagtactt caccgtttac  1560
aatgagctga ccaaggtgaa gtatgtgact gagggcatga ggaagccagc gttcctgagc  1620
ggcgagcaga agaaggctat cgtggacctg ctcttcaaga ctaaccggaa ggtgactgtg  1680
aagcagctca aggaggacta cttcaagaag attgagtgct tcgattccgt tgagattagc  1740
ggggtggagg atcggttcaa tgcttcgctc gggacatacc acgatctcct gaagatcatt  1800
aaggataagg acttcctcga caacgaggag aacgaggaca ttctcgaaga tattgtcctg  1860
accctcaccc tcttcgagga tcgggagatg atcgaggaga ggctcaagac atacgctcat  1920
ctgttcgatg ataaggtcat gaagcgctg aagcgcaggc ggtacacgg gtggggcggg  1980
ctgagccgga agctgatcaa cgggattcgg gataagcagt ccgggaagac aattctcgac  2040
ttcctcaagt ccgacgggtt cgctaaccgg aacttcatgc agctcattca tgatgactcg  2100
ctgacattca aggaggatat tcagaaggcg caggtttcgg gcagggcga ctcgctccac  2160
gagcatattg cgaatctggc gggctccccc gcgattaaga agggcattct gcaaaccgtc  2220
aaggtggttg atgagctggt caaggtcatg gggcggcata agccagagaa tattgtcatc  2280
gagatggcgc gggagaatca gaccacacag aaggggcaga gaactcacg ggagcggatg  2340
aagcgcatcg aggagggcat caaggagctg ggtcgcaga tcctgaagga catcccgtg  2400
gagaacactc agctgcaaaa tgagaagctg tacctctact acctcagaa cgggagggac  2460
atgtatgtgg atcaggagct ggatattaat aggctgagcg attacgatgt cgaccacatt  2520
gtcccacagt cgttcctgaa ggacgacagc attgacaaca aggtgctgac ccgctcgcat  2580
aagaacaggg gcaagagcga taatgttcca agcgaggagg ttgtgaagaa gatgaagaac  2640
tactggcggc agctcctgaa cgcgaagctc atcacacagc ggaagttcga caacctcacc  2700
aaggctgagc gcgggggcct gagcgagctg gacaaggcgg ggttcattaa gaggcagctg  2760
gtcgagacac ggcagattac aaagcatgtt gcgcagattc tcgattcccg gatgaacacc  2820
aagtacgatg agaacgataa gctgattcgg gaggtcaagg taattaccct gaagtccaag  2880
```

```
ctggtgtccg acttcaggaa ggacttccag ttctacaagg ttcgggagat caacaactac 2940
caccacgcgc atgatgccta cctcaacgcg gtcgtgggga ccgctctcat caagaagtac 3000
ccaaagctgg agtcagagtt cgtctacggg gattacaagg tttacgacgt gcggaagatg 3060
atcgctaaga gcgagcagga gattggcaag gctaccgcta agtacttctt ctactccaac 3120
atcatgaact tcttcaagac agagattacc ctcgcgaatg gcgagatcga gaagaggccc 3180
ctcatcgaga caaatgggga gacagggagg attgtctggg ataaggggcg ggatttcgcg 3240
accgtccgga aggtcctgtc gatgccccag gttaatattg tcaagaagac tgaggtccag 3300
actggcggct tctcaaagga gtcgattctc caaagagga actccgataa gctcattgct 3360
cggaagaagg attgggaccc caagaagtac ggggattcg actcccccac tgttgcttac 3420
tctgttctgg ttgttgctaa ggtggagaag gggaagtcga agaagctgaa gagcgtgaag 3480
gagctgctcg ggattacaat tatggagagg tcatccttcg agaagaatcc catcgacttc 3540
ctggaggcca agggctacaa ggaggtgaag aaggacctga ttattaagct gcccaagtac 3600
tcgctcttcg agctggagaa tgggcggaag cggatgctgc cgtccgcggg ggagctgcaa 3660
aaggggaacg agctggcgct cccctccaag tatgtgaatt tcctctacct ggcgtcgcac 3720
tacgagaagc tgaaggggtc cccagaggat aatgagcaga agcagctctt cgtcgagcag 3780
cataagcact acctggacga gattatcgag cagattagcg agttctcgaa gcgggtcatc 3840
ctcgcggatg cgaacctgga taaggtgctc agcgcctaca ataagcaccg ggacaagccg 3900
attcgggagc aggcggagaa tattattcac ctcttcacac tcaccaacct cggggcacca 3960
gctgcgttca agtacttcga cactactatc gaccggaagc ggtacaccct cgacgaaggag 4020
gtgctcgacg ccaccctcat tcaccagtcg atcacaggcc tgtacgagac acggattgac 4080
ctgtcccagc tcgggggcga c                                         4101

SEQ ID NO: 59        moltype = DNA   length = 4101
FEATURE              Location/Qualifiers
source               1..4101
                     mol_type = other DNA
                     organism = synthetic construct
SEQUENCE: 59
gacaagaagt actccattgg cctggcgatt gggacaaact cggtggggtg ggccgtgatt 60
acggatgagt acaaggttcc aagcaagaag ttcaaggtcc tcgggaacac agatcggcat 120
tcgattaaga agaatctcat tggggcgctc ctcttcgact cggggagac agccgaggct 180
accaggctca gcggacagc caggcggcgg tacacaaggc ggaagaatcg catctgctac 240
ctccaggaga tttctcgaa tgagatggcg aaggtggacg acagcttctt ccatcggctg 300
gaggagtcct tcctggtgga ggaggataag aagcacgaga ggcatccaat tttcgggaac 360
atcgtggacg aggttgcgta ccatgagaag taccctacaa tctaccatct gcggaagaag 420
ctggttgact ccacagacaa ggcggacctg aggctgatct acctcgctct ggcccacatg 480
attaagttcc gcgggcattt cctgatcgag ggggacctga atcccgacaa ttcggatgtg 540
gacaagctct tcatccagct ggtgcagacc tacaaccagc tgttcgagga gaatcccatc 600
aatgcgtcgg gcgttgacgc taaggccatt ctgtccgcta ggctgtcgaa gagcaggagg 660
ctggagaacc tgatcgccca gctgccaggc gagaagaaga atgggctctt cgggaatctg 720
attgcgctct ccctggggct gacaccgaac ttcaagagca atttcgatct ggctgaggac 780
gcgaagctcc agctctcgaa ggacacttac gacgatgacc tcgataacct cctcgcgcag 840
atcggggacc agtacgctga tctcttcctc gccgctaaga acctctcgga tgctatccga 900
ctctccgaca ttctccgggt taataccgag attacaaagg ccccactgtc ggcgtccatg 960
atcaagcggt acgatgagca tcatcaggat ctcaccctgc tcaaggccct cgtgcggcag 1020
cagctgcccg agaagtacaa ggagattttt ttcgaccaga gcaagaatgg gtacgctggc 1080
tacattgacg gcgggccctc acaggaggag ttctacaagt tcatcaagcc aatcctggag 1140
aagatggatg gcacagagga gctgctggtg aagctcaacc gggaggatct gctcaggaag 1200
cagcggacgt tcgacaacgg gtcgattccc atcagatcc acctggggga gctgcacgcg 1260
atcctgcgcc ggcaggagga tttctaccct tcctgaagg ataatcggga gaagatcgag 1320
aagattctca ccttccggat tccctactac gtcgggccac tcgcgcgggg caatagcagg 1380
ttcgcctgga tgacacggaa gagcgaggag acaatcaccc cctgaacttc gaggaggtt 1440
gtcgacaagg gggcgtccgc ccagtcattc attgagcgga tgaccaattt cgacaagaat 1500
ctgccaaatg agaaggttct cccaaagcat agcctcctct acgagtactt cactgtttac 1560
aacgcgctga caaggtgaa gtatgtgacc gagggcatgc ggaagccgcc gttcctgtcc 1620
ggcgagcaga agaaggccat tgtggacctc ctgttcaaga ccaatcgcaa ggtcacagtc 1680
aagcagctca ggaggatta cttcaagaag atcgagtgct tcgactcggt tgagattagc 1740
ggggtggagg atcggttcaa cgcgagcctc ggcacttacc acgacctcct gaagatcatc 1800
aaggataagg acttcctcga caacgaggag aacgaggata ttctggagga catcgtgctc 1860
accctgacgc tgttcgagga tcggggaatg atcgaggagc gcctgaagac ctacgctcat 1920
ctcttcgatg ataaggtcat gaagcagctg aagaggagc ggtacaccgg tgggcgccgc 1980
ctgagcagga agctcattaa cgggatcagg gacaagcaga gcggcaagac catcctggac 2040
ttcctcaaga gcgatggctt cgccaaccgg aatttcatgc agctcatcca cgacgactcc 2100
ctcaccttca aggaggcat tcagaaggct caggtcagcg gccaggtgca ctcgctcgta 2160
gagcacatcg ctaacctggc gggcagccca gccatcaaga agggcatcct ccagacagtg 2220
aaggtcgtgg atgagctggt gaaggtcatg ggccggcata agcccgagaa tattgtgatt 2280
gagatggcgc gggagaatca gaccactcag aagggccaga gaactcgcg ggagcgcatg 2340
aagaggatcg aggaggggat taaggagctg ggcagccaga ttctcaagga gcaccccgtg 2400
gagaatacc agctccagaa cgagaagctg tacctctact acctccagaa tgggcggac 2460
atgtatgttg atcaggagct ggacatcaat cgcctctcgg attacgacgt ggaccacatc 2520
gtgcccaga gcttcctgaa ggatgatagc atcgacaata aggtcctgac ccgctccgac 2580
aagaatcgcg gcaagagcga caacgtgccg agcgaggagg tcgtgaagaa gatgaagaac 2640
tactggcggc agctgctgaa cgcgaagctc attacacagc ggaagttcga taacctgacg 2700
aaggcggaac ctccgactg gacaaggcgg gcttcattaa gaggcagctc 2760
gtggagactc gccagatcac caagcacgtg gctcagatcc tcgatagccg gatgaatacg 2820
aagtacgatg agaatgacaa gctcatccgg gaggtgaagg taatcaccct gaagtcaaag 2880
ctcgttagcg atttccggaa ggacttccag ttctacaagg tgcgggagat taacaactac 2940
catcatgcgc acgatgcgta cctcaatgcg gtggtgggca cagccctgat taagaagtac 3000
cccaagctgg agagcgagtt cgtctacggg gactacaagg tgtacgatgt tcggaagatg 3060
```

-continued

```
atcgccaaga gcgagcagga gattgggaag gccaccgcta agtacttctt ctactcgaat    3120
attatgaatt tcttcaagac cgagatcaca ctcgctaatg gggagattcg gaagcggccc    3180
ctcatcgaga ctaacgggga gactggcgag attgtgtggg acaaggggcg cgacttcgct    3240
accgtgcgca aggtcctctc gatgcccag gttaatattg ttaagaagac agaggtgcag    3300
acgggcgggt tctccaagga gtctatcctg ccgaagcgga actcggacaa gctgatcgcc    3360
cgcaagaagg attgggaccc caagaagtac gggggattcg atagcccaac cgtggcttac    3420
agcgtcctgg tggtcgccaa ggttgagaag gggaagtcga agaagctcaa gagcgttaag    3480
gagctgctgg gcatcaccat catggagcgg tccagcttcg agaagaatcc tatcgacttc    3540
ctggaggcta aggggtacaa ggaggtcaag aaggacctga tcattaagct gcccaagtac    3600
tctctgttcg agctggagaa cgggagggaag cggatgctgg cgtctgctgg cgagctacag    3660
aagggcaatg agctggcgct ccctcgaag tatgtcaact tcctctacct ggcttcccat     3720
tacgagaagc tgaagggctc gcccgaggat aatgagcaga agcagctctt cgtggagcag    3780
cacaagcact acctcgacga gatcattgag cagattcgg agttctcgaa gcgggtcatt     3840
ctcgcggacg cgaacctcga caaggtcctc tcggcgtaca acaagcaccg ggacaagccg    3900
atccggggagc aggccgagaa cattatccac ctcttcacac tgaccaacct cggcgctccc    3960
gccgcgttca agtacttcga caccaccatt gaccgcaaga gatacacatc caccaaggag    4020
gtgctggacg cgaccctcat ccaccagagc atcacaggcc tctacgagac acggatcgac    4080
ctctcgcagc tcggggggcga t                                              4101

SEQ ID NO: 60         moltype = DNA   length = 4092
FEATURE               Location/Qualifiers
source                1..4092
                      mol_type = other DNA
                      organism = synthetic construct
SEQUENCE: 60
gacaagaagt actcgatcgg cctggcgatt ggcacaaaca gcgtgggggtg ggctgtgatc    60
actgatgagt acaaggtgcc atcgaagaag ttcaaggtgc tggggaatac agaccggcat    120
tcgatcaaga agaatctcat tggcgctctc ctcttcgatt ccggcgagac tgctgaggcg    180
acccgcctga agcgcaccgc ccggcggcgc tacactcggc ggaagaatag gatttgctac    240
ctccaggaga tttttctcga atgagatggcc aaggtggatg acagcttctt ccaccgcctg    300
gaggagtcgt tcctggtcga ggaggacaag aagcatgagc ggcaccctat cttcgggaat    360
atcgttgatg aggtcgccta ccacgagaag taccccacta tctaccatct ccgcaagaag    420
ctcgtggaca gcacagataa ggccgacctc cgcctgatct acctcgccct cgcgcacatg    480
attaagttcc gggggcactt cctcattgag ggggatctga atcccgataa ctccgacgtg    540
gacaagctgt tcatccagct ggtgcagaca tacaaccagc tgttcgagga gaatcccatc    600
aacgcgagcg cgtggacgc taaggccatt ctgtcggcta ggctctcgaa gtcgaggcgg    660
ctggagaacc tgattgcgca gctccccggc gagaagaaga acgggctgtt cgggaatctc    720
atcgccctct ccctcggcct cacaccaaac ttcaagagca atttcgacct ggctgaggac    780
gctaagctgc aactctcaaa ggatacatac gatgacgaac tggacaatct cctggctcag    840
atcggcgacc agtacgctga cctgttcctc gcggccaaga atctgtcgga cgcgattctc    900
ctcagcgaca tcctgcgcgt caataccgag attacgaagg ctccactgtc tgcgtcaatg    960
attaagcggt acgatgagca tcaccaggat ctgaccctcc tgaaggcgct cgtgcggcag    1020
cagctgcccg agaagtacaa ggagatttttc ttcgatcaga caagaatgta ctacgccagc    1080
tacatcgacg ggggcgcgag ccaggaggag ttctacaagt tcatcaagcc catcctggag    1140
aagatgacg gcaccgagga gctactcgtg aagctcaatc gggaggatct cctccggaag    1200
cagcggacat tcgataacgg gtctatccca caccagatcc acctcggcga gctgcatgcg    1260
attctgcgc ggcaggagga tttctaccct ttcctgaaga acaaccggga agatcgag      1320
aagatcctca cattccggat tccatactac gtcggccccc tggcgagggg caatagccgg    1380
ttcgcgtgga tgacaaggaa gtccgaggag actattaccc cgtggaattt cgaggaggtg    1440
gttgacaagg gcgcttccgc gcagagcttc attgagcgga tgacaaactt cgacaagaat    1500
ctcccccaacg agaaggtcct gccgaagcat gcctcctgt acgagtactt caccgtctac    1560
aatgagctaa ctaaggtcaa gtatgtgaca gagggcatga ggaagccagc cttcctctca    1620
ggcgagcaga agaaggccat tgtggacctc ctgttcaaga caaccgcaa ggtgacagtg    1680
aagcagctga aggaggatta cttcaagaag attgagtgct tcgactcagt ggagatttca    1740
ggcgtggaga tcggttcaa cgcgagcctg gggacttacc acgacctgct gaagattatt    1800
aaggacaagg acttcctgga taacgaggag aatgaggaca tcctggagga tattgtgctc    1860
accctcaccc tgttcgagga cagggagatg attgaggaga ggctcaagac ctacgcgcac    1920
ctgttcgatg acaaggtcat gaagcagctg aagaggcgc gctacactgg gtggggccgc    1980
ctgtcgcgga agctgatcaa cggcattcgg gataagcagt cccggaaagc cattctggat    2040
ttcctgaagt cggacggctt cgccaacagg aatttcatgc agctgatcca cgacgactgt    2100
ctcaccttca aggaggacat tcagaaggcc caggttagcg gccaggggga ctcactccac    2160
gagcatattg ccaatctggc cggctctcca gctataaga agggcatcct gcaaacagtt    2220
aaggttgttg acgagctggt taaggtcatg gggcggcata gcccgagaa cattgtcatc    2280
gagatggctc gggagaacca gacaactcag aagggccaga agaactccag gagcggacag    2340
aagcggattg aggagggcat taaggagctg gggtcccaga tcctcaagga gcaccctgtc    2400
gagaacactc agctgcaaaa cgagaagctc tacctgtact acctccagaa cgggcgggat    2460
atgtatgtg atcaggagct ggacatcaac aggctctccg actacgacgt ggatcacatt    2520
gtcccacagt cttcctcaa ggatgattcc atcgagaaca aggtgctgac gcgcagcgac    2580
aagaataggg ggaagtcgga caacgttccg agcagggagg tcgtgaagaa gatgaagaat    2640
tactggaggc agctcctgaa tgcgaagctg atcactcaga ggaagttcga caatctgaca    2700
aaggcggaga gggcgggct ctcggagctg gataagcgg gcttcatcaa gcggcagctc    2760
gttgaaaccc ggcagatcac caagcatgtc gcccagatcc tcgatagccg catgaacacc    2820
aagtacgatg agaacgacaa gctcattcgg gaggttaagg tcattacgct gaagtccaag    2880
ctcgtcagga acttcaggaa ggatttccag ttctcagagt ttcgggagat taacaactac    2940
caccacgcgc atgatgcgta cctgaacgct gttgtcggca ctgctctcat caagaagtac    3000
ccaaagctgg agtccgagtt cgtctacggg gactacaagg tctacgatgt ccggaagatg    3060
atcgccaagt cggagcagga gatcgggaag gctactgcga agtacttctt ctacagcaac    3120
attatgaatt tcttcaagac ggagattacg ctggcgaacg gggagattag gaagaggccc    3180
ctcattgaga ctaatgggga gacaggcgag attgtttggg acaaggggcc cgacttcgcg    3240
```

```
actgtgcgga aggtcctgtc catgccacag gtgaatattg ttaagaagac agaggtgcag   3300
actgggggct tctcgaagga gagcattctc ccaaagcgga acagcgataa gctcatcgcg   3360
cgcaagaagg attgggaccc taagaagtac ggcggcttcg attctccac tgtggcctac    3420
tccgttctcg tggttgccaa ggttgagaag gggaagtcga agaagctgaa gtcggtcaag   3480
gagctgctcg ggattacaat catggagcgg agcagctcga agaagaaccc tattgatttc   3540
ctggaggcca agggctacaa ggaggttaag aaggatctca ttatcaagct ccctaagtac   3600
tctctgttcg agctggagaa tggccggaag aggatgctgg cctcggctgg cgagctacag   3660
aagggaatg agctggccct cccgtcgaag tatgtgaatt tcctgtacct cgcgtcgcac    3720
tacgaagc tcaagggcag cccggaggat aatgagcaga agcagctctt cgtggagcag    3780
cataagcact acctggacga gatcattgag cagatcagcg agttctcgaa gcgggttatt   3840
ctggctgatg ctaacctgga caaggttctg agcgcctaca ataagcatcg cgacaagccg   3900
attcgcgagc aggcggagaa tattatccac ctgttcaccc tcactaacct cggggctccc   3960
gcggccttca agtacttcga taccacaata gataggaagc ggtacacctc gacgaaggag   4020
gtcctcgacg ccacactcat ccatcagtcg attacaggcc tgtacgagac acggattgac   4080
ctctcgcagc tg                                                       4092

SEQ ID NO: 61          moltype = DNA  length = 4101
FEATURE                Location/Qualifiers
source                 1..4101
                       mol_type = other DNA
                       organism = synthetic construct
SEQUENCE: 61
gacaagaagt attccatagg cctggctatc ggcaccaaca gcgtgggctg ggccgtcatc    60
accgacgagt acaaagtgcc gagtaaaaag ttcaaagtgc tcggcaacac cgaccgccac   120
tccataaaga aaaacctgat cggggcgctc ctgttcgaca cgggcgagac ggcggaggcc   180
accgcttga aacgcacggc ccgacgcgc tacacgcggc caagaaccg gatctgttac     240
ctacaggaga tttctctaa cgagatggcg aaggtggacg actcgttctt tcaccgcctc   300
gaagagtcct tcctcgtgga ggaggacaag aaacacgagc gccacccgat cttcggcaac   360
atcgtggacg aggtggccta ccacgagaag tacccgacca tctaccacct ccggaagaaa   420
ctcgtggaca gcacggacaa ggccgacctg aggctcatct acctcgccct ggcgcacatg   480
attaagttcc ggggccactt cctgatcgag ggcgacctga acccggacaa cagcgacgtg   540
gacaagctgt tcatccagct agtccagacc tacaaccagc ttttcgagga aaaccccatc   600
aacgccagcg gggtggacgc gaaggcgatc ctgtccgccc ggctgagcaa gtcccggcgg   660
ctggagaacc tcatcgcgca gttgcccggc gagaagaaga acggctgtt cgggaacctg   720
atcgccctct ccctggggct cacccccgaac ttcaagtcca acttcgacct cgccgaggac   780
gccaaactac agctgagcaa ggacacctac gacgacgacc tcgacaacct gctggccag   840
atcgggacc agtacgcaga cctgttcctc gccgccaaga acctctccga cgccatcctg   900
ctgtcggaca tcctgcgggt gaacacggag atcacgaagg ccccgctctc ggcctcgatg   960
attaaacgct acgacgagca ccaccaggac ttgaccctcc tcaaggcgct ggtccgcagc   1020
cagcttcccg agaagtacaa ggaaatcttt ttcgatcaga gcaagaacgg gtacgccggg   1080
tacatcgacg gcggggcgtc ccaggaggag ttctacaagt tcatcaagcc catcctggag   1140
aaaatgacg ggaccgagga gctgctcgtg aagctcaacc gcgaagattt gctccgcaag   1200
cagcgcacgt tcgacaacgg gtcgatcccg caccagatcc acctgggcga gctgcacgcg   1260
atcctcaggc gtcaggaaga cttctacccc ttcctcaagg acaaccgcga gaagatagag   1320
aagattctga ccttcagaat tccttattac gtgggcccgc tggctcgggg caactcgcgc   1380
ttcgcctgga tgacgcgcaa gtccgaggag accatcaccc cgtggaactt cgaggaggtg   1440
gtggataagg gtgcctcggc ccagtccttc atcgagcgga tgaccaactt cgacaagaac   1500
ctgccgaacg agaaggtgct ccccaagcac agcctgctct acgaatattt cacggtgtac   1560
aacgagctga cgaaggtcaa gtacgtgacc gagggaatga ggaaacctgc attcctctcc   1620
ggggagcaga agaaagccat agtcgacctc ctgttcaaga ccaaccggaa ggtcaccgtc   1680
aagcagctca aggaggacta cttcaagaag atcgagtgct tcgattcagt ggagatcagc   1740
ggcgtcgagg accggttcaa cgccagcctg ggcacctacc acgacctgct caagatcatc   1800
aaggacaagg acttcctcga caacgaggag aacgaggaca cctggagga catcgtgctg   1860
accctgacgc tcttcgagga ccgcgagatg atcgaggagc gcctcaagac ctacgcccac   1920
ctgttcgacg acaaggtgat gaagcagctc aagcggcgga gatatactgg gtggggccgc   1980
ctctcccgga agctcattaa cggtatcagg gataagcagt ccgggaagac gatcctcgac   2040
ttcctcaagt cggacgggtt cgccaaccgc aacttcatgc agctcatcca cgacgactcc   2100
ctgacgttca aggaggacat ccagaaggcc caagtgtctg gtcaaggtga ctcgctccac   2160
gagcacatcg ccaacctcgc gggcagcccg gccatcaaga agggaatact ccagaccgtc   2220
aaggtggtgg acgagctggt gaaggtcatg ggccgccaca gccggagaa catcgtcatc   2280
gagatggcgc gggagaacca gaccacgcag aaggggcaga aaaatagccg tgagcgcatg   2340
aagcgcatcg aggaggggat taaggagttg ggcagccaga tcctcaagga gcaccctgtg   2400
gagaacacgc agttgcaaaa cgagaagctc tacctgtact acctccagaa cgggagggat   2460
atgtacgtgg accaagaact ggacatcaac cgcctgtccg actacgacgt ggaccacatc   2520
gtgccgcaga gcttcctcaa ggacgacagc atcgacaaca aggtgctcac ccggtccgac   2580
aagaatcggg gcaagtccga caacgtgccc agcgaggagg tcgtcaaaaa gatgaaaaac   2640
tactggcgac aactactgaa cgccaagctc atcccccagc gcaagttcga caacctcaca   2700
aaagccgagc gcggcgggtt gagcgagctg acaaggcgg gttcatcaa gcgccagctc   2760
gtcgagacgc gccagatcac gaagcacgtc gcgcagatac tcgacagccg gatgaaccac   2820
aagtacgacg agaacgacaa gctcatccgg gaggtgaagg tcatcaccct caagtcgaag   2880
ctcgtgagcg acttccgcaa ggacttccag ttctacaagg tccgggagat caacaactac   2940
caccacgccc acgatgctta tcttaacgcc gtggtgggga cggccctcat taagaaatac   3000
ccgaagctgg agtcggagtt cgtgtacggc gactacaagg tgtacgacgt caggaagatg   3060
atcgccaagt ccgaacagga gatcgggaag gccaagaagc ttctacagcaac            3120
atcatgaact tcttcaagac cgagatcacc ctcgccaacg gcgagatccg caagcgcccg   3180
ctcatcgaga cgaacgggga gaccggcgag atcgtctggg acaaggggcg cgacttcgcc   3240
actgtgcgga aggtgctgtc gatgcccccag gtcaacatcg tcaagaagac ggaggtccag   3300
acgggcgggt tcagcaagga gagcatcctg ccgaagcgca cagcgacaa gctgatcgcc   3360
cgcaaaaagg actgggatcc aaaaaagtac ggcggcttcg acagccccac cgtcgcctac   3420
```

```
agcgtcctcg tcgtcgctaa agtcgagaag ggcaagtcca aaaagctcaa gagcgtcaag    3480
gagctgctcg ggatcaccat catggagcgg tccagcttcg agaagaaccc aattgatttc    3540
ctggaggcga agggctacaa ggaggtcaag aaagacctca tcataaagct gccgaagtac    3600
tcactcttcg agctggagaa cgggcgcaag cggatgctgg cgtcggccgg agagctccaa    3660
aaggcaacg agctggcgct gccgagcaag tacgtgaact tcctctacct ggcgtcccac    3720
tacgagaagc tcaagggcag tccagaggat aacgagcaga agcagctatt cgtggagcag    3780
cacaagcact acctggacga gatcatcgag cagatcagcg agttctccaa gcgcgtcatc    3840
ctggcggacg ccaacctgga caaggtgctg tccgcgtaca caagcaccg cgacaagccg    3900
atccgcgagc aagccgagaa catcatccac ctgttcaccc tcacgaacct cggggcaccc    3960
gccgccttca aatatttcga cacgaccatc gaccgcaagc gctacaccag cacgaaggag    4020
gtgctcgacg ccaccctgat ccaccagagc atcaccgggc tgtacgagac ccgcatcgac    4080
ctctcgcagc tcggcgggga c                                              4101

SEQ ID NO: 62          moltype = DNA  length = 4101
FEATURE                Location/Qualifiers
source                 1..4101
                       mol_type = other DNA
                       organism = synthetic construct
SEQUENCE: 62
gacaagaagt acagtattgg attggccatc gggacgaaca gcgtgggctg ggccgtcatc     60
accgacgagt acaaggtgcc atccaagaag tttaaggttc tggggaatac cgaccgccac    120
tcgatcaaga aaaatctcat cggggcgctg cttttcgaca gcgaggagac ggcggaagcg    180
acgcggctca gcggacggc tcgtcgccgt tacaccggc gtaagaaccg catctgttca    240
ctccaggaga tattcagcaa cgagatggcg aaggtggacg actccttttt ccaccgtctt    300
gaggagtcct tcctggtcga ggaggacaag aagcacgagc gccacccgat cttcgggaac    360
atcgtggacg aggtggccta ccacgagaag taccccacga tctaccacct ccgcaaaaaa    420
ctcgtggact caactgacaa ggccgatttg aggcttatct acctcgccct cgcccacatg    480
attaagttcc gtgggcactt cctaatcgag ggtgacctca accccgacaa ctctgacgtg    540
gacaagctgt tcatccagct tgtgcagacc tacaatcagc tctttgagga gaatccgatc    600
aacgcatctg gtgtggacgc aaaggccatc ctcagcgcgc ggctgagcaa gtctaggcgg    660
ttggagaacc tgatcgccca actgcccggc gagaagaaaa atggcctctt cggcaacctg    720
atcgccctgt cgctggggct cacgccgaac ttcaagagta actttgacct ggcggaggac    780
gctaagctcc agctatctaa ggacacatac gacgacgacc tggacaacct gctggccag    840
atcggcgaca agtacgccga cctcttccta gccgccaaga acctgtccga cgccatcctc    900
ctcagcgaca tcctgcgcgt gaacacggag atcacgaagg ctccgctcag cgcctccatg    960
attaagcggt acgacgagca ccaccaagac ctaactttac tcaaagcccct cgtgcggcag   1020
cagcttcccg agaagtacaa agagatattt tttgatcagt ccaagaacgg ttatgcgggc   1080
tacatcgacg gcggcgcgag ccaggaggag ttctacaagt tcatcaagcc catcctggag   1140
aagatggacg gcacggagga gctgctcgtg aagctcaacc gtgaagacct cctgcgaaag   1200
cagcgaacct tcgacaacgg ttcgatcccc caccagatcc acctcgggga gctgcacgcc   1260
atcctgaggc gacaggagga cttctaccct ttcctaaagg acaaccgcga gaagattgaa   1320
aaaatcctga cgtttcgcat accctactac gtcggcccgc tggcgcgcgg caactcccgg   1380
ttcgcctgga tgacccgtaa gagcgaggag acgatccgca cgtggaactt cgaggagtc   1440
gtggacaagg gcgcgagcgc gcagagcttc atcgagcgca tgaccaactt cgacaagaac   1500
ctcccgaacg agaaggtgct cccaaagcac tccctcctgt acgagtattt caccgtgtac   1560
aacgagttga caaaggtgaa gtacgtgacg gagggaatgc ggaagcctgc gttcctctcg   1620
ggcgagcaga aaaggcaat cgtggacctg ctcttcaaga ccaaccggaa ggtgacggtg   1680
aagcagctca aggaggacta cttcaaaaaa atcgagtgct tcgactccgt gggagataagc   1740
ggcgtggagg accgattcaa cgcctccctc ggcacctacc acgacctcct taagatcatc   1800
aaggacaagg acttcctgga caacgaggag aacgaggaca tcctggagga catcgtgctc   1860
accctgaccc tcttcgagga ccgggagatg atcgaggagc gcctcaagac gtacgcccac   1920
ttgttcgacg acaaggtgat gaagcagctc aagcggcggc gatacaccgg tgggccgcc   1980
ctatcccgca aacttatcaa cggcatccgc gacaagcagt ccggcaagac gatcctggat   2040
ttcctcaagt cggacgggtt cgccaaccgg aacttcatgc agctcatcca cgacgacagc   2100
ctcacgttca aggaggacat ccagaaggcc caagtgagcg gtcaagggga cagcctccac   2160
gagcacattg cgaaccttgc tgggagccct gcgatcaaga aggggatatt gcaaaccgtg   2220
aaggtcgtgg acgagttggt gaaggtcatg gggcgacaca gcccgagaa catcgtgatc   2280
gagatggcca gggaaaatca gaccacgcag aagggccaaa aaaacagccg cgagcggatg   2340
aagcggatcg aggagggcat caaggagctg gggtcgcaga tcctcaagga gcaccccgtg   2400
gagaacacgc agctccagaa cgagaagctg tacctctatt acctacagaa cgggcgggat   2460
atgtacgtgg accaggagct agacatcaac cgcctgtccg actacgacgt ggaccatatc   2520
gtcccgcagt cgttcttgaa ggacgacagc atcgacaaca aggtgctcac aagatcggat   2580
aagaatcgag gcaagtccga caacgtgccc tcggaggagg tggtcaagaa aatgaaaaac   2640
tactggcgac agttgctgaa cgccaagctc attacgcagc ggaagttcga caacctgacg   2700
aaggctgaac gtggtgggct cagcgagcta gacaaggcgg ggttcatcaa gcggcagctc   2760
gtcgagaccc ggcagatcac caagcacgtg gcgcagatcc tggactcgcg catgaacacc   2820
aagtacgacg agaacgacaa gctcatccgt gaggtgaagg tcatcaccct taagtctaag   2880
ctggtcagtg acttccgcaa ggacttccag ttctacaagg tccgggagat caactactac   2940
caccacgcg acgacgccta cctcaacgcg gtggtgggga cggcgcttat taagaaatat   3000
cccaagctgg aaagcgagtt cgtttacggc gactacaagg tgtacgacgt ccgcaagatg   3060
atcgcaaagt cggaacagga aatcggaaag gcgacggcca aatatttctt ttactccaac   3120
atcatgaatt tttttaagac ggagatcacc ctggcgaacg ggagatccg caagcggccc   3180
ctcatcgaga ccaacgggga gacggcgag atcgtctggg acaagggccg ggacttcgcc   3240
accgtggaag gtgtttc tatgcctcaa gtcaatatcg tcaaaaagac agaggtgcag   3300
accggcgggt tcagcaagga gtctatcctg ccgaagcgca actcggacaa gctcatcgcg   3360
cgcaagaaag actgggaccc caaaaaatat ggcgggttcg actcgccgac cgtcgcctac   3420
agcgtcctcg tggtggctaa ggtcgagaag ggcaagagca aaaagctaaa gtcggtgaag   3480
gagctgctgg gcatcaccat catggagcgc tcgtctttcg agaagaatcc aatcgacttc   3540
ctagaggcga aggggtacaa ggaggtcaaa aaggatctta tcatcaaact gccgaagtac   3600
```

```
agtctgttcg agctggagaa cgggcggaag cggatgctgg ctagtgcggg cgagttgcag  3660
aagggcaacg agttggcact gccctccaag tacgtgaact tcctgtacct ggcctcccac  3720
tacgagaagc tcaaggggag ccccgaggac aacgagcaga agcagctatt cgtcgagcag  3780
cacaagcact acctggacga gatcatcgag cagatcagtg agttctccaa gcgggtcatc  3840
ctcgcggacg ccaacctgga caaggtgctg agcgcgtaca acaagcacag ggacaagcca  3900
atcagggaac aggccgagaa catcatccca ctgttcaccc tgaccaacct gggtgcaccg  3960
gctgccttca agtactttga cacgaccatc gaccggaagc gctacacctc cacgaaggag  4020
gtgctggacg ccacgctgat ccaccagagc atcaccgggc tctacgagac acggatcgac  4080
ctgagccagc ttggcgggga c                                            4101
```

```
SEQ ID NO: 63          moltype = DNA   length = 4092
FEATURE                Location/Qualifiers
source                 1..4092
                       mol_type = other DNA
                       organism = synthetic construct
SEQUENCE: 63
gacaaaaagt attccattgg actcgctatc ggcacgaaca gcgtcgggtg ggcggtcatc  60
actgacgagt acaaggtgcc gagcaagaag tttaaggtgc tgggaaacac cgacaggcac  120
tcgatcaaga aaatcttat cggggcccta ctcttcgact ccggagaaac cgccgaggcc  180
acccggttga agcgcacggc ccgccgtcgc tacaccaggc gcaagaaccg gatctgctac  240
ctccaggaga tattcagcaa tgagatggcg aaggtggacg actcgttttt tcacaggcta  300
gaggagtctt tcctcgtgga ggaggacaag aaacacgagc gccaccccat cttcggcaac  360
atcgtggatg aggtggcata tcacgagaag tacccaacca tctaccacct ccgcaaaaag  420
ctcgtggact ctaccgacaa ggccgacctc cgtctgatct acctcgcgct ggcccacatg  480
attaagttcc gaggacactt tctgatcgag ggcgacctga cccagacaa cagcgacgtg  540
gacaagctgt tcatccaact tgtccagacc tacaatgacc tcttcgagga gaaccctatc  600
aacgcctcgg gcgtggacgc gaaggccatc ctgtccgccc gcctgagcaa gtcgcggcgg  660
ctggagaacc tgatcgccca gctccccggc gaaaaaaaga acggcctctt cggcaacctc  720
atcgcgttgt cgctggggct caccccgaac ttcaagtcca acttcgacct ggccgaggac  780
gctaaactcc agctctcgaa ggatacctac gacgacgacc tcgacaacct gctggcccag  840
atcggcgacc agtacgcgga ccttttcctg gcggccaaga acctgagcga cgcgatcctc  900
cttagcgaca tactccgtgt gaacaccgag atcacgaagg cccgctctc cgcgtccatg  960
attaagcgct acgacgagca ccaccaagac cttaccctgc ttaaggcgct ggtcaggcag  1020
cagttaccgg agaagtacaa ggagatcttt tttgatcaat ctaagaacgg ttacgccggg  1080
tacatcgacg gcggcgcgtc ccaggaggag ttctacaagt tcatcaagcc gatcttggag  1140
aaaatggacg gaccgaggaa gctgctcgtg aagtcaacc gcgaagacct cctccgcaag  1200
cagcgcacct tcgacaacgg gagcatcccg caccagatcc acctgggaga gctgcacgcg  1260
atcctgcgga gacaagagga cttctacccc ttcctcaagg acaaccggga gaagattgaa  1320
aaaatactta cttttcgtat cccgtactac gtcgggcccc ttgcgaggg caactccgga  1380
ttcgcgtgga tgacccgcaa gtccgaggag accatcaccc cgtggaactt cgaggaggtg  1440
gtggacaagg gcgcgtcggc ccagtcgttc atcgagcgca tgaccaactt cgacaagaac  1500
cttccgaacg agaaggtgct cccgaagcac agcctgctct acgaatattt tactgtgtac  1560
aacgagctca cgaaggtcaa gtacgttacg gaggggatgg ggaagcccgc cttcctctcc  1620
ggcgagcaga agaaagccat tgtggatctc ctgttcaaga ccaaccgcaa ggtgacggtg  1680
aaacagctca agaggactta cttcaagaag atcgagtgct cgactccgt agagatcagc  1740
ggggtcgagg accgcttcaa cgcctcgctg ggcacgtacc acgacctgct aaagattatc  1800
aaggacaaag acttcctaga caatgaggag aacgaggaca tttctgagga catcgtgctg  1860
actctgacgc tgttcgaaga ccgcgagatg atcgaggagc ggcttaagac gtacgcccac  1920
ctgttcgacg acaaggtgat gaagcagttg aaacggcggc gctacaccgg gtggggccgc  1980
ctctccccgca agctcatcaa cggcatccgc gacaagcagt cggggaagac gatcctggac  2040
ttcctcaaga gcgacggctt cgccaaccga aacttcatgc agctaatcca cgacgacacg  2100
ctgacgttca aggaggacat ccagaaggcc caagtgagcg gccagggaga ctcgctacac  2160
gagcatatcg ccaacctggc tggcagcccg gcgattaaga aggaatcct ccaaaccgtc  2220
aaagtggtgg acgagctggt gaaggtgatg ggccgccaca gcccgagaa cattgtgatc  2280
gagatggcg gggagaacca gacgacgcag aagggccaaa aaaatagcag ggaaaggatg  2340
aagcgaatag aggaggggat caaggagctg gggagccaga ttctcaaaga gcacccggtc  2400
gagaacacac agctccagaa cgagaagctg tacctctact acctccaaaa cggccgcgat  2460
atgtacgtgg accaggaact agacatcaac cggctgagcg actatgacgt ggaccacatc  2520
gtgccgcagt ccttcctcaa ggacgactcg attgacaaca agtgctcac tagatccgac  2580
aagaacagag gcaagagcga taacgtcccg tcggaggagg tcgtcaagaa aatgaaaaac  2640
tactggcggc agctcctaaa cgccaagctc atcacgcagc gtaagttcga caacctgacg  2700
aaggcggagc ggggcgggct gagcgagctg gacaaagcgg ggttcatcaa gcggcagctc  2760
gttgagacgc ggcagatcac aaagcacgtc gcgcaaatcc tcgactccg catgaacacc  2820
aagtacgacg agaacgacaa gctcatccgg gaggtgaagg tcattaccct taaatcgaag  2880
ctcgtcagcg actttcgtaa ggacttccag ttctacaagg tcagagagat caacaactac  2940
caccacgccc acgacgccta tctgaacgcc gtggtgggca ccgcgcttat taagaagtac  3000
cccaagctga gtccgagtt cgtgtacggc gactacaagg tttatgacgt caggaagatg  3060
atcgccaagt cggaacagga gatcggaaaa gctaccgcca aatatttctt ctatagcaac  3120
atcatgaact tcttcaaaac cgagatcacc ctcgccaacg gcgagatccg gaagcgcccc  3180
ctcatcgaga ccaacgggga gaccgggag atcgtctggg acaaggggcg ggacttcgct  3240
actgtccgaa aggtgctctc catgccacaa gtgaatatcg tcaagaaaac agaggtgcag  3300
accggagggt tcagtaagga gtccatcctg cccaagcgga actccgacaa gctaattgct  3360
cgcaaaaagg attgggatcc taaaaaatat ggcggcttcg actcgcccac ggtcgcctac  3420
tctgtgctgg tcgtggcaa ggtggagaa ggcaagctca agagcgtcaag  3480
gagctgctgg ggatcacgat catggagcgt agttcgtttg agaagaatcc catcgacttc  3540
ctggaggcta agggctacaa ggaggtcaaa aaggacctca tcattaagct gccgaagtac  3600
agcctcttcg agctggagaa cgggcggaag cgtatgctcg cctccgctgg ggagttacaa  3660
aagggggaacg agctggcgct gccgtctaag tacgtcaact tcctgtacct ggcctcccac  3720
tacgagaagc tcaaggggtc gccggaggac aacgagcaga agcagctctt cgtagagcag  3780
```

```
cacaagcact acctggacga gatcatcgag cagatttcag agttctcaaa gcgggtcatc  3840
ctcgccgacg ccaacctgga caaggtgctc tcggcctaca acaagcaccg ggacaagccg  3900
atccgcgaac aggccgaaaa catcatccac ctgttcacgc tcaccaacct cggtgccccg  3960
gcggccttca agtactttga cacgaccatc gaccggaagc gctatacctc gacgaaggag  4020
gtgctggacg ccaccctgat ccaccagtcc atcaccgggc tttacgagac ccggatcgac  4080
ctctcgcagc ta                                                      4092

SEQ ID NO: 64            moltype = DNA   length = 4101
FEATURE                  Location/Qualifiers
source                   1..4101
                         mol_type = other DNA
                         organism = synthetic construct
SEQUENCE: 64
gacaagaagt atagtattgg actcgccatc ggaaccaact ctgtggggtg ggctgttatt   60
acagatgaat ataaggtgcc atccaaaaag tttaaagttc tgggcaatac tgatagacac  120
tcaatcaaga agaatctgat aggtgcactt ctgtttgata gtggagagac tgccgaggca  180
accagactta aaaggactgc aagaagaaga taccagaga gaaagaatag gatttgctat  240
ttgcaggaaa tcttcagcaa cgaaatggcc aaggttgatg actcatttt ccataggttg  300
gaggagagtt ttcttgtgga ggaagataag aagcacgaaa gacacccaat tttcggaat  360
atagtggacg aggtggctta tcatgagaag tatcccacta tctaccacct gagaaagaaa  420
cttgtggact caaccgataa ggctgatctt aggcttatat acttggccct tgcacatatg  480
atcaaattca ggggccattt tcttatcgaa ggcgatctta atcccgataa ctcagatgtg  540
gacaagctgt ttatacaact tgtgcaaacc tacaatcaac tcttcgagga gaatcccatt  600
aacgcctccg gcgtggatgc aaaagccata ctgtcagcca gactgagcaa aagtaggaga  660
ctggagaatc ttatagccca actgcccggt gaaaagaaga atgggctctt cggaaatctg  720
atcgctcttt cattgggtt gacacccaac tttaagagta acttgactt ggcagaagat  780
gcaaagttgc agctcagtaa agacacatat gacgatgacc ttgacaatct cttggcacaa  840
ataggggatc aatacgctga ccttttcctc gctgccaaga acctcagcga cgctatactg  900
ttgtccgaca ttcttaggt aataccgaa attacaaagg ccctcttag tgcaagtatg  960
atcaaaaggt atgatgagca tcaccaagac cttacactgc tgaaggctct ggttagacag  1020
caactccctg aaaagtataa ggaaatattc ttcgaccaaa gtaagaacgg gtacgccggt  1080
tatattgatg ggggcgcaag tcaagaagaa ttttacaaat tcatcaagcc aattcttgaa  1140
aagatggacg gactgagga attgctggtg aaactgaata gagggacct tcttagaaaa  1200
cagaggacat tgacaatgg gtccatccca caccagattc atctggggga actccacga  1260
atattgagga gacaagaaga cttttaccca ttccttaagg ataatagaga gaaaatcgaa  1320
aaaatcctga ctttcaggat tccttactat gttgggccac tggccagggg gaactcaaga  1380
ttcgcttgga tgacaaggaa gtcagaagaa accataaccc cttggaattt tgaagaggtg  1440
gttgataagg gggcatcagc ccagtctttc atagagagga tgaccaactt tgataaaaat  1500
cttccaaatg agaaggtttt gccaaaacat agtcttttgt acgagtactt tactgtttca  1560
aacgaattga ccaaggtgaa gtatgtgacc gagggaatga ggaagccagc attttttgtc  1620
ggggagcaaa agaaagcaat cgttgatctt ctcttcaaga ccaacagaaa agtgaccgtg  1680
aaacaactga aggaagacta cttcaaaaag atagaatgtt tcgattcagt ggaaattagc  1740
ggtgttgaag acaggttcaa tgcttcattg ggtacttacc acgacctgtt gaagataatc  1800
aaagacaagg actttctcga taatgaggag aacgaagaca tcttggaaga cattgtgctt  1860
acactcactt tgtttgagga cagggaaatg attgaggaaa gactcaaaac ttacgctcat  1920
ttgtttgatg ataaggttat gaaacaacta aaaagaagaa ggtacaccgg ctggggaaga  1980
ttgagtagaa aactgatcaa cggtattaga gataaacaat ccggaaagac tatcctcgat  2040
ttccttaaga gtgatggctt tgcaaatagg aattttatgc agctgattca tgacgactca  2100
cttaccttca agaagacat ccaaaaagct caggtgtctg ggcaaggcga cagtctgcat  2160
gaacatatag ctaacttggc tgggagtccc gccatcaaga ggggatact tcaaacagtg  2220
aaagttgtgg acgaattggt gaaggtaatg ggaaggcaca agcctgaaaa tatagtgata  2280
gaaatggcaa gggaaatca aacaacccag aagggacaga gaacagtag ggaaaggatg  2340
aaaaggatag aagaggggat caaagagctt ggtagcagaa tcctcaagga catccagtg  2400
gagaataccc aacttcaaaa cgagaaactc tatttgtact acttgcagaa cggaagagat  2460
atgtatgtgg accaagagct tgatattaac aggctgagcg atattacgct tgaccacata  2520
gtgcccaat cattcctcaa ggatgactct attgataata aggtgctgac aaggagtgac  2580
aagaatagag ggaaatccga caacgttcca tccgaggaag ttgtgaagaa gatgaagaac  2640
tactggaggc agttgctgaa cgctaagctc attcccagag gaattcga taacctgacc  2700
aaagcagaga gaggcgggct gagcgaactc gataaagcag tttcatcaa gagacaactc  2760
gtggagacta ggcaaattac taagcacgtg gctcaaatac tcgacagcag gatgaacaca  2820
aagtacgacg agaacgacaa gctcattaga gaggttaagg ttattactct gaaaagtaaa  2880
ttggttagcg atttcagaaa ggatttccaa ttctataagg ttagagagat caacaattat  2940
catcatgcac atgatgccta tctgaatgct gtggttggta cagcccttat caagaagtac  3000
cctaagctag agagcgagtt tgtgtacgga gattataagg tgtatgatgt gaggaaaatg  3060
atcgctaaaa gtgagcaaga gattggaaag gctaccgcca aatacttctt ttattccaat  3120
attatgaatt tcttcaagac agaaatcacc ctggctaacg gcgagataag gaagaggccg  3180
cttatcgaaa ctaatgggga gacaggcgaa atagtgtggg acaaagggag ggatttcgca  3240
actgtgagga aggttttgag catgcctcag gtgaatatcg ttaagaaaac cgaagttcaa  3300
actggagggt tctctaagga aagcattctc cccaagagga actccgacaa gctgattgct  3360
agaaagaaag actgggaccc caagaagtat ggcggattcg actcacccac tgtggcatat  3420
agcgttctcg tggtggcaaa ggttgaaaag ggtaaatcca aaaaactcaa atccgtgaag  3480
gaactccttg gcataactat tatggaaagg agtagctttg aaaagaatcc catcgacttt  3540
ctcgaagcta agggctataa ggaagttaag aaggaccttta taatcaaact tccaaaatac  3600
tccctttttg agttggaaaa cggcagaaag agaatgttgg ccagtgccgg ggagcttcaa  3660
aagggcaacg aactggctct gcctagcaaa tatgtgaact ttttgtatct ggcatcacac  3720
tacgagaaac ttaaggctc tcctgaggac aacgagcaaa aacagctctt tgttgaacag  3780
cataagcact acctcgacga gattattgag cagatcagcg agttctcaaa gagagttatt  3840
ctggctgacg ctaatcttga caaggttttg tccgcttaca acaaacacag ggataagcca  3900
atcagggagc aggcagaaaa cataatccat ctctttaccc tgacaaacct cggtgccccc  3960
```

```
gctgctttca agtattttga tactaccatt gacaggaaga gatatacttc cactaaggaa    4020
gtgctcgacg caaccctcat acaccaaagt atcacaggcc tctatgaaac taggatagat    4080
ttgtctcaac ttgggggcga t                                              4101

SEQ ID NO: 65           moltype = DNA   length = 4101
FEATURE                 Location/Qualifiers
source                  1..4101
                        mol_type = other DNA
                        organism = synthetic construct
SEQUENCE: 65
gacaaaaagt attccatcgg gcttgctatc ggaaccaact ctgtggggtg ggcagttatt      60
accgacgaat acaaggtgcc cagcaagaag tttaaggttc tggggaacac agatagacat    120
agcataaaga aaaacctgat aggcgcactg ttgttcgact ccggggaaac agccgaagct    180
accaggctga agagaactgc aagaagaagg tacaccagaa gaaaaaacag aatatgttat    240
ctccaagaga ttttctctaa cgagatggcc aaggtggacg actcattctt tcacagactg    300
gaagaatctt tccttgtgga agaagataag aaacacgaga ggcacccctat ttttggcaat    360
atcgtggatg aggtggctta ccacgaaaaa taccctacaa tataccacct caggaaaaaa    420
ttggtttgata gtacagacaa ggccgacctc aggctcatct atttggcctc ggcccatatg    480
attaaattca gggggcactt tctcatcgag ggagatttga accccgacaa cagtgatgtt    540
gataagctct ttattcagct cgtgcagact acaatcagt tgtttgagga aaaccccatt      600
aatgcttccg ggtggacgc caaggcaatc ctttctgcaa gactctcaaa gtcaaggaga      660
ctcgaaaatc tgatagcaca gcttccagga gagaagaaga acggctctt tggaaacctg      720
atcgctctgt cactcggact cacacccaat ttcaaaagca attttgattt ggcagaggac    780
gctaagctgc aactcagtaa ggatacctac gacgatgact ggataatcct gctcgcacaa    840
attggggacc agtatgcaga cctgtttctc gcagctaaga acttgagtga cgccatattg    900
ctcagtgaca tcctcaggat taataccgag attacaagga ctccactctc tgcaagcatg    960
atcaagaggt atgacgagca ccatcaagac ctgacactcc ttaaggcgtt ggttaggcag    1020
caacttcctg aaaagtataa ggaaatcttc ttcgatcaaa gcaaaaacgg ctacgccggc    1080
tatatagacg ggggagcatc ccaagaagaa tttttataagt tcataaaacc tatattggag    1140
aagatggacg ggacagagga attgctcgtg aaactgaaca gggaggatct cctcaggaag    1200
caaaggacct tcgacaatgg ctccatccca catcagattc acctcggcga actgcacgca    1260
atactgagaa gacaagagga ctttttatcct ttcctgaagg acaacaggga gaaaatcgag    1320
aaaatcttga cattcagaat cccatactac gttgggcctc tggccagagg taacagtagg    1380
ttcgcctgga tgactaggaa atcagaggag actattacac cctggaactt tgaagaagtt    1440
gttgataagg gagcttcagc acaatcattc atcgaaagaa tgacaaactt tgacaaaaat    1500
ctgcctaatg agaaagtgct cccaaaacat tccctgctgt atgagtattt taccgtttat    1560
aacgagctta ccaaggtgaa atacgttact gaaggtatga gaaagccagc ttttctttca    1620
ggggagcaaa agaaggctat cgtggatctt ctctttaaga ccaacagaaa ggttaccgtg    1680
aagcagctta aggaagacta ctttaaaaag atcgagtgtt ttgactcagt ggaaataagc    1740
ggtgttgaag atagattcaa cgcatccttg gaacttatcc atgatcttct taagataatc    1800
aaggataaag actttctcga caacgaggaa aacgaagata tactgaggga catagttctg    1860
acacttactt tgttcgagga tagggagatg atcgaggaaa gactgaaaac atatgctcac    1920
cttttcgacg acaaagttat gaaacaactc aagagaagga gatatacagg gtgggggaga    1980
ttgagcagga aactgattaa tggtatcaga gacaaacagt caggaaaaac aatactcgac    2040
ttttttgaaat cagacgggtt cgcaaatagg aatttcatgc agcttataca cgacgattca    2100
cttacttttta agaggacat tcaaaaggct caagttagtg acaaggtgac ctccctccac    2160
gaacacatcg caaatctcgc tggcagccct gcaattaaga agggtatatc ccagacagtt    2220
aaggttgttg acgagctggt taagtgatgg ggaagacaca aacccgagaa catagtgata    2280
gagatggcca gggaaaacca aaccactcaa aaagggcaga aaaattccag agagaggatg    2340
aaaaggattg aagaaggtat caaggagctg ggtagccaaa ttctgaaaga acatcctgtg    2400
gaaaacactc aactccagaa tgagaaactc tatctgtact atctgcaaaa tgggagagat    2460
atgtatgtgg accaggaact ggacataaac aggctctcag attacgatgt ggatcatatc    2520
gtgccacagt cctttcttaa ggatgatagc atcgacaata aggtgcttac caggtccgac    2580
aagaacaggg gaaagtcaga taacgtgcct tctgaagaag ttgttaaaaa gatgaagaac    2640
tactggagac agctgcttaa cgctaagctc ataacacaga gaagtttga caacttgacc    2700
aaggccgaga gaggcggact ctcagaattg ataaggcag ggttcataaa aaggcagctg    2760
gtggaaacaa ggcagataac taaacatgtg ctcagatcc tcgatagtag gatgaataca    2820
aaatacgatg agaacgacaa gctcataagg gaggttaaag tgataactct gaaatccaaa    2880
ctggttagcg attttaggaa ggatttccag ttttacaaag ttagggagat caacaattat    2940
catcacgccc acgatgccta cttgaacgca gttgtgggta ctgcacttat caaaagtac    3000
cctaagctgg aatccgagtt tgtttatgga gactataagg tgtacgacgt tagaaaaatg    3060
attgcaaagt cagagcagga gatagggaaa gccactgcaa aatatttctt ttatagcaat    3120
atcatgaatt tctttaagac agaaatcaca ctggccaatg ggaaataag gaagaggccc    3180
ctgatcgaaa ctaatggcga gacagggggag attgtgtgga ataaaggtag ggactttgca    3240
acagtgagga aagtgctgag catgccccaa gttaatatcg ttaaaaagac cgaggttcaa    3300
acaggggct ttagtaagga aagcatttttc cccaagagga ataagtgacaa attgattgct    3360
aggaaaaaag attgggaccc caaaaagtat ggcggatttg ataggcccac tgttgcttac    3420
tccgtgctcg tggttgcaaa ggtggagaag ggaaaagagca agaaactgca gtcagttaag    3480
gaactcctg gtatcactat catggaaaga agctcctttg aggaagacct tattgacttc    3540
ctggaggcta aagggtacaa agaggttaag aaagaccttat cattaaaatt gccaaatat    3600
agtcttttcg agcttgaaaa cggaagaaag gatgcttg catccgctgg cgaattgcaa    3660
aagggcaatg agcttgctct cccttccaag tatgtgaact tcctttatct tgcctcacac    3720
tatgaaaaac tcaaaggttc acccgaagac aacgaacaaa agcaactatt tgtggaacaa    3780
cacaagcatc cctggcaga aatcattgca gaaatttctg agttttcaaa aagggtaatc    3840
ttggctgacg caaatctcga caaagttttg tcagcttaca acaaacatag agataagcca    3900
attagagagc aagctgagaa tatcatccat ctgtttaccc tgactaacct tggagcgcct    3960
gctgcttta aatatttcga caccacaatc gacaggaaga ggtacactag cactaaggaa    4020
gttctcgacg ccacccctcat ccaccagagt attacaggcc tgtacgagac aagaattgat    4080
cttttctcaac ttggtggtga c                                             4101
```

SEQ ID NO: 66          moltype = DNA  length = 4101
FEATURE                Location/Qualifiers
source                 1..4101
                       mol_type = other DNA
                       organism = synthetic construct
SEQUENCE: 66
gataagaagt actcaatcgg tctggcaatc ggaaccaact ctgtgggttg ggcagtgatt    60
acagatgagt ataaggtgcc aagcaaaaaa ttcaaggtgc tgggtaatac cgacagacac   120
agcattaaga agaatttgat tggagcactc ctctttgact cagggggaaac agcagaggca   180
acaaggctga agaggacagc aaggcggagg tacacaaggc ggaaaaacag gatatgctac   240
ctccaggaaa tctttagcaa cgagatggct aaagtggatg atagcttttt ccatagactc   300
gaagaatcct ttcttgttga agaggacaaa aagcatggaa ggcatcccat cttcggcaat   360
atagtttgatg aggttgcata ccatgagaag taccccacaa tctaccacct cagaaagaaa   420
cttgtggact ccacagataa agcagacctg aggctcatat acctcgcact cgcacacatg   480
atcaagttca gagggcactt tctcatcgaa ggtgacctga atccagataa ttcagatgtg   540
gataaactgt ttatacagct ggtgcaaaca tacaaccaac ttttcgagga aaacccaatc   600
aatgcctccg gtgttgatgc aaaggccatc ctgtcagcaa gactcagcaa aagcaggcgg   660
ctcgaaaacc tcatcgccca gcttccggt gaaaagaaga acgggctctt tggtaatctc    720
atcgcattga gccttggtct tactccaaac ttcaagagca attttgatct ggcagaggat   780
gctaaactgc aactctcaaa ggacacatat gacgatgacc ttgacaatct gttggcccag   840
atcgggggacc aatatgcaga cctcttcctg gccgcaaaga atctgtcaga tgcaatcctc   900
ttgtccgaca tactgagagt taacactgag atcacaaagg cacctctgtc cgcctccatg   960
attaagagat acgatgagca tcaccaggat ctgactttgc tcaaagccct cgttagacag  1020
cagttgccag aaaagtacaa agaaatattc tttgatcaat caaaaacgg atatgcaggg  1080
tacatcgacg gtggggcaag ccaggaagag ttctacaaat tcatcaaacc tatcctggaa  1140
aagatggatg gacagaagag gctgctggtt aagctgaata gggaagacct cctcagaaag  1200
cagaggacat ttgataacgg gagcatccct catcaaatcc acctcggtga actccatgct  1260
atcctgagaa ggcaggaaga cttttatcca tttttgaagg acaatagggga gaaatcgaa   1320
aaaatcctga cattcagaat cccatactac gttggtcctc tggcaagagg taacagtagg  1380
ttcgcatgga tgacaaggaa aagcgaggag acaatcacac cctggaattt tgaggaagtt  1440
gttgacaagg tgccagcgc acaatccttt atcgaaagaa tgacaaattt cgacaagaat   1500
ctgcctaacg aaaaggttct cccaaagcat tcactcctgt acgaatattt tacagtttat  1560
aacgaactga ctaaagttaa atacgttacc gagggtatga ggaagccagc attcctttcc  1620
ggggaacaga agaaagctat tgtggaccte ctgttcaaga caaatagaaa agtgacagtt  1680
aagcaactca agaggattac cttcaaaaag atcgaatgtt ttgactctgt ggagatcagc  1740
ggggtggagg atagattcaa cgccagcctg ggtacatatc atgatctcct gaaaatcatt  1800
aaagacaagg acttccttga caacgaggag aacgaggaca ttctggaaga cattgttctg  1860
accctcacac tctttgagga tagggagatg attgaggaaa gactgaagac ctacgcccac  1920
ctctttgacg ataaagtgat gaaacagctc aagagaagaa ggtatacagg ttgggggaga  1980
ctgagcagga agttgatcaa tgggattagg gacaaacagt ccgggaaaac aatcctcgat  2040
tttctgaagt cagacggttt cgcaaacaga aattttatgc agctcattca cgatgacagc  2100
ttgacattca aggaagacat ccaaaaggct caagtgaggg gccaagggga tagcctccaa  2160
gagcatattg caaatctggc aggttcacca gccatcaaaa agggcatact tcagacagtt  2220
aaggttgtgg acgaattggt taagttatg ggcaggcata agccagaaa tatcgttatc   2280
gaaatggcaa gggagaacca aacaactcaa aaagggcaga aaaatagcag agagaggatg  2340
aaaagaatcg aggaagggat caaggaactt gggtcccaaa tcctcaagga gcacccagtt  2400
gaaaatactc aactgcaaaa cgagaagctc tatctctact atctccaaaa cgggagggat  2460
atgtatgttg accaggagct ggatattaac agactgtcag attatgatgt tgatcatatc  2520
gtgccccagt cattcctgaa ggacgattcc atcgacaaca agttctcac aaggtccgat  2580
aaaaacaggg gcaagtccga taacgttcca agcgaagaag tggtgaaaaa gatgaaaaac  2640
tattggagac aacttctgaa tgcaaagttg attactcaga gaaagtttga caacctcaca  2700
aaagcagaaa gaggcgggct tagcgaactc gataaggcag ggtttatcaa aagacagctg  2760
gttgagacaa ggcagatcac aaaacatgtg gcacagatcc ttgactcaag gatgaatacc  2820
aagtgatatg agaatgataa gttgatcagg gaggttaaga ttatcacact caaatccaaa  2880
ctggtgtcag acttcaggaa agactttcaa ttttataagg tgagggagat caataactac  2940
caccatgcac atgacgccta cctgaacgca gtggtgggta cagcattgat taaaaaatac  3000
cctaagctgg agtctgagtt tgtgtacggg gactacaagg tgtacgacgt gaggaaaatg  3060
atagccaagt ccgagcagga gatcgggaaa gcaacagcta agtatttctt ttacagtaat  3120
atcatgaatt tctttaaaac tgagattact ctggcaaacg gggagatcag gaaaagaccc  3180
ctcatcgaga ctaatggtga aacaggtgag atcgtttggg acaaggggag ggatttgct   3240
actgttagaa aagttctgag tatgccacaa gtgaatattg tgaaaagac agaagttcag  3300
acaggtgggt tctccaaaga atccatcctg cccaagagaa attcagacaa gctcatcgca  3360
agaaagaagg actgggaccc taagaagtac acgaggattg acagcccac cgtggcctat  3420
tccgtgcttg ttgtgcaaa ggtggagaaa gggaagagca aaaaactgaa atccgtgaaa  3480
gaactgctgg gaattaccat catggaaaga agctcctttg agaagaaccc aatcgacttc  3540
ctggaagcaa aaggatataa ggaagtgaaa aaggacctca ttatcaagct cccaaaatac  3600
tcacttttcg agttggaaa cggtagaaag aggatgctgg caagcgcagg ggaacttcag  3660
aaaggcaatg agctggcatt gccatcaaag tatgtgaatt tcctctactt ggccagccat  3720
tacgagaaac ttaaaggtag cccagaagat aacgagcaaa aacagctctt tgtggaacag  3780
cataagcatt atctggatga gatcatagaa caaatctcag agttttccaa gagagttatc  3840
ctcgcagatg caaacctgga taaggttctc tcagcctata taagcatag agacaagcca  3900
attagagagc aagcagagaa cattatccac tgttcactc ttacaaacct gggggcacca  3960
gccgccttca aatatttcga tacaacaata gacagaaaga ggtataccag caccaaagaa  4020
gttctcgacg ccacactgat ccatcaatca atcaggcc tttacgaaac taggatcgac  4080
ttgtcacaac tgggtgggga t                                            4101

SEQ ID NO: 67          moltype = DNA  length = 3307
FEATURE                Location/Qualifiers

| source | 1..3307 |
| --- | --- |
| | mol_type = other DNA |
| | organism = synthetic construct |

SEQUENCE: 67

| | | | | | |
| --- | --- | --- | --- | --- | --- |
| gagcaaggac | acctacgacg | acgacttgga | caacctattg | gcccagatag | gtgaccagta | 60 |
| tgcagacctc | ttccttgcgg | ccaagaactt | gagtgacgct | atactgctca | gtgacatcct | 120 |
| gagggtgaac | actgagatca | ctaaggcccc | tctctctgcc | tcaatgatta | agcgttacga | 180 |
| cgagcatcac | caggatctca | ccctgcttaa | ggcccttgtt | cggcagcagc | tccctgagaa | 240 |
| gtacaaggag | atatttttg | accagtctaa | gaacggctac | gccggttaca | ttgacggtgg | 300 |
| ggcaagccag | gaggagttct | acaagttcat | caagccgatc | cttgagaaga | tggacggcac | 360 |
| cgaggagcta | cttgtcaagt | tgaaccggga | agacctgctc | cggaaacagc | gtacattcga | 420 |
| caacggcagc | atccctcacc | agatccacct | gggcgaacta | cacgccatcc | tccgacgtca | 480 |
| ggaggacttc | tatccattct | tgaaagataa | cagggaaaaa | atcgaaaaaa | tacttacgtt | 540 |
| tcgaatacct | tactacgtgg | ggcccttgc | tcggggaaac | tccagattcg | catgcatgac | 600 |
| caggaagtca | gaggagacca | tcacaccctg | gaactttgag | gaggtggttg | acaaaggtgc | 660 |
| ttctgcccag | tccttcattg | agcggatgac | taacttcgac | aagaacctgc | ccaacgagaa | 720 |
| ggtgctgcca | aagcacagcc | tgctctacga | atactttact | gtgtacaatg | agctgacgaa | 780 |
| ggtgaagtac | gtgacagagg | ggatgcggaa | gccgcttc | ctgagcggcg | agcaaaaaa | 840 |
| agcaatcgtg | gacctactgt | tcaagaccaa | ccgaaaggtg | acagtgaagc | agctcaagga | 900 |
| ggactacttc | aaaaaaatcg | agtgcttcga | ctctgttgag | ataagcggcg | tggaggaccg | 960 |
| attcaacgcc | tcattgggaa | cctatcacga | cctgctcaag | atcattaagg | acaaggactt | 1020 |
| cctggataat | gaggagatga | aggacatcct | ggaggatatt | gtgctgaccc | ttactctatt | 1080 |
| cgaggacagg | gagatgatcg | aggagcgact | caagacctac | gctcacctgt | tcgacgacaa | 1140 |
| ggttatgaag | caattgaagc | gtaggcgata | cacggggtgg | ggaagactct | cccgaaaact | 1200 |
| gataaacggc | atcagggaca | agcagtcagg | gaagacgatc | ttggacttcc | tgaaatccga | 1260 |
| cgggttcgcc | aaccgcaact | tcatgcagct | cattcacgac | gactcactaa | cgttcaaaga | 1320 |
| ggacattcag | aaggctcaag | tcagtgacaa | aggcgactcc | ctgcacgagc | acattgcaaa | 1380 |
| ccttgcgggc | tccccggcga | ttaaaaaggg | cattctccaa | acggttaagg | tggtggacga | 1440 |
| gctggtgaag | gtgatgggcc | gacacaagcc | tgagaacatc | gtgatcgaga | tggccaggga | 1500 |
| gaaccagact | acccagaagg | gtcagaagaa | ctctccagaa | cgtatgaagc | gtattgagga | 1560 |
| ggggattaag | gagttgggct | ctcaaatcct | caaggagcac | cctgtggaga | acactcagct | 1620 |
| ccaaaacgag | aagctgtacc | tgtactacct | gcaaaacggg | cgcgatatgt | acgtggatca | 1680 |
| ggagttggac | atcaacaggc | ttagcgatta | cgacgtggac | cacatcgtgc | cacagtcatt | 1740 |
| cttaaaggac | gacagcatcg | acaacaaggt | tctgacgagg | agcgacaaga | atcgagggaa | 1800 |
| aagtgacaat | gttccatccg | aggaggtggt | caagaaaatg | aagaactatt | ggcgtcagct | 1860 |
| tctgaacgcc | aagctcatca | cccagcgaaa | attcgacaac | ctgactaagg | ctgagcgagg | 1920 |
| cggactctcc | gagcttgaca | aggctggctt | catcaagcgg | cagttggtcg | aaaccccgaca | 1980 |
| gataacgaag | cacgttgccc | agatacttga | ctcccgtatg | aacaccaagt | acgacgagaa | 2040 |
| cgacaagctc | atcagggagg | tgaaggtcat | tacccttaag | tccaaactcg | tcagcgactt | 2100 |
| tcgtaaggac | ttccagttct | acaaggtgcg | cgagatcaat | aactaccacc | acgcacacga | 2160 |
| cgcctacctg | aacgcagtgg | ttggaaccgc | gttgattaaa | aagtacccca | agttggagtc | 2220 |
| ggagttcgtt | tacggggact | acaaggtgta | cgacgttcgg | aagatgatcg | ccaagtctga | 2280 |
| acaggagatc | gggaaagcaa | ccgccaagta | tttcttctat | agcaacatca | tgaacttctt | 2340 |
| taaaaccgag | atcacacttg | ccaatggcga | gatccgtaag | aggccgctga | tcgagacaaa | 2400 |
| tggggagact | ggcgagatcg | tgtgggacaa | gggccgcgac | ttcgcaaccg | ttcggaaagt | 2460 |
| cttgtccatg | cctcaagtca | acatcgtcaa | gaagactgag | gtgcaaacag | gcgggttctc | 2520 |
| gaaggagtcc | atactgccca | agaggaactc | agacaagctc | atagcacgca | aaaagactg | 2580 |
| ggatccaaag | aaatacgcg | ggttcgactc | gccgacagtc | gcatactccg | tgttagtggt | 2640 |
| ggctaaagtg | gaaaagggga | agtccaagaa | gctcaagtcc | gtcaaggagt | tgctcgggat | 2700 |
| caccattatg | gaacggtcct | cattcgagaa | gaatcccatt | gacttcctag | aggcgaaggg | 2760 |
| ctacaaagag | gtcaaaaagg | acctaattat | taagctcccc | aagtattcac | tcttcgaact | 2820 |
| tgaaaatggt | cgtaagcgga | tgttggcaag | cgctggagag | cttcagaagg | ggaacgagct | 2880 |
| tgcactgcct | tccaagtacg | tgaacttcct | gtacctcgcc | tctcattacg | agaagttgaa | 2940 |
| gggctcaccg | gaggacaacg | agcagaagca | gttgttcgtg | gagcagcaca | agcactacct | 3000 |
| cgacgagatc | attgaacaga | taagtgagtt | cagcaaacgg | gtgatccttg | ccgacgctaa | 3060 |
| cctggacaag | gtgctgagcg | cctacaacaa | gcacagagac | aagccgatcc | gagagcaagc | 3120 |
| ggagaacatc | atacacctgt | tcaccctcac | gaacctcggg | gctcccgcag | ccttcaaata | 3180 |
| ttttgacacg | accatcgacc | gtaaacgcta | cactagcacg | aaggaggtgc | tggacgctac | 3240 |
| cctatccac | cagtccatca | ccggcctgta | cgagacgaga | atcgacttgt | cgcagctcgg | 3300 |
| tggtgac | | | | | 3307 |

| SEQ ID NO: 68 | moltype = DNA length = 4101 |
| --- | --- |
| FEATURE | Location/Qualifiers |
| source | 1..4101 |
| | mol_type = other DNA |
| | organism = synthetic construct |

SEQUENCE: 68

| | | | | | |
| --- | --- | --- | --- | --- | --- |
| gacaaaaaat | actcaattgg | tctggcaatt | gggaccaaca | gtgtcggatg | ggccgtgatt | 60 |
| accgacgagt | acaaggtgcc | gtccaaaaaa | ttcaaggtgc | ttgggaacac | cgaccgccac | 120 |
| tcgatcaaga | aaaacctaat | cggtgcgttg | ctttttcgaca | gtggggagac | cgccgaggca | 180 |
| acacgcttaa | aacgcacagc | taggaggaga | tatacacggc | gcaagaaccg | aatatgctac | 240 |
| ttacaggaga | tattctccaa | tgagatgcg | aaggtggacg | actctttctt | ccatcggctt | 300 |
| gaggaatcct | tcctggtcga | ggaggacaag | agcacgagc | gacacccgat | attcgggaac | 360 |
| atcgttgatg | aggttggcgta | ccacgagaag | tacccaacga | tataccactt | acgcaaggag | 420 |
| ctcgtggact | ctacgacaa | ggccgacttg | cgccttatct | acttggcact | ggcccacatg | 480 |
| attaagttcc | gaggccactt | ccttatcgag | ggtgacctga | accccgataa | ctccgacgtg | 540 |
| gacaagctct | tcatccaact | cgtccagaca | tacaaccagc | tattcgagga | gaatcctatc | 600 |
| aacgcctctg | gggtggacgc | taagctatc | ctctcagccc | gcctgtcaaa | gtcgaggagg | 660 |
| ttggagaacc | taatcgccca | gcttccaggc | gagaagaaaa | atgggctgtt | cggaaaccctt | 720 |

```
atcgcactct cactgggcct aaccccgaac ttcaagtcca acttcgacct ggcagaggac   780
gcgaaattgc agttgtcgaa agacacctat gacgatgacc tggacaacct gttggcccag   840
ataggggacc agtacgccga cctgttccta gcggccaaga acctgtccga cgccatcttg   900
ctgtcggata tactgcgggt gaacaccgag atcactaaag cacctctctc cgccagcatg   960
attaagcgtt acgacgagca ccaccaagat ttgaccctgc taaaggcact tgtacggcag  1020
cagcttcccg agaagtacaa ggagatcttt ttcgaccaaa gcaagaacgg ctacgccggg  1080
tacatcgacg gaggtgccag ccaggaggag ttctacaagt tcattaagcc catcctggag  1140
aagatggacg ggactgagga actacttgtg aagctgaacc gggaagactt actacggaag  1200
cagcgtacct tcgacaacgg ttctatccca catcagatcc atcttgggga gttgcacgcg  1260
atcctgcgac gccaggagga cttttaccc ttcctgaaag acaaccgcga gaaaatcgag  1320
aagatactga ccttcagaat accttactac gtcggacccc ttgcgcgagg caactcaaga  1380
ttcgcgtgga tgaccaggaa atcagaggag accatcacac cctggaattt cgaggaggtg  1440
gttgacaagg gtgcctccgc ccagtccttt atcgaacgaa tgcccaactt cgacaagaac  1500
ttgcccaacg agaaggtgct ccccaaacac agcctcctct acgaatattt cacagtgtac  1560
aacgagctta ctaaagttaa gtatgttact gagggcatga ggaaaccgc cttcctgtca  1620
ggcgagcaga agaaagctat tgtggacctc cttttcaaga ccaaccggaa ggtgacagtg  1680
aagcagctca aggaggacta cttcaagaag atagagtgct tcgacagcgt ggagatcagc  1740
ggggtggagg acagattcaa tgcctctctc ggaacatacc acgacttgct taagatcatc  1800
aaggacaagg acttcctcga caacgaggaa aacgaggata ttctggagga tattgttctg  1860
actcttaccc tgttcgagga ccgggagatg atcgaggagc gtctcaagac ctacgcccac  1920
ctgttcgacg acaaagttat gaagcagctc aagcgtcgga gatataccgg atggggccgt  1980
ctgtctcgga agctcatcca gggatcagg gacaagcagt cagggaagac gatcttagac  2040
ttccttaagt ctgacggctt cgccaacagg aacttcatgc agttgatcca cgacgacagc  2100
cttaccttca aggaggacat ccagaaggcc aagtgagtg gccagggtga cagcctccac  2160
gagcatattg ctaatcttgc gggttcccca gcgattaaaa agggcatact tcaaaccgtt  2220
aaggtggtgg acgagcttgt caaggtgatg gggcgacaca agcccgagaa catcgtgatc  2280
gagatggcca gggagaacca gaccaccag aaggggcaga agaatagccg agaacgcatg  2340
aagcgcatcg aggaggggat taaggagcta gggagccaga tcctcaagga acatcccgtc  2400
gagaacaccc agctccagaa cgagaagcta tacctctact acttgcaaaa cgggagggat  2460
atgtacgtgg atcaggagtt ggacattaac cgcctaagcg actacgacgt agatcacatc  2520
gtgcctcagt cattcctcaa agacgacagc attgacaaca aagtcttgac ccgatccgac  2580
aagaaccgag gaaaatccga caatgtgccc tcagaggagg tcgtcaagaa aatgaagaac  2640
tattggaggc agctacttaa cgccaaactc ataacccagc ggaagttcga caacctgaca  2700
aaggctgagc ggggtgggct cagcgagctt gacaaggctg gcttcatcaa gcggcagttg  2760
gtggacaa gacagataac gaagcacgtg gctcagatcc tggactctcg catgaacacg  2820
aagtacgacg agaacgacaa attgatccgc gaggtcaagg ttattacgct caagagcaaa  2880
cttgtcagcg atttccgcaa ggacttccag ttctacaagg tgagggagat taacaactac  2940
caccatgcac atgatgccta cttgaacgca gtggtgggga ccgcgcttat taaaaagtac  3000
cctaagttgg agtcagagtt cgtttatggg gactacaagg tgtacgacgt ccggaagatg  3060
attgcaaagt ctgaacagga aatcgggaag gccaccgcca aatatttctt ctacagtaac  3120
attatgaatt ttttaagac tgaaattact ctcgcaaacg gcgagatcag gaagcgtccc  3180
ctcatcgaga caaacgggga gaccggggag atagtctggg caaggggcg ggacttcgct  3240
acggtgagga aggtgctctc gatgccacaa gtgaacatcg tcaaaaagac agaggtgcag  3300
accggtggct tctcaaagga gtcaatcctg ccaaaacgta acagcgacaa gctcatcgcc  3360
cgcaagaaag actgggaccc taagaagtat ggtgggttcg actcaccgac ggtcgcatac  3420
tccgttctgt tcgtggcaaa ggtggaaaag ggcaagtcca aaaaactgaa atccgtgaag  3480
gagttgcttg gcattaccat catggaacgc agcagcttcg agaagaaccc cattgacttc  3540
ctggaggcta aagggtacaa ggaggtcaag aaagatttaa ttattaagct acctaagtac  3600
agcttgttcg agctggagaa cggccgaaaa cgaatgctcg catccgccgg ggaacttcaa  3660
aagggcaacg agcttgcgct gccctccaag tacgtgaact tcctgtactt ggcatcccac  3720
tacgagaaac tcaagggtag cccagaggac aacgagcaga agcagctatt cgtggagcag  3780
cacaagcact acctcgacga gataatcgag cagatcagtg agttcagtaa gcgggtgata  3840
ctcgcggacg ccaacttgga caaggtgctt agtgcctaca acaagcaccg tgacaagccc  3900
atccgagaac aggctgagaa catcatccac cttttcactc tgacaaacct cggtgctccc  3960
gccgccttca aatacttcga cactaccatc gacaggaagc gctacacatc tacgaaggaa  4020
gttcttgacg ctacgcttat tcatcagtct atcacagggc tgtacgagac aaggatcgac  4080
cttagccaac tcggcgggga t                                            4101

SEQ ID NO: 69         moltype = DNA   length = 6639
FEATURE               Location/Qualifiers
source                1..6639
                      mol_type = genomic DNA
                      organism = Glycine max
SEQUENCE: 69
atgggttggc ttagcagaat ttttaaaggc tccgatcata ataagctttc ggaagggcat    60
tactataaag aggatgcggg ttattacttg ccatccactt cggggtaac aaatgtcagc   120
actcactctc ctccttaaag aaaccaataa tgttttgga agttgttact gttttgtcct   180
cactgtctat aacttgtttt gaattgcagg atgcttggaa ccagagccag aaccagaacg   240
agaatgaaga tatcgatcgt gctattgcac tgtctctggt ggaagagact cagaaagcaa   300
acaacaatgt aaatggtgag tgaattgtag ctccttcaaac attgttgctt ctgtgtattc   360
tttttttttt ttttttttgtt atcgacaaat gttaattgtt agtggaagag attcgaaccc   420
atgacctttc cctctcacct tctcccttca accaccaaac caaccttgta actccattgc   480
tgtgtattct tgcaacagag agaattgcgt gtgtgccgtt tcatttgttt gagtctttac   540
agtctatgtg actgctgcta attatgaact atgaagtatg gactaatgca attcgagaag   600
ttctgaattt gtaacactca gtgttgccgt tttctagtt attgatagtg tttttccatt   660
gtccccctt gtcttcattt tgtaattatg agatttttga tatgaatct gtgaccaaaa   720
tcatttggta aatgaaagaa ccaattgctt ctattgaat gtcttgatta aatgtgcttg   780
taaatgtggt tgccacgctt ttctttgtgc aaaatcgtg gcaatttgat attttgcatt   840
gttggcttag ttagttagtt ggtagcttga cttccattta tatgctcatt tcttgttta   900
```

```
ccatttacca ctgtgtttgg aagtattaaa aattagagtt gttttgcatt aagtccaaga   960
tagtaaccat tttgctcttt atttgccacg ggagtttctg cttatgtttt ctagaggtgg  1020
tgaagattga ctaatttgca cattttttt atatctatcc tttttaaata tatattaccc  1080
ctcctcccct cctcaaaagt aatcttgtct tgtctaaatt gtatttacct tagtatgaaa  1140
tatattacag ttttacatta acaaggttct ctgtctgttt tatagactac agatcacaat  1200
tagaagaaga tgaacaactt gccagagcta tagaacaaag tctaaatttg gagtctcctc  1260
ccagatatgg aaatgaaaat atgtatcaac caccaattca gtatttcccc atggggtcca  1320
ggtatgagat gttgggggat gacaatgtat gaatttggca tcataattca atactttttt  1380
tgtttcacca cttcaatgga tatgctgaaa gaatcatcta aagtattttt attcaccatt  1440
taccataggg tcataattat tggttctatc aattctcacc ttgatttgtg tcatatactg  1500
ccaccgctgg attgtctgga atgatctatt ttaatgtgtg ctatatcctt taattggtgc  1560
ccaacaaatt ttccttgtaa ttcccactta tttgtgttgg tcctattgaa ttatttatta  1620
actgatattg ctatgactga ttacaaataa tcatccttt tatcctcttc aaatacctg  1680
taccaaacat atcataaga tacagtagta gagtgaagac tgctgcattt gaactgatat  1740
agagccaagt attaatatat atgtctagac tccaaatttt tatacgatga attagtaaca  1800
gatacccaca agtccctatg aattaagttc cacttgcaaa gaagagatac gattatttgt  1860
caggttgtat catatgtcta gccatcacgc ttaatgctcg taaagggaga aaacttctaa  1920
ccaatgtttt cctgtttgtt ttcgattgtt ggagaaatta ttctcttcgt tcaatttgct  1980
atacctctat attatcaata atacatgtga tgcacataat ttaagttgat tagttatttg  2040
cataatagga tttgtgctgg ctgctatact gagattggtt atggacgata tctgaattgc  2100
ttgaatgcat tctggcatcc tgaatgcttc cgctgccgtg cttgcaacct accaatctct  2160
gattacgagg tgctaacatt accggccaca ttgcttgttt tcatatatgg ttttattct  2220
gtacttaatg ctttgtttta tacatattat tattgcagtt ttccacatct gggaattacc  2280
cttatcataa atcatgctat aaggaaagct accatccaaa atgtgatgtc tgcaagcact  2340
tcgtaagtat ttttaacaag ttttagggaa aattgcactt ggtaccctt agatttgctt  2400
atatgacatg cacacccatg ctatttttg acctgtcact tgttaccta ataacacccc  2460
tttagctaac attgattaac agatctgatt ctcctttgct gctactaaca attatacccc  2520
tgtcaccctc tttgtgctat ttcttcacc ttcaaaaata gaatcaggaa ggatgagatt  2580
gagagccttc aattcttctt tgtggaaata tggtagcttt cactttcctg agatgtgaca  2640
atgccattcc tgtgttgagt atgggtgtca attccctcct tgagatgtgt ccaccttgt  2700
tctccttttt tacccttca aagtgaacag gattccttg cacatcatca cttgctcaca  2760
tctctttctc actcagcatc acctacgtgc ataacaacca agatactaaa gttctggtag  2820
ttaattccta ataggaataa ataacgcacag caatacatgg tttgtgaatc agcatataaa  2880
gactaaggaa cgtcaaacca taagacctaa ccactctcaa atttgtgtca gccaacattc  2940
ccatcatctt gttaacttta tccaaaccat cacaaaaacc acaactttc cagcttctgc  3000
tactgtgaag cacaccctgt accatgacca tccatctgct atatctgcca aatatcgcct  3060
acacaccctg cagcaatcac ctcactgctc atcaccacca caaagccgcc ttcaatctca  3120
attctcaact aaacaaccac tctcctttca cagtgagcac cacctcctca atggatagtt  3180
cccaacacct cagcccaca ttccacgtct tgaaccaaaa tagctgcaca acattctctg  3240
agacaaattt tcaccatcct caaccttgt ggcattgaca ttcttgccac taaactaacc  3300
ttctcactgg aatttaccat tcttgagtgg atcactctct agagttgcat gaaccactat  3360
caatggaact ttccacttct gagaaaata agagagatgt ggcaaacctt tgctgctagg  3420
atggaggaga atgagagaag aacaagggaa agggtttagg gcttatattt ctgaaattta  3480
tagttcatgt tcttggtgag gcttttgttt ttaccacaaa tgatcatgga ggtagtataa  3540
agtgctactg gaatcacctt gttttctcca acttgtggac attgtctgag tcattcatga  3600
ttgtagttgt ttataactct catgttagat tttgaaaaag acatgctttt aagttttcac  3660
cttgacttca acctatatc tcattgcctg ttgttgttt ttggtaatat atatttttc  3720
acagattcca acaaatcctg ctggtcttat tgaatatagg gcacatccat tctggatcca  3780
gaaatattgc cctactcacg aacatgatgg tactacacgg tgttgcagct gcgagcgaat  3840
ggaggttagt atggatggag tatatttatc tgataaaata ttatttgtag tcttgcctag  3900
ggaaaggtgg atgaacttgt acagtgcaaa gtgaataaga tgtaaaattt tctctcatca  3960
tatgcagtcc caagaggcag gatatattgc tcttaaggat ggccggaagc tctgcttaga  4020
gtgtcttgat tctgctatca tggatactaa tgaatgccaa cccccttcatg ctgatataca  4080
aagatttat gaaagcctaa atatgaaact ggaccaacaa attccacttc tattggttga  4140
aagacaagca ctgaatgaag caagagaagg agagaagaat gtaagagaaa atgcatttcc  4200
atctgtttgc tataaatata ataactgata atttgattgt aatgacattc agctgtctga  4260
catactagga actatttttt ggtgtttggc attgtctgca caactaatat taaaagtaaa  4320
ataatgcctt ttgctattga tagctttgag aatgctatct ctgatgaagg ttttctatt  4380
cgtatatgt taaccacatg ctatgtcaaa tagttcaata tgactagcac gatatagaaa  4440
atttaagagc aaaaaggaaa caaaaaaagc atattccat ttggaagtct aatgcttgca  4500
ataaataata ctgtccaagt caacatgctt tcacctatga agctttaatt cattattagt  4560
tcatgattaa acagtgttt tccattttca tatttgagtc tttatcttgg gcagggccac  4620
tatcacatgc cggaaaccag agggctctgc ctctcagagg agctcagcac tgtaagagttt  4680
cctgttatgt tcagttttgg tgatgtactg acatttttt tttttaatgg ttagatgata  4740
acatttcttt agaaccaata attagcaatt tatggtacat tgcatttaaa cttgatcagt  4800
tctcgagacg acctagactt gggacaacaa tggacatgag agcacagcca tacagaccga  4860
ctacacgctg cgatgtgact gcaattctca ttttatatgg tcttccaagg taataataat  4920
ttagtgctctt tgcaacttgt gtaacttgga gataaataat aatctaaaag acaaaaagt  4980
ttcccaagta tgaaaacaac tgttaacaaa agatccatga aaccagaaaa tgtaatatgc  5040
gttcagctgg agagatctag ataatattat atgttagcat aatttcactt ttggtcccct  5100
tactctcgta attatgttaa cttgcccccc cccccccccc cccaattttt ttcactaatt  5160
tgatcctctt actattttaa ttgtataatc ttggtaagtt tttgttaatg tgacctccaa  5220
tattttacaa aaatgctgat atagcagtgc aatacagtgt cacatcagta tggatgtgct  5280
gacgtgacag tggcacagtg caatagaata tcacgtcaac attttgttaa atattggctg  5340
tcaagttaac tgatgtacca aaactaaaca attaaaataa tgagggatca aattcgagat  5400
aaaaattggg aggaccaaat ttgcaaaatg atgatagtat aagagactaa tgtacaatta  5460
agtcttgtat gttagacaaa agcagtgtat tttacacaga gctttgcta acatgactta  5520
ataaaatgaa aggagctaaa agctgctaat tgtaacattc ttcctcttt gtatccgtgg  5580
gatttagctt ttgtgaattc tctttcgtac ttaatgtaaa aacctgtgtt cttttggaat  5640
```

```
tagaagagga agttgattta aaaagtaata tctgcagcca agcaagcgtt gccttgttta      5700
tattgaatta tataatagtt ttcctatgca tgcaagatta tcttttttga atgtttgctc      5760
aagtctcctg actttcagaa tatatcttcc gaaagaaaat ccttcctccc caccaccta       5820
tttctttcac aacaactttg tcttcatcag ttgattttat ttatacatga ttttttttctt    5880
cttttcacag gttacttact ggatcaatcc tagctcattga gatgatgcat gcatggctgc    5940
ggcttaaagg tactatttta ttgttgggaa tctatttcat taggattcat tttagcagtt    6000
gagatttatc acctactatt aaaccagtgt tatttcgttg ggattgtctc tcaaattcat     6060
gctaacttgt gaaggttatc ggactctaag tcaagatgtt gaagaaggta tctgtcaggt    6120
tttgtctcat atgtggttgg agtctgaact ttcttctgca tcaggcagca actttgtatc    6180
agcctcatcc tcgtctgcat cacatacatc tagaaaaggt aaaagacctc agtttgagag    6240
gaagcttggg gagttcttca aacaccagat tgaatcagac atttcccctg tttatggagg    6300
tgggtttagg gcaggtcaaa aagcagtgag taaatatggt ctacaaagga cccttcatca    6360
tatcaggatg acagggactt ttccatatta agtacaaaga tacccctttt aacagattgt    6420
ttctcattat ttctagatat aaagcctggc ctgttattaa tagaaaccga ggccaaggtg    6480
cttaggcata agcttccacg aattgttgat tttttgtact tgtaattatt gataccgttc    6540
attcacattt tttctttga tttatcagac tgctattttt tggcattacc aacttccaac     6600
cgctgctatc tcccaaaaat aagaaaaaaa aaactttag                            6639

SEQ ID NO: 70          moltype = DNA  length = 1437
FEATURE                Location/Qualifiers
source                 1..1437
                       mol_type = other DNA
                       organism = Glycine max
SEQUENCE: 70
atgggttggc ttagcagaat ttttaaaggc tccgatcata ataagctttc ggaagggcat    60
tactataaag aggatgcggg ttattacttg ccatccactt cggggggtaac aaatgatgct    120
tggaaccaga gccagaacca gaacgagaat gaagatatcg atcgtgctat tgcactgtct    180
ctggtggaag agactcagaa agcaaacaac aatgtaaatg actacagatc acaattagaa    240
gaagatgaac aacttgccag agctatagaa caaagtctaa atttggagtc tcctcccaga    300
tatggaaatg aaaatatgta tcaaccacca attcagtatt tccccatggg gtccaggatt    360
tgtgctggct gctatactga gattggttat ggacgatatc tgaattgctt gaattgcattc    420
tggcatcctg aatgcttccg ctgccgtgct tgcaacctac caatctctga ttacgagttt    480
tccacatctg ggaattaccc ttatcataaa tcatgctata ggaaagcta ccatccaaaa     540
tgtgatgtct gcaagcactt cattccaaca aatcctgctg gtcttattga atatagggca   600
catccattct ggatccagaa atattgccct actcacgaac atggtggtac tacacgctgt   660
tgcagctgcg agcgaatgga gtcccaagag gcaggatata ttgctcttaa ggatggccgg   720
aagctctgct tagagtgtct tgattctgct atcatggata ctaatgaatg ccaaccctt    780
catgctgata tacaaagatt ttatgaaagc ctaaatatga aacttggacca acaaattcca   840
cttctattgg ttgaaagaca agcactgaat gaagcaagaa aaggagagaa gaatggccac   900
tatcacatgc cggaaccag agggctctgc ctctcagagg agctcagcac tttctcgaga   960
cgacctagac ttgggacaac aatggacatg agagcacagc catacagacc gactacacgc  1020
tgcgatgtga ctgcaattct catttttatat ggtcttccaa ggttacttac tggatcaatc  1080
ctagctcatg agatggcaa tgcatggctg cggcttaaag gttatcggac tctaagtgaa   1140
gatgttgaag aaggtatctg tcaggttttg tctcatatgt ggttggagtc tgaactttct   1200
tctgcatcag gcagcaactt tgtatcagcc tcatcctcgt ctgcatcaca tacatctaga  1260
aaaggtaaaa gacctcagtt tgagaggaag cttggggagt tcttcaaaca ccagattgaa   1320
tcagacattt cccctgttta tggaggtggg tttagggcag gtcaaaaagc agtgagtaaa   1380
tatggtctac aaaggaccct tcatcatatc aggatgacag ggacttttcc atattaa       1437

SEQ ID NO: 71          moltype = AA  length = 483
FEATURE                Location/Qualifiers
source                 1..483
                       mol_type = protein
                       organism = Glycine max
SEQUENCE: 71
MGWLSRIFKG SDHNKLSEGH YYKEDAGYYL PSTSGVTNDA WNQSQNQNEN EDIDRAIALS     60
LVEETQKANN NVNDYRSQLE EDEQLARAIE QSLNLESPPR YGNENMYQPP IQYFPMGSSY    120
LHNRICAGCY TEIGYGRYLN CLNAFWHPEC FRCRACNLPI SDYEFSTSGN YPYHKSCYKE   180
SYHPKCDVCK HFIPTNPAGL IEYRAHPFWI QKYCPTHEHD GTTRCCSCER MESQEAGYIA   240
LKDGRKLCLE CLDSAIMDTN ECQPLHADIQ RFYESLNMKL DQQIPLLLVE RQALNEAREG   300
EKNGHYHMPE TRGLCLSEEL STFSRRPRLG TTMDMRAQPY RPTTRCDVTA ILILYGLPRL   360
LTGSILAHEM MHAWLRLKGY RTLSQDVEEG ICQVLSHMWL ESELSSASGS NFVSASSSSA   420
SHTSRKGKRP QFERKLGEFF KHQIESDISP VYGGGFRAGQ KAVSKYGLQR TLHHIRMTGT   480
FPY                                                                 483

SEQ ID NO: 72          moltype = DNA  length = 392
FEATURE                Location/Qualifiers
source                 1..392
                       mol_type = other DNA
                       organism = Glycine max
SEQUENCE: 72
atgggttggc ttagcagaat ttttaaaggc tccgatcata ataagctttc ggaagggcat    60
tactataaag aggatgcggg ttattacttg ccatccactt cggggggtaac aaatgtcagc   120
actcactctc ctccttaaag aaaccaataa tgttttggaa agttgttact gttttgtcct   180
cactgtctat aacttgtttt gaattgcagg atgcttggaa ccagagccag aaccagaacg   240
agaatgaaga tatcgatcgt gctattgcac tgtctctggt ggaagagact cagaaagcaa   300
acaacaatgt aaatggtgag tgaattgtag ctccttcaaac attgttgctt ctgtgtattc   360
ttttttttt ttttttgtt atcgacaaat gt                                   392
```

```
SEQ ID NO: 73          moltype = DNA    length = 307
FEATURE                Location/Qualifiers
source                 1..307
                       mol_type = other DNA
                       organism = Glycine max
SEQUENCE: 73
ttggcttagc agaattttta aaggctccga tcataataag ctttcggaag ggcattacta   60
taaagaggat gcgggttatt acttgccatc cacttcgggg gtaacaaatg tcagcactca  120
ctctcctcct taaagaaacc aataatgttt tggaagttg ttactgtttt gtcctcactg   180
tctataactt gttttgaatt gcaggatgct tggaaccaga gccagaacca gaacgagaat  240
gaagatatcg atcgtgctat tgcactgtct ctggtggaag agactcagaa agcaaacaac  300
aatgtaa                                                            307

SEQ ID NO: 74          moltype = DNA    length = 143
FEATURE                Location/Qualifiers
source                 1..143
                       mol_type = other DNA
                       organism = Glycine max
SEQUENCE: 74
ttggcttagc agaattttta aaggctccga tcataataag ctttcggaag ggcattacta   60
taaagaggat gcgggttatt acttgccatc cacttcgggg gtaacaaatg tcagcactca  120
ctctcctcct taaagaaacc aat                                          143

SEQ ID NO: 75          moltype = DNA    length = 104
FEATURE                Location/Qualifiers
source                 1..104
                       mol_type = other DNA
                       organism = Glycine max
SEQUENCE: 75
ttggcttagc agaattttta aaggctccga tcataataag ctttcggaag ggcattacta   60
taaagaggat gcgggttatt acttgccatc cacttcgggg gtaa                   104

SEQ ID NO: 76          moltype = DNA    length = 63
FEATURE                Location/Qualifiers
source                 1..63
                       mol_type = other DNA
                       organism = Glycine max
SEQUENCE: 76
ttggcttagc agaattttta aaggctccga tcataataag ctttcggaag ggcattacta   60
taa                                                                 63

SEQ ID NO: 77          moltype = DNA    length = 223
FEATURE                Location/Qualifiers
source                 1..223
                       mol_type = other DNA
                       organism = Glycine max
SEQUENCE: 77
tgttttgtcc tcactgtcta taacttgttt tgaattgcag gatgcttgga accagagcca   60
gaaccagaac gagaatgaag atatcgatcg tgctattgca ctgtctctgg tggaagagac  120
tcagaaagca acaacaatg taaatggtga gtgaattgta gctcttcaaa cattgttgct   180
tctgtgtatt cttttttttt ttttttttgt tatcgacaaa tgt                    223

SEQ ID NO: 78          moltype = DNA    length = 143
FEATURE                Location/Qualifiers
source                 1..143
                       mol_type = other DNA
                       organism = Glycine max
SEQUENCE: 78
gatgcttgga accagagcca gaaccagaac gagaatgaag atatcgatcg tgctattgca   60
ctgtctctgg tggaagagac tcagaaagca acaacaatg taaatggtga gtgaattgta  120
gctcttcaaa cattgttgct tct                                          143

SEQ ID NO: 79          moltype = DNA    length = 103
FEATURE                Location/Qualifiers
source                 1..103
                       mol_type = other DNA
                       organism = Glycine max
SEQUENCE: 79
gaaccagaac gagaatgaag atatcgatcg tgctattgca ctgtctctgg tggaagagac   60
tcagaaagca acaacaatg taaatggtga gtgaattgta gct                     103

SEQ ID NO: 80          moltype = DNA    length = 63
FEATURE                Location/Qualifiers
source                 1..63
                       mol_type = other DNA
                       organism = Glycine max
SEQUENCE: 80
atatcgatcg tgctattgca ctgtctctgg tggaagagac tcagaaagca acaacaatg   60
taa                                                                 63
```

```
SEQ ID NO: 81              moltype = DNA   length = 248
FEATURE                    Location/Qualifiers
source                     1..248
                           mol_type = other DNA
                           organism = Glycine max
SEQUENCE: 81
aatactgtcc aagtcaacat gctttcacct atgaagcttt aattcattat tagttcatga      60
ttaaacagtg ttttccatt tcatatttg agtctttatc ttgggcaggg ccactatcac       120
atgccggaaa ccagagggct ctgcctctca gaggagctca gcactgtaag atttcctgtt    180
atgttcagtt ttggtgatgt actgacattt ttctttta atggttagag gataacattt       240
ctttagaa                                                                248

SEQ ID NO: 82              moltype = DNA   length = 168
FEATURE                    Location/Qualifiers
source                     1..168
                           mol_type = other DNA
                           organism = Glycine max
SEQUENCE: 82
aattcattat tagttcatga ttaaacagtg ttttccatt tcatatttg agtctttatc        60
ttgggcaggg ccactatcac atgccggaaa ccagagggct ctgcctctca gaggagctca    120
gcactgtaag atttcctgtt atgttcagtt ttggtgatgt actgacat                 168

SEQ ID NO: 83              moltype = DNA   length = 128
FEATURE                    Location/Qualifiers
source                     1..128
                           mol_type = other DNA
                           organism = Glycine max
SEQUENCE: 83
ttaaacagtg ttttccatt tcatatttg agtctttatc ttgggcaggg ccactatcac        60
atgccggaaa ccagagggct ctgcctctca gaggagctca gcactgtaag atttcctgtt    120
atgttcag                                                                128

SEQ ID NO: 84              moltype = DNA   length = 88
FEATURE                    Location/Qualifiers
source                     1..88
                           mol_type = other DNA
                           organism = Glycine max
SEQUENCE: 84
ttcatatttg agtctttatc ttgggcaggg ccactatcac atgccggaaa ccagagggct     60
ctgcctctca gaggagctca gcactgta                                        88

SEQ ID NO: 85              moltype = DNA   length = 47
FEATURE                    Location/Qualifiers
source                     1..47
                           mol_type = other DNA
                           organism = Glycine max
SEQUENCE: 85
ttgggcaggg ccactatcac atgccggaaa ccagagggct ctgcctc                    47

SEQ ID NO: 86              moltype = DNA   length = 297
FEATURE                    Location/Qualifiers
source                     1..297
                           mol_type = other DNA
                           organism = Glycine max
SEQUENCE: 86
atgggttggc ttagcagaat ttttaaaggc tccgatcata ataagctttc ggaagggcat     60
tactataaag aggatgcggg ttattacttg ccatccactt cggggtaac aaatgatgct     120
tggaaccaga gccagaacca gaacgagaat gaagatatcg atcgtgctat tgcactgtct   180
ctggtggaag agactcagaa agcaaacaac aatgtaaatg actacagatc acaattagaa   240
gaagatgaac aacttgccag agctatagaa caaagtctaa atttggagtc tcctccc       297

SEQ ID NO: 87              moltype = DNA   length = 262
FEATURE                    Location/Qualifiers
source                     1..262
                           mol_type = other DNA
                           organism = Glycine max
SEQUENCE: 87
atgggttggc ttagcagaat ttttaaaggc tccgatcata ataagctttc ggaagggcat     60
tactataaag aggatgcggg ttattacttg ccatccactt cggggtaac aaatgatgct     120
tggaaccaga gccagaacca gaacgagaat gaagatatcg atcgtgctat tgcactgtct   180
ctggtggaag agactcagaa agcaaacaac aatgtaaatg actacagatc acaattagaa   240
gaagatgaac aacttgccag ag                                              262

SEQ ID NO: 88              moltype = DNA   length = 222
FEATURE                    Location/Qualifiers
source                     1..222
                           mol_type = other DNA
                           organism = Glycine max
```

```
SEQUENCE: 88
atgggttggc ttagcagaat ttttaaaggc tccgatcata ataagctttc ggaagggcat    60
tactataaag aggatgcggg ttattacttg ccatccactt cggggg taac aaatgatgct   120
tggaaccaga gccagaacca gaacgagaat gaagatatcg atcgtgctat tgcactgtct   180
ctggtggaag agactcagaa agcaaacaac aatgtaaatg ac                      222

SEQ ID NO: 89           moltype = DNA   length = 154
FEATURE                 Location/Qualifiers
source                  1..154
                        mol_type = other DNA
                        organism = Glycine max
SEQUENCE: 89
atgggttggc ttagcagaat ttttaaaggc tccgatcata ataagctttc ggaagggcat    60
tactataaag aggatgcggg ttattacttg ccatccactt cggggg taac aaatgatgct   120
tggaaccaga gccagaacca gaacgagaat gaag                               154

SEQ ID NO: 90           moltype = DNA   length = 135
FEATURE                 Location/Qualifiers
source                  1..135
                        mol_type = other DNA
                        organism = Glycine max
SEQUENCE: 90
atgggttggc ttagcagaat ttttaaaggc tccgatcata ataagctttc ggaagggcat    60
tactataaag aggatgcggg ttattacttg ccatccactt cggggg taac aaatgatgct   120
tggaaccaga gccag                                                    135

SEQ ID NO: 91           moltype = DNA   length = 114
FEATURE                 Location/Qualifiers
source                  1..114
                        mol_type = other DNA
                        organism = Glycine max
SEQUENCE: 91
atgggttggc ttagcagaat ttttaaaggc tccgatcata ataagctttc ggaagggcat    60
tactataaag aggatgcggg ttattacttg ccatccactt cggggg taac aaat        114

SEQ ID NO: 92           moltype = DNA   length = 74
FEATURE                 Location/Qualifiers
source                  1..74
                        mol_type = other DNA
                        organism = Glycine max
SEQUENCE: 92
atgggttggc ttagcagaat ttttaaaggc tccgatcata ataagctttc ggaagggcat    60
tactataaag agga                                                      74

SEQ ID NO: 93           moltype = DNA   length = 223
FEATURE                 Location/Qualifiers
source                  1..223
                        mol_type = other DNA
                        organism = Glycine max
SEQUENCE: 93
tgcgggttat tacttgccat ccacttcggg ggtaacaaat gatgcttgga accagagcca    60
gaaccagaac gagaatgaag atatcgatcg tgctattgca ctgtctctgg tggaagagac   120
tcagaaagca acaacaatg taaatgacta cagatcacaa ttagaagaag atgaacaact    180
tgccagagct atagaacaaa gtctaaattt ggagtctcct ccc                     223

SEQ ID NO: 94           moltype = DNA   length = 148
FEATURE                 Location/Qualifiers
source                  1..148
                        mol_type = other DNA
                        organism = Glycine max
SEQUENCE: 94
gatgcttgga accagagcca gaaccagaac gagaatgaag atatcgatcg tgctattgca    60
ctgtctctgg tggaagagac tcagaaagca acaacaatg taaatgacta cagatcacaa    120
ttagaagaag atgaacaact tgccagag                                      148

SEQ ID NO: 95           moltype = DNA   length = 108
FEATURE                 Location/Qualifiers
source                  1..108
                        mol_type = other DNA
                        organism = Glycine max
SEQUENCE: 95
gaaccagaac gagaatgaag atatcgatcg tgctattgca ctgtctctgg tggaagagac    60
tcagaaagca acaacaatg taaatgacta cagatcacaa ttagaaga                 108

SEQ ID NO: 96           moltype = DNA   length = 68
FEATURE                 Location/Qualifiers
source                  1..68
                        mol_type = other DNA
                        organism = Glycine max
```

```
SEQUENCE: 96
atatcgatcg tgctattgca ctgtctctgg tggaagagac tcagaaagca aacaacaatg    60
taaatgac                                                             68

SEQ ID NO: 97           moltype = DNA  length = 257
FEATURE                 Location/Qualifiers
source                  1..257
                        mol_type = other DNA
                        organism = Glycine max
SEQUENCE: 97
aagattttat gaaagcctaa atatgaaact ggaccaacaa attccacttc tattggttga    60
aagacaagca ctgaatgaag caagagaagg agagaagaat ggccactatc acatgccgga   120
aaccagaggg ctctgcctct cagaggagct cagcactttc tcgagacgac ctagacttgg   180
gacaacaatg gacatgagag cacagccata cagaccgact cacgctgcg atgtgactgc    240
aattctcatt ttatatg                                                  257

SEQ ID NO: 98           moltype = DNA  length = 177
FEATURE                 Location/Qualifiers
source                  1..177
                        mol_type = other DNA
                        organism = Glycine max
SEQUENCE: 98
attccacttc tattggttga aagacaagca ctgaatgaag caagagaagg agagaagaat    60
ggccactatc acatgccgga aaccagaggg ctctgcctct cagaggagct cagcactttc   120
tcgagacgac ctagacttgg gacaacaatg gacatgagag cacagccata cagaccg      177

SEQ ID NO: 99           moltype = DNA  length = 137
FEATURE                 Location/Qualifiers
source                  1..137
                        mol_type = other DNA
                        organism = Glycine max
SEQUENCE: 99
aagacaagca ctgaatgaag caagagaagg agagaagaat ggccactatc acatgccgga    60
aaccagaggg ctctgcctct cagaggagct cagcactttc tcgagacgac ctagacttgg   120
gacaacaatg gacatga                                                  137

SEQ ID NO: 100          moltype = DNA  length = 97
FEATURE                 Location/Qualifiers
source                  1..97
                        mol_type = other DNA
                        organism = Glycine max
SEQUENCE: 100
caagagaagg agagaagaat ggccactatc acatgccgga aaccagaggg ctctgcctct    60
cagaggagct cagcactttc tcgagacgac ctagact                             97

SEQ ID NO: 101          moltype = DNA  length = 57
FEATURE                 Location/Qualifiers
source                  1..57
                        mol_type = other DNA
                        organism = Glycine max
SEQUENCE: 101
ggccactatc acatgccgga aaccagaggg ctctgcctct cagaggagct cagcact        57

SEQ ID NO: 102          moltype = AA   length = 99
FEATURE                 Location/Qualifiers
source                  1..99
                        mol_type = protein
                        organism = Glycine max
SEQUENCE: 102
MGWLSRIFKG SDHNKLSEGH YYKEDAGYYL PSTSGVTNDA WNQSQNQNEN EDIDRAIALS    60
LVEETQKANN NVNDYRSQLE EDEQLARAIE QSLNLESPP                           99

SEQ ID NO: 103          moltype = AA   length = 49
FEATURE                 Location/Qualifiers
source                  1..49
                        mol_type = protein
                        organism = Glycine max
SEQUENCE: 103
MGWLSRIFKG SDHNKLSEGH YYKEDAGYYL PSTSGVTNDA WNQSQNQNE                49

SEQ ID NO: 104          moltype = AA   length = 50
FEATURE                 Location/Qualifiers
source                  1..50
                        mol_type = protein
                        organism = Glycine max
SEQUENCE: 104
NEDIDRAIAL SLVEETQKAN NNVNDYRSQL EEDEQLARAI EQSLNLESPP                50

SEQ ID NO: 105          moltype = AA   length = 59
```

```
FEATURE                 Location/Qualifiers
source                  1..59
                        mol_type = protein
                        organism = Glycine max
SEQUENCE: 105
IPLLLVERQA LNEAREGEKN GHYHMPETRG LCLSEELSTF SRRPRLGTTM DMRAQPYRP      59

SEQ ID NO: 106          moltype = AA  length = 39
FEATURE                 Location/Qualifiers
source                  1..39
                        mol_type = protein
                        organism = Glycine max
SEQUENCE: 106
LNEAREGEKN GHYHMPETRG LCLSEELSTF SRRPRLGTT                            39

SEQ ID NO: 107          moltype = AA  length = 19
FEATURE                 Location/Qualifiers
source                  1..19
                        mol_type = protein
                        organism = Glycine max
SEQUENCE: 107
GHYHMPETRG LCLSEELST                                                  19

SEQ ID NO: 108          moltype = AA  length = 9
FEATURE                 Location/Qualifiers
source                  1..9
                        mol_type = protein
                        organism = Glycine max
SEQUENCE: 108
MPETRGLCL                                                              9

SEQ ID NO: 109          moltype = DNA  length = 5101
FEATURE                 Location/Qualifiers
source                  1..5101
                        mol_type = genomic DNA
                        organism = Glycine max
SEQUENCE: 109
atgggttggt ttaccaagtt gcttaagggc tctgatcata aaattttca aggacaatac      60
catggcaaat atggagagga cagaatttgg gataatcatc atagttcaat ggtaaacaaa    120
gtttttcctt ttctagtaag aattaaaagc attgccacaa gtcacaacta cgtcattgag    180
ctagcctttt atctgaattt agctttgaga ttagcatgaa gctaacaaag tactacttcc    240
tctgagacat aagcagataa tctgcatttg taatagttac aaactgaatg caggatgatt    300
tgactgatat tgagaaagaa gacattgacc atgcaattgc actttctctg tcagaggagg    360
atcataaagg gaaaaagtt gttggtaaga tttatgcttt tgcaccttgg tagttaaagt     420
tcatttcctg gttagtttgg ctcaaattta atgctgttat gattctgcat actgcatatg    480
aggtacctaa actctaagat ctgaatcaa ccaaaatgct cgatgattta gtacaagctc     540
ttacttacct cttgtattat ttcctgtctt tctatgccta tttcagtgtc ttcttcattc    600
ttgtttaagt agattatgct ttgtgaacac cccaaaaaaa ggtcatgctt tgttgatgaa    660
aggctatgat gctatcagtt gagtctttca tttacatctg aatcagaatg gaactaagaa    720
ataaattttt aaattactac aattagcttc tagattactt aaaatataa atttaacatg     780
catataagaa ttatggggat attctgattc tggtgtttca cttaagttgc aactcaaagt    840
gcttaaagta tatttcttag ttaagagtcc attgaagaat ttttttcaaaa aatacaaaaa   900
agagtacatt gaagaaaatc tgaagtttca tttggtttat gtgttcagaa agtgcatgtg    960
ttaatcaatt aattatttcc acaccaaagc ataaccaaaa ggtctcatgt tttttgtctc   1020
ataatacccct agattatgac tctcaatctg aagatgagga actttgtaaa attgatgatg  1080
aggaggatga acatcttgtt aaagttcatc tagatgatga tgaacgtctt gctaaaattc   1140
agcaagaaga agaagaacgt cttgctaaaa ttcaacaaga agatgagcat cttgctaaaa   1200
ttcaacaaga agaagaagaa cgtcttgcta aaattcaaca agaagatgaa tgtcttgcta   1260
aaattcaaca agaggatgaa cgtcttgcta aagctcaact tgaggaagac tgcaacttg    1320
ctagggcaat tcaagaaagc ttgaaaattg gttctcctcc tcaatatgac aatggttctt   1380
caattctatc tttttcctcac cttttccccc ctggatacag gtaattgttg gtatgatcac  1440
atcttttatc tatatagcaa gtccttatac tgtttttgga aattgttgaa gtacactagt   1500
tctaaatgaa cagaccaata atgtaattgt gccaaaaata agaaaaacaa aaaattttcca  1560
aactgaatat gttttgaaac ttcaatttaa gtattgctga tttgagtgat aggtcataca   1620
actaactgat ctggacttca tacaagctaa tcaatcttat tttatgagat tctagtctga   1680
atcattgaac tgggataaat gctgtattgg gattttatgc atgacacctt ggtgtgcgtt   1740
ggttttcctt agtgttctta agtacctttc aattagatga aaattttaaa aaatagtagt   1800
tattaaaatg aacattccat aaatttgatta cttaagtctt attatggtg atcctgagca   1860
cttcctgtag aatagcttgg agtgatttca tgatcatcta ataataaaa ttgaaatact    1920
ctcctctgtt gcaatattgt ggacctatat aatcgacatc tttgaaattt atttttcaag   1980
gtttcatgaa tctttattaa ttattagaaa caaagattta accttttttc tgtaaaatct   2040
gcctgcagaa tctgtgctgg atgcaagact gagattggcc aaggaagatt tttaagttgc   2100
atgggaggtg tctggcatcc agaatgcttc tgctgccatg catgccatct tccaatcact   2160
gattatgagg ttagagacta gagtcttgtt ttcttttgct gcttgtttcg caaagctgaa   2220
tttaattaca ataagttgaa accttgtttt tttggtgaaa gaaaaagttg aaaattattc   2280
ttagcttcat aaatgaaggt cttcaattta tttctcttgt ttgtcaatct caatatgatt   2340
atgcttaatt cgtcccttta cagttttcca tgtctagcaa tcgcccttac cataaatcat   2400
gctatagggga gaagcatcac ccaagatgtg atgtttgcaa gaacttttgta agtatcttca  2460
ccagttgttt tcactcaca gttgtctatt agccttggtt tggttgtggg gaaggaagta    2520
```

```
ctattcaaca gcaaatttc aaaaaatagt gtgggtccta caccatttt ttttctcta 2580
ctttaattca aatatttctt ctcaattctt ttctcttcca cacaaccaaa catactctta 2640
gtcaatactg tgtgcttgtt ttctttcaaa ggtttctatc aatttgatg tgctttagaa 2700
gctttacaag atgcatatac aaggaagact gttgatattg agttgttctt gcttctcaga 2760
tagatcagaa ttccaaacta tacttgagaa agttctgctg aactcagcag ttgttaatc 2820
tttataacaa atcatgggct attgatctta ctgaaataac atcatgggag ctcttcatga 2880
agctaatatt tgtatatttt tatattttgg gccagacagt ctgtttgggc ccagcccaat 2940
gtggttatac ctcttggggt ttatacatgc atagactcaa atcttaatat tttgaatgta 3000
atgttaggat ttgagctatt gtatcctgca cctcccatta cattctggaa agcccattcc 3060
ggaatgcaaa tttacattcc ggaatgggat ttccggaatg cagtgaggtg taggatgcaa 3120
tagtggggagt gcctatgctg tgtaatgtgc ataaacccca atgtggctat ccctcttggg 3180
atttcataat ttttttaaag acttggatac ttcatcgata cgtattggtg aagtatccaa 3240
tagtattggt atcggatacg tgaaaaaaat tgaagtattc gctcttcatg aacagacctt 3300
aagtttgcgt ttttttttta aaaaaaaatg gcagtaagat atattgttca gtaaactaga 3360
attattggtt ctttccttgt agatcccaac taattcatct ggcctcattg agtatagagc 3420
tcatcctttc tggctacaaa aatactgccc atcgcatgag cttgatggca cttctcgttg 3480
ttgtagttgc gaaagaatgg aggttagtta tattgactcc caaatctttt catcctatta 3540
ttatcaatta gaagctaact gttggatcct tcctctcctc ccccattccc tgtcccgttt 3600
tcttgccttt tcaatcaatg cagccaaggg atacaaaata tcttttgctt gatgatggtc 3660
gaaagctatg tttagagtgt ctagactcat caattatgga tactcatgaa tgccaacctc 3720
tttaccttga aatacaagaa ttttatgaag gttaaatat gaaattggag caacaaattc 3780
ctatgctctt ggttgagaga caagcgctga atgaggctat ggagggagaa agaaatgtaa 3840
gtgttaatgt gtttaacttc ccatttcatt catggaatgc tgttatttct attctttcta 3900
gtgtcctgtc gaaatgttct tttatttctc actattgaat gtagggtcat caccacttac 3960
ccgaaactag aggactatgc ttgtcagaag agcaaactgt caccactgta gggatttctc 4020
acttgcaaat tgaatcttca catctcaattc tgctataga actctgtgta tcaaatagtg 4080
attttattac ttttatatat ttcatgtaat actagattc aaggaggcca aggattgcag 4140
caggctaccg agccatagac atgataactg aaccttatag gctgatccgt tgttgtgaag 4200
tgacagccat tcttgttttg tatggccttc ctaggtatcc ttcttgtaca atctactttc 4260
ataatctaca gtgcttgcat atgacattcc tcatatataa ttcaatttt ttttatgttt 4320
ataggttgtt aacaggatca atcctagctc atgagatgat gcatgcatgg cttaggctta 4380
aaggtattca gccattaaca tgatccagaa aagtttatat atttgtttca tggtgccaag 4440
ttggacaaaa tttctgggtt tttgacaggt tatcctaacc tcagtccaga agttgaagaa 4500
ggaatctgcc aagttttggc tcatatgtgg ttagaatcag agctctattc tggatttggg 4560
aatgatggtg catcatcctc aacatcatct ttgtcttcgt catcaccttc ctcctcttct 4620
gtctcaacaa agaagggtaa acggtccgac tttgagaaga aacttggtga ttttttaaa 4680
caccagattg agtcagatac ctcctcagct tatggagatg gattcagatt gggtaaccaa 4740
gcaatggtca agtatgggct taaaaggacc cttgaccata tccatatgac aggaagtttt 4800
ccatattaaa aattgaaaat ttgaaagata tgattcctg acctatacaa tggccattac 4860
cacagcttgg ttaataaatt atatagttca aagtttccaa gatcatatag tttaacatta 4920
gagaaaataa ggaataaaat tgctcctctt acgttgcggt cccttaattt cgtgtcaaat 4980
gtggcaccgc atgccttata tgtataatta aatactactc aggaactgaa gcaatgaaag 5040
tatagaatta attttgtatc tcttgtgttt tgctgatata ggtttcctca ttgggaaatt 5100
t                                                              5101
```

SEQ ID NO: 110       moltype = DNA  length = 1689
FEATURE              Location/Qualifiers
source               1..1689
                      mol_type = other DNA
                      organism = Glycine max

```
SEQUENCE: 110
atgggttggt ttaccaagtt gcttaagggc tctgatcata aaattttca aggacaatac 60
catggcaaat atggagagga cagaatttgg gataatcatc atagttcaat ggatgatttg 120
actgatattg agaagaaga cattgaccat gcaattgcac tttctctgtc agaggaggat 180
cataaaggga aaaaagttgt tgatgaggaa cttttgtaaaa ttgatgatga ggaggatgaa 240
catcttgtta aagttcatct agatgaagat gaacgtcttg ctaaaattca gcaagaagaa 300
gaagaacgtc ttgctaaaat tcaacaagaa gatgagcatc ttgctaaaat tcaacaagaa 360
gaagaagaac gtcttgctaa aattcaacaa gaagatgaat gtcttgctaa aattcaacaa 420
gaggatgaac gtcttgctaa agctcaactt gaggaagacg agcaacttgc taggggcaatt 480
caagaaagct tgaaaattgg ttctcctcct caatatgaca atggttcttc aattctatct 540
tttcctcacc tttttccccc tggatacaga atctgtgctg gatgcaagac tgagattggc 600
caaggaagat ttttaagttg catgggaggt gtctggcatc cagaatgctt ctgctgccat 660
gcatgccatc ttccaatcac tgattatgag ttttccatgt ctagcaatcg cccttaccat 720
aaatcatgct ataggggagaa gcatcaccca agatgtgattg tttgcaagaa ctttatccca 780
actaattcat ctggcctcat tgagtataga gctcatcctt tctggctaca aaaatactgc 840
ccatcgcatg agcttgatgg cacttctcgt tgttgtagtt gcgaaagaat ggagccaagg 900
gatacaaaat atcttttgct tgatgatggt cgaaagctat gtttagagtg tctagactca 960
tcaattatga atactcatga atgccaacct ctttaccttg aaatacaaga atttttatgaa 1020
ggttaaaata tgaaattgga gcaacaaatt cctatgctct tggttgagag acaagcgctg 1080
aatgaggcta tggagggaga aagaatggt catcaccact acccgaaaac tagaggacta 1140
tgcttgtcag aagagcaaac tgtcaccact atttcaagga ggccaaggat tgcagcaggc 1200
taccgagcca tagacatgat aactgaacct tataggctga tccgttgttg tgaagtgaca 1260
gccattcttg ttttgtatgg ccttcctagg ttgttaacag atcaatcct agctcatgag 1320
atgatgcatg catggcttag gcttaaaggt tatcctaacc tcagtccaga agttgaagaa 1380
ggaatctgcc aagttttggc tcatatgtgg ttagaatcag agctctattc tggatttggg 1440
aatgatggtg catcatcctc aacatcatct ttgtcttcgt catcaccttc ctcctcttct 1500
gtctcaacaa agaagggtaa acggtccgac tttgagaaga aacttggtga ttttttaaa 1560
caccagattg agtcagatac ctcctcagct tatggagatg gattcagatt gggtaaccaa 1620
gcaatggtca agtatgggct taaaaggacc cttgaccata tccatatgac aggaagtttt 1680
```

```
ccatattaa                                                                       1689

SEQ ID NO: 111          moltype = AA  length = 563
FEATURE                 Location/Qualifiers
source                  1..563
                        mol_type = protein
                        organism = Glycine max
SEQUENCE: 111
MGWFTKLLKG SDHKILRGQY HGKYGEDRIW DNHHSSMDDL TDIEKEDIDR AIALSLSEED   60
HKGKKVVDEE LCKIDDDEED EHLVKVHLDE DERLAKIQQE EEERLAKIQQ EDEHLAKIQQ  120
EEEERLAKIQ QEDECLAKIQ QEDERLAKAQ LEEDEQLARA IQESLKIGSP PQYDNGSSIL  180
SFPHLFPPGY RICAGCKTEI GQGRFLSCMG GVWHPECFCC HACHLPITDY EFSMSSNRPY  240
HKSCYREKHH PRCDVCKNFI PTNSSGLIEY RAHPFWLQKY CPSHELDGTS RCCSCERMEP  300
RDTKYLLLDD GRKLCLECLD SSIMDTHECQ PLYLEIQEFY EGLNMKLEQQ IPMLLVERQA  360
LNEAMEGEKN GHHHLPETRG LCLSEEQTVT TISRRPRIAA GYRAIDMITE PYRLIRCCEV  420
TAILVLYGLP RLLTGSILAH EMMHAWLRLK GYPNLSPEVE EGICQVLAHM WLESELYSGF  480
GNDGASSSTS SLSSSSPSSS SVSTKKGKRS DFEKKLGDFF KHQIESDTSS AYGDGFRLGN  540
QAMVKYGLKR TLDHIHMTGS FPY                                         563

SEQ ID NO: 112          moltype = DNA  length = 425
FEATURE                 Location/Qualifiers
source                  1..425
                        mol_type = other DNA
                        organism = Glycine max
SEQUENCE: 112
atgggttggt ttaccaagtt gcttaagggc tctgatcata aaatttttca aggacaatac   60
catggcaaat atggagagga cagaatttgg gataatcatc atagttcaat ggtaaacaaa  120
gttttttcctt ttctagtaag aattaaaagc attgccacaa gtcacaacta cgtcattgag  180
ctagcctttt atctgaattt agctttgaga ttagcatgaa gctaacaaag tactacttcc  240
tctgagacat aagcagataa tctgcatttg taatagttac aaactgaatg caggatgatt  300
tgactgatat tgagaaagaa gacattgacc atgcaattgc actttctctg tcagaggagg  360
atcataaagg gaaaaagtt gttggtaaga tttatgctttt gcaccttgg tagttaaagt  420
tcatt                                                              425

SEQ ID NO: 113          moltype = DNA  length = 315
FEATURE                 Location/Qualifiers
source                  1..315
                        mol_type = other DNA
                        organism = Glycine max
SEQUENCE: 113
tctgatcata aaatttttca aggacaatac catggcaaat atggagagga cagaatttgg   60
gataatcatc atagttcaat ggtaaacaaa gttttttcctt ttctagtaag aattaaaagc  120
attgccacaa gtcacaacta cgtcattgag ctagcctttt atctgaattt agctttgaga  180
ttagcatgaa gctaacaaag tactacttcc tctgagacat aagcagataa tctgcatttg  240
taatagttac aaactgaatg caggatgatt tgactgatat tgagaaagaa gacattgacc  300
atgcaattgc acttt                                                   315

SEQ ID NO: 114          moltype = DNA  length = 132
FEATURE                 Location/Qualifiers
source                  1..132
                        mol_type = other DNA
                        organism = Glycine max
SEQUENCE: 114
atgggttggt ttaccaagtt gcttaagggc tctgatcata aaatttttca aggacaatac   60
catggcaaat atggagagga cagaatttgg gataatcatc atagttcaat ggtaaacaaa  120
gttttttcctt tt                                                     132

SEQ ID NO: 115          moltype = DNA  length = 102
FEATURE                 Location/Qualifiers
source                  1..102
                        mol_type = other DNA
                        organism = Glycine max
SEQUENCE: 115
ttaccaagtt gcttaagggc tctgatcata aaatttttca aggacaatac catggcaaat   60
atggagagga cagaatttgg gataatcatc atagttcaat gg                     102

SEQ ID NO: 116          moltype = DNA  length = 62
FEATURE                 Location/Qualifiers
source                  1..62
                        mol_type = other DNA
                        organism = Glycine max
SEQUENCE: 116
tctgatcata aaatttttca aggacaatac catggcaaat atggagagga cagaatttgg   60
ga                                                                  62

SEQ ID NO: 117          moltype = DNA  length = 223
FEATURE                 Location/Qualifiers
source                  1..223
                        mol_type = other DNA
```

```
                        organism = Glycine max
SEQUENCE: 117
ctttgagatt agcatgaagc taacaaagta ctacttcctc tgagacataa gcagataatc    60
tgcatttgta atagttacaa actgaatgca ggatgatttg actgatattg agaaagaaga   120
cattgaccat gcaattgcac tttctctgtc agaggaggat cataaaggga aaaaagttgt   180
tggtaagatt tatgcttttg caccttggta gttaaagttc att                    223

SEQ ID NO: 118          moltype = DNA   length = 143
FEATURE                 Location/Qualifiers
source                  1..143
                        mol_type = other DNA
                        organism = Glycine max
SEQUENCE: 118
tgagacataa gcagataatc tgcatttgta atagttacaa actgaatgca ggatgatttg    60
actgatattg agaaagaaga cattgaccat gcaattgcac tttctctgtc agaggaggat   120
cataaaggga aaaaagttgt tgg                                          143

SEQ ID NO: 119          moltype = DNA   length = 103
FEATURE                 Location/Qualifiers
source                  1..103
                        mol_type = other DNA
                        organism = Glycine max
SEQUENCE: 119
tgcatttgta atagttacaa actgaatgca ggatgatttg actgatattg agaaagaaga    60
cattgaccat gcaattgcac tttctctgtc agaggaggat cat                    103

SEQ ID NO: 120          moltype = DNA   length = 63
FEATURE                 Location/Qualifiers
source                  1..63
                        mol_type = other DNA
                        organism = Glycine max
SEQUENCE: 120
actgaatgca ggatgatttg actgatattg agaaagaaga cattgaccat gcaattgcac    60
ttt                                                                 63

SEQ ID NO: 121          moltype = DNA   length = 263
FEATURE                 Location/Qualifiers
source                  1..263
                        mol_type = other DNA
                        organism = Glycine max
SEQUENCE: 121
taatgtgttt aacttcccat ttcattcatg gaatgctgtt atttctattc tttctagtgt    60
cctgtcgaaa tgttcttta tttctcacta ttgaatgtag ggtcatcacc acttacccga   120
aactagagga ctatgcttgt cagaagagca aactgtcacc actgtaggga tttctcactt   180
gcaaattgaa tcttcacatc taattctgct atagaagatc tgtgtatcaa atagtgattt   240
tattactttt atatatttca tgt                                          263

SEQ ID NO: 122          moltype = DNA   length = 184
FEATURE                 Location/Qualifiers
source                  1..184
                        mol_type = other DNA
                        organism = Glycine max
SEQUENCE: 122
atttctattc tttctagtgt cctgtcgaaa tgttctttta tttctcacta ttgaatgtag    60
ggtcatcacc acttacccga aactagagga ctatgcttgt cagaagagca aactgtcacc   120
actgtaggga tttctcactt gcaaattgaa tcttcacatc taattctgct atagaagatc   180
tgtg                                                               184

SEQ ID NO: 123          moltype = DNA   length = 143
FEATURE                 Location/Qualifiers
source                  1..143
                        mol_type = other DNA
                        organism = Glycine max
SEQUENCE: 123
cctgtcgaaa tgttctttta tttctcacta ttgaatgtag ggtcatcacc acttacccga    60
aactagagga ctatgcttgt cagaagagca aactgtcacc actgtaggga tttctcactt   120
gcaaattgaa tcttcacatc taa                                          143

SEQ ID NO: 124          moltype = DNA   length = 103
FEATURE                 Location/Qualifiers
source                  1..103
                        mol_type = other DNA
                        organism = Glycine max
SEQUENCE: 124
tttctcacta ttgaatgtag ggtcatcacc acttacccga aactagagga ctatgcttgt    60
cagaagagca aactgtcacc actgtaggga tttctcactt gca                    103

SEQ ID NO: 125          moltype = DNA   length = 63
FEATURE                 Location/Qualifiers
```

```
                         source          1..63
                                         mol_type = other DNA
                                         organism = Glycine max
SEQUENCE: 125
ggtcatcacc acttacccga aactagagga ctatgcttgt cagaagagca aactgtcacc      60
act                                                                   63

SEQ ID NO: 126           moltype = DNA   length = 35
FEATURE                  Location/Qualifiers
source                   1..35
                         mol_type = other DNA
                         organism = Glycine max
SEQUENCE: 126
acccgaaact agaggactat gcttgtcaga agagc                                 35

SEQ ID NO: 127           moltype = DNA   length = 243
FEATURE                  Location/Qualifiers
source                   1..243
                         mol_type = other DNA
                         organism = Glycine max
SEQUENCE: 127
atgggttggt ttaccaagtt gcttaagggc tctgatcata aaattttca aggacaatac       60
catggcaaat atggagagga cagaatttgg gataatcatc atagttcaat ggatgatttg     120
actgatattg agaagaaga cattgaccat gcaattgcac tttctctgtc agaggaggat     180
cataaaggga aaaagttgt tgatgaggaa ctttgtaaaa ttgatgatga ggaggatgaa     240
cat                                                                  243

SEQ ID NO: 128           moltype = DNA   length = 172
FEATURE                  Location/Qualifiers
source                   1..172
                         mol_type = other DNA
                         organism = Glycine max
SEQUENCE: 128
atgggttggt ttaccaagtt gcttaagggc tctgatcata aaattttca aggacaatac       60
catggcaaat atggagagga cagaatttgg gataatcatc atagttcaat ggatgatttg     120
actgatattg agaagaaga cattgaccat gcaattgcac tttctctgtc ag              172

SEQ ID NO: 129           moltype = DNA   length = 132
FEATURE                  Location/Qualifiers
source                   1..132
                         mol_type = other DNA
                         organism = Glycine max
SEQUENCE: 129
atgggttggt ttaccaagtt gcttaagggc tctgatcata aaattttca aggacaatac       60
catggcaaat atggagagga cagaatttgg gataatcatc atagttcaat ggatgatttg     120
actgatattg ag                                                        132

SEQ ID NO: 130           moltype = DNA   length = 103
FEATURE                  Location/Qualifiers
source                   1..103
                         mol_type = other DNA
                         organism = Glycine max
SEQUENCE: 130
tttaccaagt tgcttaaggg ctctgatcat aaaattttc aaggacaata ccatggcaaa       60
tatggagagg acagaatttg ggataatcat catagttcaa tgg                      103

SEQ ID NO: 131           moltype = DNA   length = 63
FEATURE                  Location/Qualifiers
source                   1..63
                         mol_type = other DNA
                         organism = Glycine max
SEQUENCE: 131
ctctgatcat aaaattttc aaggacaata ccatggcaaa tatggagagg acagaatttg       60
gga                                                                   63

SEQ ID NO: 132           moltype = DNA   length = 223
FEATURE                  Location/Qualifiers
source                   1..223
                         mol_type = other DNA
                         organism = Glycine max
SEQUENCE: 132
gcttaagggc tctgatcata aaattttca aggacaatac catggcaaat atggagagga       60
cagaatttgg gataatcatc atagttcaat ggatgatttg actgatattg agaagaaga     120
cattgaccat gcaattgcac tttctctgtc agaggaggat cataaaggga aaaagttgt     180
tgatgaggaa ctttgtaaaa ttgatgatga ggaggatgaa cat                      223

SEQ ID NO: 133           moltype = DNA   length = 143
FEATURE                  Location/Qualifiers
source                   1..143
```

```
                                      mol_type = other DNA
                                      organism = Glycine max
SEQUENCE: 133
catggcaaat atggagagga cagaatttgg gataatcatc atagttcaat ggatgatttg    60
actgatattg agaaagaaga cattgaccat gcaattgcac tttctctgtc agaggaggat   120
cataaaggga aaaaagttgt tga                                           143

SEQ ID NO: 134              moltype = DNA   length = 103
FEATURE                     Location/Qualifiers
source                      1..103
                            mol_type = other DNA
                            organism = Glycine max
SEQUENCE: 134
cagaatttgg gataatcatc atagttcaat ggatgatttg actgatattg agaaagaaga    60
cattgaccat gcaattgcac tttctctgtc agaggaggat cat                     103

SEQ ID NO: 135              moltype = DNA   length = 63
FEATURE                     Location/Qualifiers
source                      1..63
                            mol_type = other DNA
                            organism = Glycine max
SEQUENCE: 135
atagttcaat ggatgatttg actgatattg agaaagaaga cattgaccat gcaattgcac    60
ttt                                                                  63

SEQ ID NO: 136              moltype = DNA   length = 263
FEATURE                     Location/Qualifiers
source                      1..263
                            mol_type = other DNA
                            organism = Glycine max
SEQUENCE: 136
agaattttat gaaggtttaa atatgaaatt ggagcaacaa attcctatgc tcttggttga    60
gagacaagcg ctgaatgagg ctatggaggg agaaaagaat ggtcatcacc acttacccga   120
aactagagga ctatgcttgt cagaagagca aactgtcacc actatttcaa ggaggccaag   180
gattgcagca ggctaccgag ccatagacat gataactgaa cctataggc tgatccgttg    240
ttgtgaagtg acagccattc ttg                                           263

SEQ ID NO: 137              moltype = DNA   length = 183
FEATURE                     Location/Qualifiers
source                      1..183
                            mol_type = other DNA
                            organism = Glycine max
SEQUENCE: 137
attcctatgc tcttggttga gagacaagcg ctgaatgagg ctatggaggg agaaaagaat    60
ggtcatcacc acttacccga aactagagga ctatgcttgt cagaagagca aactgtcacc   120
actatttcaa ggaggccaag gattgcagca ggctaccgag ccatagacat gataactgaa   180
cct                                                                 183

SEQ ID NO: 138              moltype = DNA   length = 143
FEATURE                     Location/Qualifiers
source                      1..143
                            mol_type = other DNA
                            organism = Glycine max
SEQUENCE: 138
gagacaagcg ctgaatgagg ctatggaggg agaaaagaat ggtcatcacc acttacccga    60
aactagagga ctatgcttgt cagaagagca aactgtcacc actatttcaa ggaggccaag   120
gattgcagca ggctaccgag cca                                           143

SEQ ID NO: 139              moltype = DNA   length = 103
FEATURE                     Location/Qualifiers
source                      1..103
                            mol_type = other DNA
                            organism = Glycine max
SEQUENCE: 139
ctatggaggg agaaaagaat ggtcatcacc acttacccga aactagagga ctatgcttgt    60
cagaagagca aactgtcacc actatttcaa ggaggccaag gat                     103

SEQ ID NO: 140              moltype = AA    length = 82
FEATURE                     Location/Qualifiers
source                      1..82
                            mol_type = protein
                            organism = Glycine max
SEQUENCE: 140
MGWFTKLLKG SDHKILRGQY HGKYGEDRIW DNHHSSMDDL TDIEKEDIDR AIALSLSEED    60
HKGKKVVDEE LCKIDDDEED EH                                             82

SEQ ID NO: 141              moltype = AA    length = 41
FEATURE                     Location/Qualifiers
source                      1..41
```

```
                            mol_type = protein
                            organism = Glycine max
SEQUENCE: 141
MGWFTKLLKG SDHKILRGQY HGKYGEDRIW DNHHSSMDDL T                    41

SEQ ID NO: 142              moltype = AA   length = 41
FEATURE                     Location/Qualifiers
source                      1..41
                            mol_type = protein
                            organism = Glycine max
SEQUENCE: 142
DIEKEDIDRA IALSLSEEDH KGKKVVDEEL CKIDDDEEDE H                    41

SEQ ID NO: 143              moltype = AA   length = 61
FEATURE                     Location/Qualifiers
source                      1..61
                            mol_type = protein
                            organism = Glycine max
SEQUENCE: 143
IPMLLVERQA LNEAMEGEKN GHHHLPETRG LCLSEEQTVT TISRRPRIAA GYRAIDMITE 60
P                                                                61

SEQ ID NO: 144              moltype = AA   length = 41
FEATURE                     Location/Qualifiers
source                      1..41
                            mol_type = protein
                            organism = Glycine max
SEQUENCE: 144
LNEAMEGEKN GHHHLPETRG LCLSEEQTVT TISRRPRIAA G                    41

SEQ ID NO: 145              moltype = AA   length = 21
FEATURE                     Location/Qualifiers
source                      1..21
                            mol_type = protein
                            organism = Glycine max
SEQUENCE: 145
GHHHLPETRG LCLSEEQTVT T                                          21

SEQ ID NO: 146              moltype = AA   length = 9
FEATURE                     Location/Qualifiers
source                      1..9
                            mol_type = protein
                            organism = Glycine max
SEQUENCE: 146
LPETRGLCL                                                        9

SEQ ID NO: 147              moltype = DNA   length = 23
FEATURE                     Location/Qualifiers
source                      1..23
                            mol_type = other DNA
                            organism = synthetic construct
SEQUENCE: 147
aaggctccga tcataataag ctt                                        23

SEQ ID NO: 148              moltype = DNA   length = 23
FEATURE                     Location/Qualifiers
source                      1..23
                            mol_type = other DNA
                            organism = synthetic construct
SEQUENCE: 148
tgagtctctt ccaccagaga cag                                        23

SEQ ID NO: 149              moltype = DNA   length = 23
FEATURE                     Location/Qualifiers
source                      1..23
                            mol_type = other DNA
                            organism = synthetic construct
SEQUENCE: 149
aaggacaata ccatggcaaa tat                                        23

SEQ ID NO: 150              moltype = DNA   length = 23
FEATURE                     Location/Qualifiers
source                      1..23
                            mol_type = other DNA
                            organism = synthetic construct
SEQUENCE: 150
actgatattg agaaagaaga cat                                        23

SEQ ID NO: 151              moltype = DNA   length = 23
```

```
FEATURE                 Location/Qualifiers
source                  1..23
                        mol_type = other DNA
                        organism = synthetic construct
SEQUENCE: 151
ttgggcaggg ccactatcac atg                                          23

SEQ ID NO: 152          moltype = DNA   length = 23
FEATURE                 Location/Qualifiers
source                  1..23
                        mol_type = other DNA
                        organism = synthetic construct
SEQUENCE: 152
tcacatgccg gaaaccagag ggc                                          23

SEQ ID NO: 153          moltype = DNA   length = 23
FEATURE                 Location/Qualifiers
source                  1..23
                        mol_type = other DNA
                        organism = synthetic construct
SEQUENCE: 153
agaggcagag ccctctggtt tcc                                          23

SEQ ID NO: 154          moltype = DNA   length = 4799
FEATURE                 Location/Qualifiers
source                  1..4799
                        mol_type = other DNA
                        organism = synthetic construct
SEQUENCE: 154
atgggttggt ttaccaagtt gcttaagggc tctgatcata aaattttca aggacaatac    60
caggagagga cagaatttgg gataatcatc atagttcaat ggtaaacaaa gttttttcctt  120
ttctagtaag aattaaaagc attgccacaa gtcacaacta cgtcattgag ctagcctttt  180
atctgaattt agctttgaga ttagcatgaa gctaacaaag tactacttcc tctgagacat  240
aagcagataa tctgcatttg taatagttac aaactgaatg caggatgatt tgactgatat  300
tgagaaagaa gacattgacc atgcaattgc acttctctg tcagaggagg atcataaagg   360
gaaaaaagtt gttggtaaga tttatgcttt tgcaccttgg tagttaaagt tcatttcctg   420
gttagtttgg ctcaaattta atgctgttat gattctgcat actgcatatg aggtacctaa   480
actctaagat ctgaatctaa ccaaaatgct cgatgattta gtacaagctc ttacttacct   540
cttgtattat ttcctgtctt tctatgccta tttcagtgtc tcttcattc ttgtttaagt    600
agattatgct ttgtgaacac cccaaaaaaa ggtcatgctt tgttgatgaa aggctatgat   660
gctatcagtt gagtctttca tttacatctg aatcagaatg gaactaagaa ataaattttt   720
aaattactac aattagcttc tagattactt taaaatataa atttaacatg catataagaa   780
ttatggggat attctgattc tggtgtttca cttaagttgc aactcaaagt gcttaaagta   840
tatttcttag ttaagagtcc attgaagaat ttttcaaaa aatacaaaaa agagtacatt    900
gaagaaaatc tgaagtttca tttggtttat gtgttcagaa agtgcatgtg ttaatcaatt   960
aattatttcc acaccaaagc ataaccaaaa ggtctcatgt tttttgtctc ataatacct   1020
agattatgac tctcaatctg aagatgagga acttttgtaaa attgatgatg aggaggatga  1080
acatcttgtt aaagttcatc tagatgaaga tgaacgtctt gctaaaattc agcaagaaga  1140
agaagaacgt cttgctaaaa ttcaacaaga agatgagcat cttgctaaaa ttcaacaaga  1200
agaagaagaa cgtcttgcta aaattcaaca agaagatgaa tgtcttgcta aaattcaaca  1260
agaggatgaa cgtcttgcta aagctcaact tgaggaagac gagcaacttg ctagggcaat  1320
tcaagaaagc ttgaaaattg gttctcctcc tcaatatgac aatggttctt caattctatc  1380
ttttcctcac cttttccccc ctggatacag gtaattgttg gtatgatcac atcttttatc  1440
tatatagcaa gtccttatac tgttttttgga aattgttgaa gtacactagt tctaaatgaa  1500
cagaccaata atgtaattgt gccaaaaata agaaaaacaa aaaattttcca aactgaatat  1560
gttttgaaac ttcaatttaa gtattgctga tttgagtgat aggtcataca actaactgat  1620
ctggacttca tacaagctaa tcaatcttat tttatgagat tctagtctga atcattgaac  1680
tgggataaat gctgtattgg gattttatgc atgacacctt ggtgtgcgtt ggttttcctt  1740
agtgttctta gtaccttca aattagatga aaatttttaaa aaatagtagt tattaaaatg   1800
aacattttcat aatttgatta cttaagttctt atttatggtg atcctgagca cttcctgtag  1860
aatagcttgg agtgatttca tgatcatcta ataataaaa ttgaaatact ctcctctgtt   1920
gcaatattgt ggacctatat aatcgacatc tttgaaattt attttttcaag gtttcatgaa   1980
tctttattaa ttattagaaa caaagattta acctttttc tgtaaaatct gcctgcagaa   2040
tctgtgctgg atgcaagact gagattggcc aaggaagatt tttaagttgc atgggaggtg   2100
tctggcatcc agaatgcttc tgctgccatg catgccatct tccaatcact gattatgagg   2160
ttagagacta gagtctgttt tcttttgct gcttgtttcg caaagctgaa tttaattaca    2220
ataagttgaa accttgtttt tttggtgaaa gaaaagttg aaaattattc ttagcttcat    2280
aaatgaaggt cttcaattta ttttctcttgt ttgtcaatct caatatgatt atgcttaatt   2340
cgtcccttta cagttttcca tgtctagcaa tcgcccttac cataaatcat gctatagga    2400
gaagcatcac ccaagatgtg atgtttgcaa gaacttgta agtatcttca ccagttgttt    2460
ttcactcaca gttgtctatt agccttggtt tggttgtggg gaaggaagta ctattcaaca   2520
gcaaatttc aaaaaatagt gtgggtccta caccatttt tttttctcta ctttaattca    2580
aatatttctt ctcaattctt ttctcttcca cacaaccaaa catactctta gtcaatactg   2640
tgtgcttgtt tcttttcaaa ggtttctatc aattttgatg tgcttttagaa gcttacaag   2700
atgcatatac aaggaagact gttgatattg agttgttctt gcttctcaga tagatcagaa   2760
ttccaaacta tacttgagaa agttctgctg aactcagcag ttgtttaatc tttataacaa   2820
atcatgggct attgatctta ctgaaataac atcatgggag ctcttcatga agctaatatt   2880
tgtatatttt tatattttgg gccagacagt ctgtttgggc ccagcccaat gtggttatac    2940
ctcttggggt ttatacatgc atagactcaa atcttaatat tttgaatgta atgttaggat   3000
```

```
ttgagctatt gtatcctgca cctcccatta cattctggaa agcccattcc ggaatgcaaa  3060
tttacattcc ggaatgggat ttccggaatg cagtgaggtg taggatgcaa tagtgggagt  3120
gcctatgctg tgtaatggtg ataaacccca atgtggctat ccctcttggg atttcataat  3180
ttttttaaag acttggatac ttcatcgata cgtattggtg aagtatccaa tagtattggt  3240
atcggatacg tgaaaaaaat tgaagtattc gctcttcatg aacagacctt aagtttgcgt  3300
tttttttta aaaaaaaatg gcagtaagat atattgttca gtaaactaga attattggtt  3360
ctttccttgt agatcccaac taattcatct ggcctcattg agtatagagc tcatcctttc  3420
tggctacaaa aatactgccc atcgcatgag cttgatggca cttctcgttg ttgtagttgc  3480
gaaagaatgg aggttagtta tattgactcc caaatctttt catcctatta ttatcaatta  3540
gaagctaact gttggatcct tcctctcctc ccccattccc tgtcccgttt tcttgccttt  3600
tcaatcaatg cagccaaggg atacaaaata tcttttgctt gatgatggtc gaaagctatg  3660
tttagagtgt ctagactcat caattatgga tactcatgaa tgccaacctc tttaccttga  3720
aatacaagaa ttttatgaag gtttaaatat gaaattggag caacaaattc ctatgctctt  3780
ggttgagaga caagcgctga atgaggctat ggagggagaa aagaatgtaa gtgttaatgt  3840
gtttaacttc ccatttcatt catggaatgc tgttatttct attctttcta gtgtcctgtc  3900
gaaatgttct tttatttctc actattgaat gtagggtcat caccacttac ccgaaactag  3960
aggactatgc ttgtcagaag agcaaactgt caccactgta gggatttctc acttgcaaat  4020
tgaatcttca catctaattc tgctatagaa gatctgtgta tcaaatagtg attttattac  4080
ttttatatat ttcatgtaat actagatttc aaggaggcca aggattgcag caggctaccg  4140
agccatagac atgataactg aaccttatag gctgatccgt tgttgtgaag tgacagccat  4200
tcttgttttg tatggccttc ctaggtatcc ttcttgtaca atctactttc ataatctaca  4260
gtgcttgcat atgacattcc tcatatataa ttcaattttt tttatgttt ataggttgtt  4320
aacaggatca atcctagctc atgagatgat gcatgcatgg cttaggctta aaggtattca  4380
gccattaaca tgatccagaa aagtttatat atttgtttca tggtgccaag ttggacaaaa  4440
tttctggggtt tttgacaggt tatcctaacc tcagtccaga agttgaagaa ggaatctgcc  4500
aagttttggc tcatatgtgg ttagaatcag agctctattc tggattttggg aatgatggtg  4560
catcatcctc aacatcatct ttgtcttcgt catccaccttc ctcctcttct gtctcaacaa  4620
agaagggtaa acgtccgac tttgagaaga aacttggtga tttttttaaa caccagattg  4680
agtcagatac ctcctcagct tatggagatg gattcagatt gggtaaccaa gcaatggtca  4740
agtatgggct taaaaggacc cttgaccata tccatatgac aggaagtttt ccatattaa   4799

SEQ ID NO: 155           moltype = DNA   length = 4802
FEATURE                  Location/Qualifiers
source                   1..4802
                         mol_type = other DNA
                         organism = synthetic construct
SEQUENCE: 155
atgggttggt ttaccaagtt gcttaagggc tctgatcata aaattttttca aggacaatac   60
catgtggaga ggacagaatt tgggataatc atcatagttc aatggtaaac aaagttttc   120
cttttctagt aagaattaaa agcattgcca caagtcacaa ctacgtcatt gagctagcct  180
tttatctgaa tttagctttg agattagcat gaagctaaca aagtactact tcctctgaga  240
cataagcaga taatctgcat ttgtaatagt tacaaactga atgcaggatg atttgactga  300
tattgagaaa gaagacattg accatgcaat tgcacttttc ctgtcagagg aggatcataa  360
agggaaaaaa gttgttggta agatttatgc ttttgcacct tggtagttaa agttcatttc  420
ctggttagtt tggctcaaat ttaatgctgt tatgattctg catactgcat atgaggtacc  480
taaactctaa gatctgaatc taaccaaaat gctcgatgat ttagtacaag ctcttactta  540
cctcttgtat tatttcctgt cttttctatgc ctatttcagt gtcttcttca ttcttgttta  600
agtagattat gctttgtgaa cacccccaaaa aaaggtcatg ctttgttgat gaaaggctat  660
gatgctatca gttgagtctt tcatttacat ctgaatcaga atggaactaa gaaataaatt  720
tttaaattac tacaattagc ttctagatta ctttaaaata taaatttaac atgcatataa  780
gaattatggg gatattctga ttctggtgtt tcacttaagt tgcaactcaa agtgcttaaa  840
gtatatttct tagttaagag tccattgaag aattttttca aaaaatacaa aaaagagtac  900
attgaagaaa atctgaagtt tcatttggtt tatgtgttca gaaagtgcat gtgttaatca  960
attaattatt tccacaccaa agcataacca aaaggtctca tgtttttttgt ctcataatac 1020
cctagattat gactctcaat ctgaagatga ggaacttttgt aaaattgatg atgaggagga 1080
tgaacatctt gttaaagttc atctagatga agatgaacgt cttgctaaaa ttcagcaaga 1140
agaagaagaa cgtcttgcta aaattcaaca agaagatgag catcttgcta aaattcaaca 1200
agaagaagaa gaacgtcttg ctaaaattca acaagaagat gaatgtcttg ctaaaattca 1260
acaagaggat gaacgtcttg ctaaagctca acttgaggaa gacgagcaac ttgctagggc 1320
aattcaagaa agcttgaaaa ttggttctct tcctcaatat gacaatggtt cttcaattcc 1380
atcttttcct caccttttcc cccctggata caggtaattg ttggtatgat cacatctttt 1440
atctatatag caagtcctta tactgttttt ggaaattgtt gaagtacact agttctaaat 1500
gaacagacca ataatgtaat tgtgccaaaa ataagaaaaa caaaaaattt ccaaactgaa 1560
tatgttttga aacttcaatt taagtattgc tgatttgagt gataggtcat acaactaact 1620
gatctggact tcatacaagc taatcaatct tattttatga gattctagtc tgaatcattg 1680
aactgggata aatgctgtat tgggatttta tgcatgacac cttggtgtgc gttggttttc 1740
cttagtgttc ttaagtacct ttcaattaga tgaaaatttt aaaaaatagt agttattaaa 1800
atgaacattt cataatttga ttacttaagt cttatttatg tgtgatcctga gcacttcctg 1860
tagaatagct tggagtgatt tcatgatcat ctaataaata aattgaaat actctcctct 1920
gttgcaatat tgtggaccta tataatcgac atctttgaaa tttattttttc aaggtttcat 1980
gaatctttat taattattag aaacaaagat ttaacctttt ttctgtaaaa tctgcctgca 2040
gaatctgtgc tggatgcaag actgagattg gccaaggaag attttaagt tgcatgggag 2100
gtgtctggca tccagaatgc ttctgctgcc atgcatgcca tcttccaatc actgattatg 2160
aggttagga ctagagtctt gtttttctttt gctgcttgtt tcgcaaagct gaatttaatt 2220
acaataagtt gaaaccttgt ttttttggtg aaagaaaaag ttgaaaatta tcttagctt 2280
cataaatgaa ggtcttcaat ttatttctct tgtttgtcaa tctcaatatg attatgctta 2340
attcgtccct ttacagtttt ccatgtctag caatcgccct taccataaat catgctatag 2400
ggagaagcat caccccaagat gtgatgtttg caagaacttt gtaagtatct tcaccagttg 2460
ttttttcactc acagttgtct attagccttg gtttggttgt ggggaaggaa gtactattca 2520
```

```
acagcaaatt ttcaaaaaat agtgtgggtc ctacaccatt ttttttttct ctactttaat    2580
tcaaatattt cttctcaatt cttttctctt ccacacaacc aaacatactc ttagtcaata    2640
ctgtgtgctt gttttctttc aaaggtttct atcaatttg atgtgcttta gaagctttac    2700
aagatgcata tacaaggaag actgttgata ttgagttgtt cttgcttctc agatagatca    2760
gaattccaaa ctatacttga gaaagttctg ctgaactcga cagttgttta atctttataa    2820
caaatcatgg gctattgatc ttactgaaat aacatcatgg gagctcttca tgaagctaat    2880
atttgtatat ttttatattt tgggccagac agtctgtttg ggcccagccc aatgtggtta    2940
tacctcttgg ggtttataca tgcatagact caaatcttaa tattttgaat gtaatgttag    3000
gatttgagct attgtatcct gcaccctccca ttacattcgt gaaagcccat tccggaatgc    3060
aaatttacat tccggaatgg gatttccgga atgcagtgag gtgtaggatg caatagtggg    3120
agtgcctatg ctgtgtaatg tgcataaacc ccaatgtggc tatccctctt gggatttcat    3180
aattttttta aagacttgga tacttcatcg atacgtattg gtgaagtatc caatagtatt    3240
ggtatcggat acgtgaaaaa aattgaagta ttcgctcttc atgaacagac cttaagtttg    3300
cgtttttttt ttaaaaaaaa atggcagtaa gatatattgt tcagtaaact agaattattg    3360
gttctttcct tgtagatccc aactaattca tctggcctca ttgagtatag agctcatcct    3420
ttctggctac aaaaatactg cccatcgcat gagcttgatg gcacttctcg ttgttgtagt    3480
tgcgaaagaa tggaggttag ttatattgac tcccaaatct tttcatccta ttattatcaa    3540
ttagaagcta actgttggat ccttcctctc ctccccccatt ccctgtcccg ttttcttgcc    3600
ttttcaatca atgcagccaa gggatacaaa atatctttg cttgatgatg gtcgaaagct    3660
atgtttagag tgtctagact catcaattat ggatactcat gaatgccaac ctctttacct    3720
tgaaatacaa gaatttatg aaggtttaaa tatgaaattg agcaacaaa ttcctatgct    3780
cttggttgga agacaagcgc tgaatgaggc tatggaggga gaaaagaatg taagtgttaa    3840
tgtgtttaac ttcccattc attcatggaa tgctgttatt tctattcttt ctagtgtcct    3900
gtcgaaatgt tctttatttt ctcactattg aatgtagggt catcaccact tacccgaaac    3960
tagaggacta tgcttgtcag aagagcaaac tgtcaccact gtagggattt ctcacttgca    4020
aattgaatct tcacatctaa ttctgctata gaagatctgt gtatcaaata gtgattttat    4080
tactttata tatttcatgt aatactagat ttcaaggagg ccaaggattg cagcaggcta    4140
ccgagccata gacatgataa ctgaacctta taggctgatc cgttgttgtg aagtgacagc    4200
cattcttgtt ttgtatggcc ttcctaggta tccttcttgt acaatctact ttcataatct    4260
acagtgcttg catatgacat tcctcatata taattcaatt ttttttatg ttttataggtt    4320
gttaacagga tcaatcctag ctcatgagat gatgcatgca tggcttaggc ttaaaggtat    4380
tcagccatta acatgatcca gaaaagttta tatatttgtt tcatggtgcc aagttggaca    4440
aaatttctgg gttttgaca ggttatccta acctcagtcc agaagttgaa gaggaatcc    4500
gccaagtttt ggctcatatg tggttagaat tctggattt tctggattt gggaatgatg    4560
gtgcatcatc ctcaacatca tctttgtctt cgtcatcacc ttcctcctct tctgtctcaa    4620
caaagaaggg taaacggtcc gactttgaga agaaacttgg tgatttttt aaacaccaga    4680
ttgagtcaga tacctcctca gcttatgag atggattcag attgggtaac caagcaatgg    4740
tcaagtatgg gcttaaaagg acccttgacc atatccatat gacaggaagt tttccatatt    4800
aa                                                                   4802

SEQ ID NO: 156           moltype = DNA   length = 4801
FEATURE                  Location/Qualifiers
source                   1..4801
                         mol_type = other DNA
                         organism = synthetic construct
SEQUENCE: 156
atgggttggt ttaccaagtt gcttaagggc tctgatcata aaattttca aggacaatac      60
caatggagag gacagaattt gggataatca tcatagttca atggtaaaca aagttttcc     120
tttttctagta agaattaaaa gcattgccac aagtcacaac tacgtcattg agctagcctt    180
ttatctgaat ttagctttga gattagcatg aagctaacaa agtactactt cctctgagac    240
ataagcagat aatctgcatt tgtaatagtt acaaactgaa tgcaggatga tttgactgat    300
attgagaaag aagacattga ccatgcaatt gcactttctc tgtcagagga ggatcataaa    360
gggaaaaaag ttgttggtaa gatttatgct tttgcacctt ggtagttaaa gttcatttcc    420
tggttagttt ggctcaaatt taatgctgtt atgattctgc atactgcata tgaggtacct    480
aaactctaag atctgaatct aaccaaaatg ctcgatgatt tagtacaagc tcttacttac    540
ctcttgtatt atttcctgtc tttcatgcc tatttcagtg tcttcttcat tcttgtttaa    600
gtagattatg ctttgtgaac accccaaaaa aaggtcatgc tttgttgatg aaaggctatg    660
atgctatcag ttgagtcttt catttacatc tgaatcagaa tggaactaag aaataaattt    720
ttaaattact acaattagct tctagattac tttaaaaaat aaattttaaca tgcatataag    780
aattatgggg atattctgat tctggtgttt cacttaagtt gcaactcaaa gtgcttaaag    840
tatatttctt agttaagagt ccattgaaga atttttcaa aaaatacaaa aaagagtaca    900
ttgaagaaaa tctgaagttt catttggttt atgtgttcag aaagtgcatg tgttaatcaa    960
ttaattattt ccacaccaaa gcataaccaa aaggtctcat gttttttgtc tcataatacc   1020
ctagattatg actctcaatc tgaagatgag gaacttgta aattgatga tgaggaggat   1080
gaacatcttg ttaaagttca tctagatgaa gatgaacgtc ttgctaaaat tcagcaagaa   1140
gaagaagaac gtcttgctaa aattcaacaa gaagatgagc atcttgctaa aattcaacaa   1200
gaagaagaag aacgtcttgc taaaattcaa caagaagatg aatgtcttgc taaaattcaa   1260
caagaggatg aacgtcttgc taaagctcaa cttgaggaag acgagcaact tgctagggca   1320
attcaagaaa gcttgaaaat tggttctcct cctcaatatg acaatgttc ttcaattcta   1380
tcttttcctc acctttcccc cctggatac aggtaattgt tggtatgatc acatcttta   1440
tctatatagc aagtccttat actgttttg gaaattgttg aagtacacta gttcaaatg   1500
aacagaccaa taatgtaatt gtgccaaaaa taagaaaaac aaaaaattc caaactgaat   1560
atgtttgaa acttcaattt aagtattgct gatttgagtg ataggtcata caactaactg   1620
atctgactt catacaagct aatcaatct attttatgag attctagtct gaatcattga   1680
actgggataa atgctgtatt gggattttat gcatgacacc ttggtgtgcg ttggttttcc   1740
ttagtgttct taagtacctt tcaattagat gaaaattta aaaaaatagta gttattaaaa   1800
tgaacatttc ataattgat tacttaagtc ttatttatgg tgatcctgag cacttcctgt   1860
agaatagctt ggagtgattt catgatcatc taataaaataa aattgaaata ctctcctctg   1920
ttgcaatatt gtggacctat ataatcgaca tctttgaaat ttatttttca aggtttcatg   1980
```

```
aatctttatt aattattaga aacaaagatt taaccttttt tctgtaaaat ctgcctgcag    2040
aatctgtgct ggatgcaaga ctgagattgg ccaaggaaga ttttaagtt gcatgggagg     2100
tgtctggcat ccagaatgct tctgctgcca tgcatgccat cttccaatca ctgattatga    2160
ggttagagac tagagtcttg ttttcttttg ctgcttgttt cgcaaagctg aatttaatta    2220
caataagttg aaaccttgtt tttttggtga aagaaaaagt tgaaaattat tcttagcttc    2280
ataaatgaag gtcttcaatt tatttctctt gtttgtcaat ctcaatatga ttatgcttaa    2340
ttcgtcccct tacagttttc catgtctagc aatcgcccct accataaatc atgctatagg    2400
gagaagcatc acccaagatg tgatgtttgc aagaactttg taagtatctt caccagttgt    2460
ttttcactca cagttgtcta ttagccttgg tttggttgtg gggaaggaag tactattcaa    2520
cagcaaattt tcaaaaaata gtgtgggtcc tacaccattt ttttttctc tactttaatt    2580
caaatatttc ttctcaattc ttttctcttc cacacaacca aacatactct tagtcaatac    2640
tgtgtgcttg ttttctttca aaggtttcta tcaattttga tgtgctttag aagctttaca    2700
agatgcatat acaaggaaga ctgttgatat tgagttgttc ttgcttctca gatagatcag    2760
aattccaaac tatacttgag aaagttctgc tgaactcagc agttgtttaa tcttataac    2820
aaatcatggg ctattgatct tactgaaata acatcatggg agctcttcat gaagctaata    2880
tttgtatatt tttatatttt gggccagaca gtctgtttgg gcccagccca atgtggttat    2940
acctcttggg gtttatacat gcatagactc aaatcttaat attttgaatg taatgttagg    3000
atttgagcta ttgtatcctg cacctcccat tacattcttg aaagcccatt ccggaatgca    3060
aatttacatt ccggaatggg atttccggaa tgcagtgagg tgtaggatgc aatagtggga    3120
gtgcctatgc tgtgtaatgt gcataaaccc caatgtggct atccctcttg ggatttcata    3180
atttttttaa agacttggat acttcatcga tacgtattgg tgaagtatcc aatagtattg    3240
gtatcggata cgtgaaaaaa attgaagtat tcgctcttca gaacagaca ttaagtttgc    3300
gttttttttt taaaaaaaaa tggcagtaag atatattgtt cagtaaacta gaattattgg    3360
ttctttcctt gtagatccca actaattcat ctggcctcat tgagtataga gctcatcctt    3420
tctggctaca aaaatactgc ccatcgcatg agcttgatgg cacttctcgt tgttgtagtt    3480
gcgaaagaat ggaggttagt tatattgact cccaaatctt ttcatcctat tattatcaat    3540
tagaagctaa ctgttggatc cttcctctcc tcccccattc cctgtcccgt tttcttgcct    3600
tttcaatcaa tgcagccaag ggatacaaaa tatcttttgc ttgatgatgg tcgaaagcta    3660
tgtttagagt gtctagactc atcaattatg gatactcatg aatgccaacc tctttacctt    3720
gaaatacaag aattttatga aggtttaaat atgaaattgg agcaacaaat tcctatgctc    3780
ttggttgaga gacaagcgct gaatgaggct atggagggag aaaagaatgt aagtgttaat    3840
gtgtttaact tcccatttca ttcatggaat gctgttattt ctattctttc tagtgtcctg    3900
tcgaaatgtt cttttatttc tcactattga atgtagggtc atcaccactt acccgaaact    3960
agaggactat gcttgtcaga agagcaaact gtcaccactg tagggatttc tcacttgcaa    4020
attgaatctt cacatctaat tctgctatag aagatctgtg tatcaaatag tgatttatt     4080
actttatat atttcatgta atactagatt tcaaggaggc caaggattgc agcaggctac    4140
cgagccatag acatgataac tgaacctttat aggctgatcc gttgttgtga agtgacagcc    4200
attcttgttt tgtatggcct tcctaggtat ccttcttgta caatctactt tcataatcta    4260
cagtgcttgc atatgacatt cctcatatat aattcaattt ttttttatgt ttataggttg    4320
ttaacaggat caatcctagc tcatgagatg atgcatgcat ggcttaggct taaaggtatt    4380
cagccattaa catgatccag aaaagtttat atatttgttt catggtgcca agttggacaa    4440
aatttctggg ttttttgacag gttatcctaa cctcagtcca gaagttgaag aaggaatctg    4500
ccaagttttg gctcatatgt ggttagaatc agagctctat tctggatttg ggaatgatgg    4560
tgcatcatcc tcaacatcat ctttgtcttc gtcatcacct tcctcctctt ctgtctcaac    4620
aaagaagggt aaacggtccg actttgagaa gaaacttggt gatttttta aacaccagat    4680
tgagtcagat acctcctcag cttatggaga tggattcaga ttgggtaacc aagcaatggt    4740
caagtatggg cttaaaagga cccttgacca tatccatatg acaggaagtt ttccatatta    4800
a                                                                   4801
SEQ ID NO: 157      moltype = DNA  length = 6385
FEATURE             Location/Qualifiers
source              1..6385
                    mol_type = other DNA
                    organism = synthetic construct
SEQUENCE: 157
atgggttggc ttagcagaat ttttaaaggc tccgatcata ataagctttc ggaagggcat      60
tactataaag aggatgcggg ttattacttg ccatccactt cgggggtaac aaatgtcagc     120
actcactctc ctccttaaag aaaccaataa tgttttggaa agttgttact gttttgtcct     180
cactgtctat aacttgtttt gaattgcagg atgcttggaa ccagagccag aaccagaacg     240
agaatgaaga tatcgatcgt gctattgcac tggtggaaga gactcagaaa gcaaacaaca     300
atgtaaatgg tgagtgaatt gtagctcttc aaacattgtt gcttctgtgt attctttttt     360
ttttttttt tgttatcgac aaatgttaat tgttagtgga agagattcga acccatgacc      420
tttcccctc accttctccc ttcaaccacc aaaccaacct tgtaactcca ttgctgtgta    480
ttcttgcaac agagaaatt gcgtgtgtgc cgtttcattt gtttagtct ttacagtcta     540
tgtgactgct gctaattatg aactatgaag tatggactaa tgcaattcga gaagttctga    600
atttgtaaca ctcagtgttg ccgttttttct agttattgat agtgttttc cattgtcccc    660
ctttgtcttc attttgtaat tatgagattt ttgatatgaa atctgtgacc aaaatcattt    720
ggtaaatgaa agaaccaatt gctttctatt gaatgtcttg attaaatgtg cttgtaaatg    780
tggttgccac gcttttcttt gtgcaaaatc tgtgcaatt tgatattttg cattgttggc    840
ttagttagtt agttggtagc ttgacttcca tttatatgct cattcttgt tttaccattt    900
accactgtgt ttggaagtat taaaaattag agttgttttg cattaagtcc aagatagtaa    960
ccattttgct ctttatttgc cacgggagtt tctgcttatg ttttctagag gtggtgaaga   1020
ttgactaatt tgcacatttt tttatatct atccttttta aatatatatt accccctctc    1080
ccctcctcaa aagtaatctt gtcttgtcta aattgtatt gtcttagtat gaaatatatt    1140
acagttttac attaacaagg ttctctgtct gttttataga ctacagatca caattagaag   1200
aagatgaaca acttgccaga gctatagaac aaagtctaaa ttggagtct cctcccagat     1260
atggaaatga aaatatgtat caaccaccaa ttcagtattt ccccatgggg tccaggtatg    1320
agatgttggg ggatgacaat gtatgaattt ggcatcataa ttcaatactt ttttttgtttc   1380
accacttcaa tggatatgct gaaagaatca tctaaagtat ttttattcac catttaccat   1440
```

```
agggtcataa ttattggttc tatcaattct caccttgatt tgtgtcatat actgccaccg   1500
ctggattgtc tggaatgatc tatttaatg tgtgctatat cctttaattg gtgcccaaca    1560
aattttcctt gtaattccca cttatttgtg ttggtcctat tgaattattt attaactgat   1620
attgctatga ctgattacaa ataatcatcc tttttatcct cttcaaatac cttgtaccaa   1680
acatatcata aagatacagt agtagagtga agactgctgc atttgaactg atatagagcc   1740
aagtattaat atatatgtct agactccaaa tttttatacg atgaattagt aacagatacc   1800
cacaagtccc tatgaattaa gttccacttg caaagaagag atacgattat ttgtcaggtt   1860
gtatcatatg tctagccatc acgcttaatg ctcgtaaagg gagaaaactt ctaaccaatg   1920
ttttcctgtt tgttttcgat tgttggagaa attattctct tcgttcaatt tgctatacct   1980
ctatattatc aataacat gtgatgcaca taatttaagt tgattagtta tttgcataat     2040
aggatttgtg ctggctgcta tactgagatt ggttatggac gatatctgaa ttgcttgaat   2100
gcattctggc atcctgaatg cttccgctgc cgtgcttgca acctaccaat ctctgattac   2160
gaggtgctaa cattaccggc cacattgctt gttttcatat atggttttta ttctgtactt   2220
aatgctttgt tttatacata ttattattgc agttttccac atctgggaat taccctatc   2280
ataaatcatg ctataaggaa agctaccatc caaaatgtga tgtctgcaag cacttcgtaa   2340
gtattttaa caagttttag ggaaaattgc acttggtacc cctagatttt gcttatatga    2400
catgcacacc catgctattt tttgacctgt cacttgttac cctaataaca ccccttttagc  2460
taacattgat taacagatct gattctcctt tgctgctact aacaattata ccccctgtcac  2520
cctcttgtg ctattttctt caccttcaaa aatagaatca ggaaggatga gattgagagc    2580
cttcaattct tctttgtgga aatatggtag ctttcacttt cctgagatgt gacaatgcca   2640
ttcctgtgtt gagtatgggt gtcaattccc tccttgagat gtgtccaccc ttgttctcct   2700
tttttaccct ttcaaagtga acaggattcc cttgcacatc atcacttgct cacatctctt   2760
tctcactcag catcacctac gtgcataaca accaagatac taaagttctg gtagttaatt   2820
tctaatagga ataaataacg acagcaatac atggtttgtg aatcagcata taaagactaa   2880
ggaacgtcaa accataagac ctaaccactc tcaaatttgt gtcagccaac attcccatca   2940
tcttgttaac tttatccaaa ccatcacaaa aaccacaaca tttccagctt ctgctactgt   3000
gaagcacacc ctgtaccatg accatccatc tgctatatct gccaaatatc gcctacacac   3060
cctgcagcaa tcacctcact gctcatcacc accacaaagc cgccttcaat ctcaattctc    3120
aactaaacaa cacctctcct ttcacagtga gcaccacctc ctcaatggat agttcccaac   3180
acctcagccc cacattccac gtcttgaacc aaaatagctg cacaacattc tctgagacaa    3240
attttcacca tcctcaacct ttgtggcatt gacattcttg ccactaaact aaccttctca   3300
ctggaattta ccattcttga gtggatcact ctctagagtt gcatgaacca ctatcaatgg   3360
aactttccac ttctgagaaa aataagagag atgtggcaaa cctttgctgc taggatggag   3420
gagaatgaga gaagaacaag ggaaagggtt tagggctttat atttctgaaa tttatagttc   3480
atgttcttgg tgaggctttt gttttacca caaatgatca tggaggtagt ataaagtgct    3540
actggaatca ccttgtttct ccaaacttgt ggacattgtc tgagtcattc atgattgtag   3600
ttgtttataa ctctcatgtt agattttgaa aagacatgc ttttaagttt tcaccttgac     3660
ttcaaccta tatctcattg cctgttgttg ttttttggta atatatattt tttcacagat    3720
tccaacaaat cctgctggtc ttattgaata tagggcacat ccattctgga tccagaaata   3780
ttgccctact cacgaacatg atggtactac acgctgttgc agctgcgagc gaatggaggt   3840
tagtatggat ggagtatatt tatctgataa aatattattt gtagtcttgc ctagggaaag   3900
gtggatgaac ttgtacagtg caaagtgaat agaatgtaaa attttctctc atcatatgca   3960
gtcccaagag gcaggatata ttgctcttaa ggatggccgg aagctctgct tagagtgtct   4020
tgattctgct atcatggata ctaatgaatg ccaaccccett catgctgata tacaaagatt   4080
ttatgaaagc ctaaatatga aactggacca acaaattcca cttctattgg ttgaaagaca   4140
agcactgaat gaagcaagag aaggagagaa gaatgtaaga gaaaatgcat ttccatctgt   4200
ttgctataaa tataataact gataatttga ttgtaatgac attcagctgt ctgacatact   4260
aggaactatt ttttggtgtt tggcattgtc tgcacaacta atattaaaag taaaataatg   4320
ccttttgcta ttgatagctt tgagaatgct atctctgatg aaggtttttc tattcgtgat   4380
atgttaacca catgctatgt caaatagttc aatatgacta gcacgatata gaaaatttaa   4440
gagcaaaaag gaaacaaaaa aagcatattc acatttggaa gtctaatgct tgcaataaat   4500
aatactgtcc aagtcaacat gctttcacct atgaagcttt aattcattat tagttcatga   4560
ttaaacagtg ttttttccatt ttcatatttg agtctttatc ttgggcaggg ccactatcac   4620
atgccggaaa ccagagggct ctgcctctca gaggagctca gcactgtaag atttcctgtt   4680
atgttcagtt ttggtgatgt actgacattt tttcttttta atggttagat gataacattt   4740
ctttagaacc aataattagc aatttatggt acattgcatt taaacttgat cagttctcga   4800
gacgacctag acttgggaca acaatggaca tgagagcaca gccatacaga ccgactacac   4860
gctgcgatgt gactgcaatt tcatttttat atggtcttcc aaggtaataa taatttagtg   4920
cttttgcaac ttgtgtaact tggagataaa taataatcta aaagacaaaa aagtttccca   4980
agtatgaaaa caactgttaa caaaagatcc atgaaaccag aaaatgtaat atgcgttcag   5040
ctggagagat ctagataata ttatatgtta gcataatttc acttttggtc cccttactct   5100
cgtaattatg ttaacttgcc cccccccccc ccccccccaa tttttcact aatttgatcc    5160
tcttactatt ttaattgtat aatcttggta agttttttgtt aatgtgacct ccaatatttt    5220
acaaaaatgc tgatatagca gtgcaataca gtgtcacatc agatggatg tgctgacgtg    5280
acagtggcac agtgcaatag aatatcacgt caacattttg ttaaatattg gctgtcaagt   5340
taactgatgt accaaaacta aacaattaaa ataatgaggg atcaaattcg agataaaaat   5400
tgggaggacc aaatttgcaa aatgatgata gtaagagaa ctaatgtaca attaagtctt    5460
gtatgttaga caaaagcagt gtattttaca cagagctttt gctaacatga cttaataaaa   5520
tgaaaggaac taaaagctgc taattgtaac attcttcctc tttttgtatcc gtgggattta   5580
gcttttgtga attctctttc gtacttaatg taaaaacctg tgttcttttg gaattagaag   5640
aggaagttga tttaaaaagt aatatctgca gccaagcaag cgttgccttg tttatattga   5700
attatataat agttttccta tgcatgcaag attatctttt ttgaatgttt gctcaagtct   5760
cctgactttc agaatatatc ttccgaaaga aaatccttcc tccccaccac cctatttctt   5820
tcacaacaac tttgtcttca tcagttgatt ttatttatac atgattttt tcttctttc      5880
acaggttact tactgatca atcctagctc atgagatgat gcatgcatgg ctgcggctta   5940
aaggtactat tttattgttg ggaatctatt tcattaggat tcattttagc agttgagatt   6000
tatcacctac tattaaacca gtgttatttc gttgggattg tctctcaaat tcatgctaac   6060
ttgtgaaggt tatcggactc taagtcaaga tgttaagaa ggtatctgtc aggttttgtc     6120
tcatatgtgg ttggagtctg aactttcttc tgcatcaggc agcaactttg tatcagcctc   6180
```

```
atcctcgtct gcatcacata catctagaaa aggtaaaaga cctcagtttg agaggaagct  6240
tggggagttc ttcaaacacc agattgaatc agacatttcc cctgtttatg gaggtgggtt  6300
tagggcaggt caaaaagcag tgagtaaata tggtctacaa aggacccttc atcatatcag  6360
gatgacaggg acttttccat attaa                                        6385

SEQ ID NO: 158         moltype = DNA   length = 4796
FEATURE                Location/Qualifiers
source                 1..4796
                       mol_type = other DNA
                       organism = synthetic construct
SEQUENCE: 158
atgggttggt ttaccaagtt gcttaagggc tctgatcata aaattttca aggacaatac     60
cataggacag aatttgggat aatcatcata gttcaatggt aaacaaagtt tttccttttc    120
tagtaagaat taaaagcatt gccacaagtc acaactacgt cattgagcta gccttttatc    180
tgaatttagc tttgagatta gcatgaagct aacaaagtac tacttcctct gagacataag    240
cagataatct gcatttgtaa tagttacaaa ctgaatgcag gatgatttga ctgatattga    300
gaaagaagac attgaccatg caattgcact ttctctgtca gaggaggatc ataaagggaa    360
aaaagttgtt ggtaagattt atgcttttgc accttggtag ttaaagttca tttcctggtt    420
agtttggctc aaatttaatg ctgttatgat tctgcatact gcatatgagg tacctaaact    480
ctaagatctg aatctaacca aaatgctcga tgatttagta caagctctta cttacctctt    540
gtattatttc ctgtctttct atgcctattt cagtgtcttc ttcattcttg tttaagtaga    600
ttatgctttg tgaacacccc aaaaaaaggt catgctttgt tgatgaaagg ctatgatgct    660
atcagttgag tctttcattt acatctgaat cagaatggaa ctaagaaata aatttttaaa    720
ttactacaat tagcttctag attactttaa aatataaatt taacatgcat ataagaatta    780
tggggatatt ctgattctgg tgtttcactt aagttgcaac tcaaagtgct taagtatat     840
ttcttagtta agagtccatt gaagaatttt tccaaaaaat acaaaaaaga gtacattgaa    900
gaaaatctga agtttcattt ggtttatgtg ttcagaaagt gcatgtgtta atcaattaat    960
tatttccaca ccaaagcata accaaaaggt ctcatgtttt ttgtctcata taccctaga    1020
ttatgactct caatctgaag atgaggaact ttgtaaaatt gatgatgagg aggatgaaca   1080
tcttgttaaa gttcatctag atgaagatga acgtcttgct aaaattcagc aagaagaaga   1140
agaacgtctt gctaaaattc aacaagaaga tgagcatctt gctaaaattc aacaagaaga   1200
agaagaacgt cttgctaaaa ttcaacaaga agatgaatgt cttgctaaaa ttcaacaaga   1260
ggatgaacgt cttgctaaag ctcaacttga ggaagacgag caacttgcta gggcaattca   1320
agaaagcttg aaaattggtt ctcctcctca atatgacaat ggttcttcaa ttctatcttt   1380
tcctcacctt ttccccccctg gatacaggta attgttggta tgatcacatc ttttatctat   1440
atagcaagtc cttatactgt ttttggaaat tgttgaagta cactagttct aaatgaacag   1500
accaataatg taattgtgcc aaaaataaga aaaacaaaaa atttccaaac tgaatatgtt   1560
ttgaaacttc aatttaagta ttgctgattt gagtgatagg tcatacaact aactgatctg   1620
gacttcatac aagctaatca atcttatttt atgagattct agtctgaatc attgaactgg   1680
gataaatgct gtattgggat tttatgcatg acaccttggt gtgcgttggt tttccttagt   1740
gttcttaagt accttttcaat tagatgaaaa ttttaaaaaa tagtagttat taaaatgaac   1800
atttcataat ttgattactt aagtcttatt tatggtgatc ctgagcactt cctgtagaat   1860
agcttggagt gatttcatga tcatctaata aataaaattg aaatactctc ctctgttgca   1920
atattgtgga cctatataat cgacatcttt gaaatttatt tttcaaggtt tcatgaatct   1980
ttattaatta ttagaaacaa agatttaacc tttttttctgt aaaatctgcc tgcagaatct  2040
gtgctggatg caagactgag attggccaag gaagattttt aagttgcatg ggaggtgtct   2100
ggcatccaga atgcttctgc tgccatgcat gccatcttcc aatcactgat tatgaggtta   2160
gagactagag tcttgttttc ttttgctgct tgtttcgcaa agctgaattt aattacaata   2220
agttgaaacc ttgttttttt ggtgaaagaa aaagttgaaa attattctta gcttcataaa   2280
tgaaggtctt caatttattt ctcttgtttg tcaatctcaa tatgattatg cttaattcgt   2340
cccttttacag ttttccatgt ctagcaatcg ccottaccat aaatcatgct ataggagaa   2400
gcatcaccca agatgtgatg tttgcaagaa ctttgtaagt atcttcacca gttgttttc    2460
actcacagtt gtctattagc cttggtttgg ttgtggggaa ggaagtacta ttcaacagca   2520
aatttttcaaa aaatagtgtg ggtcctacac cattttttttt ttctctactt taattcaaat   2580
atttcttctc aatttcttttc tcttccacac aaccaaacat aacttagtc aatactgtgt   2640
gcttgttttc tttcaaaggt ttctatcaat tttgatgtgc tttagaagct ttacaagatg   2700
catatacaag gaagactgtt gatattgagt tgttcttgct tctcagatag atcagaattc   2760
caaactatac ttgagaaagt tctgctgaac tcagcagttg tttaatcttt ataacaaatc   2820
atgggctatt gatcttactg aaataacatc atgggagctc ttcatgaagc taatatttgt   2880
atattttttat atttttgggcc agacagtctg tttgggccca gcccaatgtg gttatacctc   2940
ttgggggttta tacatgcata gactcaaatc ttaatatttt gaatgtaatg ttaggatttg   3000
agctattgta tcctgcacct cccattacat tctggaaagc ccattccgga atgcaaattt   3060
acattccgga atgggatttc cggaatgcag tgaggtgtag gatgcaatag tgggagtgcc   3120
tatgctgtgt aatgtgcata aaccccaatg tggcatccc tcttgggatt tcataatttt   3180
tttaaagact tggatacttc atcgatacgt attggtgaag tatccaatag tattggtatc   3240
ggatacgtga aaaaaattga agtattcgct cttcatgaac agaccttaag tttgcgtttt   3300
tttttttaaaa aaaaatggca gtaagatata ttgttcagta aactagaatt attggttctt   3360
tccttgtaga tcccaactaa ttcatctggc ctcattgagt atagagctca tccttttctgg  3420
ctacaaaaat actgcccatc gcatgagctt gatgtcaatt ctcgttgttg tagttgcgaa   3480
agaatggagg ttagttatat tgactcccaa atctttttcat cctattatta tcaattagaa   3540
gctaactgtt ggatccttcc tctcctcccc cattccctgt cccgttttct tgccttttca   3600
atcaatgcag ccaagggata caaatatct tttgcttgat gatggtcgaa agctatgttt    3660
agagtgtcta gactcatcaa ttatggatac tcatgaatgc aacctctttt accttgaaat   3720
acaagaattt tatgaaggtt taaatatgaa attggagcaa ttaattccta tgtctcttggt  3780
tgagagacaa cgcgctgaat gaggctatgga gggagaaaag aatgtaagtg ttaatgttga   3840
taacttccca tttcattcat ggaatgctgt tatttctatt cttttctagtg tcctgtcgaa   3900
atgttctttt atttctcact attgaatgta gggtcatcac cacttacccg aaactagagg   3960
actatgcttg tcagaagagc aaactgtcac cactgtaggg atttctcact tgcaaattga   4020
atcttcacat ctaattctgc tatagaagat ctgtgtatca aatagtgatt ttattacttt   4080
```

```
tatatatttc atgtaatact agatttcaag gaggccaagg attgcagcag gctaccgagc    4140
catagacatg ataactgaac cttataggct gatccgttgt tgtgaagtga cagccattct    4200
tgttttgtat ggccttccta ggtatccttc ttgtacaatc tactttcata atctacagtg    4260
cttgcatatg acattcctca tatataattc aattttttt tatgtttata ggttgttaac     4320
aggatcaatc ctagctcatg agatgatgca tgcatggctt aggcttaaag gtattcagcc    4380
attaacatga tccagaaaag tttatatatt tgtttcatgg tgccaagttg gacaaaattt    4440
ctgggttttt gacaggttat cctaacctca gtccagaagt tgaagaagga atctgccaag    4500
ttttggctca tatgtggtta gaatcagagc tctattctgg atttgggaat gatggtgcat    4560
catcctcaac atcatctttg tcttcgtcat caccttcctc ctcttctgtc tcaacaaaga    4620
agggtaaacg gtccgacttt gagaagaaac ttggtgattt ttttaaacac cagattgagt    4680
cagataccctc ctcagcttat ggagatggat tcagattggg taaccaagca atggtcaagt   4740
atgggcttaa aaggaccctt gaccatatcc atatgacagg aagttttcca tattaa        4796

SEQ ID NO: 159          moltype = DNA  length = 10
FEATURE                 Location/Qualifiers
source                  1..10
                        mol_type = other DNA
                        organism = Glycine max
SEQUENCE: 159
tggcaaatat                                                             10

SEQ ID NO: 160          moltype = DNA  length = 13
FEATURE                 Location/Qualifiers
source                  1..13
                        mol_type = other DNA
                        organism = Glycine max
SEQUENCE: 160
ggcaaatatg gag                                                         13
```

MODIFICATION OF UBIQUITIN BINDING PEPTIDASE GENES IN PLANTS FOR YIELD TRAIT IMPROVEMENT

STATEMENT OF PRIORITY

This application claims the benefit, under 35 U.S.C. § 119 (e), of U.S. Provisional Application No. 63/238,394 filed on Aug. 30, 2021, the entire contents of which is incorporated by reference herein.

STATEMENT REGARDING ELECTRONIC FILING OF A SEQUENCE LISTING

A Sequence Listing in XML text format, entitled 1499-71_ST26.xml, 285,324 bytes in size, generated on Aug. 11, 2022 and filed herewith, is hereby incorporated by reference into the specification for its disclosures.

FIELD OF THE INVENTION

This invention relates to compositions and methods for modifying Ubiquitin Binding Peptidase (DA1) genes in plants, optionally to improve yield traits. The invention further relates to plants having increased improved yield traits produced using the methods and compositions of the invention.

BACKGROUND OF THE INVENTION

Intensive breeding across row crops has led to incremental increases in plant yield. However, genetic gain from breeding has started to plateau and assembling multiple small-effect genes in a breeding program has substantially increased research and development costs. Single gene solutions have been challenging for a complex trait such as yield, where background genetics and environment combine to reduce the impact of individual genes. Breeding has been successful by combining many individual genes with small contributing effects but is requiring greater resources to find unique combinations with improved effects. To increase the rate of yield gain, novel variation needs to be introduced in important genes and pathways that contribute to yield.

Transgenic approaches involving stable transformation to increase yield have largely been unsuccessful and there are no commercially relevant single gene approaches that have successfully created a step change in yield.

The present invention addresses these shortcomings in the art by providing new compositions and methods for improving/enhancing yield traits in plants, including soybean, corn, and other plant species.

SUMMARY OF THE INVENTION

One aspect of the invention provides a plant or plant part thereof comprising at least one mutation in an endogenous Ubiquitin Binding Peptidase (DA1) gene encoding a ubiquitin binding peptidase (DA1) polypeptide, optionally wherein the mutation is a non-natural mutation.

A second aspect of the invention provides a plant cell, comprising an editing system comprising: (a) a CRISPR-Cas effector protein; and (b) a guide nucleic acid (e.g., gRNA, gDNA, crRNA, crDNA, sgRNA, sgDNA) comprising a spacer sequence with complementarity to an endogenous target gene encoding a ubiquitin binding peptidase (DA1) polypeptide.

A third aspect of the invention provides a plant cell comprising at least one mutation within an endogenous Ubiquitin Binding Peptidase (DA1) gene, wherein the at least one non- is a substitution, insertion, or deletion that is introduced using an editing system that comprises a nucleic acid binding domain that binds to a target site in the endogenous DA1 gene, optionally wherein the mutation is a non-natural mutation.

A fourth aspect of the invention provides a method of producing/breeding a transgene-free edited plant, comprising: crossing the plant of the invention with a transgene free plant, thereby introducing the at least one mutation into the plant that is transgene-free; and selecting a progeny plant that comprises the at least one mutation and is transgene-free, thereby producing a transgene free edited plant, optionally wherein the mutation is a non-natural mutation.

A fifth aspect of the invention provides a method of providing a plurality of plants having one or more improved yield traits, the method comprising planting two or more plants of the invention in a growing area, thereby providing a plurality of plants having one or more improved yield traits (optionally increased seed size (e.g., seed area and/or seed weight) as compared to a plurality of control plants not comprising the at least one mutation.

A sixth aspect of the invention provides a method of generating variation in a ubiquitin binding peptidase (DA1) polypeptide, comprising: introducing an editing system into a plant cell, wherein the editing system is targeted to a region of a Ubiquitin Binding Peptidase (DA1) gene that encodes the DA1 polypeptide, and contacting the region of the DA1 gene with the editing system, thereby introducing a mutation into the DA1 gene and generating variation in the DA1 polypeptide of the plant cell.

A seventh aspect provides a method for editing a specific site in the genome of a plant cell, the method comprising: cleaving, in a site-specific manner, a target site within an endogenous Ubiquitin Binding Peptidase (DA1) gene in the plant cell, the endogenous DA1 gene: (a) comprising a nucleotide sequence having at least 80% sequence identity to any one of SEQ ID NOs:69, 70, 109, or 110, (b) comprising a region having at least 90% sequence identity to any one of SEQ ID NOs:72-101 or 112-139, (c) encoding an amino acid sequence having at least 80% sequence identity to SEQ ID NO:71 or SEQ ID NO:111, (d) encoding a region having at least 90% sequence identity to an amino acid sequence of any one of SEQ ID NOs:102-108 or 140-, thereby generating an edit in the endogenous DA1 gene of the plant cell and producing a plant cell comprising the edit in the endogenous DA1 gene.

An eighth aspect provides a method for making a plant, the method comprising: (a) contacting a population of plant cells comprising an endogenous Ubiquitin Binding Peptidase (DA1) gene with a nuclease linked to a nucleic acid binding domain (e.g., editing system) that binds to a sequence (i) having at least 80% sequence identity to a nucleotide sequence of any one of SEQ ID NOs:69, 70, 109, or 110, (ii) comprising a region having at least 90% identity to any one of SEQ ID NOs:72-101 or 112-139; (iii) encoding an amino acid sequence having at least 80% sequence identity to SEQ ID NO:71 or SEQ ID NO:111, and/or (iv) encoding a region having at least 90% sequence identity to any one of SEQ ID NOs:102-108 or 140-146, and/or; (b) selecting a plant cell from the population of plant cells in which an endogenous DA1 gene has been mutated, thereby producing a plant cell comprising a mutation in the endogenous DA1 gene; and (c) growing the selected plant cell into a plant.

A ninth aspect provides a method for improving one or more yield traits in a plant, comprising: (a) contacting a plant cell comprising an endogenous Ubiquitin Binding Peptidase (DA1) gene with a nuclease targeting the endogenous DA1 gene, wherein the nuclease is linked to a nucleic acid binding domain (e.g., editing system) that binds to a target site in the endogenous DA1 gene, wherein the endogenous DA1 gene: (i) comprises a sequence having at least 80% sequence identity to the nucleotide sequence of any one of SEQ ID NOs:69, 70, 109, or 110; (ii) comprises a region having at least 90% identity to any one of SEQ ID NOs: 72-101 or 112-139; (iii) encodes an amino acid sequence having at least 80% sequence identity to SEQ ID NO:71 or SEQ ID NO:111; and/or (iv) encodes an amino acid sequence comprising a region having at least 90% sequence identity to any one of SEQ ID NOs:102-108 or 140-146 to produce a plant cell comprising a mutation in the endogenous DA1 gene; and (b) growing the plant cell into a plant comprising the mutation in the endogenous DA1 gene thereby producing a plant having a mutated endogenous DA1 gene and one or more improved yield traits.

A tenth aspect provides a method of producing a plant or part thereof comprising at least one cell having a mutated Ubiquitin Binding Peptidase (DA1) gene, the method comprising contacting a target site in an endogenous DA1 gene in the plant or plant part with a nuclease comprising a cleavage domain and a nucleic acid binding domain, wherein the nucleic acid binding domain binds to a target site in the endogenous DA1 gene, wherein the endogenous DA1 gene (a) comprises a sequence having at least 80% sequence identity to a nucleotide sequence of any one of SEQ ID NOs:69, 70, 109, or 110; (b) comprises a region having at least 90% identity to any one of SEQ ID NOs: 72-101 or 112-139; (c) encodes an amino acid sequence having at least 80% sequence identity to SEQ ID NO:71 or SEQ ID NO:111; and/or (d) encodes an amino acid sequence comprising a region having at least 90% identity to any one of SEQ ID NOs:102-108 or 140-146, thereby producing the plant or part thereof comprising at least one cell having a mutation in the endogenous DA1 gene.

An eleventh aspect of the invention provides a method for producing a plant or part thereof comprising a mutated endogenous Ubiquitin Binding Peptidase (DA1) gene and exhibiting one or more improved yield traits, the method comprising contacting a target site in an endogenous DA1 gene in the plant or plant part with a nuclease comprising a cleavage domain and a nucleic acid binding domain, wherein the nucleic acid binding domain binds to a target site in the endogenous DA1 gene, wherein the endogenous DA1 gene: (a) comprises a sequence having at least 80% sequence identity to a nucleotide sequence of any one of SEQ ID NOs:69, 70, 109, or 110; (b) comprises a region having at least 90% identity to any one of SEQ ID NOs: 72-101 or 112-139; (c) encodes an amino acid sequence having at least 80% sequence identity to SEQ ID NO:71 or SEQ ID NO:111; and/or (d) encodes an amino acid sequence comprising a region having at least 90% identity to any one of SEQ ID NOs:102-108 or 140-146, thereby producing the plant or part thereof comprising an endogenous DA1 gene having a mutation and exhibiting one or more improved yield traits.

A twelfth aspect provides a guide nucleic acid that binds to a target site in a Ubiquitin Binding Peptidase (DA1) gene, wherein the target site is in a region of the DA1 gene having at least 90% sequence identity to any one of SEQ ID NOs:72-101 or 112-139, optionally a region of the DA1 gene having at least 90% sequence identity to any one of SEQ ID NOs:74-76, 78-80, 82-85, 89-96, 99-101, 114-116, 119, 120, 123-126, 128-131, 133-135, 138, or 139, optionally at least 90% sequence identity to any one of SEQ ID NOs:82-85, 99-101, 123-126, 138, or 139.

In a thirteenth aspect, a system is provided that comprises a guide nucleic acid of the invention and a CRISPR-Cas effector protein that associates with the guide nucleic acid.

A fourteenth aspect provides a gene editing system comprising a CRISPR-Cas effector protein in association with a guide nucleic acid, wherein the guide nucleic acid comprises a spacer sequence that binds to an endogenous Ubiquitin Binding Peptidase (DA1) gene. In a fifteenth aspect, a complex comprising a guide nucleic acid and a CRISPR-Cas effector protein comprising a cleavage domain is provided, wherein the guide nucleic acid binds to a target site in a Ubiquitin Binding Peptidase (DA1) gene, wherein the endogenous DA1 gene: (a) comprises a sequence having at least 80% sequence identity to a nucleotide sequence of any one of SEQ ID NOs:69, 70, 109, or 110; (b) comprises a region having at least 90% identity to any one of SEQ ID NOs:72-101 or 112-139; (c) encodes an amino acid sequence having at least 80% sequence identity to SEQ ID NO:74 or SEQ ID NO:114; and/or (d) encodes an amino acid sequence comprising a region having at least 90% identity to any one of SEQ ID NOs:105-111 or 143-149, and the cleavage domain cleaves a target strand in the DA1 gene.

In a sixteenth aspect, an expression cassette is provided, the expression cassette comprising (a) a polynucleotide encoding CRISPR-Cas effector protein comprising a cleavage domain and (b) a guide nucleic acid that binds to a target site in an Ubiquitin Binding Peptidase (DA1) gene, wherein the guide nucleic acid comprises a spacer sequence that is complementary to and binds to (i) a portion of a nucleic acid having at least 80% sequence identity to any one of SEQ ID NOs:69, 70, 109, or 110; (ii) a portion of a nucleic acid having at least 90% sequence identity to any one of SEQ ID NOs:72-101 or 112-139; (iii) a portion of a nucleic acid encoding an amino acid sequence having at least 80% sequence identity to any one of SEQ ID NO:71 or SEQ ID NO:111; and/or (iv) a portion of a nucleic acid encoding an amino acid sequence having at least 90% identity to any one of SEQ ID NOs:102-108 or 140-146.

In a seventeenth aspect, a modified ubiquitin binding peptidase (DA1) polypeptide is provided, the modified DA1 polypeptide comprising a mutation in an amino acid residue located in a region of a DA1 polypeptide comprising an amino acid sequence having at least 90% sequence identity to any one of SEQ ID NOs:102-108 or 140-146, optionally in a region of a DA1 polypeptide comprising an amino acid sequence having at least 90% sequence identity to any one of SEQ ID NOs:103-108, 141, 142 or 144-146, optionally having at least 90% sequence identity to any one of SEQ ID NOs:105-108 or 144-146.

In an additional aspect, a method of creating a mutation in a Ubiquitin Binding Peptidase (DA1) gene in a plant is provided, the method comprising: (a) targeting a gene editing system to a portion of the DA1 gene that (i) comprises a sequence having at least 90% sequence identity to any one of SEQ ID NOs:72-101 or 112-139; and/or (ii) encodes a sequence having at least 90% identity to any one of SEQ ID NOs:102-108 or 140-146, and (b) selecting a plant that comprises a modified amino acid residue located in a region of the DA1 gene encoding an amino acid sequence having at least 90% sequence identity to any one of SEQ ID NOs:102-108 or 140-146, optionally located in a region of the DA1 gene encoding an amino acid sequence having at least 90% sequence identity to any one of SEQ ID NOs:

103-108, 141, 142, or 144-146, optionally in a region having at least 90% sequence identity to any one of SEQ ID NOs:105-108 or 144-146.

In another aspect, plants are provided that comprise in their genome one or more mutated Ubiquitin Binding Peptidase (DA1) genes produced by the methods of the invention.

A further aspect of the invention provides a soybean plant or plant part thereof comprising at least one mutation in at least one endogenous Ubiquitin Binding Peptidase (DA1) gene having the gene identification number (gene ID) of Glyma.14g077800 and/or Glyma.11g062400, optionally wherein the mutation is a non-natural mutation.

In a further aspect, a guide nucleic acid is provided that binds to a target nucleic acid in a Ubiquitin Binding Peptidase (DA1) gene having the gene identification number (gene ID) of Glyma.14g077800 and/or Glyma.11g062400. Further provided are polypeptides, polynucleotides, nucleic acid constructs, expression cassettes and vectors for making a plant of this invention.

These and other aspects of the invention are set forth in more detail in the description of the invention below.

BRIEF DESCRIPTION OF THE SEQUENCES

SEQ ID NOs:1-17 are exemplary Cas12a amino acid sequences useful with this invention.

SEQ ID NOs:18-20 are exemplary Cas12a nucleotide sequences useful with this invention.

SEQ ID NO:21-22 are exemplary regulatory sequences encoding a promoter and intron.

SEQ ID NOs:23-29 are exemplary cytosine deaminase sequences useful with this invention.

SEQ ID NOs:30-40 are exemplary adenine deaminase amino acid sequences useful with this invention.

SEQ ID NO:41 is an exemplary uracil-DNA glycosylase inhibitor (UGI) sequences useful with this invention.

SEQ ID NOs:42-44 provide example peptide tags and affinity polypeptides useful with this invention.

SEQ ID NOs:45-55 provide example RNA recruiting motifs and corresponding affinity polypeptides useful with this invention.

SEQ ID NOs:56-57 are exemplary Cas9 polypeptide sequences useful with this invention.

SEQ ID NOs:58-68 are exemplary Cas9 polynucleotide sequences useful with this invention.

SEQ ID NO:69 is an example DA1-1 genomic sequence from soybean.

SEQ ID NO:70 is an example DA1-1 coding sequence from soybean.

SEQ ID NO:71 is an example DA1-1 polypeptide sequence from soybean.

SEQ ID NOs:72-101 are example portions or regions of soybean DA1-1 genomic and coding sequences.

SEQ ID NOs:102-108 are example portions or regions of DA1-1 polypeptide from soybean.

SEQ ID NO:109 is an example DA1-2 genomic sequence from soybean.

SEQ ID NO:110 is an example DA1-2 coding sequence from soybean.

SEQ ID NO:111 is an example DA1-2 polypeptide sequence from soybean.

SEQ ID NOs:112-139 are example portions or regions of soybean DA1-2 genomic and coding sequences.

SEQ ID NOs:140-146 are example portions or regions from a DA1-2 polypeptide from soybean.

SEQ ID NOs:147-150 and 151-153 are example spacer sequences for nucleic acid guides useful with this invention.

SEQ ID NOs:154, 155, 156 and 158 are example DA1-2 genes edited as described herein in soybean.

SEQ ID NO:157 is an example DA1-1 gene edited as described herein in soybean.

SEQ ID NO:159 and SEQ ID NO:160 are example regions that have been deleted from a DA1 gene. SEQ ID NO:159 is a portion deleted from SEQ ID NO:109 (SEQ ID NO:154) and SEQ ID NO:160 is a portion deleted from SEQ ID NO:69 (SEQ ID NO:157).

DETAILED DESCRIPTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, +1%, +0.5%, or even ±0.1% of X. A range provided herein for a measurable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 5%, 10%, 15%, 20%, 25%, 50%, 75%, 100%, 150%, 200%, 300%, 400%, 500% or more as compared to a control. For example, a plant comprising a mutation in a Ubiquitin Binding Peptidase (DA1) gene as described herein can exhibit an improved yield trait (e.g., one or more improved yield traits; e.g., optionally an increase in yield (bu/acre), an increase in biomass, an increase in seed size, an increase in seed weight, an increased number of pods, an increased number of pods per node, an increased number of seeds per pod) as compared to a control plant devoid of the at least one mutation. A control plant is typically the same plant as the edited plant, but the control plant has not been similarly edited and therefore is devoid of the mutation. A control plant maybe an isogenic plant and/or a wild type plant. Thus, a control plant can be the same breeding line, variety, or cultivar as the subject plant into which a mutation as described herein is introgressed, but the control breeding line, variety, or cultivar is free of the mutation. In some embodiments, a comparison between a plant of the invention and a control plant is made under the same growth conditions, e.g., the same environmental conditions (soil, hydration, light, heat, nutrients, and the like).

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 96%, 97%, 98%, 99%, 99.5%, 99.6%, 99.7%, 99.8%, 99.9%, or 100% as compared to a control. In particular embodiments, the reduction can result in no or essentially no (i.e., an insignificant amount, e.g., less than about 10% or even 5%) detectable activity or amount.

As used herein, the terms "express," "expresses," "expressed" or "expression," and the like, with respect to a nucleic acid molecule and/or a nucleotide sequence (e.g., RNA or DNA) indicates that the nucleic acid molecule and/or a nucleotide sequence is transcribed and, optionally, translated. Thus, a nucleic acid molecule and/or a nucleotide sequence may express a polypeptide of interest or, for example, a functional untranslated RNA.

A "heterologous" or a "recombinant" nucleotide sequence is a nucleotide sequence not naturally associated with a host cell into which it is introduced, including non-naturally occurring multiple copies of a naturally occurring nucleotide sequence. A "heterologous" nucleotide/polypeptide may originate from a foreign species, or, if from the same species, is substantially modified from its native form in composition and/or genomic locus by deliberate human intervention.

A "native" or "wild type" nucleic acid, nucleotide sequence, polypeptide or amino acid sequence refers to a naturally occurring or endogenous nucleic acid, nucleotide sequence, polypeptide or amino acid sequence. In some contexts, a "wild type" nucleic acid is a nucleic acid that is not edited as described herein and can differ from an "endogenous" gene that may be edited as described herein (e.g., a mutated endogenous gene). In some contexts, a "wild type" nucleic acid (e.g., unedited) may be heterologous to the organism in which the wild type nucleic acid is found (e.g., a transgenic organism). As an example, a "wild type endogenous Ubiquitin Binding Peptidase (DA1) gene" is a DA1 gene that is naturally occurring in or endogenous to the reference organism, e.g., a plant, e.g., a soybean plant, a maize plant, and may be subject to modification as described herein, after which, such a modified endogenous gene is no longer wild type. In some embodiments, an endogenous DA1 gene is an endogenous DA1-1 gene or an endogenous DA1-2 gene.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "allele" refers to one of two or more different nucleotides or nucleotide sequences that occur at a specific locus.

A "null allele" is a nonfunctional allele caused by a genetic mutation that results in a complete lack of production of the corresponding protein or produces a protein that is nonfunctional.

A "recessive mutation" is a mutation in a gene that produces a phenotype when homozygous but the phenotype is not observable when the locus is heterozygous.

A "dominant mutation" is a mutation in a gene that produces a mutant phenotype in the presence of a non-mutated copy of the gene. A dominant mutation may be a loss or a gain of function mutation, a hypomorphic mutation, a hypermorphic mutation or a weak loss of function or a weak gain of function.

A "dominant negative mutation" is a mutation that produces an altered gene product (e.g., having an aberrant function relative to wild type), which gene product adversely affects the function of the wild-type allele or gene product. For example, a "dominant negative mutation" may block a function of the wild type gene product. A dominant negative mutation may also be referred to as an "antimorphic mutation."

A "semi-dominant mutation" refers to a mutation in which the penetrance of the phenotype in a heterozygous organism is less than that observed for a homozygous organism.

A "weak loss-of-function mutation" is a mutation that results in a gene product having partial function or reduced function (partially inactivated) as compared to the wildtype gene product.

A "hypomorphic mutation" is a mutation that results in a partial loss of gene function, which may occur through reduced expression (e.g., reduced protein and/or reduced RNA) or reduced functional performance (e.g., reduced activity), but not a complete loss of function/activity. A "hypomorphic" allele is a semi-functional allele caused by a genetic mutation that results in production of the corresponding protein that functions at anywhere between 1% and 99% of normal efficiency.

A "hypermorphic mutation" is a mutation that results in increased expression of the gene product and/or increased activity of the gene product.

A "locus" is a position on a chromosome where a gene or marker or allele is located. In some embodiments, a locus may encompass one or more nucleotides.

As used herein, the terms "desired allele," "target allele" and/or "allele of interest" are used interchangeably to refer to an allele associated with a desired trait. In some embodiments, a desired allele may be associated with either an increase or a decrease (relative to a control) of or in a given trait, depending on the nature of the desired phenotype.

A marker is "associated with" a trait when said trait is linked to it and when the presence of the marker is an indicator of whether and/or to what extent the desired trait or trait form will occur in a plant/germplasm comprising the marker. Similarly, a marker is "associated with" an allele or chromosome interval when it is linked to it and when the presence of the marker is an indicator of whether the allele or chromosome interval is present in a plant/germplasm comprising the marker.

As used herein, the terms "backcross" and "backcrossing" refer to the process whereby a progeny plant is crossed back to one of its parents one or more times (e.g., 1, 2, 3, 4, 5, 6, 7, 8, etc.). In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. *Marker-assisted Backcrossing: A Practical Example*, in TECHNIQUES ET UTILISATIONS DES MARQUEURS MOLECULAIRES LES COLLOQUES, Vol. 72, pp. 45-56 (1995); and Openshaw et al., *Marker-assisted Selection in Backcross Breeding*, in PROCEEDINGS OF THE SYMPOSIUM "ANALYSIS OF MOLECULAR MARKER DATA," pp. 41-43 (1994). The initial cross gives rise to the F1 generation. The term "BC1" refers to the second use of the recurrent parent, "BC2" refers to the third use of the recurrent parent, and so on.

As used herein, the terms "cross" or "crossed" refer to the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

As used herein, the terms "introgression," "introgressing" and "introgressed" refer to both the natural and artificial transmission of a desired allele or combination of desired alleles of a genetic locus or genetic loci from one genetic background to another. For example, a desired allele at a specified locus can be transmitted to at least one (e.g., one or more) progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele may be a selected allele of a marker, a QTL, a transgene, or the like. Offspring comprising the desired allele can be backcrossed one or more times (e.g., 1, 2, 3, 4, or more times) to a line having a desired genetic background, selecting for the desired allele, with the result being that the desired allele becomes fixed in the desired genetic background. For example, a marker associated with increased yield under non-water stress conditions may be introgressed from a donor into a recurrent parent that does not comprise the marker and does not exhibit increased yield under non-water stress conditions. The resulting offspring could then be backcrossed one or more times and selected until the progeny possess the genetic marker(s) associated with increased yield under non-water stress conditions in the recurrent parent background.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell or can be separate from the organism or cell. In general, germplasm provides genetic material with a specific genetic makeup that provides a foundation for some or all of the hereditary qualities of an organism or cell culture. As used herein, germplasm includes cells, seed or tissues from which new plants may be grown, as well as plant parts that can be cultured into a whole plant (e.g., leaves, stems, buds, roots, pollen, cells, etc.).

As used herein, the terms "cultivar" and "variety" refer to a group of similar plants that by structural or genetic features and/or performance can be distinguished from other varieties within the same species.

As used herein, the terms "exotic," "exotic line" and "exotic germplasm" refer to any plant, line or germplasm that is not elite. In general, exotic plants/germplasms are not derived from any known elite plant or germplasm, but rather are selected to introduce one or more desired genetic elements into a breeding program (e.g., to introduce novel alleles into a breeding program).

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

A "haplotype" is the genotype of an individual at a plurality of genetic loci, i.e., a combination of alleles. Typically, the genetic loci that define a haplotype are physically and genetically linked, i.e., on the same chromosome segment. The term "haplotype" can refer to polymorphisms at a particular locus, such as a single marker locus, or polymorphisms at multiple loci along a chromosomal segment.

As used herein, the term "heterologous" refers to a nucleotide/polypeptide that originates from a foreign species, or, if from the same species, is substantially modified from its native form in composition and/or genomic locus by deliberate human intervention.

A plant in which at least one (e.g., one or more, e.g., 1, 2, 3, or 4, or more) endogenous DA1 gene (e.g., an endogenous DA1-1 gene, an endogenous DA1-2 gene) is modified as described herein (e.g., comprises a modification as described herein) may have improved yield traits as compared to a plant that does not comprise (is devoid of) the modification in the at least one endogenous DA1 gene. As used herein, "improved yield traits" refers to any plant trait associated with growth, for example, biomass, yield, nitrogen use efficiency (NUE), inflorescence size/weight, fruit yield, fruit quality, fruit size, seed size (e.g., seed area, seed size), seed number, foliar tissue weight, nodulation number, nodulation mass, nodulation activity, number of seed heads, number of tillers, number of branches, number of flowers, number of tubers, tuber mass, bulb mass, number of seeds, total seed mass, rate of leaf emergence, rate of tiller/branch emergence, rate of seedling emergence, length of roots, number of roots, size and/or weight of root mass, or any combination thereof. In some aspects, "improved yield traits" may include, but are not limited to, increased inflorescence production, increased fruit production (e.g., increased number, weight and/or size of fruit; e.g., increased number, weight, and/or length of ears for, e.g., maize), increased fruit quality, increased number, size and/or weight of roots, increased meristem size, increased seed size (e.g., seed area and/or seed weight), increased biomass, increased leaf size, increased nitrogen use efficiency, increased height, increased internode number and/or increased internode length as compared to a control plant or part thereof (e.g., a plant that does not comprise a mutated endogenous DA1 nucleic acid as described herein). In some aspects, improved yield traits can be expressed as quantity of grain produced per area of land (e.g., bushels per acre of land). In some embodiments, the one or more improved yield traits is an increase in seed number.

As used herein, an "increased seed size" can mean a seed that is increased in area and/or an increase in seed weight (e.g., 100-seed weight). In some embodiments, a seed may be increased in area by up to about 70% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, 50, 51, 52, 53, 54, 55, 56, 57, 58, 59, 60, 61, 62, 63, 64, 65, 66, 67, 68, 69, 70%) as compared to a seed from a control plant (e.g., a plant not comprising the mutation in an endogenous DA1 gene as described herein). In some embodiments, an seed may be increased in weight by up to about 50% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 45, 46, 47, 48, 49, or 50%) as compared to a seed from a control plant (e.g., a plant not comprising the mutation in an endogenous DA1 gene as described herein). In some embodiments, an increase in seed size can include an increase in both seed area and seed size. An increased seed size may be measured, for example, by 100-seed weight.

As used herein a "control plant" means a plant that does not contain an edited DA1 gene or gene as described herein that imparts an enhanced/improved trait (e.g., yield trait) or altered phenotype. A control plant is used to identify and select a plant edited as described herein and that has an enhanced trait or altered phenotype as compared to the control plant. A suitable control plant can be a plant of the parental line used to generate a plant comprising a mutated DA1 gene(s), for example, a wild type plant devoid of an edit in an endogenous DA1 gene as described herein. A suitable control plant can also be a plant that contains recombinant nucleic acids that impart other traits, for example, a transgenic plant having enhanced herbicide tolerance. A suitable control plant can in some cases be a progeny of a heterozygous or hemizygous transgenic plant line that is devoid of the mutated DA1 gene as described herein, known as a negative segregant, or a negative isogenic line.

An enhanced trait (e.g., improved yield trait) may include, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, increased yield, increased nitrogen use efficiency, and/or increased water use efficiency as compared to a control plant. An altered phenotype may be, for example, plant height, biomass, canopy area, anthocyanin content, chlorophyll content, water applied, water content, and water use efficiency.

In some embodiments, a plant of this invention may comprise one or more improved yield traits including, but not limited to, In some embodiments, the one or more improved yield traits includes higher yield (bu/acre), increased biomass, increased plant height, increased stem diameter, increased leaf area, increased number of flowers, increased kernel row number, optionally wherein ear length is not substantially reduced, increased kernel number, increased kernel size, increased ear length, decreased tiller number, decreased tassel branch number, increased number of pods, including an increased number of pods per node and/or an increased number of pods per plant, increased number of seeds per pod, increased number of seeds, increased seed size, and/or increased seed weight (e.g., increase in 100-seed weight) as compared to a control plant devoid of the at least one mutation. In some embodiments, a plant of this invention may comprise one or more improved yield traits including, but not limited to, optionally an increase in yield (bu/acre), seed size (including kernel size), seed weight (including kernel weight), increased kernel row number (optionally wherein ear length is not substantially reduced), increased number of pods, increased number of seeds per pod and an increase in ear length as compared to a control plant or part thereof.

As used herein a "trait" is a physiological, morphological, biochemical, or physical characteristic of a plant or particular plant material or cell. In some instances, this characteristic is visible to the human eye and can be measured mechanically, such as seed or plant size, weight, shape, form, length, height, growth rate and development stage, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example, by employing Northern analysis, RT-PCR, microarray gene expression assays, or reporter gene expression systems, or by agricultural observations such as hyperosmotic stress tolerance or yield. However, any technique can be used to measure the amount of, the comparative level of, or the difference in any selected chemical compound or macromolecule in the transgenic plants.

As used herein an "enhanced trait" means a characteristic of a plant resulting from mutations in a DA1 gene(s) as described herein. Such traits include, but are not limited to, an enhanced agronomic trait characterized by enhanced plant morphology, physiology, growth and development, yield, nutritional enhancement, disease, or pest resistance, or environmental or chemical tolerance. In some embodiments, an enhanced trait/altered phenotype may be, for example, decreased days from planting to maturity, increased stalk size, increased number of leaves, increased plant height growth rate in vegetative stage, increased ear size, increased ear dry weight per plant, increased number of kernels per ear, increased weight per kernel, increased number of kernels per plant, decreased ear void, extended grain fill period, reduced plant height, increased number of root branches, increased total root length, drought tolerance, increased water use efficiency, cold tolerance, increased nitrogen use efficiency, and/or increased yield. In some embodiments, a trait is increased yield under nonstress conditions or increased yield under environmental stress conditions. Stress conditions can include both biotic and abiotic stress, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, ear size, ear tip filling, kernel abortion, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), flowering time and duration, ear number, ear size, ear weight, seed number per ear or pod, seed size, composition of seed (starch, oil, protein) and characteristics of seed fill.

Also used herein, the term "trait modification" encompasses altering the naturally occurring trait by producing a detectable difference in a characteristic in a plant comprising a mutation in an endogenous DA1 gene as described herein relative to a plant not comprising the mutation, such as a wild-type plant, or a negative segregant. In some cases, the trait modification can be evaluated quantitatively. For example, the trait modification can entail an increase or decrease in an observed trait characteristic or phenotype as compared to a control plant. It is known that there can be natural variations in a modified trait. Therefore, the trait modification observed can entail a change of the normal distribution and magnitude of the trait characteristics or phenotype in the plants as compared to a control plant.

The present disclosure relates to a plant with improved economically relevant characteristics, more specifically increased yield. More specifically the present disclosure relates to a plant comprising a mutation(s) in a DA1 gene(s) as described herein, wherein the plant has increased yield as compared to a control plant devoid of said mutation(s). In some embodiments, plants produced as described herein exhibit increased yield or improved yield trait components as compared to a control plant. In some embodiments, a plant of the present disclosure exhibits an improved trait that is related to yield, including but not limited to increased nitrogen use efficiency, increased nitrogen stress tolerance, increased water use efficiency and/or increased drought tolerance, as defined and discussed infra.

Yield can be defined as the measurable produce of economic value from a crop. Yield can be defined in the scope of quantity and/or quality. Yield can be directly dependent on several factors, for example, the number and size of organs, plant architecture (such as the number of branches, plant biomass, e.g., increased root biomass, steeper root angle and/or longer roots, and the like), flowering time and duration, grain fill period. Root architecture and development, photosynthetic efficiency, nutrient uptake, stress tolerance, early vigor, delayed senescence and functional stay green phenotypes may be factors in determining yield. Optimizing the above-mentioned factors can therefore contribute to increasing crop yield.

Reference herein to an increase/improvement in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens.

"Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; or (ii)

increased early vigor, defined herein as an improved seedling aboveground area approximately three weeks post-germination.

"Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor, for example, can be a combination of the ability of seeds to germinate and emerge after planting and the ability of the young plants to grow and develop after emergence. Plants having early vigor also show increased seedling survival and better establishment of the crop, which often results in highly uniform fields with the majority of the plants reaching the various stages of development at substantially the same time, which often results in increased yield. Therefore, early vigor can be determined by measuring various factors, such as kernel weight, percentage germination, percentage emergence, seedling growth, seedling height, root length, root and shoot biomass, canopy size and color and others.

Further, increased yield can also manifest as increased total seed yield, which may result from one or more of an increase in seed biomass (seed weight) due to an increase in the seed weight on a per plant and/or on an individual seed basis an increased number of, for example, flowers/panicles per plant; an increased number of pods; an increased number of nodes; an increased number of flowers ("florets") per panicle/plant; increased seed fill rate; an increased number of filled seeds; increased seed size (length, width, area, perimeter, and/or weight), which can also influence the composition of seeds; and/or increased seed volume, which can also influence the composition of seeds. In one embodiment, increased yield can be increased seed yield, for example, increased seed weight; increased number of filled seeds; and/or increased harvest index.

Increased yield can also result in modified architecture, or can occur because of modified plant architecture.

Increased yield can also manifest as increased harvest index, which is expressed as a ratio of the yield of harvestable parts, such as seeds, over the total biomass The disclosure also extends to harvestable parts of a plant such as, but not limited to, seeds, leaves, fruits, flowers, bolls, pods, siliques, nuts, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Typically, plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein, "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein, "water deficit" refers to the conditions or environments that provide less than optimal amounts of water needed for adequate/successful growth and development of plants.

As used herein, "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein with respect to nucleic acids, the term "fragment" or "portion" refers to a nucleic acid that is reduced in length relative (e.g., reduced by 1, 2, 3, 4, 5, 6, 7, 8, 9, 10, 11, 12, 13, 14, 15, 16, 17, 18, 19, 20, 20, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 400, 450, 500, 550, 600, 650, 700, 750, 800, 850, or 900 or more nucleotides or any range or value therein) to a reference nucleic acid and that comprises, consists essentially of and/or consists of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to a corresponding portion of the reference nucleic acid. Such a nucleic acid fragment may be, where appropriate, included in a larger polynucleotide of which it is a constituent. As an example, a repeat sequence of guide nucleic acid of this invention may comprise a "portion" of a wild type CRISPR-Cas repeat sequence (e.g., a wild type CRISPR-Cas repeat; e.g., a repeat from the CRISPR Cas system of, for example, a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or a Cas14c, and the like).

In some embodiments, a nucleic acid fragment may comprise, consist essentially of or consist of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 320, 330, 340, 350, 360, 370, 380, 390, 395, 400, 410, 415, 420, 425, 430, 435, 440, 445, 450, 500, 550, 600, 650, 700, 750, 800, 850, 900, 950, 1000, 1100, 1150, 1200, 1250, 1300, 1350, 1400, 1450, 1500, 1550, 1600, 1650, 1700, 1750, or 1800 or more consecutive nucleotides, or any range or value therein, of a nucleic acid encoding an DA1 polypeptide, optionally a fragment of an DA1 gene may be about 10, 20, 30, 35, 40, 45, 50, 55, 60, 65, 70, 75, 80, 85, 90, 95, 100, 110, 115, 120, 125, 130, 135, 140, 145, 150 consecutive nucleotides to about 155, 160, 165, 170, 175, 180, 185, 190, 195, 200, 205, 210, 215, 220, 225, 230, 240, 245, 250, 255, 260, 265, 270, 275, 280, 285, 290, 295, 300, 305, 310, 315, 320, 325, 330, 340, 345, 350, 355, 360, 365, 370, 375, 380, 385, 390, 395, or 400, or more consecutive nucleotides in length, or any range or value therein (e.g., a fragment or portion of any one of SEQ ID NOs:69, 70, 109, or 110 (e.g., SEQ ID NOs:72-101 or 112-139).

In some embodiments, a "sequence-specific nucleic acid binding domain" may bind to one or more fragments or portions of nucleotide sequences (e.g., DNA, RNA) encoding, for example, ubiquitin binding peptidase (DA1) polypeptide as described herein.

As used herein with respect to polypeptides, the term "fragment" or "portion" may refer to a polypeptide that is reduced in length relative to a reference polypeptide and that comprises, consists essentially of and/or consists of an amino acid sequence of contiguous amino acids identical or almost identical (e.g., 90%, 91%, 92%, 93%, 94%, 95%, 96%, 97%, 98%, 99% identical) to a corresponding portion of the reference polypeptide. Such a polypeptide fragment may be, where appropriate, included in a larger polypeptide of which it is a constituent. In some embodiments, a polypeptide fragment may comprise, consist essentially of, or consist of at least about 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175, 200, 225, 250, 260, 270, 280, or 290 or more consecutive amino acids of a reference polypeptide. In some embodiments, a polypeptide fragment may comprise, consist essentially of or consist of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 230, 240, or 250 or more consecutive amino acid residues, or any range or value therein, of a DA1 polypeptide (e.g., a fragment or a portion of SEQ ID NOs:71 or 111 (e.g., SEQ ID NOs:102-108 or 140-146)).

In some embodiments, such a deletion when comprised in a plant can result in the plant exhibiting one or more improved yield traits, as compared to a plant not comprising said deletion. A DA1 gene may be edited in one or more than one location (and using one or more different editing tools), thereby providing a DA1 gene comprising one or more than one mutation. In some embodiments, a DA1 polypeptide mutated as described herein may comprise one or more than one edit that may result in a polypeptide having one or more than one amino acid deletion (e.g., 1, 2, 3, 4, 5, 6, 7, 8, 9, or 10 or more amino acid deletions (e.g., a truncated polypeptide), optionally a deletion of more than one consecutive amino acids). In some embodiments, an DA1 polypeptide mutated as described herein may comprise one or more than one edit that may result in a polypeptide having one or more than one amino acid substitution, optionally wherein the polypeptide comprises 1, 2, 3, 4, 5 or 6 or more amino acid substitutions.

In some embodiments, a "portion" or "region" in reference to a nucleic acid means at least 2, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 120, 130, 140, 141, 142, 143, 144, 145, 150, 160, 170, 180, 190, 200, 210, 220, 230, 240, 250, 260, 270, 280, 285, 290, 300, 310, 320, 330, 340, 350, 360, 370, 380, 390, 395, 400, 405, 410, 415, 420, 425, 430, 435, 440, 445, 450, 500, 600, 700, 800, 900, 1000, 1100, 1200, 1300, 1400, 1500, 1600, or 1700 or more consecutive nucleotides from a gene (e.g., consecutive nucleotides from a DA1 gene), optionally a "portion" or "region" of an DA1 gene may be about 5, 6, 7, 8, 9, 10, 20, 30, 35, 40, 45, 50, 55, 60, 65, 70, 75, 80, 85, 90, 95, 100, 110, 115, 120, 125, 130, 135, 140, 145, 150 consecutive nucleotides to about 155, 160, 165, 170, 175, 180, 185, 190, 195, 200, 205, 210, 215, 220, 225, 230, 240, 245, 250, 255, 260, 265, 270, 275, 280, 285, 290, 295, 300, 305, 310, 315, 320, 325, 330, 340, 345, 350, 355, 360, 365, 370, 375, 380, 385, 390, 395, or 400, or more consecutive nucleotides in length, or any range or value therein (e.g., a portion or region of any one of SEQ ID NOs:69, 70, 109, or 110 (e.g., SEQ ID NOs:72-101 or 112-139, optionally SEQ ID NOs:74-76, 78-80, 82-85, 89-96, 99-101, 114-116, 119, 120, 123-126, 128-131, 133-135, 138, or 139, optionally SEQ ID NOs:82-85, 99-101, 123-126, 138, or 139)).

In some embodiments, a "portion" or "region" of a DA1 polypeptide sequence may be about 5 to about 250 or more consecutive amino acid residues in length (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 120, 130, 140, 141, 142, 143, 144, 145, 150, 160, 170, 180, 190, 200, 210, 220, 230, 240, or 250, or more consecutive amino acid residues in length (e.g., a portion of any one of SEQ ID NO:71 or SEQ ID NO:111 (e.g., SEQ ID NOs:102-108 or 140-146, optionally SEQ ID NOs:103-108, 141, 142, or 144-146, or SEQ ID NOs:105-108 or 144-146).

As used herein with respect to nucleic acids, the term "functional fragment" refers to nucleic acid that encodes a functional fragment of a polypeptide. A "functional fragment" with respect to a polypeptide is a fragment of a polypeptide that retains one or more of the activities of the native reference polypeptide.

The term "gene," as used herein, refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The term "mutation" refers to point mutations (e.g., missense, or nonsense, or insertions or deletions of single base pairs that result in frame shifts), insertions, deletions, inversions and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue. A truncation can include a truncation at the C-terminal end of a polypeptide or at the N-terminal end of a polypeptide. A truncation of a polypeptide can be the result of a deletion of the corresponding 5' end or 3' end of the gene encoding the polypeptide. A frameshift mutation can occur when deletions or insertions of one or more base pairs are introduced into a gene, optionally resulting in an out-of-frame mutation or an in-frame mutation. Frameshift mutations in a gene can result in the production of a polypeptide that is longer, shorter or the same length as the wild type polypeptide depending on when the first stop codon occurs following the mutated region of the gene. As an example, an out-of-frame mutation that produces a premature stop codon can produce a polypeptide that is shorter that the wild type polypeptide, or, in some embodiments, the polypeptide may be absent/undetectable. A DNA inversion is the result of a rotation of a genetic fragment within a region of a chromosome.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement," as used herein, can mean 100% complementarity with the comparator nucleotide sequence or it can mean less than 100% complementarity (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity) to the comparator nucleotide sequence.

Different nucleic acids or proteins having homology are referred to herein as "homologues." The term homologue includes homologous sequences from the same and from other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%8, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent sequence identity" can refer to the percentage of identical amino acids in an amino acid sequence as compared to a reference polypeptide.

As used herein, the phrase "substantially identical," or "substantial identity" in the context of two nucleic acid molecules, nucleotide sequences, or polypeptide sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, about 100 nucleotides to about 200 nucleotides, about 100 nucleotides to about 300 nucleotides, about 100 nucleotides to about 400 nucleotides, about 100 nucleotides to about 500 nucleotides, about 100 nucleotides to about 600 nucleotides, about 100 nucleotides to about 800 nucleotides, about 100 nucleotides to about 900 nucleotides, or more in length, or any range therein, up to the full length of the sequence. In some embodiments, nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40, 50, 60, 70, or 80 nucleotides or more).

In some embodiments of the invention, the substantial identity exists over a region of consecutive amino acid residues of a polypeptide of the invention that is about 3 amino acid residues to about 20 amino acid residues, about 5 amino acid residues to about 25 amino acid residues, about 7 amino acid residues to about 30 amino acid residues, about 10 amino acid residues to about 25 amino acid residues, about 15 amino acid residues to about 30 amino acid residues, about 20 amino acid residues to about 40 amino acid residues, about 25 amino acid residues to about 40 amino acid residues, about 25 amino acid residues to about 50 amino acid residues, about 30 amino acid residues to about 50 amino acid residues, about 40 amino acid residues to about 50 amino acid residues, about 40 amino acid residues to about 70 amino acid residues, about 50 amino acid residues to about 70 amino acid residues, about 60 amino acid residues to about 80 amino acid residues, about 70 amino acid residues to about 80 amino acid residues, about 90 amino acid residues to about 100 amino acid residues, or more amino acid residues in length, and any range therein, up to the full length of the sequence. In some embodiments, polypeptide sequences can be substantially identical to one another over at least about 8 consecutive amino acid residues (e.g., about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 130, 140, 150, 175, 200, 225, 250, 300, 350 or more amino acids in length or more consecutive amino acid residues). In some embodiments, two or more DA1 polypeptides may be identical or substantially identical (e.g., at least 70% to 99.9% identical; e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% identical or any range or value therein) over at least 8 consecutive amino acids to about 350 consecutive amino acids. In some embodiments, two or more DA1 polypeptides may be identical or substantially identical over at least 8, 9, 10, 11, 12, 13, 14, or 15 consecutive amino acids to about 20, 21, 22, 23, 24, 25, 26, 27, 28, 29, 30, 31, 32, 33, 34, 35, 36, 37, 38, 39, or 40 consecutive amino acids).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention (e.g., expression cassettes and/or vectors) may be codon optimized for expression. In some embodiments, the polynucleotides, nucleic acid constructs, expression cassettes, and/or vectors of the editing systems of the invention (e.g., comprising/encoding a sequence-specific nucleic acid binding domain (e.g., a sequence-specific nucleic acid binding domain (e.g., DNA binding domain) from a polynucleotide-guided endonuclease, a zinc finger nuclease, a transcription activator-like effector nuclease (TALEN), an Argonaute protein, and/or a CRISPR-Cas endonuclease (e.g., CRISPR-Cas effector protein) (e.g., a Type I CRISPR-Cas effector protein, a Type II CRISPR-Cas effector protein, a Type III CRISPR-Cas effector protein, a Type IV CRISPR-Cas effector protein, a Type V CRISPR-Cas effector protein or a Type VI CRISPR-Cas effector protein)), a nuclease (e.g., an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN)), deaminase proteins/domains (e.g., adenine deaminase, cytosine deaminase), a polynucleotide encoding a reverse transcriptase protein or domain, a polynucleotide encoding a 5'-3' exonuclease polypeptide, and/or affinity polypeptides, peptide tags, etc.) may be codon optimized for expression in a plant. In some embodiments, the codon optimized nucleic acids, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acids, polynucleotides, expression cassettes, and/or vectors that have not been codon optimized.

In any of the embodiments described herein, a polynucleotide or nucleic acid construct of the invention may be operatively associated with a variety of promoters and/or other regulatory elements for expression in a plant and/or a cell of a plant. Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," in reference to polypeptides, refers to the attachment of one polypeptide to another. A polypeptide may be linked to another polypeptide (at the N-terminus or the C-terminus) directly (e.g., via a peptide bond) or through a linker.

The term "linker" is art-recognized and refers to a chemical group, or a molecule linking two molecules or moieties, e.g., two domains of a fusion protein, such as, for example, a nucleic acid binding polypeptide or domain and peptide tag and/or a reverse transcriptase and an affinity polypeptide that binds to the peptide tag; or a DNA endonuclease polypeptide or domain and peptide tag and/or a reverse transcriptase and an affinity polypeptide that binds to the peptide tag. A linker may be comprised of a single linking molecule or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide.

In some embodiments, a peptide linker useful with this invention may be about 2 to about 100 or more amino acids in length, for example, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 2 to about 40, about 2 to about 50, about 2 to about 60, about 4 to about 40, about 4 to about 50, about 4 to about 60, about 5 to about 40, about 5 to about 50, about 5 to about 60, about 9 to about 40, about 9 to about 50, about 9 to about 60, about 10 to about 40, about 10 to about 50, about 10 to about 60, or about 2, 3, 4, 5, 6, 7, 8, 9, 10, 11, 12, 13, 14, 15, 16, 17, 18, 19, 20, 21, 22, 23, 24, 25 amino acids to about 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more amino acids in length (e.g., about 105, 110, 115, 120, 130, 140 150 or more amino acids in length). In some embodiments, a peptide linker may be a GS linker.

As used herein, the term "linked," or "fused" in reference to polynucleotides, refers to the attachment of one polynucleotide to another. In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covenant linkage or binding, including e.g., Watson-Crick base-pairing, or through one or more linking nucleotides.

In some embodiments, a polynucleotide motif of a certain structure may be inserted within another polynucleotide sequence (e.g., extension of the hairpin structure in the guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in *Genetic Engineering of Plants*, T. Kosuge, C. Meredith and A. Hollaender (eds.), Plenum Press, pp. 211-227).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. Gene 403:132-142 (2007); Li et al. *Mol Biol. Rep.* 37:1143-1154 (2010)). PrbcS1 and Pactin are constitutive promoters and Pnr and Pdca1 are inducible promoters.

Pnr is induced by nitrate and repressed by ammonium (Li et al. Gene 403:132-142 (2007)) and Pdca1 is induced by salt (Li et al. *Mol Biol. Rep.* 37:1143-1154 (2010)). In some embodiments, a promoter useful with this invention is RNA polymerase II (Pol II) promoter. In some embodiments, a U6 promoter or a 7SL promoter from *Zea mays* may be useful with constructs of this invention. In some embodiments, the U6c promoter and/or 7SL promoter from *Zea mays* may be useful for driving expression of a guide nucleic acid. In some embodiments, a U6c promoter, U6i promoter and/or 7SL promoter from *Glycine max* may be useful with constructs of this invention. In some embodiments, the U6c promoter, U6i promoter and/or 7SL promoter from *Glycine max* may be useful for driving expression of a guide nucleic acid.

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *Arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2_USP from maize (Wang et al. *Genome* 60(6):485-495 (2017)), LAT52 and LAT59 from tomato (Twell et al. *Development* 109(3):705-713 (1990)), Zm13 (U.S. Pat. No. 10,421,972), PLA2-6 promoter from *Arabidopsis* (U.S. Pat. No. 7,141,424), and/or the ZmC5 promoter from maize (International PCT Publication No. WO1999/042587.

Additional examples of plant tissue-specific/tissue preferred promoters include, but are not limited to, the root hair-specific cis-elements (RHEs) (Kim et al. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SANMS) (Vander Mijnsbrugge et al. (1996) *Plant and Cell Physiology*, 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), *petunia* chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) Plant *Cell* 1:1175-1183), and chalcone synthase promoters (Franken et al. (1991) *EMBO J.* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron (see, e.g., SEQ ID NO:21 and SEQ ID NO:22).

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a one or more polynucleotides of the invention (e.g., a polynucleotide encoding a sequence-specific nucleic acid binding domain, a polynucleotide encoding a deaminase protein or domain, a polynucleotide encoding a reverse transcriptase protein or domain, a polynucleotide encoding a 5'-3' exonuclease polypeptide or domain, a guide nucleic acid and/or reverse transcriptase (RT) template), wherein polynucleotide(s) is/are operably associated with one or more control sequences (e.g., a promoter, terminator and the like). Thus, in some embodiments, one or more expression cassettes may be provided, which are designed to express, for example, a nucleic acid construct of the invention (e.g., a polynucleotide encoding a sequence-specific nucleic acid binding domain, a polynucleotide encoding a nuclease polypeptide/domain, a polynucleotide encoding a deaminase protein/domain, a polynucleotide encoding a reverse transcriptase protein/domain, a polynucleotide encoding a 5'-3' exonuclease polypeptide/domain, a polynucleotide encoding a peptide tag, and/or a polynucleotide encoding an affinity polypeptide, and the like, or comprising a guide nucleic acid, an extended guide nucleic acid, and/or RT template, and the like). When an expression cassette of the present invention comprises more than one polynucleotide, the polynucleotides may be operably linked to a single promoter that drives expression of all of the polynucleotides or the polynucleotides may be operably linked to one or more separate promoters (e.g., three polynucleotides may be driven by one, two or three promoters in any combination). When two or more separate promoters are used, the promoters may be the same promoter, or they may be different promoters. Thus, a polynucleotide encoding a sequence specific nucleic acid binding domain, a polynucleotide encoding a nuclease protein/domain, a polynucleotide encoding a CRISPR-Cas effector protein/domain, a polynucleotide encoding an deaminase protein/domain, a polynucleotide encoding a reverse transcriptase polypeptide/domain (e.g., RNA-dependent DNA polymerase), and/or a polynucleotide encoding a 5'-3' exonuclease polypeptide/domain, a guide nucleic acid, an extended guide nucleic acid and/or RT template when comprised in a single expression cassette may each be operably linked to a single promoter, or separate promoters in any combination.

An expression cassette comprising a nucleic acid construct of the invention may be chimeric, meaning that at least one (e.g., one or more) of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to, for example, a gene encoding a sequence-specific nucleic acid binding protein, a gene encoding a nuclease, a gene encoding a reverse transcriptase, a gene encoding a deaminase, and the like, or may be native to a host cell, or may be native to another source (e.g., foreign or heterologous to, for example, to a promoter, to a gene encoding a sequence-specific nucleic acid binding protein, a gene encoding a nuclease, a gene encoding a reverse transcriptase, a gene encoding a deaminase, and the like, or to the host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

In addition to expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct (e.g., expression cassette(s)) comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self-transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g., autonomous replicating plasmid with an origin of replication). Additionally, included are shuttle vectors by which is meant a DNA vehicle capable, naturally or by design, of replication in two different host organisms, which may be selected from actinomycetes and related species, bacteria and eukaryotic (e.g., higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid or polynucleotide of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). As an example, a target nucleic acid may be contacted with a sequence-specific nucleic acid binding protein (e.g., polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein)) and a deaminase or a nucleic acid construct encoding the same, under conditions whereby the sequence-specific nucleic acid binding protein, the reverse transcriptase and/or the deaminase are expressed and the sequence-specific nucleic acid binding protein binds to the target nucleic acid, and the reverse transcriptase and/or deaminase may be fused to either the sequence-specific nucleic acid binding protein or recruited to the sequence-specific nucleic acid binding protein (via, for example, a peptide tag fused to the sequence-specific nucleic acid binding protein and an affinity tag fused to the reverse transcriptase and/or deaminase) and thus, the deaminase and/or reverse transcriptase is positioned in the vicinity of the target nucleic acid, thereby modifying the target nucleic acid. Other methods for recruiting reverse transcriptase and/or deaminase may be used that take advantage of other protein-protein interactions, and also RNA-protein interactions and chemical interactions may be used for protein-protein and protein-nucleic acid recruitment.

As used herein, "modifying" or "modification" in reference to a target nucleic acid includes editing (e.g., mutating), covalent modification, exchanging/substituting nucleic acids/nucleotide bases, deleting, cleaving, nicking, and/or altering transcriptional control of a target nucleic acid. In some embodiments, a modification may include one or more single base changes (SNPs) of any type.

"Introducing," "introduce," "introduced" (and grammatical variations thereof) in the context of a polynucleotide of interest means presenting a nucleotide sequence of interest (e.g., polynucleotide, RT template, a nucleic acid construct, and/or a guide nucleic acid) to a plant, plant part thereof, or cell thereof, in such a manner that the nucleotide sequence gains access to the interior of a cell.

The terms "transformation" or transfection" may be used interchangeably and as used herein refer to the introduction of a heterologous nucleic acid into a cell. Transformation of a cell may be stable or transient. Thus, in some embodiments, a host cell or host organism (e.g., a plant) may be stably transformed with a polynucleotide/nucleic acid molecule of the invention.

In some embodiments, a host cell or host organism may be transiently transformed with a polynucleotide/nucleic acid molecule of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention (e.g., one or more expression cassettes comprising polynucleotides for editing as described herein) may be transiently introduced into a cell with a guide nucleic acid and as such, no DNA is maintained in the cell.

A nucleic acid construct of the invention may be introduced into a plant cell by any method known to those of skill in the art. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2318 (2013)) General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

In some embodiments of the invention, transformation of a cell may comprise nuclear transformation. In other embodiments, transformation of a cell may comprise plastid transformation (e.g., chloroplast transformation). In still further embodiments, nucleic acids of the invention may be introduced into a cell via conventional breeding techniques. In some embodiments, one or more of the polynucleotides, expression cassettes and/or vectors may be introduced into a plant cell via *Agrobacterium* transformation.

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

The present invention is directed to modification of Ubiquitin Binding Peptidase (DA1) genes (e.g., DA1-1 genes, DA1-2 genes) in plants through editing technology to provide plants that exhibit one or more improved yield traits. Mutations that may be useful for producing plants with one or more improved yield traits include, for example, substitutions, deletions, and/or insertions. In some aspects, a mutation generated by the editing technology can be a point mutation.

In some embodiments, the invention provides a plant or plant part thereof comprising at least one mutation in an endogenous Ubiquitin Binding Peptidase (DA1) gene encoding a ubiquitin binding peptidase (DA1) polypeptide. In some embodiments, the at least one mutation may be a non-natural mutation. In some embodiments, an endogenous DA1 gene may be an endogenous DA1-1 gene or an endogenous DA1-2 gene, wherein the encoded DA1 polypeptide is a DA1-1 polypeptide or a DA1-2 polypeptide, respectively. In some embodiments, the at least one mutation may be a null mutation, dominant mutation, semi-dominant mutation, or a dominant negative mutation. In some embodiments, the at least one mutation may be a recessive mutation, optionally wherein the recessive mutation is a null mutation. In some embodiments a mutation in a DA1 gene as described herein comprises a nucleic acid sequence having at least 90% (e.g., 90%, 91%, 92%, 93%, 94%, 95%, 96%, 97%, 98%, 99%, 99.5%. 99.9% or 100%) sequence identity to any one of SEQ ID NOs:154-158.

As used herein, a "non-natural mutation" refers to a mutation that is generated though human intervention and differs from mutations found in the same gene that have occurred in nature (e.g., occurred naturally)).

In some embodiments, a plant cell is provided, the plant cell comprising an editing system, the editing system comprising: (a) a CRISPR-Cas effector protein; and (b) a guide nucleic acid (e.g., gRNA, gDNA, crRNA, crDNA, sgRNA, sgDNA) comprising a spacer sequence with complementarity to an endogenous target gene encoding a ubiquitin binding peptidase (DA1) polypeptide. The editing system may be used to generate a mutation in the endogenous target gene encoding a DA1 polypeptide. In some embodiments, the endogenous target gene is an endogenous Ubiquitin Binding Peptidase (DA1) gene, optionally an endogenous DA1-1 gene or an endogenous DA1-2 gene, and the DA1 polypeptide is DA1-1 polypeptide or a DA1-2 polypeptide. In some embodiments, the mutation is a non-natural mutation. In some embodiments, a guide nucleic acid of an editing system may comprise the nucleotide sequence (a spacer sequence, e.g., one or more spacers) of any one of SEQ ID NOs:147-153 (e.g., SEQ ID NO:147 (PWsp1495), SEQ ID NO:148 (PWsp1496), SEQ ID NO:149 (PWsp1497), SEQ ID NO:150 (PWsp1498), SEQ ID NO:151 (PWsp1555), SEQ ID NO:152 (PWsp1686) and/or SEQ ID NO:153 (PWsp1687)). In some embodiments, spacers may target specific DA1 genes. For example, spacers having the SEQ ID NOs:147-153 may target a DA1 gene having at least 80% sequence identity to SEQ ID NO:69. In another example, spacers having the SEQ ID NOs:147-149 may target a DA1 gene having at least 80% sequence identity to SEQ ID NO:109. In some embodiments, the mutated DA1 gene that is generated may have a sequence that is at least 90% sequence identity to any one SEQ ID NOs:154-158.

A mutation in a DA1 gene of the plant, plant part thereof, or the plant cell useful for this invention may be any type of mutation, including a base substitution, a base deletion, and/or a base insertion. In some embodiments, the at least one mutation may be a non-natural mutation. In some embodiments, a mutation may comprise a base substitution to an A, a T, a G, or a C, optionally the base substitution may be from an A to a G or a G to an A. In some embodiments, a mutation may be a deletion of at least one base pair (e.g., 1 base pair to about 100 base pairs; e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 consecutive base pairs; e.g., 1 to about 50 consecutive base pairs, 1 to about 30 consecutive base pairs, 1 to about 15 consecutive base pairs) or an insertion of at least one base pair (e.g., 1 base pair to about 15 base pairs; e.g., 1, 2, 3, 4, 5, 6, 7, 8, 9, 10, 11, 12, 13, 14, or 15 consecutive base pairs), optionally wherein the deletion or insertion is an in-frame deletion, an in-frame insertion, an out-of-frame deletion, or an out-of-frame insertion. As an example, a deletion as described herein may result in a DA1 gene having at least 90% (e.g., 90%, 91%, 92%, 93%, 94%, 95%, 96%, 97%, 98%, 99%, 99.5%, 99.9% or 100%) sequence identity to any one of SEQ ID NOs:154-158.

A mutation in a DA1 gene may be located in the 5' region or the 3' region of the DA1 gene. In some embodiments, a mutation of a DA1 gene may be within a portion or region of the endogenous DA1 gene that encodes the DA1 polypeptide (e.g., the coding regions (exons)), which may be in the 5' or 3' region of the gene. In some embodiments, the at least one mutation may be an in-frame insertion or in-frame deletion, optionally wherein mutation of a DA1 gene may result in a DA1 polypeptide having an amino acid substitution as compared to a wild type mature DA1 polypeptide. In some embodiments, the in-frame insertion or in-frame deletion may be a dominant mutation, semi-dominant mutation, or a dominant negative mutation. In some embodiments, the mutation may be an out-of-frame deletion or an out-of-frame insertion that may result in a truncated polypeptide, or little or no detectible polypeptide. In some embodiments, the out-of-frame deletion or out-of-frame insertion may be a null mutation, optionally a recessive mutation. In some embodiments, a mutation located in the 5' region of the DA1 gene may be a deletion or an insertion that results in a premature stop codon (e.g., an out-of-frame base insertion or an out-of-frame base deletion) and a truncated DA1 polypeptide or, optionally results in little or no detectable DA1 polypeptide. In some embodiments, a mutation located in the 3' region of a DA1 gene may be a deletion or an insertion that results in an amino acid substitution in the encoded DA1 polypeptide.

The types of editing tools that may be used to generate these and other mutations in DA1 genes include any base editors or cutters, which are guided to a target site using spacers having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) complementarity to a portion or a region of a DA1 gene as described herein.

In some embodiments, a mutation of a DA1 gene is within a portion or region of the endogenous DA1 gene having at least 90% sequence identity to any one of the nucleotide sequences of SEQ ID NOs:72-101 or 112-139, optionally a portion or region of the endogenous DA1 gene having at least 90% sequence identity to any one of the nucleotide sequences SEQ ID NOs:74-76, 78-80, 82-85, 89-96, 99-101, 114-116, 119, 120, 123-126, 128-131, 133-135, 138, or 139, optionally in a region having at least 90% sequence identity to any one of SEQ ID NOs:82-85, 99-101, 123-126, 138, or 139.

In some embodiments, the at least one mutation in an endogenous DA1 gene results in a mutation of one or more amino acid residue(s) located in a region of the DA1 polypeptide having at least 90% sequence identity to any one of the amino acid sequences of SEQ ID NOs:102-108 or 140-146, optionally comprising an amino acid sequence having at least 90% sequence identity to any one of SEQ ID NOs:103-108, 141, 142 or 144-146, optionally in a region having at least 90% sequence identity to any one of SEQ ID NOs:105-108 or 144-146, optionally wherein the at least one mutation may be a non-natural mutation.

In some embodiments, the at least one mutation may result in a substitution of one or more of the amino acid residues located in a region having at least 90% (e.g., 90%, 91%, 92%, 93%, 94%, 95%, 96%, 97%, 98%, 99%, 99.5% or 100%, or any value or range therein) sequence identity to any one of the amino acid sequences of SEQ ID NOs:102-108 or 140-146, optionally a substitution of one or more amino acid residues located in a region having at least 90% sequence identity to any one of SEQ ID NOs:103-108, 141, 142 or 144-146, optionally in a region having at least 90% sequence identity to any one of SEQ ID NOs:105-108 or 144-146. In some embodiments, a substitution of one or more of the amino acid residues may be a substitution of one amino acid residue to about ten amino acid residues in the DA1 polypeptide (e.g., 1, 2, 3, 4, 5, 6, 7, 8, 9 or 10 amino acid residues). In some embodiments, the at least one mutation may result in a substitution of an amino acid residue located: at position 312 with reference to amino acid position numbering of SEQ ID NO:71 or at position 379 with reference to amino acid position numbering of SEQ ID NO:111, optionally wherein the substitution is arginine (R) to lysine (K) (R>K). In some embodiments, the at least one mutation may be a non-natural mutation.

An endogenous DA1 gene useful with this invention (e.g., an endogenous target gene) encodes a ubiquitin binding peptidase (DA1) polypeptide and includes an endogenous DA1-1 gene or an endogenous DA1-2 gene, which encode a DA1-1 polypeptide or an DA1-2 polypeptide, respectively. In some embodiments, an endogenous DA1 gene (e.g., endogenous target gene) (1) may comprise a nucleic acid sequence having at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.5% or 100%, or any value or range therein) sequence identity to any one of SEQ ID NOs:69, 70, 109, or 110, (2) may comprise a region of a DA1 gene having at least 90% sequence identity to any one of SEQ ID NOs:72-101 or 112-139, (3) may encode a polypeptide having at least 80% sequence identity to SEQ ID NO:71 or SEQ ID NO:111, and/or (4) may encode a region of a DA1 polypeptide having at least 90% (e.g., 90%, 91%, 92%, 93%, 94%, 95%, 96%, 97%, 98%, 99%, 99.5% or 100%, or any value or range therein) sequence identity to any one of SEQ ID NOs:102-108 or 140-146.

In some embodiments, a plant (e.g., a corn plant, a soybean plant) comprising at least one (e.g., one or more) mutation in an endogenous DA1 gene (optionally wherein the least one mutation may be a non-natural mutation) exhibits one or more improved yield traits as compared to a plant devoid of the at least one mutation (e.g., an isogenic plant (e.g., wild type unedited plant or a null segregant). In some embodiments, the one or more improved yield traits include, but are not limited to, increased yield (bu/acre), increased biomass, increased plant height, increased stem diameter, increased leaf area, increased flower number, increased kernel number, increased kernel size, increased ear length, increased number of pods, including an increased number of pods per node and/or an increased number of pods per plant, increased number of seeds per pod, increased number of seeds, increased seed size, and/or increased seed weight (e.g., increase in 100-seed weight). In some embodiments, the one or more improved yield traits may include, but is not limited to, an increase in yield (bu/acre), increased seed size (including kernel size), increased seed weight (including kernel weight), increased number of pods, and/or increased number of seeds per pod. In some embodiments, the at least one mutation in a plant may comprise a mutated DA1 gene having at least 90% (e.g., 90%, 91%, 92%, 93%, 94%, 95%, 96%, 97%, 98%, 99%, 99.5%. 99.9% or 100%) sequence identity to any one of SEQ ID NOs:154-158.

In some embodiments, a plant may be regenerated from a plant part and/or plant cell of the invention comprising a mutation in a DA1 gene as described herein, wherein the regenerated plant comprises the mutation in the endogenous DA1 gene and a phenotype of improvement in one or more yield traits as compared to a plant devoid of the same mutation in the DA1 gene.

In some embodiments, a plant cell is provided, the plant cell comprising at least one (e.g., one or more) mutation within an endogenous Ubiquitin Binding Peptidase (DA1) gene, wherein the at least one mutation is a substitution, insertion, or deletion that is introduced using an editing system that comprises a nucleic acid binding domain that binds to a target site in the endogenous DA1 gene. In some embodiments, the substitution, insertion, or deletion results in, for example, an amino acid substitution. In some embodiments, the substitution, insertion, or deletion results in, for example, a premature stop codon. In some embodiments, the substitution, insertion, or deletion results in, for example, a truncated DA1 protein and/or the absence of the DA1 protein (e.g., the truncation results in no or little detectable protein). In some embodiments, the at least one mutation may be a non-natural mutation. In some embodiments, the at least one mutation is a point mutation. In some embodiments, the at least one mutation within the DA1 gene is an insertion and/or a deletion, optionally the at least one mutation is an in-frame insertion or in-frame deletion and/or an out-of-frame insertion or out-of-frame deletion. In some embodiments, the plant cell that comprises at least one mutation in a DA1 gene may comprise a mutated DA1 gene as described herein having at least 90% (e.g., 90%, 91%, 92%, 93%, 94%, 95%, 96%, 97%, 98%, 99%, 99.5%. 99.9% or 100%) sequence identity to any one of SEQ ID NOs: 154-158.

In some embodiments, the target site in the DA1 gene of the plant cell is within a region of the endogenous DA1 gene, the region having at least 90% sequence identity to any one of the nucleotide sequences of SEQ ID NOs:72-101 or 112-139, optionally at least 90% (e.g., 90%, 91%, 92%, 93%, 94%, 95%, 96%, 97%, 98%, 99%, 99.5%. 99.9% or 100%) sequence identity to any one of SEQ ID NOs:74-76, 78-80, 82-85, 89-96, 99-101, 114-116, 119, 120, 123-126, 128-131, 133-135, 138, or 139, optionally at least 90% sequence identity to any one of SEQ ID NOs:82-85, 99-101, 123-126, 138, or 139. In some embodiments, the target site in the DA1 gene is within a region of the endogenous DA1 gene that encodes an amino acid sequence having at least 90% sequence identity to any one of SEQ ID NOs:102-108 or 140-146, optionally a substitution of any one or more amino acid residues located in a region having at least 90% sequence identity to any one of SEQ ID NOs:103-108, 141, 142, or 144-146, optionally a substitution of any one or more amino acid residues located in a region having at least 90% sequence identity to any one of SEQ ID NOs:105-108 or 144-146.

In some embodiments, a mutation may be made following cleavage by an editing system that comprises a nuclease and a nucleic acid binding domain that binds to a target site within a sequence having least 80% sequence identity to a sequence encoding of any one of SEQ ID NOs:69, 70, 109, or 110, or a sequence having at least 90% sequence identity to a sequence encoding any one of SEQ ID NOs:72-101 or 112-139, optionally at least 90% sequence identity to any one of SEQ ID NOs:74-76, 78-80, 82-85, 89-96, 99-101, 114-116, 119, 120, 123-126, 128-131, 133-135, 138, or 139, optionally at least 90% sequence identity to any one of SEQ ID NOs:82-85, 99-101, 123-126, 138, or 139, and the at least one mutation within a DA1 gene is made following cleavage by the nuclease. In some embodiments, the at least one mutation results in a modified amino acid residue located: at position 312 with reference to amino acid position numbering of SEQ ID NO:71 or at position 379 with reference to amino acid position numbering of SEQ ID NO:111, optionally wherein the substitution is arginine (R) to lysine (K) (R>K). In some embodiments, the at least one mutation may be a non-natural mutation. In some embodiments, the mutation may be a deletion, optionally wherein the mutation results in a DA1 gene having at least 90% sequence identity to any one of SEQ ID NOs:154-158.

In some embodiments, the at least one mutation may result in a recessive allele, a dominant allele, dominant negative allele, semi-dominant allele, or a null allele.

In some embodiments, the plant cell is regenerated into a plant that comprises the at least one mutation, optionally wherein the plant regenerated from the plant cell exhibits a phenotype of at least one (one or more) improved yield trait when compared to a wild-type plant not comprising/devoid of the allele (e.g., an isogenic wild type plant), optionally wherein the one or more improved yield traits includes, but is not limited to, increased yield (bu/acre), increased biomass, increased plant height, increased stem diameter, increased leaf area, increased flower number, increased kernel number, increased kernel size, increased ear length, increased number of pods, including an increased number of pods per node and/or an increased number of pods per plant, increased number of seeds per pod, increased number of seeds, increased seed size, and/or increased seed weight (e.g., increase in 100-seed weight) as compared to a control plant devoid of the at least one mutation. In some embodiments, the one or more improved yield traits resulting from a mutation as described herein includes, but is not limited to, an increase in yield (bu/acre), seed size (including kernel size), seed weight (including kernel weight), increased number of pods and/or increased number of seeds per pod as compared to a control plant devoid of the at least one mutation, optionally wherein the mutation may be a non-natural mutation.

In some embodiments, a method of producing/breeding a transgene-free edited plant (e.g., a soybean plant, a canola plant) is provided, the method comprising: crossing a plant of the present invention (e.g., a plant comprising one or more mutations (e.g., non-natural mutations) in one or more DA1 genes and having one or more improved yield traits) with a transgene free plant, thereby introducing the mutation into the plant that is transgene-free; and selecting a progeny plant that comprises the mutation and is transgene-free, thereby producing a transgene free edited plant.

Also provided herein is a method of providing a plurality of plants (e.g., canola plants, soybean plants) having one or more improved yield traits, the method comprising planting two or more plants of the invention (e.g., 2, 3, 4, 5, 6, 7, 8, 9, 10, 20, 30, 40, 50, 100, 200, 300, 400, 500, 1000, 2000, 3000, 400, 5000, or 10,000 or more plants comprising one or more mutations (e.g., non-natural mutations) in one or more DA1 genes and having one or more improved yield traits) in a growing area (e.g., a field (e.g., a cultivated field, an agricultural field), a growth chamber, a greenhouse, a recreational area, a lawn, and/or a roadside and the like), thereby providing a plurality of plants having one or more improved yield traits as compared to a plurality of control plants devoid of the mutation.

The invention further provides a method of generating variation in generating variation in a ubiquitin binding peptidase (DA1) polypeptide, comprising: introducing an editing system into a plant cell, wherein the editing system is targeted to a region of a Ubiquitin Binding Peptidase (DA1) gene (e.g., DA1-1, DA1-2) that encodes the DA1 polypeptide, and contacting the region of the DA1 gene with the editing system, thereby introducing a mutation into the DA1 gene and generating variation in the DA1 polypeptide of the plant cell. In some embodiments, the DA1 polypeptide is DA1-1 polypeptide, or a DA1-2 polypeptide, which is encoded by a DA1-1 gene or a DA1-2 gene, respectively. In some embodiments, the DA1 gene comprises a nucleotide sequence having at least 80% sequence identity to any one of SEQ ID NOs:69, 70, 109, or 110 and/or encodes an amino acid sequence having at least 80% sequence identity to SEQ ID NO:71 or SEQ ID NO:111, and the mutation is made following cleavage by the editing system that comprises a nuclease and a nucleic acid binding domain that binds to a target site within a sequence having at least 80% sequence identity to any one of the nucleotide sequences of SEQ ID NOs:69, 70, 109, or 110. In some embodiments, the variation that is generated in a DA1 gene as described herein results in a nucleic acid sequence having at least 90% sequence identity to any one of SEQ ID NOs:154-158.

In some embodiments, the region of the DA1 gene that is targeted for generating variation in a DA1 polypeptide comprises at least 90% sequence identity to any one of SEQ ID NOs:72-101 or 112-139, optionally comprises at least 90% sequence identity to any one of SEQ ID NOs:74-76, 78-80, 82-85, 89-96, 99-101, 114-116, 119, 120, 123-126, 128-131, 133-135, 138, or 139, optionally at least 90% sequence identity to any one of SEQ ID NOs:82-85, 99-101, 123-126, 138, or 139. In some embodiments, the region of the DA1 polypeptide in which variation is generated comprises an amino acid sequence having at least 90% sequence identity to any one of SEQ ID NOs:102-108 or 140-146, optionally comprises at least 90% sequence identity to any one of SEQ ID NOs:103-108, 141, 142 or 144-146, optionally a region having at least 90% sequence identity to any one of SEQ ID NOs:105-108 or 144-146.

In some embodiments, a method for editing a specific site in the genome of a plant cell is provided, the method comprising: cleaving, in a site-specific manner, a target site within an endogenous Ubiquitin Binding Peptidase (DA1) gene (e.g., DA1-1, DA1-2) in the plant cell, the endogenous DA1 gene: (a) comprising a nucleotide sequence having at least 80% sequence identity to any one of SEQ ID NOs:69, 70, 109, or 110, (b) comprising a region having at least 90% sequence identity to any one of SEQ ID NOs:72-101 or 112-139, (c) encoding an amino acid sequence having at least 80% sequence identity to SEQ ID NO:71 or SEQ ID NO:111, (d) encoding a region having at least 90% sequence identity to an amino acid sequence of any one of SEQ ID NOs:102-108 or 140-146, thereby generating an edit in the endogenous DA1 gene of the plant cell and producing a plant cell comprising the edit in the endogenous DA1 gene. In some embodiments, the endogenous DA1 gene is an endogenous DA1-1 gene or an endogenous DA1-2 gene. In some embodiments, the edit results in a DA1 gene having at least 90% sequence identity to any one of SEQ ID NOs: 154-158, optionally wherein the DA1 gene is a DA1-1 gene having at least 90% sequence identity to SEQ ID NO:157, and/or the DA1 gene is a DA1-2 gene having at least 90% sequence identity to any one of SEQ ID NOs:154-156 or 158. In some embodiments, the plant cell is from a soybean plant or a canola plant.

In some embodiments, the edit in the endogenous DA1 gene results in a mutation including, but not limited to, a base deletion, a base substitution, or a base insertion. In some embodiments, the at least one mutation may be in the 5' region or the 3' region of a DA1 gene. In some embodiments, the mutation may be a non-natural mutation. In some embodiments, the edit may be a nucleotide substitution of an A to a G or a G to an A. In some embodiments, the edit may result in at least one mutation that is an insertion of at least one base pair (e.g., 1, 2, 3, 4, 5, 6, 7, 8, 9, 10, 11, 12, 13, 14, or 15 base pairs, e.g., about 1-15 base pairs, e.g., 1 base pair to about 15 consecutive base pairs). In some embodiments, the edit may result in at least one mutation that is a deletion, optionally wherein the deletion is about 1 to about 100 consecutive base pairs in length, e.g., about 1-50 consecutive base pairs, about 1-30 consecutive base pairs or about 1-15 consecutive base pairs in length. A deletion or insertion useful with this invention may be an in-frame insertion, in-frame deletion, an out-of-frame insertion or an out-of-frame deletion. In some embodiments, an out-of-frame insertion or out-of-frame deletion may result in a premature stop codon and truncated protein, optionally wherein the out-of-frame insertion or out-of-frame deletion results in no or little detectable protein (e.g., a knock-out or null mutation, optionally wherein the mutation is recessive). In some embodiments, an edit as described herein results in a mutated DA1 gene comprising a nucleic acid sequence having at least 90% sequence identity to any one of SEQ ID NOs:154-158 optionally wherein the DA1 gene is a DA1-1 gene having at least 90% sequence identity to SEQ ID NO:157, and/or the DA1 gene is a DA1-2 gene having at least 90% sequence identity to any one of SEQ ID NOs: 154-156 or 158.

In some embodiments, an edit results in variation of amino acids in the coding region of the encoded DA1 polypeptide. As an example, an edit may result in variation in a sequence having at least 80% sequence identity to any one of SEQ ID NOs:69, 70, 109, or 110, a sequence having at least 90% identity to any one of SEQ ID NOs:74-76, 78-80, 82-85, 89-96, 99-101, 114-116, 119, 120, 123-126, 128-131, 133-135, 138, or 139, optionally having at least 90% sequence identity to any one of SEQ ID NOs:82-85, 99-101, 123-126, 138, or 139. In some embodiments, the edit is a base substitution of an A to a G or a G to an A that produces an amino acid substitution of an arginine (R) to a lysine (K) (R>K).

In some embodiments, a method of editing may further comprise regenerating a plant from the plant cell comprising the edit in the endogenous DA1 gene, thereby producing a plant comprising the edit in its endogenous DA1 gene and having a phenotype of one or more improved yield traits when compared to a control plant that is devoid of the edit. In some embodiments, a regenerated plant may comprise a mutated DA1 gene as described herein, optionally wherein the mutated DA1 gene comprises a nucleic acid sequence having at least 90% sequence identity to any one of SEQ ID NOs:154-158.

In some embodiments, a method for making a plant is provided, the method comprising (a) contacting a population of plant cells comprising an endogenous Ubiquitin Binding Peptidase (DA1) gene with a nuclease linked to a nucleic acid binding domain (e.g., editing system) that binds to a sequence (i) having at least 80% sequence identity to a nucleotide sequence of any one of SEQ ID NOs:69, 70, 109, or 110, (ii) comprising a region having at least 90% identity to any one of SEQ ID NOs:72-101 or 112-139; (iii) encoding an amino acid sequence having at least 80% sequence identity to SEQ ID NO:71 or SEQ ID NO:111, and/or (iv) encoding a region having at least 90% sequence identity to any one of SEQ ID NOs:102-108 or 140-146, and/or; (b) selecting a plant cell from the population of plant cells in which an endogenous DA1 gene has been mutated, thereby producing a plant cell comprising a mutation in the endogenous DA1 gene; and (c) growing the selected plant cell into a plant. In some embodiments, the plant that is produced comprises a mutated DA1 gene having at least 90% sequence identity to any one of SEQ ID NOs:154-158.

In some embodiments, a method of improving one or more yield traits in a plant is provided, the method comprising (a) contacting a plant cell comprising an endogenous Ubiquitin Binding Peptidase (DA1) gene with a nuclease targeting the endogenous DA1 gene, wherein the nuclease is linked to a nucleic acid binding domain (e.g., editing system) that binds to a target site in the endogenous DA1 gene, wherein the endogenous DA1 gene: (i) comprises a sequence having at least 80% sequence identity to the nucleotide sequence of any one of SEQ ID NOs:69, 70, 109, or 110; (ii) comprises a region having at least 90% identity to any one of SEQ ID NOs:72-101 or 112-139; (iii) encodes an amino acid sequence having at least 80% sequence identity to SEQ ID NO:71 or SEQ ID NO:111; and/or (iv) encodes an amino acid sequence comprising a region having at least 90% sequence identity to any one of SEQ ID NOs:102-108 or 140-146 to produce a plant cell comprising a mutation in the endogenous DA1 gene; and (b) growing the plant cell into a plant comprising the mutation in the endogenous DA1 gene thereby producing a plant having a mutated endogenous DA1 gene and one or more improved yield traits. In some embodiments, the plant having one or more improved yield traits comprises a mutated endogenous DA1 gene having at least 90% sequence identity to any one of SEQ ID NOs:154-158.

In some embodiments, a method for producing a plant or part thereof comprising at least one cell having a mutated endogenous Ubiquitin Binding Peptidase (DA1) gene, the method comprising contacting a target site in an endogenous DA1 gene (e.g., an endogenous DA1-1 gene, an endogenous DA1-2 gene) in the plant or plant part with a nuclease comprising a cleavage domain and a nucleic acid binding domain, wherein the nucleic acid binding domain binds to a target site in the endogenous DA1 gene, wherein the endogenous DA1 gene (a) comprises a sequence having at least 80% sequence identity to a nucleotide sequence of any one of SEQ ID NOs:69, 70, 109, or 110; (b) comprises a region having at least 90% identity to any one of SEQ ID NOs: 72-101 or 112-139; (c) encodes an amino acid sequence having at least 80% sequence identity to SEQ ID NO:71 or SEQ ID NO:111; and/or (d) encodes an amino acid sequence comprising a region having at least 90% identity to any one of SEQ ID NOs:102-108 or 140-146, thereby producing the plant or part thereof comprising at least one cell having a mutation in the endogenous DA1 gene. In some embodiments, the mutated endogenous DA1 gene comprised in the at least one cell of the plant or part thereof comprises a sequence having at least 90% sequence identity to any one of SEQ ID NOs: NOs:154-158.

Also provided herein is a method for producing a plant or part thereof comprising a mutated endogenous Ubiquitin Binding Peptidase (DA1) gene and exhibiting one or more improved yield traits, the method comprising contacting a target site in an endogenous DA1 gene (e.g., an endogenous DA1-1 gene, an endogenous DA1-2 gene) in the plant or plant part with a nuclease comprising a cleavage domain and a nucleic acid binding domain, wherein the nucleic acid binding domain binds to a target site in the endogenous DA1 gene, wherein the endogenous DA1 gene: (a) comprises a sequence having at least 80% sequence identity to a nucleotide sequence of any one of SEQ ID NOs:69, 70, 109, or 110; (b) comprises a region having at least 90% identity to any one of SEQ ID NOs:72-101 or 112-139; (c) encodes an amino acid sequence having at least 80% sequence identity to SEQ ID NO:71 or SEQ ID NO:111; and/or (d) encodes an amino acid sequence comprising a region having at least 90% identity to any one of SEQ ID NOs:102-108 or 140-146, thereby producing the plant or part thereof comprising an endogenous DA1 gene having a mutation and exhibiting one or more improved yield traits. In some embodiments, the one or more improved yield traits includes, but is not limited to, increased yield (bu/acre), increased biomass, increased plant height, increased stem diameter, increased leaf area, increased flower number, increased kernel number, increased kernel size, increased ear length, increased number of pods, including an increased number of pods per node and/or an increased number of pods per plant, increased number of seeds per pod, increased number of seeds, increased seed size, and/or increased seed weight (e.g., increase in 100-seed weight), optionally wherein the one or more improved yield traits may be, for example, an increase in yield (bu/acre), an increase in seed size (including kernel size), an increase in seed weight (including kernel weight), an increased number of pods, and/or an increased number of seeds per pod, as compared to a control plant devoid of the at least one mutation. In some embodiments, the mutated endogenous DA1 gene comprised in the plant or part thereof comprises a nucleic acid sequence having at least 90% sequence identity to any one of SEQ ID NOs:154-158.

In some embodiments, a nuclease may cleave an endogenous DA1 gene, thereby introducing the mutation into the endogenous DA1 gene. A nuclease useful with the invention may be any nuclease that can be utilized to edit/modify a target nucleic acid. Such nucleases include, but are not limited to a zinc finger nuclease, transcription activator-like effector nucleases (TALEN), endonuclease (e.g., Fok1) and/or a CRISPR-Cas effector protein. Likewise, any nucleic acid binding domain useful with the invention may be any DNA binding domain or RNA binding domain that can be utilized to edit/modify a target nucleic acid. Such nucleic acid binding domains include, but are not limited to, a zinc finger, transcription activator-like DNA binding domain (TAL), an argonaute and/or a CRISPR-Cas effector DNA binding domain.

In some embodiments, a nucleic acid binding domain (e.g., DNA binding domain) is comprised in a nucleic acid binding polypeptide. A "nucleic acid binding protein" or "nucleic acid binding polypeptide" as used herein refers to a polypeptide that binds and/or is capable of binding a nucleic acid in a site- and/or sequence-specific manner. In some embodiments, a nucleic acid binding polypeptide may be a sequence-specific nucleic acid binding polypeptide (e.g., a sequence-specific DNA binding domain) such as, but not limited to, a sequence-specific binding polypeptide and/or domain from, for example, a polynucleotide-guided endonuclease, a CRISPR-Cas effector protein (e.g., a CRISPR-Cas endonuclease), a zinc finger nuclease, a transcription activator-like effector nuclease (TALEN) and/or an Argonaute protein. In some embodiments, a nucleic acid binding polypeptide comprises a cleavage polypeptide (e.g., a nuclease polypeptide and/or domain) such as, but not limited to, an endonuclease (e.g., Fok1), a polynucleotide-guided endonuclease, a CRISPR-Cas endonuclease, a zinc finger nuclease, and/or a transcription activator-like effector nuclease (TALEN). In some embodiments, the nucleic acid binding polypeptide associates with and/or is capable of associating with (e.g., forms a complex with) one or more nucleic acid molecule(s) (e.g., forms a complex with a guide nucleic acid as described herein) that can direct or guide the nucleic acid binding polypeptide to a specific target nucleotide sequence (e.g., a gene locus of a genome) that is complementary to the one or more nucleic acid molecule(s) (or a portion or region thereof), thereby causing the nucleic acid binding polypeptide to bind to the nucleotide sequence at the specific target site. In some embodiments, the nucleic acid binding polypeptide is a CRISPR-Cas effector protein as described herein. In some embodiments, reference is made to specifically to a CRISPR-Cas effector protein for simplicity, but a nucleic acid binding polypeptide as described herein may be used. In some embodiments, a polynucleotide and/or a nucleic acid construct of the invention can be an "expression cassette" or can be comprised within an expression cassette.

In some embodiments, a method of editing an endogenous Ubiquitin Binding Peptidase (DA1) gene in a plant or plant part is provided, the method comprising contacting a target site in an endogenous DA1 gene in the plant or plant part with a cytosine base editing system comprising a cytosine deaminase and a nucleic acid binding domain that binds to a target site in the endogenous DA1 gene, wherein the endogenous DA1 gene: (a) comprises a sequence having at least 80% sequence identity to a nucleotide sequence of any one of SEQ ID NOs:69, 70, 109, or 110; (b) comprises a region having at least 90% identity to any one of SEQ ID NOs:72-101 or 112-139; (c) encodes an amino acid sequence having at least 80% sequence identity to SEQ ID NO:71 or SEQ ID NO:111; and/or (d) encodes an amino acid sequence comprising a region having at least 90% identity to any one of SEQ ID NOs:102-108 or 140-146, thereby editing the endogenous DA1 gene in the plant or part thereof and producing a plant or part thereof comprising at least one cell having a mutation in the endogenous DA1 gene. In some embodiments, editing as described herein may result in a deletion and a mutated DA1 gene having at least 90% sequence identity to any one of SEQ ID NOs:154-158.

In some embodiments, a method of editing an endogenous Ubiquitin Binding Peptidase (DA1) gene (e.g., DA1-1, DA1-2) in a plant or plant part is provided, the method comprising contacting a target site in an DA1 gene in the plant or plant part with an adenosine base editing system comprising an adenosine deaminase and a nucleic acid binding domain that binds to a target site in the DA1 gene, wherein the DA1 gene (a) comprises a sequence having at least 80% sequence identity to a nucleotide sequence of any one of SEQ ID NOs:69, 70, 109, or 110; (b) comprises a region having at least 90% identity to any one of SEQ ID NOs:72-101 or 112-139; (c) encodes an amino acid sequence having at least 80% sequence identity to SEQ ID NO:71 or SEQ ID NO:111; and/or (d) encodes an amino acid sequence comprising a region having at least 90% identity to any one of SEQ ID NOs:102-108 or 140-146, thereby editing the endogenous DA1 gene in the plant or part thereof and producing a plant or part thereof comprising at least one cell having a mutation in the endogenous DA1 gene. In some embodiments, editing an endogenous DA1 gene as described herein may result in a deletion and a mutated DA1 gene having at least 90% sequence identity to any one of SEQ ID NOs:154-158.

In some embodiments, a method of creating a mutation in a Ubiquitin Binding Peptidase (DA1) gene (e.g., DA1-1, DA1-2) in a plant is provided, comprising: (a) targeting a gene editing system to a portion of the DA1 gene that (i) comprises a sequence having at least 90% sequence identity to any one of SEQ ID NOs:72-101 or 112-139; and/or (ii) encodes a sequence having at least 90% identity to any one of SEQ ID NOs:102-108 or 140-146, and (b) selecting a plant that comprises a modified amino acid residue located in a region of the DA1 gene encoding an amino acid sequence having at least 90% sequence identity to any one of SEQ ID NOs:102-108 or 140-146, optionally wherein the modification may be a substitution at position 312 with reference to amino acid position numbering of SEQ ID NO:71 or at position 379 with reference to amino acid position numbering of SEQ ID NO:111. In some embodiments, when the amino acid modification is an amino acid substitution, the substitution is arginine (R) to lysine (K) (R>K). In some embodiments, the mutation may be located in a region of the DA1 gene encoding an amino acid sequence having at least 90% sequence identity to any one of SEQ ID NOs:103-108, 141, 142, or 144-146, optionally in a region having at least 90% sequence identity to any one of SEQ ID NOs:105-108 or 144-146. In some embodiments, the mutation that is created may be a deletion and the resultant mutated DA1 gene may have at least 90% sequence identity to any one of SEQ ID NOs:154-158.

A mutation useful with the invention may be a substitution, an insertion and/or a deletion, optionally wherein the insertion or deletion may be an in-frame insertion, in-frame deletion, an out-of-frame insertion, or an out-of-frame deletion. In some embodiments, a mutation may comprise a base substitution to an A, a T, a G, or a C, optionally the base substitution may be from an A to a G or a G to an A. In some embodiments, the mutation may be a deletion (in-frame or out-of-frame) of about 1 base pair to about 100 consecutive base pairs (e.g., 1 base pair to about 100 base pairs; e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 consecutive base pairs or any range or value therein; e.g., 1 to about 50 consecutive base pairs, 1 to about 30 consecutive base pairs, 1 to about 15 consecutive base pairs, e.g., 1 base pair to about 15 base pairs; e.g., 1, 2, 3, 4, 5, 6, 7, 8, 9, 10, 11, 12, 13, 14, or 15 consecutive base pairs) (see, e.g., SEQ ID NOs:154-158). In some embodiments, the mutation may be an insertion (in-frame or out-of-frame) of at least one base pair (e.g., 1 base pair to about 15 base pairs; e.g., 1, 2, 3, 4, 5, 6, 7, 8, 9, 10, 11, 12, 13, 14, or 15 consecutive base pairs). A mutation in a DA1 gene may be located in the 5' region or the 3' region of the DA1 gene, optionally wherein the mutation may be within a portion or region of the endogenous DA1 gene that encodes the DA1 polypeptide (e.g., the coding regions (exons)), which may be in the 5' or 3' region of the gene. In some embodiments, a mutation of a DA1 gene that is an in-frame insertion or in-frame deletion may result in a DA1 polypeptide having an amino acid substitution as compared to a wild type mature DA1 polypeptide. In some embodiments, the in-frame insertion or in-frame deletion may be a dominant mutation, semi-dominant mutation, or a dominant negative mutation. In some embodiments, a mutation of a DA1 gene that is an out-of-frame deletion or an out-of-frame insertion may result in a truncated polypeptide or may result in little or no detectible polypeptide. In some embodiments, the out-of-frame deletion or out-of-frame insertion may be a null mutation, optionally a recessive mutation. In some embodiments, a out-of-frame deletion or an out-of-frame insertion may be located in the 5' region of the DA1 gene that results in a premature stop codon (e.g., an out-of-frame base insertion or an out-of-frame base deletion) and a truncated DA1 polypeptide or, optionally results in little or no detectable DA1 polypeptide. In some embodiments, an in-frame insertion or in-frame may be located in the 3' region of a DA1 gene and results in an amino acid substitution in the encoded DA1 polypeptide. In some embodiments, a mutation provided by methods of the invention may be a non-natural mutation.

In some embodiments, a mutation may result in a modified amino acid residue is located in a region of the encoded DA1 polypeptide having at least 90% sequence identity to any one of SEQ ID NOs:102-108 or 140-146, optionally comprising an amino acid sequence having at least 90% sequence identity to any one of SEQ ID NOs:103-108, 141, 142 or 144-146, optionally in a region having at least 90% sequence identity to any one of SEQ ID NOs:105-108 or 144-146. In some embodiments, the mutation results in a modified amino acid residue at position 312 with reference to amino acid position numbering of SEQ ID NO:71 or at position 379 with reference to amino acid position numbering of SEQ ID NO:111. In some embodiments, the modification is a substitution of one or more amino acids, optionally a substitution of an arginine (R) for a lysine (K) (R>K).

In some embodiments, a method of detecting a mutant Ubiquitin Binding Peptidase (DA1) gene (e.g., DA1-1, DA1-2) is provided, the method comprising detecting in the genome of a plant an endogenous DA1 gene encoding a DA1 polypeptide comprising a mutation, optionally wherein the mutation is located in a region of the DA1 polypeptide having at least 90% sequence identity to any one of the amino acid sequences of SEQ ID NOs:103-108, 141, 142 or 144-146, optionally in a region having at least 90% sequence identity to any one of SEQ ID NOs:105-108 or 144-146. In some embodiments, a method of detecting a mutant DA1 gene is provided, the method comprising detecting in the genome of a plant a nucleic acid encoding the amino acid sequence of SEQ ID NO:71 or SEQ ID NO:111, wherein the amino acid sequence of SEQ ID NO:71 or SEQ ID NO:111 comprises a mutation in one or more of the amino acid residues located in a region of the DA1 polypeptide having at least 90% sequence identity to any one of SEQ ID NOs:103-108, 141, 142 or 144-146, optionally in a region having at least 90% sequence identity to any one of SEQ ID NOs:105-108 or 144-146. In some embodiments, the mutation is the result of a nucleotide substitution of an A to a G or a G to an A. In some embodiments, a mutated DA1 polypeptide comprises at least one mutation comprising a substitution of arginine (R) for lysine (K) (R>K). In some embodiments, the mutated DA1 gene that is detected may have at least 90% sequence identity to any one of SEQ ID NOs:154-158.

In some embodiments, the present invention provides a method of producing a plant comprising a mutation in an endogenous Ubiquitin Binding Peptidase (DA1) gene (e.g., DA1-1, DA1-2) and at least one polynucleotide of interest, the method comprising crossing a plant of the invention comprising at least one mutation in an endogenous DA1 gene (a first plant) with a second plant that comprises the at least one polynucleotide of interest to produce progeny plants; and selecting progeny plants comprising at least one mutation in the DA1 gene and the at least one polynucleotide of interest, thereby producing the plant comprising a mutation in an endogenous DA1 gene and at least one polynucleotide of interest.

The present invention further provides a method of producing a plant comprising a mutation in an endogenous DA1 gene and at least one polynucleotide of interest, the method comprising introducing at least one polynucleotide of interest into a plant of the present invention comprising at least one mutation in a DA1 gene, thereby producing a plant comprising at least one mutation in a DA1 gene and at least one polynucleotide of interest. In some embodiments, the plant is a corn plant. In some embodiments, the plant is a soybean plant.

In some embodiments, also provided is a method of producing a plant comprising a mutation in an endogenous DA1 gene and exhibiting a phenotype of improved yield traits, improved plant architecture and/or improved defense traits, the method comprising crossing a first plant, which is a plant of the present invention comprising at least one mutation in a DA1 gene, with a second plant that exhibits a phenotype of improved yield traits, improved plant architecture and/or improved defense traits; and selecting progeny plants comprising the mutation in the DA1 gene and a phenotype of improved yield traits, improved plant architecture and/or improved defense traits, thereby producing the plant comprising a mutation in an endogenous DA1 gene and exhibiting a phenotype of improved yield traits, improved plant architecture and/or improved defense traits as compared to a control plant.

Further provided is a method of controlling weeds in a container (e.g., pot, or seed tray and the like), a growth chamber, a greenhouse, a field, a recreational area, a lawn, or on a roadside, the method comprising applying an herbicide to one or more (a plurality) plants of the invention (e.g., a plant comprising at least one mutation, optionally a non-natural mutation, in a DA1 gene (e.g., DA1-1, DA1-2) as described herein) growing in a container, a growth chamber, a greenhouse, a field, a recreational area, a lawn, or on a roadside, thereby controlling the weeds in the container, the growth chamber, the greenhouse, the field, the recreational area, the lawn, or on the roadside in which the one or more plants are growing.

In some embodiments, a method of reducing insect predation on a plant is provided, the method comprising applying an insecticide to one or more plants of the invention, optionally, wherein the one or more plants are growing in a container, a growth chamber, a greenhouse, a field, a recreational area, a lawn, or on a roadside, thereby reducing insect predation on the one or more plants.

In some embodiments, a method of reducing fungal disease on a plant is provided, the method comprising applying a fungicide to one or more plants of the invention, optionally, wherein the one or more plants are growing in a container, a growth chamber, a greenhouse, a field, a recreational area, a lawn, or on a roadside, thereby reducing fungal disease on the one or more plants.

A polynucleotide of interest may be any polynucleotide that can confer a desirable phenotype or otherwise modify the phenotype or genotype of a plant. In some embodiments, a polynucleotide of interest may be polynucleotide that confers herbicide tolerance, insect resistance, nematode resistance, disease resistance, increased yield, increased nutrient use efficiency or abiotic stress resistance.

Thus, plants or plant cultivars which are to be treated with preference in accordance with the invention include all plants which, through genetic modification, received genetic material which imparts particular advantageous useful properties ("traits") to these plants. Examples of such properties are better plant growth, vigor, stress tolerance, standability, lodging resistance, nutrient uptake, plant nutrition, and/or yield, in particular improved growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products.

Further examples of such properties are an increased resistance against animal and microbial pests, such as against insects, arachnids, nematodes, mites, slugs and snails owing, for example, to toxins formed in the plants. Among DNA sequences encoding proteins which confer properties of tolerance to such animal and microbial pests, in particular insects, mention will particularly be made of the genetic material from *Bacillus thuringiensis* encoding the Bt proteins widely described in the literature and well known to those skilled in the art. Mention will also be made of proteins extracted from bacteria such as *Photorhabdus* (WO97/17432 and WO98/08932). In particular, mention will be made of the Bt Cry or VIP proteins which include the Cry1A, Cry1Ab, Cry1Ac, Cry2A, Cry3A, Cry3B2, Cry9c Cry2Ab, Cry3Bb and Cry1F proteins or toxic fragments thereof and also hybrids or combinations thereof, especially the Cry1F protein or hybrids derived from a Cry1F protein (e.g. hybrid Cry1A-Cry1F proteins or toxic fragments thereof), the Cry1A-type proteins or toxic fragments thereof, preferably the Cry1Ac protein or hybrids derived from the Cry1Ac protein (e.g. hybrid Cry1Ab-Cry1Ac proteins) or the Cry1Ab or Bt2 protein or toxic fragments thereof, the Cry2Ae, Cry2Af or Cry2Ag proteins or toxic fragments thereof, the Cry1A.105 protein or a toxic fragment thereof, the VIP3Aa19 protein, the VIP3Aa20 protein, the VIP3A proteins produced in the COT202 or COT203 cotton events, the VIP3Aa protein or a toxic fragment thereof as described in Estruch et al. (1996), Proc Natl Acad Sci US A. 28; 93(11):5389-94, the Cry proteins as described in WO2001/47952, the insecticidal proteins from *Xenorhabdus* (as described in WO98/50427), *Serratia* (particularly from *S. entomophila*) or *Photorhabdus* species strains, such as Tc-proteins from *Photorhabdus* as described in WO98/08932. Also any variants or mutants of any one of these proteins differing in some amino acids (1-10, preferably 1-5) from any of the above named sequences, particularly the sequence of their toxic fragment, or which are fused to a transit peptide, such as a plastid transit peptide, or another protein or peptide, is included herein.

Another and particularly emphasized example of such properties is conferred tolerance to one or more herbicides, for example imidazolinones, sulphonylureas, glyphosate or phosphinothricin. Among DNA sequences encoding proteins (i.e., polynucleotides of interest) which confer properties of tolerance to certain herbicides on the transformed plant cells and plants, mention will be particularly be made to the bar or PAT gene or the *Streptomyces coelicolor* gene described in WO2009/152359 which confers tolerance to glufosinate herbicides, a gene encoding a suitable EPSPS (5-Enolpyruvylshikimat-3-phosphat-Synthase) which confers tolerance to herbicides having EPSPS as a target, especially herbicides such as glyphosate and its salts, a gene encoding glyphosate-n-acetyltransferase, or a gene encoding glyphosate oxidoreductase. Further suitable herbicide tolerance traits include at least one ALS (acetolactate synthase) inhibitor (e.g., WO2007/024782), a mutated *Arabidopsis* ALS/AHAS gene (e.g., U.S. Pat. No. 6,855,533), genes encoding 2,4-D-monooxygenases conferring tolerance to 2,4-D (2,4-dichlorophenoxyacetic acid) and genes encoding Dicamba monooxygenases conferring tolerance to dicamba (3,6-dichloro-2-methoxybenzoic acid).

Further examples of such properties are increased resistance against phytopathogenic fungi, bacteria and/or viruses owing, for example, to systemic acquired resistance (SAR), systemin, phytoalexins, elicitors and also resistance genes and correspondingly expressed proteins and toxins.

Particularly useful transgenic events in transgenic plants or plant cultivars which can be treated with preference in accordance with the invention include Event 531/PV-GHBK04 (cotton, insect control, described in WO2002/040677), Event 1143-14A (cotton, insect control, not deposited, described in WO2006/128569); Event 1143-51B (cotton, insect control, not deposited, described in WO2006/128570); Event 1445 (cotton, herbicide tolerance, not deposited, described in US-A 2002-120964 or WO2002/034946); Event 17053 (rice, herbicide tolerance, deposited as PTA-9843, described in WO2010/117737); Event 17314 (rice, herbicide tolerance, deposited as PTA-9844, described in WO2010/117735); Event 281-24-236 (cotton, insect control-herbicide tolerance, deposited as PTA-6233, described in WO2005/103266 or US-A 2005-216969); Event 3006-210-23 (cotton, insect control-herbicide tolerance, deposited as PTA-6233, described in US-A 2007-143876 or WO2005/103266); Event 3272 (corn, quality trait, deposited as PTA-9972, described in WO2006/098952 or US-A 2006-230473); Event 33391 (wheat, herbicide tolerance, deposited as PTA-2347, described in WO2002/027004), Event 40416 (corn, insect control-herbicide tolerance, deposited as ATCC PTA-11508, described in WO 11/075593); Event 43A47 (corn, insect control-herbicide tolerance, deposited as ATCC PTA-11509, described in WO2011/075595); Event 5307 (corn, insect control, deposited as ATCC PTA-9561, described in WO2010/077816); Event ASR-368 (bent grass, herbicide tolerance, deposited as ATCC PTA-4816, described in US-A 2006-162007 or WO2004/053062); Event B16 (corn, herbicide tolerance, not deposited, described in US-A 2003-126634); Event BPS-CV127-9 (soybean, herbicide tolerance, deposited as NCIMB No. 41603, described in WO2010/080829); Event BLR1 (oilseed rape, restoration of male sterility, deposited as NCIMB 41193, described in WO2005/074671), Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO2006/128571); Event CE46-02A (cotton, insect control, not deposited, described in WO2006/128572); Event COT102 (cotton, insect control, not deposited, described in US-A 2006-130175 or WO2004/039986); Event COT202 (cotton, insect control, not deposited, described in US-A 2007-067868 or WO2005/054479); Event COT203 (cotton, insect control, not deposited, described in WO2005/054480); Event DAS21606-3/1606 (soybean, herbicide tolerance, deposited as PTA-11028, described in WO2012/033794), Event DAS40278 (corn, herbicide tolerance, deposited as ATCC PTA-10244, described in WO2011/

022469); Event DAS-44406-6/pDAB8264.44.06.1 (soybean, herbicide tolerance, deposited as PTA-11336, described in WO2012/075426), Event DAS-14536-7/pDAB8291.45.36.2 (soybean, herbicide tolerance, deposited as PTA-11335, described in WO2012/075429), Event DAS-59122-7 (corn, insect control-herbicide tolerance, deposited as ATCC PTA 11384, described in US-A 2006-070139); Event DAS-59132 (corn, insect control-herbicide tolerance, not deposited, described in WO2009/100188); Event DAS68416 (soybean, herbicide tolerance, deposited as ATCC PTA-10442, described in WO2011/066384 or WO2011/066360); Event DP-098140-6 (corn, herbicide tolerance, deposited as ATCC PTA-8296, described in US-A 2009-137395 or WO 08/112019); Event DP-305423-1 (soybean, quality trait, not deposited, described in US-A 2008-312082 or WO2008/054747); Event DP-32138-1 (corn, hybridization system, deposited as ATCC PTA-9158, described in US-A 2009-0210970 or WO2009/103049); Event DP-356043-5 (soybean, herbicide tolerance, deposited as ATCC PTA-8287, described in US-A 2010-0184079 or WO2008/002872); Event EE-I (brinjal, insect control, not deposited, described in WO 07/091277); Event Fil 17 (corn, herbicide tolerance, deposited as ATCC 209031, described in US-A 2006-059581 or WO 98/044140); Event FG72 (soybean, herbicide tolerance, deposited as PTA-11041, described in WO2011/063413), Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO98/044140); Event GHB119 (cotton, insect control-herbicide tolerance, deposited as ATCC PTA-8398, described in WO2008/151780); Event GHB614 (cotton, herbicide tolerance, deposited as ATCC PTA-6878, described in US-A 2010-050282 or WO2007/017186); Event GJ11 (corn, herbicide tolerance, deposited as ATCC 209030, described in US-A 2005-188434 or WO98/044140); Event GM RZ13 (sugar beet, virus resistance, deposited as NCIMB-41601, described in WO2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO2003/013224 or US-A 2003-097687); Event LLRICE06 (rice, herbicide tolerance, deposited as ATCC 203353, described in U.S. Pat. No. 6,468,747 or WO2000/026345); Event LLRice62 (rice, herbicide tolerance, deposited as ATCC 203352, described in WO2000/026345), Event LLRICE601 (rice, herbicide tolerance, deposited as ATCC PTA-2600, described in US-A 2008-2289060 or WO2000/026356); Event LY038 (corn, quality trait, deposited as ATCC PTA-5623, described in US-A 2007-028322 or WO2005/061720); Event MIR162 (corn, insect control, deposited as PTA-8166, described in US-A 2009-300784 or WO2007/142840); Event MIR604 (corn, insect control, not deposited, described in US-A 2008-167456 or WO2005/103301); Event MON15985 (cotton, insect control, deposited as ATCC PTA-2516, described in US-A 2004-250317 or WO2002/100163); Event MON810 (corn, insect control, not deposited, described in US-A 2002-102582); Event MON863 (corn, insect control, deposited as ATCC PTA-2605, described in WO2004/011601 or US-A 2006-095986); Event MON87427 (corn, pollination control, deposited as ATCC PTA-7899, described in WO2011/062904); Event MON87460 (corn, stress tolerance, deposited as ATCC PTA-8910, described in WO2009/111263 or US-A 2011-0138504); Event MON87701 (soybean, insect control, deposited as ATCC PTA-8194, described in US-A 2009-130071 or WO2009/064652); Event MON87705 (soybean, quality trait-herbicide tolerance, deposited as ATCC PTA-9241, described in US-A 2010-0080887 or WO2010/037016); Event MON87708 (soybean, herbicide tolerance, deposited as ATCC PTA-9670, described in WO2011/034704); Event MON87712 (soybean, yield, deposited as PTA-10296, described in WO2012/051199), Event MON87754 (soybean, quality trait, deposited as ATCC PTA-9385, described in WO2010/024976); Event MON87769 (soybean, quality trait, deposited as ATCC PTA-8911, described in US-A 2011-0067141 or WO2009/102873); Event MON88017 (corn, insect control-herbicide tolerance, deposited as ATCC PTA-5582, described in US-A 2008-028482 or WO2005/059103); Event MON88913 (cotton, herbicide tolerance, deposited as ATCC PTA-4854, described in WO2004/072235 or US-A 2006-059590); Event MON88302 (oilseed rape, herbicide tolerance, deposited as PTA-10955, described in WO2011/153186), Event MON88701 (cotton, herbicide tolerance, deposited as PTA-11754, described in WO2012/134808), Event MON89034 (corn, insect control, deposited as ATCC PTA-7455, described in WO 07/140256 or US-A 2008-260932); Event MON89788 (soybean, herbicide tolerance, deposited as ATCC PTA-6708, described in US-A 2006-282915 or WO2006/130436); Event MSl 1 (oilseed rape, pollination control-herbicide tolerance, deposited as ATCC PTA-850 or PTA-2485, described in WO2001/031042); Event MS8 (oilseed rape, pollination control-herbicide tolerance, deposited as ATCC PTA-730, described in WO2001/041558 or US-A 2003-188347); Event NK603 (corn, herbicide tolerance, deposited as ATCC PTA-2478, described in US-A 2007-292854); Event PE-7 (rice, insect control, not deposited, described in WO2008/114282); Event RF3 (oilseed rape, pollination control-herbicide tolerance, deposited as ATCC PTA-730, described in WO2001/041558 or US-A 2003-188347); Event RT73 (oilseed rape, herbicide tolerance, not deposited, described in WO2002/036831 or US-A 2008-070260); Event SYHTOH2/SYN-000H2-5 (soybean, herbicide tolerance, deposited as PTA-11226, described in WO2012/082548), Event T227-1 (sugar beet, herbicide tolerance, not deposited, described in WO2002/44407 or US-A 2009-265817); Event T25 (corn, herbicide tolerance, not deposited, described in US-A 2001-029014 or WO2001/051654); Event T304-40 (cotton, insect control-herbicide tolerance, deposited as ATCC PTA-8171, described in US-A 2010-077501 or WO2008/122406); Event T342-142 (cotton, insect control, not deposited, described in WO2006/128568); Event TC1507 (corn, insect control-herbicide tolerance, not deposited, described in US-A 2005-039226 or WO2004/099447); Event VIP1034 (corn, insect control-herbicide tolerance, deposited as ATCC PTA-3925, described in WO2003/052073), Event 32316 (corn, insect control-herbicide tolerance, deposited as PTA-11507, described in WO2011/084632), Event 4114 (corn, insect control-herbicide tolerance, deposited as PTA-11506, described in WO2011/084621), event EE-GM3/FG72 (soybean, herbicide tolerance, ATCC Accession No PTA-11041) optionally stacked with event EE-GM1/LL27 or event EE-GM2/LL55 (WO2011/063413A2), event DAS-68416-4 (soybean, herbicide tolerance, ATCC Accession No PTA-10442, WO2011/066360A1), event DAS-68416-4 (soybean, herbicide tolerance, ATCC Accession No PTA-10442, WO2011/066384A1), event DP-040416-8 (corn, insect control, ATCC Accession No PTA-11508, WO2011/075593A1), event DP-043A47-3 (corn, insect control, ATCC Accession No PTA-11509, WO2011/075595A1), event DP-004114-3 (corn, insect control, ATCC Accession No PTA-11506, WO2011/084621A1), event DP-032316-8 (corn, insect control, ATCC Accession No PTA-11507, WO2011/084632A1), event MON-88302-9 (oilseed rape, herbicide tolerance, ATCC Accession No PTA-10955, WO2011/153186A1), event DAS-21606-3 (soybean, herbicide tolerance, ATCC Accession No. PTA-11028, WO2012/033794A2), event MON-87712-4 (soybean, quality trait, ATCC Accession No. PTA-10296, WO2012/051199A2), event DAS-44406-6 (soybean, stacked herbicide tolerance, ATCC Accession No. PTA-11336, WO2012/075426A1), event DAS-14536-7 (soybean, stacked herbicide tolerance, ATCC Accession No. PTA-11335, WO2012/075429A1), event SYN-000H2-5 (soybean, herbicide tolerance, ATCC Accession No. PTA-11226, WO2012/082548A2), event DP-061061-7 (oilseed rape, herbicide tolerance, no deposit No available, WO2012071039A1), event DP-073496-4 (oilseed rape, herbicide tolerance, no deposit No available, US2012131692), event 8264.44.06.1 (soybean, stacked herbicide tolerance, Accession No PTA-11336, WO2012075426A2), event 8291.45.36.2 (soybean, stacked herbicide tolerance, Accession No. PTA-11335, WO2012075429A2), event SYH-TOH2 (soybean, ATCC Accession No. PTA-11226, WO2012/082548A2), event MON88701 (cotton, ATCC Accession No PTA-11754, WO2012/134808A1), event KK179-2 (alfalfa, ATCC Accession No PTA-11833, WO2013/003558A1), event pDAB8264.42.32.1 (soybean, stacked herbicide tolerance, ATCC Accession No PTA-11993, WO2013/010094A1), event MZDT09Y (corn, ATCC Accession No PTA-13025, WO2013/012775A1).

The genes/events (e.g., polynucleotides of interest), which impart the desired traits in question, may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails, as well as the increased resistance of the plants to one or more herbicides.

Commercially available examples of such plants, plant parts or plant seeds that may be treated with preference in accordance with the invention include commercial products, such as plant seeds, sold or distributed under the GENUITY®, DROUGHTGARD®, SMARTSTAX®, RIB COMPLETE®, ROUNDUP READY®, VT DOUBLE PRO®, VT TRIPLE PRO®, BOLLGARD II®, ROUNDUP READY 2 YIELD®, YIELDGARD®, ROUNDUP READY® 2 XTEND™, INTACTA RR2 PRO®, VISTIVE GOLD®, and/or XTENDFLEX™ trade names.

A Ubiquitin Binding Peptidase (DA1) gene useful with this invention includes any DA1 gene in which a mutation as described herein can confer improvement in one or more yield traits in a plant or part thereof comprising the mutation. In some embodiments, an endogenous DA1 gene (a) comprises a sequence having at least 80% sequence identity to a nucleotide sequence of any one of SEQ ID NOs:69, 70, 109, or 110; (b) comprises a region having at least 90% identity to any one of SEQ ID NOs:72-101 or 112-139; (c) encodes an amino acid sequence having at least 80% sequence identity to SEQ ID NO:71 or SEQ ID NO:111; and/or (d) encodes an amino acid sequence comprising a region having at least 90% identity to any one of SEQ ID NOs:102-108 or 140-146.

In some embodiments, the at least one mutation in an endogenous DA1 gene in a plant may be a base substitution, a base deletion and/or a base insertion. In some embodiments, the at least one mutation may be a non-natural mutation. In some embodiments, the at least one mutation in an endogenous DA1 gene in a plant may result in a plant having the phenotype of one or more improved yield traits as compared to a control plant devoid of the edit/mutation, optionally wherein the improved yield trait can include but is not limited to, higher yield (bu/acre), increased yield (bu/acre), increased biomass, increased plant height, increased stem diameter, increased leaf area, increased flower number, increased kernel number, increased kernel size, increased ear length, increased number of pods, including an increased number of pods per node and/or an increased number of pods per plant, increased number of seeds per pod, increased number of seeds, increased seed size, and/or increased seed weight (e.g., increase in 100-seed weight). In some embodiments, the one or more improved yield traits includes, but not limited to, an increase in yield (bu/acre), an increase in seed size (including kernel size), an increase in seed weight (including kernel weight), an increase in the number of pods, and/or an increase in the number of seeds per pod. In some embodiments, a mutation in an endogenous DA1 gene may be a base substitution, a base deletion and/or a base insertion of at least 1 base pair. In some embodiments, a base substitution, a base deletion and/or a base insertion may be about 2 nucleotides to about 100 nucleotides (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 base pairs, or any range or value therein, e.g., 1 to about 50 base pairs, 1 to about 30 base pairs, 1 to about 15 base pairs, or any range or value therein), optionally where the mutation is at about 2 to about 100 consecutive nucleotides (e.g., 1 to about 50 consecutive base pairs, 1 to about 30 consecutive base pairs, 1 to about 15 consecutive base pairs)). In some embodiments, such a base substitution, base deletion and/or base insertion may result in a substitution, a deletion and/or an insertion of one or more amino acid residues, optionally one amino acid residue to about ten consecutive amino acid residues (e.g., 1, 2, 3, 4, 5, 6, 7, 8, 9 or 10 consecutive amino acid residues) of the DAT polypeptide. In some embodiments, the at least one mutation may be a base substitution to an A, a T, a G, or a C. In some embodiments, the at least one mutation may be, for example, a base substitution to from a G to an A, and/or an A to a G. A mutation may be a point mutation. In some embodiments, the mutation may result in a substitution of one or more amino acid residues located in a region having at least 90% sequence identity to any one of the amino acid sequences of SEQ ID NOs:103-108, 141, 142 or 144-146, optionally in a region having at least 90% sequence identity to any one of SEQ ID NOs: 105-108 or 144-146, optionally the mutation may result in a substitution of an amino acid residue located: at position 312 with reference to amino acid position numbering of SEQ ID NO:71 or at position 379 with reference to amino acid position numbering of SEQ ID NO:111. In some embodiments, a substitution may be a substitution of arginine (R) for lysine (K) (R>K). In some embodiments, the at least one mutation in an endogenous DA1 gene of a plant or plant part may be a deletion, wherein the mutated DA1 gene comprises a sequence having at least 90% identity to any one of SEQ DI NOs:154-158.

In some embodiments, a mutation in an endogenous DA1 gene may be made following cleavage by an editing system that comprises a nuclease and a nucleic acid binding domain that binds to a target site within a target nucleic acid (e.g., a DA1 gene), the target nucleic acid comprising a sequence having at least 80% sequence identity to any one of the nucleotide sequences of SEQ ID NOs:69, 70, 109, or 110, and/or encoding an amino acid sequence having at least 80% sequence identity to any one of SEQ ID NO:71 or SEQ ID NO:111, optionally wherein the target site is located in a region of the DA1 gene: the region comprising a sequence having at least 90% identity to any one of SEQ ID NOs: 72-101 or 112-139 and/or encoding a sequence having at least 90% sequence identity to an amino acid sequence of any one of SEQ ID NOs:102-108 or 140-146.

Further provided are guide nucleic acids (e.g., gRNA, gDNA, crRNA, crDNA) that bind to a target site in a Ubiquitin Binding Peptidase (DA1) gene (DA1-1, DA1-2), wherein the target site is in a region of the DA1 gene having at least 90% sequence identity to any one of the nucleotide sequences of SEQ ID NOs:72-101 or 112-139. In some embodiments, the guide nucleic acid comprises a spacer comprising any one of the nucleotide sequences of SEQ ID NOs:147-143, optionally SEQ ID NOs:147-150 or SEQ ID NOs:151-153.

In some embodiments, a soybean plant or plant part thereof is provided that comprises at least one mutation in at least one endogenous Ubiquitin Binding Peptidase (DA1) gene having the gene identification number (gene ID) of Glyma.14g077800 and/or Glyma.11g062400 (see, Soybean Knowledge Base (SoyKB)), optionally wherein the at least one mutation may be a non-natural mutation. In some embodiments, the mutation in an endogenous DA1 gene of a soybean plant or part thereof may result in a mutated DA1 gene having at least 90% sequence identity to any one of SEQ ID NOs:154-158.

In some embodiments, a guide nucleic acid is provided that binds to a target nucleic acid in a Ubiquitin Binding Peptidase (DA1) gene having the gene identification number (gene ID) of Glyma.14g077800 and/or Glyma.11g062400.

In some embodiments, a system is provided comprising a guide nucleic acid comprising a spacer (e.g., one or more spacers) having the nucleotide sequence of any one of SEQ ID NOs:143-151 or SEQ ID NOs:151-153, and a CRISPR-Cas effector protein that associates with the guide nucleic acid. In some embodiments, the system may further comprise a tracr nucleic acid that associates with the guide nucleic acid and a CRISPR-Cas effector protein, optionally wherein the tracr nucleic acid and the guide nucleic acid are covalently linked.

As used herein, "a CRISPR-Cas effector protein in association with a guide nucleic acid" refers to the complex that is formed between a CRISPR-Cas effector protein and a guide nucleic acid in order to direct the CRISPR-Cas effector protein to a target site in a gene.

The invention further provides a gene editing system comprising a CRISPR-Cas effector protein in association with a guide nucleic acid and the guide nucleic acid comprises a spacer sequence that binds to a Ubiquitin Binding Peptidase (DA1) gene, optionally wherein the DA1 gene (a) comprises a sequence having at least 80% sequence identity to a nucleotide sequence of any one of SEQ ID NOs:69, 70, 109, or 110; (b) comprises a region having at least 90% identity to any one of SEQ ID NOs:72-101 or 112-139; (c) encodes an amino acid sequence having at least 80% sequence identity to SEQ ID NO:71 or SEQ ID NO:111; and/or (d) encodes an amino acid sequence comprising a region having at least 90% identity to any one of SEQ ID NOs:102-108 or 140-146. In some embodiments, a spacer sequence of the guide nucleic acid may comprise the nucleotide sequence of any of SEQ ID NOs:147-153. In some embodiments, the gene editing system may further comprise a tracr nucleic acid that associates with the guide nucleic acid and a CRISPR-Cas effector protein, optionally wherein the tracr nucleic acid and the guide nucleic acid are covalently linked.

The present invention further provides a complex comprising a CRISPR-Cas effector protein comprising a cleavage domain and a guide nucleic acid, wherein the guide nucleic acid binds to a target site in an endogenous Ubiquitin Binding Peptidase (DA1) gene, wherein the endogenous DA1 gene: (a) comprises a sequence having at least 80% sequence identity to a nucleotide sequence of any one of SEQ ID NOs:69, 70, 109, or 110; (b) comprises a region having at least 90% identity to any one of SEQ ID NOs: 72-101 or 112-139; (c) encodes an amino acid sequence having at least 80% sequence identity to SEQ ID NO:71 or SEQ ID NO:111; and/or (d) encodes an amino acid sequence comprising a region having at least 90% identity to any one of SEQ ID NOs:102-108 or 140-146, and the cleavage domain cleaves a target strand in the DA1 gene.

In some embodiments, an expression cassette(s) is/are provided that comprise (a) a polynucleotide encoding CRISPR-Cas effector protein comprising a cleavage domain and (b) a guide nucleic acid that binds to a target site in an endogenous Ubiquitin Binding Peptidase (DA1) gene, wherein the guide nucleic acid comprises a spacer sequence that is complementary to and binds to (i) a portion of a nucleic acid having at least 80% sequence identity to any one of SEQ ID NOs:69, 70, 109, or 110; (ii) a portion of a nucleic acid having at least 90% sequence identity to any one of SEQ ID NOs:72-101 or 112-139; (iii) a portion of a nucleic acid encoding an amino acid sequence having at least 80% sequence identity to any one of SEQ ID NO:71 or SEQ ID NO:111; and/or (iv) a portion of a nucleic acid encoding an amino acid sequence having at least 90% identity to any one of SEQ ID NOs:102-108 or 140-146.

In some embodiments a ubiquitin binding peptidase (DA1) polypeptide (DA1-1, DA1-2) is provided comprising a mutation in an amino acid residue located in a region of the DA1 polypeptide comprising an amino acid sequence having at least 90% sequence identity to any one of SEQ ID NOs:103-108, 141, 142 or 144-146, optionally in a region having at least 90% sequence identity to any one of SEQ ID NOs:105-108 or 144-146, optionally the mutation may result in a substitution of an amino acid residue located: at position 312 with reference to amino acid position numbering of SEQ ID NO:71 or at position 379 with reference to amino acid position numbering of SEQ ID NO:111. In some embodiments, a substitution may be a substitution of arginine (R) for lysine (K) (R>K). In some embodiments, a modified DA1 polypeptide may be encoded by a nucleic acid sequence having at least 90% sequence identity to any one of SEQ ID NOs:154-158.

Also provided are nucleic acids encoding mutated DA1 polypeptides, optionally wherein when present in a plant or plant part, the mutated DA1 polypeptide/mutated DA1 gene results in the plant comprising a phenotype of one or more improved yield traits as compared to a plant or plant part devoid of the mutation. In some embodiments, the nucleic acids encoding mutated DA1 polypeptides may have at least 90% sequence identity to any one of SEQ ID NOs:154-158.

Nucleic acid constructs of the invention (e.g., a construct comprising a sequence specific nucleic acid binding domain (e.g., sequence specific DNA binding domain), a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids (e.g., endogenous DA1 genes, e.g., endogenous DA1-1 gene, endogenous DA1-2 gene) and/or their expression.

Any plant comprising an endogenous DA1 gene that is capable of conferring at least one improved yield trait, when modified as described herein, may be modified (e.g., mutated, e.g., base edited, cleaved, nicked, etc.) as described herein (e.g., using the polypeptides, polynucleotides, RNPs, nucleic acid constructs, expression cassettes, and/or vectors of the invention) to improve one or more yield traits in the plant. A plant exhibiting an improved yield trait may show an improvement of about 5% to about 100% (e.g., about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% or more or any range or value therein; e.g., about 5% to about 10%, about 5% to about 15%, about 5% to about 20%, about 10% to about 50%, about 10% to about 80%, about 10% to about 90%, about 10% to about 100%, about 20% to about 50%, about 20% to about 80%, about 20% to about 90%, about 20% to about 100%, about 30% to about 50%, about 30% to about 80%, about 30% to about 90%, about 30% to about 100%, about 50% to about 100%, about 75% to about 100% or more, and any range or value therein) in the yield trait as compared to a plant or part thereof that is devoid of the mutated endogenous DA1 gene.

An editing system useful with this invention can be any site-specific (sequence-specific) genome editing system now known or later developed, which system can introduce mutations in a target specific manner. For example, an editing system (e.g., site- or sequence-specific editing system) can include, but is not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or more polypeptides and/or one or more polynucleotides that when expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (DNA binding domain), a nuclease, and/or other polypeptide, and/or a polynucleotide.

In some embodiments, an editing system can comprise one or more sequence-specific nucleic acid binding domains (DNA binding domains) that can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN). In some embodiments, an editing system can comprise one or more polypeptides that include, but are not limited to, a deaminase (e.g., a cytosine deaminase, an adenine deaminase), a reverse transcriptase, a Dna2 polypeptide, and/or a 5' flap endonuclease (FEN). In some embodiments, an editing system can comprise one or more polynucleotides, including, but is not limited to, a CRISPR array (CRISPR guide) nucleic acid, extended guide nucleic acid, and/or a reverse transcriptase template.

In some embodiments, a method of modifying or editing Ubiquitin Binding Peptidase (DA1) gene may comprise contacting a target nucleic acid (e.g., a nucleic acid encoding a ubiquitin binding peptidase (DA1) polypeptide, e.g., a DA1-1 polypeptide, a DA1-2 polypeptide) with a base-editing fusion protein (e.g., a sequence specific DNA binding protein (e.g., a CRISPR-Cas effector protein or domain) fused to a deaminase domain (e.g., an adenine deaminase and/or a cytosine deaminase) and a guide nucleic acid, wherein the guide nucleic acid is capable of guiding/targeting the base editing fusion protein to the target nucleic acid, thereby editing a locus within the target nucleic acid. In some embodiments, a base editing fusion protein and guide nucleic acid may be comprised in one or more expression cassettes. In some embodiments, the target nucleic acid may be contacted with a base editing fusion protein and an expression cassette comprising a guide nucleic acid. In some embodiments, the sequence-specific nucleic acid binding fusion proteins and guides may be provided as ribonucleoproteins (RNPs). In some embodiments, a cell may be contacted with more than one base-editing fusion protein and/or one or more guide nucleic acids that may target one or more target nucleic acids in the cell.

In some embodiments, a method of modifying or editing a Ubiquitin Binding Peptidase (DA1) gene may comprise contacting a target nucleic acid (e.g., a nucleic acid encoding a DA1 polypeptide) with a sequence-specific nucleic acid binding fusion protein (e.g., a sequence-specific DNA binding protein (e.g., a CRISPR-Cas effector protein or domain) fused to a peptide tag, a deaminase fusion protein comprising a deaminase domain (e.g., an adenine deaminase and/or a cytosine deaminase) fused to an affinity polypeptide that is capable of binding to the peptide tag, and a guide nucleic acid, wherein the guide nucleic acid is capable of guiding/targeting the sequence-specific nucleic acid binding fusion protein to the target nucleic acid and the sequence-specific nucleic acid binding fusion protein is capable of recruiting the deaminase fusion protein to the target nucleic acid via the peptide tag-affinity polypeptide interaction, thereby editing a locus within the target nucleic acid. In some embodiments, the sequence-specific nucleic acid binding fusion protein may be fused to the affinity polypeptide that binds the peptide tag and the deaminase may be fused to the peptide tag, thereby recruiting the deaminase to the sequence-specific nucleic acid binding fusion protein and to the target nucleic acid. In some embodiments, the sequence-specific binding fusion protein, deaminase fusion protein, and guide nucleic acid may be comprised in one or more expression cassettes. In some embodiments, the target nucleic acid may be contacted with a sequence-specific binding fusion protein, deaminase fusion protein, and an expression cassette comprising a guide nucleic acid. In some embodiments, the sequence-specific nucleic acid binding fusion proteins, deaminase fusion proteins and guides may be provided as ribonucleoproteins (RNPs).

In some embodiments, methods such as prime editing may be used to generate a mutation in an endogenous DA1 gene. In prime editing, RNA-dependent DNA polymerase (reverse transcriptase, RT) and reverse transcriptase templates (RT template) are used in combination with sequence specific nucleic acid binding domains that confer the ability to recognize and bind the target in a sequence-specific manner, and which can also cause a nick of the PAM-containing strand within the target. The nucleic acid binding domain may be a CRISPR-Cas effector protein and in this case, the CRISPR array or guide RNA may be an extended guide that comprises an extended portion comprising a primer binding site (PSB) and the edit to be incorporated into the genome (the template). Similar to base editing, prime editing can take advantages of the various methods of recruiting proteins for use in the editing to the target site, such methods including both non-covalent and covalent interactions between the proteins and nucleic acids used in the selected process of genome editing.

As used herein, a "CRISPR-Cas effector protein" is a protein or polypeptide or domain thereof that cleaves or cuts a nucleic acid, binds a nucleic acid (e.g., a target nucleic acid and/or a guide nucleic acid), and/or that identifies, recognizes, or binds a guide nucleic acid as defined herein. In some embodiments, a CRISPR-Cas effector protein may be an enzyme (e.g., a nuclease, endonuclease, nickase, etc.) or portion thereof and/or may function as an enzyme. In some embodiments, a CRISPR-Cas effector protein refers to a CRISPR-Cas nuclease polypeptide or domain thereof that comprises nuclease activity or in which the nuclease activity has been reduced or eliminated, and/or comprises nickase activity or in which the nickase has been reduced or eliminated, and/or comprises single stranded DNA cleavage activity (ss DNAse activity) or in which the ss DNAse activity has been reduced or eliminated, and/or comprises self-processing RNAse activity or in which the self-processing RNAse activity has been reduced or eliminated. A CRISPR-Cas effector protein may bind to a target nucleic acid.

In some embodiments, a sequence-specific nucleic acid binding domain may be a CRISPR-Cas effector protein. In some embodiments, a CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be Type II CRISPR-Cas effector protein, for example, a Cas9 effector protein. In some embodiments, a CRISPR-Cas effector protein may be Type V CRISPR-Cas effector protein, for example, a Cas12 effector protein.

In some embodiments, a CRISPR-Cas effector protein may include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g., Cas9 nickase, Cas12a nickase.

A CRISPR Cas9 effector protein or CRISPR Cas9 effector domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes, S. thermophilus*), *Lactobacillus* spp., *Bifidobacterium* spp., *Kandleria* spp., *Leuconostoc* spp., *Oenococcus* spp., *Pediococcus* spp., *Weissella* spp., and/or *Olsenella* spp. Example Cas9 sequences include, but are not limited to, the amino acid sequences of SEQ ID NO:56 and SEQ ID NO:57 or the nucleotide sequences of SEQ ID NOs:58-68.

In some embodiments, the CRISPR-Cas effector protein may be a Cas9 polypeptide derived from *Streptococcus pyogenes* and recognizes the PAM sequence motif NGG, NAG, NGA (Mali et al, Science 2013; 339(6121): 823-826). In some embodiments, the CRISPR-Cas effector protein may be a Cas9 polypeptide derived from *Streptococcus thermophiles* and recognizes the PAM sequence motif NGGNG and/or NNAGAAW (W=A or T) (See, e.g., Horvath et al, Science, 2010; 327(5962): 167-170, and Deveau et al, J Bacteriol 2008; 190(4): 1390-1400). In some embodiments, the CRISPR-Cas effector protein may be a Cas9 polypeptide derived from *Streptococcus mutans* and recognizes the PAM sequence motif NGG and/or NAAR (R=A or G) (See, e.g., Deveau et al, J BACTERIOL 2008; 190(4): 1390-1400). In some embodiments, the CRISPR-Cas effector protein may be a Cas9 polypeptide derived from *Streptococcus aureus* and recognizes the PAM sequence motif NNGRR (R=A or G). In some embodiments, the CRISPR-Cas effector protein may be a Cas9 protein derived from *S. aureus*, which recognizes the PAM sequence motif N GRRT (R=A or G). In some embodiments, the CRISPR-Cas effector protein may be a Cas9 polypeptide derived from *S. aureus*, which recognizes the PAM sequence motif N GRRV (R=A or G). In some embodiments, the CRISPR-Cas effector protein may be a Cas9 polypeptide that is derived from *Neisseria meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the CRISPR-Cas effector protein may be a Cas13a protein derived from Leptotrichia shahii, which recognizes a protospacer flanking sequence (PFS) (or RNA PAM (rPAM)) sequence motif of a single 3' A, U, or C, which may be located within the target nucleic acid.

In some embodiments, the CRISPR-Cas effector protein may be derived from Cas12a, which is a Type V Clustered Regularly Interspaced Short Palindromic Repeats (CRISPR)-Cas nuclease, see, e.g., amino acid sequences of SEQ ID NOs:1-17, nucleic acid sequences of SEQ ID NOs:18-20. Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as deadCas12a (e.g., dCas12a). In some embodiments, a Cas12a domain or Cas12a polypeptide having a mutation in its nuclease active site may have impaired activity, e.g., may have nickase activity.

Any deaminase domain/polypeptide useful for base editing may be used with this invention. In some embodiments, the deaminase domain may be a cytosine deaminase domain or an adenine deaminase domain. A cytosine deaminase (or cytidine deaminase) useful with this invention may be any known or later identified cytosine deaminase from any organism (see, e.g., U.S. Pat. No. 10,167,457 and Thuronyi et al. *Nat. Biotechnol.* 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally occurring cytosine deaminase, including but not limited to a primate (e.g., a human, monkey, chimpanzee, gorilla), a dog, a cow, a rat or a mouse. Thus, in some embodiments, a cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same (e.g., SEQ ID NO:27, SEQ ID NO:28 or SEQ ID NO:29). In some embodiments, the cytosine deaminase may be an APOBEC1 deaminase having the amino acid sequence of SEQ ID NO:23. In some embodiments, the cytosine deaminase may be an APOBEC3A deaminase having the amino acid sequence of SEQ ID NO:24. In some embodiments, the cytosine deaminase may be an CDA1 deaminase, optionally a CDA1 having the amino acid sequence of SEQ ID NO:25. In some embodiments, the cytosine deaminase may be a FERNY deaminase, optionally a FERNY having the amino acid sequence of SEQ ID NO:26. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., an evolved deaminase). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of SEQ ID NO:23, SEQ ID NO:24, SEQ ID NO:25 or SEQ ID NO:26 (e.g., at least 80%, at least 85%, at least 90%, at least 92%, at least 95%, at least 96%, at least 97%, at least 98%, at least 99%, or at least 99.5% identical to the amino acid sequence of SEQ ID NO:23, SEQ ID NO:24, SEQ ID NO:25, SEQ ID NO:26, SEQ ID NO:27, SEQ ID NO:28 or SEQ ID NO:29). In some embodiments, a polynucleotide encoding a cytosine deaminase may be codon optimized for expression in a plant and the codon optimized polypeptide may be about 70% to 99.5% identical to the reference polynucleotide.

In some embodiments, a nucleic acid construct of this invention may further encode a uracil glycosylase inhibitor (UGI) (e.g., uracil-DNA glycosylase inhibitor) polypeptide/domain. Thus, in some embodiments, a nucleic acid construct encoding a CRISPR-Cas effector protein and a cytosine deaminase domain (e.g., encoding a fusion protein comprising a CRISPR-Cas effector protein domain fused to a cytosine deaminase domain, and/or a CRISPR-Cas effector protein domain fused to a peptide tag or to an affinity polypeptide capable of binding a peptide tag and/or a deaminase protein domain fused to a peptide tag or to an affinity polypeptide capable of binding a peptide tag) may further encode a uracil-DNA glycosylase inhibitor (UGI), optionally wherein the UGI may be codon optimized for expression in a plant. In some embodiments, the invention provides fusion proteins comprising a CRISPR-Cas effector polypeptide, a deaminase domain, and a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and a UGI may be fused to any combination of peptide tags and affinity polypeptides as described herein, thereby recruiting the deaminase domain and UGI to the CRISPR-Cas effector polypeptide and a target nucleic acid.

In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

A "uracil glycosylase inhibitor" useful with the invention may be any protein that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:41 or a polypeptide having about 70% to about 99.5% sequence identity to the amino acid sequence of SEQ ID NO:41 (e.g., at least 80%, at least 85%, at least 90%, at least 92%, at least 95%, at least 96%, at least 97%, at least 98%, at least 99%, or at least 99.5% identical to the amino acid sequence of SEQ ID NO:41). For example, in some embodiments, a UGI domain may comprise a fragment of the amino acid sequence of SEQ ID NO:41 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:41. In some embodiments, a UGI domain may be a variant of a known UGI (e.g., SEQ ID NO:41) having about 70% to about 99.5% sequence identity (e.g., 70%, 71%, 72%, 73%, 74%, 75%, 76%, 77%, 78%, 79% 80%, 8%1%, 82%, 83%, 84%, 85%, 86%, 87%, 88%, 89%, 90%, 91%, 92%, 93%, 94%, 95%, 96%, 97%, 98%, 99%, 99.5% sequence identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

An adenine deaminase (or adenosine deaminase) useful with this invention may be any known or later identified adenine deaminase from any organism (see, e.g., U.S. Pat. No. 10,113,163, which is incorporated by reference herein for its disclosure of adenine deaminases). An adenine deaminase can catalyze the hydrolytic deamination of adenine or adenosine. In some embodiments, the adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid.

In some embodiments, an adenosine deaminase may be a variant of a naturally occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%9, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli*, *Staphylococcus aureus*, *Haemophilus influenzae*, *Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:30. In some embodiments, a mutated/evolved *E. coli* TadA* comprises the amino acid sequence of SEQ ID NOs:31-40 (e.g., SEQ ID NOs: 31, 32, 33, 34, 35, 36, 37, 38, 39 or 40). In some embodiments, a polynucleotide encoding a TadA/TadA* may be codon optimized for expression in a plant.

A cytosine deaminase catalyzes cytosine deamination and results in a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid.

In some embodiments, the adenine deaminase encoded by the nucleic acid construct of the invention generates an A→G conversion in the sense (e.g., "+"; template) strand of the target nucleic acid or a T→C conversion in the antisense (e.g., "−", complementary) strand of the target nucleic acid.

The nucleic acid constructs of the invention encoding a base editor comprising a sequence-specific nucleic acid binding protein and a cytosine deaminase polypeptide, and nucleic acid constructs/expression cassettes/vectors encoding the same, may be used in combination with guide nucleic acids for modifying target nucleic acid including, but not limited to, generation of C→T or G→A mutations in a target nucleic acid including, but not limited to, a plasmid sequence; generation of C→T or G→A mutations in a coding sequence to alter an amino acid identity; generation of C→T or G→A mutations in a coding sequence to generate a stop codon; generation of C→T or G→A mutations in a coding sequence to disrupt a start codon; generation of point mutations in genomic DNA to disrupt function; and/or generation of point mutations in genomic DNA to disrupt splice junctions.

The nucleic acid constructs of the invention encoding a base editor comprising a sequence-specific nucleic acid binding protein and an adenine deaminase polypeptide, and expression cassettes and/or vectors encoding the same may be used in combination with guide nucleic acids for modifying a target nucleic acid including, but not limited to, generation of A→G or T→C mutations in a target nucleic acid including, but not limited to, a plasmid sequence; generation of A→G or T→C mutations in a coding sequence to alter an amino acid identity; generation of A→G or T→C mutations in a coding sequence to generate a stop codon; generation of A→G or T→C mutations in a coding sequence to disrupt a start codon; generation of point mutations in genomic DNA to disrupt function; and/or generation of point mutations in genomic DNA to disrupt splice junctions.

The nucleic acid constructs of the invention comprising a CRISPR-Cas effector protein or a fusion protein thereof may be used in combination with a guide RNA (gRNA, CRISPR array, CRISPR RNA, crRNA), designed to function with the encoded CRISPR-Cas effector protein or domain, to modify a target nucleic acid. A guide nucleic acid useful with this invention comprises at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex (e.g., a CRISPR-Cas effector fusion protein (e.g., CRISPR-Cas effector domain fused to a deaminase domain and/or a CRISPR-Cas effector domain fused to a peptide tag or an affinity polypeptide to recruit a deaminase domain and optionally, a UGI) to the target nucleic acid, wherein the target nucleic acid may be modified (e.g., cleaved or edited) or modulated (e.g., modulating transcription) by the deaminase domain.

As an example, a nucleic acid construct encoding a Cas9 domain linked to a cytosine deaminase domain (e.g., fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) linked to a cytosine deaminase domain or adenine deaminase domain (e.g., fusion protein) may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof; a repeat of a Type II Cas9 CRISPR-Cas system, or fragment thereof; a repeat of a Type V C2c1 CRISPR Cas system, or a fragment thereof; a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made, and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids Res.* 35(Web Server issue):W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g., protospacer) (e.g., a portion of consecutive nucleotides of a sequence that (a) comprises a sequence of consecutive nucleotides having at least 80% sequence identity to any one of SEQ ID NOs:69, 70, 109, or 110; (b) comprises a region having at least 90% sequence identity to any one of SEQ ID NOs:72-101 or 112-139; (c) encodes a sequence of consecutive amino acids having at least 80% sequence identity to any one of SEQ ID NO:71 or SEQ ID NO:111; and/or (d) or encodes a region having at least 90% sequence identity to any one of SEQ ID NOs:102-108 or 140-146. In some embodiments, a spacer sequence (e.g., one or more spacers) may include, but is not limited to, the nucleotide sequences of any one of SEQ ID NOs:147-150 and/or 151-153. The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more (e.g., 99.1, 99.2, 99.3, 99.4, 99.5, 99.6, 99.7, 99.8, 99.9, or 100%)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length.

In some embodiments, the 5' region of a spacer sequence of a guide nucleic acid may be identical to a target DNA, while the 3' region of the spacer may be substantially complementary to the target DNA (e.g., Type V CRISPR-Cas), or the 3' region of a spacer sequence of a guide nucleic acid may be identical to a target DNA, while the 5' region of the spacer may be substantially complementary to the target DNA (e.g., Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%9, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA.

In some embodiments, a seed region of a spacer may be about 8 to about 10 nucleotides in length, about 5 to about 6 nucleotides in length, or about 6 nucleotides in length.

As used herein, a "target nucleic acid", "target DNA," "target nucleotide sequence," "target region," or a "target region in the genome" refers to a region of a plant's genome that is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

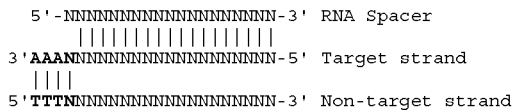

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention (e.g., one or more components of an editing system of the invention). In some embodiments, expression cassettes and/or vectors comprising the nucleic acid constructs of the invention and/or one or more guide nucleic acids may be provided. In some embodiments, a nucleic acid construct of the invention encoding a base editor (e.g., a construct comprising a CRISPR-Cas effector protein and a deaminase domain (e.g., a fusion protein)) or the components for base editing (e.g., a CRISPR-Cas effector protein fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

Fusion proteins of the invention may comprise sequence-specific nucleic acid binding domains (e.g., sequence-specific DNA binding domains), CRISPR-Cas polypeptides, and/or deaminase domains fused to peptide tags or affinity polypeptides that interact with the peptide tags, as known in the art, for use in recruiting the deaminase to the target nucleic acid. Methods of recruiting may also comprise guide nucleic acids linked to RNA recruiting motifs and deaminases fused to affinity polypeptides capable of interacting with RNA recruiting motifs, thereby recruiting the deaminase to the target nucleic acid. Alternatively, chemical interactions may be used to recruit polypeptides (e.g., deaminases) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26(5): 910-924 (2017)); Gilbreth (*Curr Opin Struc Biol* 22(4):413-420 (2013)), U.S. Pat. No. 9,982,053, each of which are incorporated by reference in their entireties for the teachings relevant to affibodies, anticalins, monobodies and/or DARPins. Example peptide tag sequences and their affinity polypeptides include, but are not limited to, the amino acid sequences of SEQ ID NOs:42-44.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases). Example RNA recruiting motifs and their affinity polypeptides include, but are not limited to, the sequences of SEQ ID NOs:45-55.

In some embodiments, a polypeptide fused to an affinity polypeptide may be a reverse transcriptase and the guide nucleic acid may be an extended guide nucleic acid linked to an RNA recruiting motif. In some embodiments, an RNA recruiting motif may be located on the 3' end of the extended portion of an extended guide nucleic acid (e.g., 5'-3', repeat-spacer-extended portion (RT template-primer binding site)-RNA recruiting motif). In some embodiments, an RNA recruiting motif may be embedded in the extended portion.

In some embodiments of the invention, an extended guide RNA and/or guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited, to a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide Pumilio/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide Pumilio/fem-3 mRNA binding factor (PUF).

In some embodiments, the components for recruiting polypeptides and nucleic acids may those that function through chemical interactions that may include, but are not limited to, rapamycin-inducible dimerization of FRB-FKBP; Biotin-streptavidin; SNAP tag; Halo tag; CLIP tag; DmrA-DmrC heterodimer induced by a compound; bifunctional ligand (e.g., fusion of two protein-binding chemicals together, e.g., dihyrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

Further provided herein are cells comprising one or more polynucleotides, guide nucleic acids, nucleic acid constructs, expression cassettes or vectors of the invention.

The nucleic acid constructs of the invention (e.g., a construct comprising a sequence specific DNA binding domain, a CRISPR-Cas effector domain, a deaminase domain, reverse transcriptase (RT), RT template and/or a guide nucleic acid, etc.) and expression cassettes/vectors comprising the same may be used as an editing system of this invention for modifying target nucleic acids and/or their expression.

A target nucleic acid of any plant or plant part (or groupings of plants, for example, into a genus or higher order classification) may be modified (e.g., mutated, e.g., base edited, cleaved, nicked, etc.) using the polypeptides, polynucleotides, ribonucleoproteins (RNPs), nucleic acid constructs, expression cassettes, and/or vectors of the invention including an angiosperm, a gymnosperm, a monocot, a dicot, a C3, C4, CAM plant, a bryophyte, a fern and/or fern ally, a microalgae, and/or a macroalgae. A plant and/or plant part that may be modified as described herein may be a plant and/or plant part of any plant species/variety/cultivar. In some embodiments, a plant that may be modified as described herein is a monocot. In some embodiments, a plant that may be modified as described herein is a dicot.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell. A "protoplast" is an isolated plant cell without a cell wall or with only parts of the cell wall. Thus, in some embodiments of the invention, a transgenic cell comprising a nucleic acid molecule and/or nucleotide sequence of the invention is a cell of any plant or plant part including, but not limited to, a root cell, a leaf cell, a tissue culture cell, a seed cell, a flower cell, a fruit cell, a pollen cell, and the like. In some aspects of the invention, the plant part can be a plant germplasm. In some aspects, a plant cell can be non-propagating plant cell that does not regenerate into a plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, a "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

In some embodiments of the invention, a transgenic tissue culture or transgenic plant cell culture is provided, wherein the transgenic tissue or cell culture comprises a nucleic acid molecule/nucleotide sequence of the invention. In some embodiments, transgenes may be eliminated from a plant developed from the transgenic tissue or cell by breeding of the transgenic plant with a non-transgenic plant and selecting among the progeny for the plants comprising the desired gene edit and not the transgenes used in producing the edit.

Any plant comprising an endogenous Ubiquitin Binding Peptidase (DA1) gene may be modified as described herein to improve one or more yield traits. Non-limiting examples of plants that may be modified as described herein may include, but are not limited to, turf grasses (e.g., bluegrass, bentgrass, ryegrass, fescue), feather reed grass, tufted hair grass, miscanthus, arundo, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, papaya, and lychee, a field crop plant such as clover, alfalfa, timothy, evening primrose, meadow foam, corn/maize (field, sweet, popcorn), hops, jojoba, buckwheat, safflower, quinoa, wheat, rice, barley, rye, millet, sorghum, oats, triticale, sorghum, tobacco, kapok, a leguminous plant (beans (e.g., green and dried), lentils, peas, soybeans), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), *Cannabis* (e.g., *Cannabis sativa, Cannabis indica,* and *Cannabis ruderalis*), lauraceae (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify, for example, soybean or canola.

In some embodiments, a plant that may be modified as described herein may include, but is not limited to, corn, soybean, canola, wheat, rice, cotton, sugarcane, sugar beet, barley, oats, alfalfa, sunflower, safflower, oil palm, sesame, coconut, tobacco, potato, sweet potato, cassava, coffee, apple, plum, apricot, peach, cherry, pear, fig, banana, citrus, cocoa, avocado, olive, almond, walnut, strawberry, watermelon, pepper, grape, tomato, cucumber, or a *Brassica* spp (e.g., *B. napus, B. oleracea, B. rapa, B. juncea,* and/or *B. nigra*). In some embodiments, a plant that may be modified as described herein is a dicot. In some embodiments, a plant that may be modified as described herein is a monocot. In some embodiments, a plant that may be modified as described herein is canola (e.g., *Brassica napus, Brassica rapa, Brassica juncea*). In some embodiments, a plant that may be modified as described herein is soybean (i.e., *Glycine max*).

The invention will now be described with reference to the following examples. It should be appreciated that these examples are not intended to limit the scope of the claims to the invention but are rather intended to be exemplary of certain embodiments. Any variations in the exemplified methods that occur to the skilled artisan are intended to fall within the scope of the invention.

EXAMPLES

Example 1. Modification of Ubiquitin Binding Peptidase (DA1) Genes in Soybean

A strategy to generate edits in endogenous Ubiquitin Binding Peptidase (DA1) (e.g., DA1-1, DA1-2) genes in soybean was developed. Specifically, the DA genes from soybean having the gene identification number (gene ID) of Glyma. 14g077800 (SEQ ID NO:69 (genomic), SEQ ID NO: 70 (coding)) and/or Glyma. 11g062400 (SEQ ID NO:109 (genomic), SEQ ID NO: 110 (coding)) were targeted to obtain, for example, plants with altered seed development. Without wishing to be limited by any particular theory, it is believed that this type of mutation occurs by unrestricting cell proliferation in the integuments, which may result from edits to the DA1 genes as described herein when expressed, for example, in the seeds.

To generate a range of alleles, multiple Cas12a guide nucleic acids comprising spacers (see Table 1) having complementarity to a region of the DA1 gene encoding a near amino acid 312 or 379 with reference to the amino acid numbering of SEQ ID NO:71 or SEQ ID NO:111, respectively, were designed and placed into a construct.

Lines carrying edits in the DA1 genes are screened and those that show sequencing reads having edits in the targeted gene are advanced to the next generation.

TABLE 1

Example spacers for targeting soybean DA1 genes

| Spacer name | SEQ ID NO: | Target gene SEQ ID NO (gene ID no) |
|---|---|---|
| PWsp1495 | 147 | 69 (Glyma.14g077800), 109 (Glyma.11g062400) |
| PWsp1496 | 148 | 69, 109 |
| PWsp1497 | 149 | 69, 109 |
| PWsp1498 | 150 | 69, 109 |
| PWsp1555 | 151 | 69 |
| PWsp1686 | 152 | 69 |
| PWsp1687 | 153 | 69 |

Example 2. Edited Alleles

The edited soybean lines generated as described in Example 1 were evaluated for edits in the DA1 genes Glyma.14g077800 (SEQ ID NO:69) and Glyma.11g062400 (SEQ ID NO:109). A range of edits were identified which segregated in the subsequent generations. Edited alleles are further described in Table 2 below.

TABLE 2

Edited alleles

| Gene and allele name | Edit description | Mutation type |
|---|---|---|
| Allele A Glyma.14g077800 (SEQ ID NO: 157, CE123633 L213) | 6 bp deletion (GTCTCT) at position 272 of SEQ ID NO: 69 | In-frame deletion |
| Allele A Glyma.11g062400 (SEQ ID NO: 154; CE123488) | 10 bp deletion (TGGCAAATAT, SEQ ID NO: 159) at position 63 of SEQ ID NO: 109 | Out-of-frame mutation |
| Allele B Glyma.11g062400 (SEQ ID NO: 155, CE123607) | 7 bp deletion (GCAAATA) at position 65 of SEQ ID NO: 109 | Out-of-frame mutation |
| Allele C Glyma.11g062400 (SEQ ID NO: 156, CE123633 L212) | 8 bp deletion (TGGCAAAT) at position 63 of SEQ ID NO: 109 | Out-of-frame mutation |
| Allele D Glyma.11g062400 (SEQ ID NO: 158, CE123696) | 13 bp deletion (GGCAAATATGGAG, SEQ ID NO: 160) at position 64 of SEQ ID NO: 109 | Out-of-frame mutation |

Example 3: Phenotype Analysis

Soybean seed was germinated, and the plants grown in the greenhouse to the R6 stage of growth. Plant architectural features associated with yield were evaluated and the resulting observations are outlined in Table 3 and Table 4, below. These observations suggest that edits in the DA1 genes influence plant architecture that may affect yield.

TABLE 3

Phenotypic observations

| Glyma.14g077800 allele | Glyma.11g062400 allele | # of plants | Pods per node on mainstem | Pods per plant | Seeds per plant | Seeds per pod | Seed weight | 100 Seed Weight |
|---|---|---|---|---|---|---|---|---|
| Silent edits in intron | Allele A homozygous | 1 | 2.7 | 186 | 451 | 2.42 | 57.22 | 12.7 |
| Silent edits in intron | Allele A heterozygous | 2 | 3.3 | 188.5 | 471 | 2.50 | 56.30 | 12 |
| Silent edits in intron | Allele B heterozygous | 2 | 3 | 190.5 | 503 | 2.63 | 66.32 | 13 |
| Silent edits in intron | Allele B heterozygous | 1 | 2.9 | 210 | 611 | 2.91 | 89.74 | 14.7 |
| Allele A heterozygous (includes silent edits in intron) | Allele C heterozygous; Allele D heterozygous | 1 | 2.6 | 211 | 571 | 2.71 | 77.90 | 13.6 |

TABLE 3-continued

| | Phenotypic observations | | | | | | | |
|---|---|---|---|---|---|---|---|---|
| Glyma.14g077800 allele | Glyma.11g062400 allele | # of plants | Pods per node on mainstem | Pods per plant | Seeds per plant | Seeds per pod | Seed weight | 100 Seed Weight |
| Silent edits in intron | Allele C homozygous | 1 | 3.2 | 222 | 502 | 2.26 | 59.60 | 11.9 |
| Allele A heterozygous (silent edits in intron) | Allele C heterozygous; Allele D heterozygous | 1 | 3.2 | 191 | 488 | 2.55 | 57.85 | 11.9 |
| Allele A heterozygous (silent edits in intron) | Allele D homozygous | 1 | 2.7 | 179 | 379 | 2.12 | 52.20 | 13.8 |
| Silent edits in intron | Allele A heterozygous | 1 | 2.4 | 214 | 534 | 2.50 | 65.35 | 12.2 |
| Silent edits in intron | Allele A homozygous | 1 | 2.6 | 209 | 516 | 2.47 | 64.99 | 12.6 |
| Silent edits in intron | Allele A heterozygous | 1 | 3 | 187 | 489 | 2.6 | 59.5 | 12.2 |
| Silent edits in intron | Allele A heterozygous | 1 | 2.7 | 176 | 442 | 2.5 | 57.3 | 13 |
| Transformation control* | Transformation control* | 10 | 3.2 | 198 | 448.3 | 2.3 | 55.3 | 12.4 |
| Wild type-unedited | Wild type-unedited | 10 | 3.4 | 192.9 | 476.1 | 2.5 | 60.3 | 12.7 |

*A plant that has gone through the transformation process to express the β-glucuronidase (GUS) reporter gene, but which is not edited.

TABLE 4

| | Phenotypic observations | | | | | | |
|---|---|---|---|---|---|---|---|
| Glyma.14g077800 allele | Glyma.11g062400 allele | # of plants | Plant Height | Nodes on Mainstem | Number of branches | Pods on branches | Pods on Mainstem |
| Silent edits in intron | Glyma.11g062400 Allele A homozygous | 1 | 98 | 27 | 11 | 112 | 74 |
| Silent edits in intron | Glyma.11g062400 Allele A heterozygous | 2 | 101.5 | 25.5 | 12.5 | 103.5 | 85 |
| Silent edits in intron | Glyma.11g062400 Allele B heterozygous | 2 | 97 | 26.5 | 11 | 111.5 | 79 |
| Silent edits in intron | Glyma.11g062400 Allele B heterozygous | 1 | 92 | 26 | 11 | 135 | 75 |
| Allele A heterozygous (includes silent edits in intron) | Allele C heterozygous; Allele D heterozygous | 1 | 88 | 24 | 13 | 149 | 62 |
| Silent edits in intron | Allele C homozygous | 1 | 94 | 26 | 13 | 139 | 83 |
| Allele A heterozygous (silent edits in intron) | Allele C heterozygous; Allele D heterozygous | 1 | 92 | 25 | 11 | 111 | 80 |
| Allele A heterozygous (silent edits in intron) | Allele D homozygous | 1 | 90 | 24 | 11 | 115 | 64 |
| Silent edits in intron | Allele A heterozygous | 1 | 99 | 26 | 10 | 151 | 63 |
| Silent edits in intron | Allele A homozygous | 1 | 98 | 26 | 10 | 142 | 67 |
| Silent edits in intron | Allele A heterozygous | 1 | 98 | 25. | 11 | 113 | 74 |
| Silent edits in intron | Allele A heterozygous | 1 | 98 | 26 | 10 | 105 | 71 |
| Transformation control* | Transformation control* | 10 | 102.9 | 25.1 | 12.4 | 118.9 | 79.1 |

TABLE 4-continued

Phenotypic observations

| Glyma.14g077800 allele | Glyma.11g062400 allele | # of plants | Plant Height | Nodes on Mainstem | Number of branches | Pods on branches | Pods on Mainstem |
|---|---|---|---|---|---|---|---|
| Wild type-unedited | Wild type-unedited | 10 | 98.7 | 25.6 | 12.2 | 106.3 | 86.6 |

*A plant that has gone through the transformation process to express the β-glucuronidase (GUS) reporter gene, but which is not edited.

The foregoing is illustrative of the present invention and is not to be construed as limiting thereof. The invention is defined by the following claims, with equivalents of the claims to be included therein.

That which is claimed is:

1. A soybean plant or part thereof comprising at least one non-natural mutation in an endogenous Ubiquitin Binding Peptidase (DA1) gene encoding a ubiquitin binding peptidase (DA1) polypeptide, wherein the endogenous DA1 gene comprises a nucleotide sequence having at least 80% sequence identity to SEQ ID NO:109, wherein the at least one non-natural mutation comprises a mutation in a region of the endogenous DA1 gene having at least 90% sequence identity to a nucleotide sequence of any one of SEQ ID NOs:112-120 or 127-135, and
wherein the soybean plant comprising the at least one non-natural mutation has a phenotype of one or more improved yield traits as compared to a soybean plant devoid of the at least one non-natural mutation.

2. The soybean plant or part thereof of claim 1, wherein the endogenous DA1 gene (a) comprises a nucleotide sequence having at least 80% sequence identity to SEQ ID NO:110; (b) comprises a region having at least 90% sequence identity to a nucleotide sequence of any one of SEQ ID NOs:112-139; (c) encodes the DA1 polypeptide having at least 80% sequence identity to SEQ ID NO:111; and/or (d) encodes a region having at least 90% sequence identity to any one of SEQ ID NOs:140-146.

3. The soybean plant or part thereof of claim 1, wherein the at least one non-natural mutation in the endogenous DA1 gene results in a mutation of one or more amino acid residue(s) located in a region of the encoded DA1 polypeptide having at least 90% sequence identity to any one of SEQ ID NOs:140-142.

4. The soybean plant or part thereof of claim 1, wherein the at least one non-natural mutation results in a substitution, insertion, or deletion of one or more amino acid residue(s) located in a region having at least 90% sequence identity to any one of SEQ ID NOs:140-142.

5. The soybean plant or part thereof of claim 1, further comprising a substitution of an amino acid residue located at position 379 with reference to amino acid position numbering of SEQ ID NO:111.

6. The soybean plant or part thereof of claim 1, wherein the at least one non-natural mutation results in a mutated DA1 gene in the soybean plant or part thereof, the mutated DA1 gene having at least 90% sequence identity to any one of SEQ ID NOs:154-156, or 158.

7. The soybean plant or part thereof of claim 1, wherein the at least one non-natural mutation results in a modified DA1 polypeptide in the soybean plant or part thereof, the modified DA1 polypeptide comprising a mutation in an amino acid residue located in a region of a DA1 polypeptide comprising an amino acid sequence having at least 90% sequence identity to any one of SEQ ID NOs:140-142.

8. A soybean plant cell comprising at least one non-natural mutation within an endogenous Ubiquitin Binding Peptidase (DA1) gene, wherein the endogenous DA1 gene comprises a nucleotide sequence having at least 80% sequence identity to SEQ ID NO:109, wherein the at least one non-natural mutation is a substitution, insertion, or deletion that is introduced using an editing system that comprises a nucleic acid binding domain that binds to a target site in the endogenous DA1 gene, and wherein the at least one non-natural mutation comprises a mutation in a region of the endogenous DA1 gene having at least 90% sequence identity to a nucleotide sequence of any one of SEQ ID NOs: 112-120 or 127-135.

9. The soybean plant cell of claim 8, wherein the target site is within a region of the endogenous DA1 gene, the region encoding an amino acid sequence having at least 90% sequence identity to any one of SEQ ID NOs:140-142.

10. The soybean plant cell of claim 9, wherein the editing system further comprises a nuclease, wherein the nucleic acid binding domain binds to the target site in a sequence having least 80% sequence identity to any one of SEQ ID NOs:109 or 110 and/or in a sequence having at least 90% sequence identity to the nucleotide sequence of any one of SEQ ID NOs:112-120 or 127-135, and wherein the at least one non-natural mutation within the DA1 gene is made following cleavage by the nuclease.

11. The soybean plant cell of claim 8, wherein the at least one non-natural mutation within the DA1 gene is an insertion and/or a deletion.

12. The soybean plant cell of claim 8, further comprising a substitution of an amino acid residue located: at position 379 with reference to amino acid position numbering of SEQ ID NO:111.

13. The soybean plant cell of claim 8, wherein the at least one non-natural mutation results in a mutated DA1 gene comprising a nucleotide sequence having at least 90% sequence identity to any one of SEQ ID NOs:154-156 or 158.

14. A method for producing a soybean plant or part thereof comprising at least one cell having a mutated endogenous Ubiquitin Binding Peptidase (DA1) gene, the method comprising;
    contacting a target site in an endogenous DA1 gene in the soybean plant or part thereof with a nuclease comprising a cleavage domain and a nucleic acid binding domain, wherein the nucleic acid binding domain binds to a target site in the endogenous DA1 gene, wherein the endogenous DA1 gene comprises a nucleotide sequence having at least 80% sequence identity to SEQ ID NO: 109, thereby producing the soybean plant or part thereof comprising the at least one cell having the mutated endogenous DA1 gene;
    and
    wherein the mutated endogenous DA1 gene comprises a non-natural mutation in a region of the endogenous DA1 gene having at least 90% sequence identity to a nucleotide sequence of any one of SEQ ID NOs:112-120 or 127-135.

15. The method of claim 14, wherein the non-natural mutation is a substitution, an insertion, and/or a deletion.

16. The method of claim 14, wherein the non-natural mutation is an insertion and/or a deletion that results in an amino acid substitution and/or a premature stop codon.

17. The method of claim 14, wherein the non-natural mutation results in a modified amino acid residue located in a region having at least 90% sequence identity to any one of SEQ ID NOs:140-142.

18. The method of claim 14, wherein the mutated endogenous DA1 gene further comprises a substitution at position 379 with reference to amino acid position numbering of SEQ ID NO:111.

19. A guide nucleic acid that binds to a target site in a Ubiquitin Binding Peptidase (DA1) gene, wherein the target site is in a region of the DA1 gene having at least 90% sequence identity to any one of SEQ ID NOs:112-120 or 127-135.

20. The soybean plant or part thereof of claim 1, wherein the at least one non-natural mutation is a deletion.

* * * * *

UNITED STATES PATENT AND TRADEMARK OFFICE
CERTIFICATE OF CORRECTION

Page 1 of 1

PATENT NO. : 12,359,215 B2
APPLICATION NO. : 17/822822
DATED : July 15, 2025
INVENTOR(S) : Mathew et al.

It is certified that error appears in the above-identified patent and that said Letters Patent is hereby corrected as shown below:

In the Specification

Column 26, Lines 13-14: Please remove the paragraph break between "nucleotides." and "In some"

Column 28, Line 23: Please correct "PLA2-6" to read --PLA$_2$-ô--

Column 28, Line 35: Please correct "(SANMS)" to read --(SAMS)--

Column 32, Lines 25-26: Please remove the paragraph break between "invention." and "In some"

Column 50, Line 44: Please correct "SYHTOH2/SYN-000H2-5" to read --SYHT0H2/SYN-000H2-5--

Column 51, Lines 27-28: Please correct "SYHTOH2" to read --SYHT0H2--

Column 52, Line 54: Please correct "DAT" to read --DA1--

Column 61, Lines 8-9: Please remove the paragraph break between "acid." and "In some"

Column 72, Line 47: Please correct "DA" to read --*DA1*--

Signed and Sealed this
Thirtieth Day of December, 2025

John A. Squires
*Director of the United States Patent and Trademark Office*